US011634425B2

(12) United States Patent
Cockerill et al.

(10) Patent No.: US 11,634,425 B2
(45) Date of Patent: Apr. 25, 2023

(54) PHARMACEUTICAL COMPOUNDS

(71) Applicant: ReViral Limited, Stevenage (GB)

(72) Inventors: George Stuart Cockerill, Stevenage (GB); James Good, Stevenage (GB); Edward James Cochrane, Nottingham (GB)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 17/845,187

(22) Filed: Jun. 21, 2022

(65) Prior Publication Data

US 2022/0324873 A1 Oct. 13, 2022

Related U.S. Application Data

(63) Continuation of application No. 17/636,510, filed as application No. PCT/GB2020/052008 on Aug. 20, 2020.

(30) Foreign Application Priority Data

Aug. 20, 2019 (GB) ...................................... 1911944

(51) Int. Cl.
| | |
|---|---|
| *A61K 31/5513* | (2006.01) |
| *C07D 487/04* | (2006.01) |
| *A61P 31/14* | (2006.01) |
| *A61K 45/06* | (2006.01) |
| *C07D 519/00* | (2006.01) |

(52) U.S. Cl.
CPC ........ *C07D 487/04* (2013.01); *A61K 31/5513* (2013.01); *A61K 45/06* (2013.01); *A61P 31/14* (2018.01); *C07D 519/00* (2013.01)

(58) Field of Classification Search
CPC .................................................. A61K 31/5513
USPC .................................................... 514/210.21
See application file for complete search history.

(56) References Cited

U.S. PATENT DOCUMENTS

| 7,417,152 B2 * | 8/2008 | Tung .................... C07D 401/14 548/312.4 |
| 2017/0022221 A1 * | 1/2017 | Shook .................. C07D 417/14 |
| 2022/0306639 A1 | 9/2022 | Cockerill |

FOREIGN PATENT DOCUMENTS

| WO | 2004026843 A1 | 4/2004 |
| WO | 2004106310 A1 | 12/2004 |
| WO | 2005089769 A1 | 9/2005 |
| WO | 2005089770 A1 | 9/2005 |
| WO | 2005089771 A1 | 9/2005 |
| WO | 2005090319 A1 | 9/2005 |
| WO | 2006113140 A2 | 10/2006 |
| WO | 2011027156 A1 | 3/2011 |
| WO | 2011151651 A1 | 12/2011 |
| WO | 2011151652 A1 | 12/2011 |
| WO | 2016166546 A1 | 10/2016 |
| WO | 2018033714 A1 | 2/2018 |
| WO | 2018085378 A1 | 5/2018 |
| WO | 2018129287 A1 | 7/2018 |
| WO | 2018152413 A1 | 8/2018 |
| WO | 2018226801 A1 | 12/2018 |
| WO | 2019094920 A1 | 5/2019 |
| WO | 2020190935 A1 | 9/2020 |
| WO | 2021079121 A1 | 4/2021 |
| WO | 2021084280 A1 | 5/2021 |
| WO | 2022008911 A1 | 1/2022 |
| WO | 2022008912 A1 | 1/2022 |

OTHER PUBLICATIONS

Chapman et al., RSV604, A Novel Inhibitor of Respiratory Syncytial Virus Replication, Antimicrobial Agents and Chemotherapy, 2007, 51(9):3346-3353.

* cited by examiner

*Primary Examiner* — Raymond J Henley, III
(74) *Attorney, Agent, or Firm* — Quarles & Brady LLP

(57) ABSTRACT

Benzodiazepine derivatives of formula (I): (I) wherein: each of $R^1$ and $R^2$ is independently H or halo; either (i) T is N, Z is C, -a- and -c- are bonds, and -b- and -d- are absent; or (ii) T is C, Z is N, -b- and -d- are bonds, and -a- and -c- are absent; each of $R^3$ and $R^4$ is independently halo, —$OR^6$, —$NR^6R^7$—$COR^8$, —$C(O)OR^8$, —$CON(R^8)_2$ or —$R^6$; $R^5$ is H or halo; each of $R^6$ and $R^7$ is independently H or a group selected from $C_1$-$C_6$ alkyl, $C_3$-$C_{10}$ cycloalkyl, C6-C10 aryl, 4- to 10-membered heterocyclyl and 4- to 10-membered heteroaryl, the group being unsubstituted or substituted; $R^8$ is H or $C_1$-$C_6$ alkyl, each $R^8$ being the same or different when two are present; n is 0 or 1; and one of V, W, X and Y is N or CH and the other three are CH; and the pharmaceutically acceptable salts thereof are inhibitors of RSV and can therefore be used to treat or prevent an RSV infection.

2 Claims, No Drawings

PHARMACEUTICAL COMPOUNDS

CROSS-REFERENCE TO RELATED APPLICATIONS

This application is a continuation of U.S. application Ser. No. 17/636,510 filed on Feb. 18, 2022, which is the U.S. National Stage of PCT/GB2020/052008 filed Aug. 20, 2020, which published as WO 2021/032992 on Feb. 25, 2021, and which claims priority to GB 1911944.9 with filing date Aug. 20, 2019. The entire content of each of the above-referenced applications is incorporated herein by reference.

FIELD OF THE INVENTION

The present invention relates to benzodiazepine derivatives and to their use in treating or preventing a respiratory syncytial virus (RSV) infection.

BACKGROUND TO THE INVENTION

RSV is a negative-sense, single-stranded RNA virus of the Paramyxoviridae family. RSV is readily transmitted by secretions from an infected person via surfaces or hand-to-hand transfer. Unlike influenza, it is not transmitted by small-particle aerosols. Following successful inoculation, the incubation period is between four and six days during which time the virus spreads from the nasopharynx to the lower respiratory tract by fusion of infected with uninfected cells and by sloughing of the necrotic epithelium. In infants, coupled with increased mucus secretion and oedema, this can lead to mucus plugging causing hyper-inflation and collapse of distal lung tissue indicative of bronchiolitis. Hypoxia is common and the ability to feed is often impaired because of respiratory distress. In RSV pneumonia, inflammatory infiltration of the airways consists of mononuclear cells and is more generalised, with involvement of the bronchioles, bronchi and alveoli. The duration and degree of viral shedding has been found to correlate with the clinical signs and severity of disease.

RSV is the leading cause of serious respiratory tract infections in infants and young children throughout the world. The highest morbidity and mortality occurs in those born prematurely and for those with chronic lung or heart disease, although many infants hospitalised for RSV infection are otherwise healthy. Severe RSV infection in infancy can lead to several years of recurrent wheezing and is linked to the later development of asthma.

RSV is also a major cause of morbidity and mortality in the elderly and in immunocompromised children and adults as well as those with chronic obstructive pulmonary disease (COPD) and congestive heart failure (CHF).

RSV has a seasonal incidence; it is highly predictable and occurs in the winters of both hemispheres, from September to May in Europe and North America, peaking in December and January, and can occur throughout the year in tropical countries. It affects >90% of infants and young children by the age of two years and as natural immunity is short-lived; many will be re-infected each year. As with influenza, in elderly people, RSV causes around 10% of winter hospitalisations with an associated mortality of 10%.

Current anti-RSV treatment involves the use of a monoclonal antibody to RSV, called palivizumab. Such use of palivizumab is a prophylactic, rather than therapeutic, treatment of RSV. Although this antibody is often effective, its use is restricted to preterm infants and infants at high risk. Indeed, its limited utility means that it is unavailable for many people in need of anti-RSV treatment. There is therefore an urgent need for effective alternatives to existing anti-RSV treatment.

Small molecules have also been proposed as inhibitors of RSV. These include benzimidazoles and benzodiazepines. For instance, the discovery and initial development of RSV604, a benzodiazepine compound having sub-micromolar anti-RSV activity, is described in Antimicrobial Agents and Chemotherapy, September 2007, 3346-3353 (Chapman et al). Benzodiazepine inhibitors of RSV are also disclosed in publications including WO2004/026843 and WO2005/089770 (Arrow Therapeutics Limited); WO2016/166546 and WO2018/033714 (Durham University); and WO2017/015449, WO2018/129287 and WO2018/226801 (Enanta Pharmaceuticals, Inc.).

There exists a need to identify further compounds that have anti-RSV activity, in particular compounds having a combination of potent anti-viral activity and favourable pharmacokinetic properties.

SUMMARY OF THE INVENTION

It has now been found that a novel series of benzodiazepine derivatives have potent anti-RSV activity with favourable pharmacokinetics and physicochemical properties.

Accordingly, the present invention provides a compound which is a benzodiazepine derivative of formula (I):

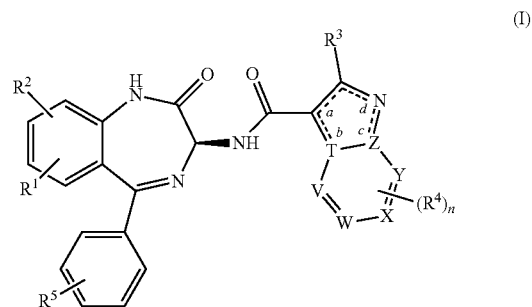

wherein:

each of $R^1$ and $R^2$ is independently H or halo;

either (i) T is N, Z is C, ---a--- and ---c--- are bonds, and ---b--- and ---d--- are absent; or (ii) T is C, Z is N, ---b--- and ---d--- are bonds, and ---a--- and ---c--- are absent;

each of $R^3$ and $R^4$ is independently halo, —$OR^6$, —$NR^6R^7$, —$COR^8$, —$C(O)OR^8$, —$CON(R^8)_2$ or —$R^6$;

$R^5$ is H or halo;

each of $R^6$ and $R^7$ is independently H or a group selected from $C_1$-$C_6$ alkyl, $C_3$-$C_{10}$ cycloalkyl, $C_6$-$C_{10}$ aryl, 4- to 10-membered heterocyclyl and 4- to 10-membered heteroaryl, the group being unsubstituted or substituted;

$R^8$ is H or $C_1$-$C_6$ alkyl, each $R^8$ being the same or different when two are present;

n is 0 or 1;

and one of V, W, X and Y is N or CH and the other three are CH;

or a pharmaceutically acceptable salt thereof.

Compounds of the invention possess two N atoms in the five-membered ring of the bicyclic heteroaryl ring that is linked via an amide group to the benzodiazepine ring system. This structural feature is thought to be important to the properties of the compounds discussed further below.

DETAILED DESCRIPTION OF THE INVENTION

When any group, ring, substituent or moiety defined herein is substituted, it is typically substituted by Q as defined below.

A $C_{1-6}$ alkyl group or moiety is linear or branched. A $C_{1-6}$ alkyl group is typically a $C_{1-4}$ alkyl group, or a $C_{4-6}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). For the avoidance of doubt, where two alkyl moieties are present in a group, the alkyl moieties may be the same or different. A $C_{1-6}$ alkyl group is unsubstituted or substituted, typically by one or more groups Q as defined below. For example, a $C_{1-6}$ alkyl group is unsubstituted or substituted by 1, 2 or 3 groups Q as defined below.

Q is halo, nitro, —CN, OH, $C_{1-6}$ alkoxy, $C_{1-6}$ hydroxyalkyl, $C_{1-6}$ alkoxyalkyl, unsubstituted $C_{1-6}$ alkyl, $C_{1-6}$ alkylthio, $C_{1-6}$ haloalkyl, $C_{1-4}$ haloalkoxy, —$CO_2R'''$, —$NR'_2$, —SR', —S(=O)R', —S(=O)$_2$R', $C_{3}$-$C_{10}$ cycloalkyl, 4- to 10-membered heterocyclyl, $C_6$-$C_{10}$ aryl or 4- to 10-membered heteroaryl, wherein each R' is independently selected from H, $C_{1-6}$ alkyl, $C_{3-10}$ cycloalkyl, 4 to 10-membered heterocyclyl, $C_6$-$C_{10}$ aryl and 4- to 10-membered heteroaryl.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups Q as defined above.

A $C_{1-6}$ alkylthio group is linear or branched. It is typically a $C_{1-4}$ alkylthio group, for example a methylthio, ethylthio, propylthio, i-propylthio, n-propylthio, n-butylthio, sec-butylthio or tert-butylthio group. A $C_{1-6}$ alkylthio group is unsubstituted or substituted, typically by one or more groups Q as defined above.

A halogen or halo group is F, Cl, Br or I. Typically it is F or Cl. A $C_{1-6}$ alkyl group substituted by halogen may be denoted "$C_{1-6}$ haloalkyl", which means a $C_{1-6}$ alkyl group as defined above in which one or more hydrogens is replaced by halo. Likewise a $C_{1-6}$ alkoxy group substituted by halogen may be denoted "$C_{1-6}$ haloalkoxy", which means a $C_{1-6}$ alkoxy group as defined above in which one or more hydrogens is replaced by halo. Typically, $C_{1-6}$ haloalkyl or $C_{1-6}$ haloalkoxy is substituted by 1, 2 or 3 said halogen atoms. Haloalkyl and haloalkoxy groups include perhaloalkyl and perhaloalkoxy groups such as —$CX_3$ and —$OCX_3$ wherein X is a halogen, for example —$CF_3$—$CCl_3$—$OCF_3$ and —$OCCl_3$.

A $C_{1-6}$ hydroxyalkyl group is a $C_{1-6}$ alkyl group as defined above, substituted by one or more OH groups. Typically, it is substituted by one, two or three OH groups. Preferably, it is substituted by a single OH group.

A $C_{1-6}$ alkoxyalkyl group is a $C_{1-6}$ alkyl group as defined above, substituted by a $C_{1-6}$ alkoxy group as defined above. It may, for instance, be methoxyalkyl or ethoxyalkyl, in which the alkyl moiety is a $C_{1-6}$ alkyl group as defined above A $C_6$-$C_{10}$ aryl group is an aromatic carbocyclic group containing from 6 to 10 carbon atoms. It is monocyclic or a fused bicyclic ring system in which an aromatic ring is fused to another aromatic carbocyclic ring. Examples of a $C_6$-$C_{10}$ aryl group include phenyl and naphthyl. When substituted, an aryl group is typically substituted by a group Q as defined above, for instance by 1, 2 or 3, groups selected from a group Q as defined above. More particularly, a substituted aryl group such as a substituted phenyl group is substituted by 1 or 2 groups selected from $C_1$-$C_6$ alkyl, halo, —$OR^8$ and —$N(R^8)_2$ wherein $R^8$ is H or $C_1$-$C_6$ alkyl, each $R^8$ being the same or different when two are present.

A $C_{3-10}$ cycloalkyl group is a saturated hydrocarbon ring having from 3 to 10 carbon atoms. A $C_{3-10}$ cycloalkyl group may be, for instance, $C_3$-$C_7$ cycloalkyl such as cyclopropyl, cyclobutyl, cyclopentyl, cyclohexyl, or cycloheptyl. Typically it is $C_3$-$C_6$ cycloalkyl, or $C_4$-$C_6$ cycloalkyl, for example cyclobutyl, cyclopentyl or cyclohexyl. In one embodiment it is cyclobutyl. A $C_{3-10}$ cycloalkyl group is unsubstituted or substituted, typically by one or more groups Q as defined above.

A 4- to 10-membered heteroaryl group or moiety is a 4- to 10-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a monocyclic 5- to 7-membered heteroaryl group, for instance a 5- or 6-membered N-containing heteroaryl group. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl and pyrazolyl groups. Furanyl, thienyl, imidazolyl, pyridyl and pyrimidyl groups are preferred. It may alternatively be a bicyclic heteroaryl group, for instance an 8- to 10-membered bicyclic heteroaryl group. Examples include quinolyl, isoquinolyl, quinazolyl, quinoxalinyl, indolyl, isoindolyl, indazolyl, imidazopyridazinyl, pyrrolopyridinyl, pyrazolopyrimidinyl and pyrrolopyrimidinyl. When substituted, a heteroaryl group (monocyclic or bicyclic) is typically substituted by one or more, e.g. 1, 2 or 3, groups selected from $C_{1-4}$ alkyl and a group Q as defined above.

A 4- to 10-membered heterocyclyl group is a monocyclic or bicyclic non-aromatic, saturated or unsaturated ring system containing 5 to 10 carbon atoms and at least one atom or group selected from N, O, S, SO, $SO_2$ and CO, more typically N or O. When the ring system is bicyclic, one ring may be saturated and one ring unsaturated.

Typically, it is a $C_{4-10}$ ring system in which 1, 2 or 3 of the carbon atoms in the ring are replaced with an atom or group selected from O, S, $SO_2$, CO and NH. More typically it is a monocyclic ring, preferably a monocyclic $C_4$-$C_6$ ring. Examples of a 4- to 10-membered heterocyclyl group include azetidinyl, piperidyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, tetrahydrofuranyl and tetrahydropyranyl, piperidin-2,6-dionyl and piperidin-2-onyl moieties. In particular, a 4- to 10-membered heterocyclyl group may be azetidinyl, piperidyl, piperazinyl, morpholinyl or thiomorpholinyl.

When substituted, a heterocyclic group (monocyclic or bicyclic) is typically substituted by one or more, e.g. 1, 2 or 3, groups selected from unsubstituted $C_{1-4}$ alkyl and a group Q as defined above. It may also be substituted by a bridgehead atom which links two of the ring atoms, typically two ring carbon atoms. For instance, a piperazine group or a morpholine group may be substituted by a carbon bridgehead. The resulting bicyclic structure may be, respectively, a 2,5-diazabicyclo[2.2.1]heptane or 2-oxa-5-azabicyclo [2.2.1]heptane group.

For the avoidance of doubt, although the above definitions of heteroaryl and heterocyclyl groups refer to an "N" atom which can be present in the ring, it will be evident to a skilled chemist that any such N atom will be protonated (or will carry a substituent as defined above) if it is attached to each of its adjacent ring atoms via a single bond. Such protonated forms are embraced within the present definitions of heteroaryl and heterocyclyl groups.

In one embodiment of formula (I) as defined above, $R^2$ is a halo substituent, in particular F, at the 9-position of the benzodiazepinyl ring system. Examples of such compounds are those of the following formula (I'):

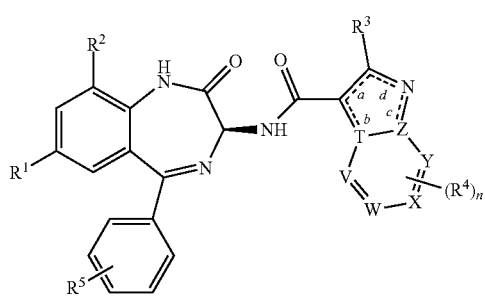

(I')

wherein $R^1$ is H or halo, $R^2$ is H or halo and the remaining groups and variables are as defined above for formula (I). Typically $R^1$ is H or F and $R^2$ is H or F. For instance, $R^1$ is H or F and $R^2$ is F.

In one embodiment of formulae (I), T is N and Z is C. In such compounds ___a___ and ___c___ are bonds while ___b___ and ___d___ are absent. Such compounds have the ___e___ following formula (Ia):

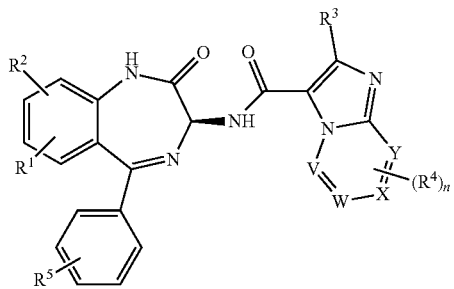

(Ia)

in which all the groups and variables are as defined above for formula (I) or (I').

In another embodiment of formula (I), T is C and Z is N. In such compounds ___b___ and ___d___ are bonds while ___a___ and ___c___ are absent. Such compounds have the following formula (b):

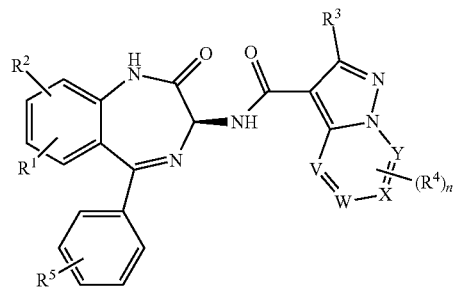

(Ib)

in which all the groups and variables are as defined above for formula (I) or (I').

In the above formulae (I), (I'), (Ia) and (Ib), V is typically N and each of W, X and Y is CH. Examples of such structures include benzodiazepinyl imidazopyridazines of the following formula (Ia') and benzodiazepinyl pyrazolopyrimidines of the following formula (Ib'):

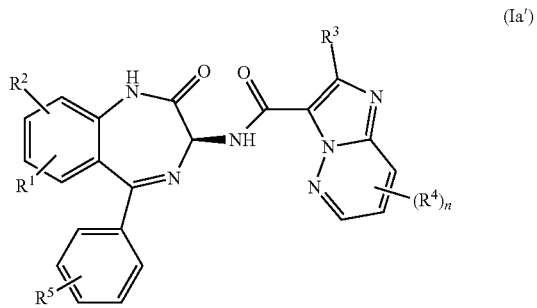

(Ia')

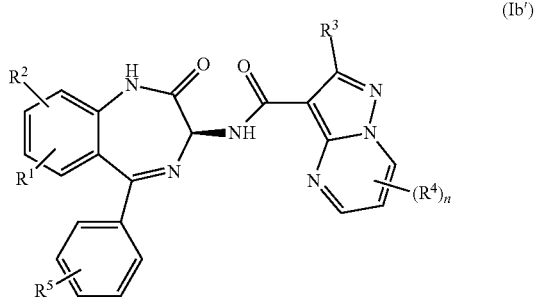

(Ib')

In formulae (Ia') and (Ib') each of $R^1$ to $R^5$ and n is as defined above for formula (I) or (I').

In one embodiment of compounds of the invention having any of the structural formulae (I), (I'), (Ia), (Ib), (Ia') and (Ib') as defined above, $R^1$ is H or F and $R^2$ is F at ring position 9 of the benzodiazepinyl ring system.

In one embodiment of compounds of formulae (Ia') and (Ib'), $R^1$ and $R^2$ take the definitions and ring positions defined for formula (I') above. Such compounds are benzodiazepinyl imidazopyridazines of the following formula (Ia''):

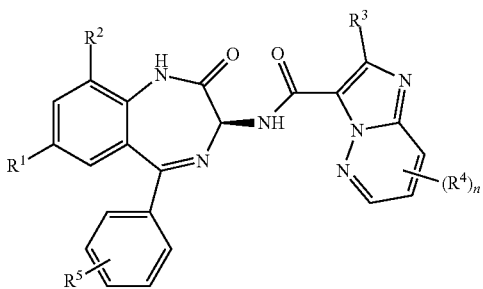

(Ia")

wherein each of $R^1$ to $R^5$ and n is as defined above for formula (I'); and benzodiazepinyl pyrazolopyrimidines of the following formula (Ib"):

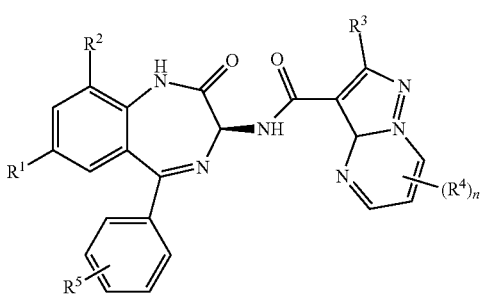

(Ib")

wherein each of $R^1$ to $R^5$ and n is as defined above for formula (I').

In compounds of the invention having any of the structural formulae defined above, $R^3$ is typically a group selected from $C_1$-$C_6$ alkyl, $C_3$-$C_{10}$ cycloalkyl, $C_6$-$C_{10}$ aryl, 4- to 10-membered heterocyclyl and 4- to 10-membered heteroaryl, the group being unsubstituted or substituted by one or two groups Q as defined above. For instance, $R^3$ as defined above may be unsubstituted or substituted by a group selected from $C_1$-$C_6$ alkyl, $C_3$-$C_6$ cycloalkyl, $C_1$-$C_6$ alkoxy, $C_1$-$C_6$ alkoxyalkyl, $C_1$-$C_6$ trifluoroalkyl, halo, —$OR^8$, —$N(R^8)_2$ in which $R^8$ is H, $C_1$-$C_6$ alkyl or $C_3$-$C_6$ cycloalkyl, each $R^8$ being the same or different when two are present, and —$N(R^9)_2$ in which the $R^9$ groups together form a ring selected from morpholine, piperidine, piperazine and pyrrolidine, which ring is unsubstituted or substituted by $C_1$-$C_6$ alkyl.

In compounds of the invention having any of the structural formulae defined above, $R^3$ is more typically a group selected from $C_1$-$C_6$ alkyl, $C_1$-$C_6$ haloalkyl (such as $C_1$-$C_6$ difluoroalkyl or $C_1$-$C_6$ trifluoroalkyl), dihydroindole, phenoxy and phenyl, the group being unsubstituted or substituted by 1, 2 or 3 groups selected from halo, —$OR^8$ and —$N(R^8)_2$ in which $R^8$ is H, $C_1$-$C_6$ alkyl or $C_3$-$C_6$ cycloalkyl, each $R^8$ being the same or different when two are present.

In one embodiment of the structural formulae defined above, $R^3$ is a group of the following formula (II):

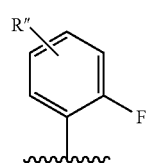

(II)

in which R" is H, halo, —$OR^8$ or —$N(R^8)_2$ as defined above.

In another embodiment of the structural formulae defined above, $R^3$ is a 4- to 10-membered heteroaryl group, for instance selected from pyridyl, pyrrolopyridyl and indazolyl. The 4- to 10-membered heteroaryl group is unsubstituted or substituted by a group Q as defined above, for instance by a group selected from $C_1$-$C_6$ alkyl, $C_3$-$C_6$ cycloalkyl, $C_1$-$C_6$ alkoxy, $C_1$-$C_6$ alkoxyalkyl, $C_1$-$C_6$ trifluoroalkyl, halo, —$OR^8$, —$N(R^8)_2$ in which $R^8$ is H, $C_1$-$C_6$ alkyl or $C_3$-$C_6$ cycloalkyl, each $R^8$ being the same or different when two are present, and —$N(R^9)_2$ in which the $R^9$ groups together form a ring selected from morpholine, piperidine, piperazine and pyrrolidine, which ring is unsubstituted or substituted by $C_1$-$C_6$ alkyl or by a bridgehead carbon atom that links two ring atoms.

Examples of $R^3$ groups include the following:

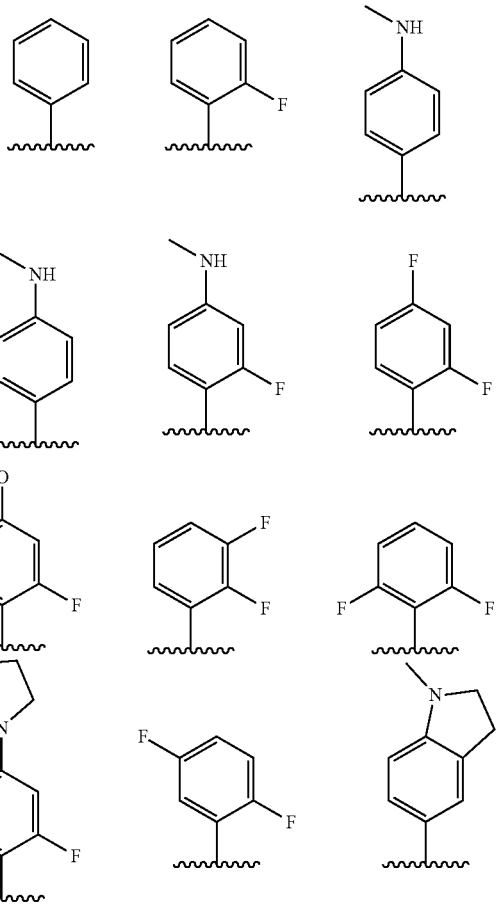

-continued

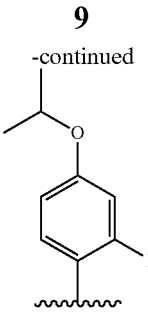

In compounds of the invention having any of the structural formulae defined above, $R^4$ bonds to any available carbon atom in the six-membered ring. In effect, therefore, in the structural formulae (I), (I'), (Ia), (Ib), (Ia') and (Ib') as defined above the group $R^4$, when present, replaces H in one of the ring CH groups represented by any of V, W, X and Y. Hence one of V, W, X and Y is N, CH or $CR^4$ and the other three are CH or $CR^4$, subject to there being only one $CR^4$ present.

In one embodiment of compounds of the invention having any of the structural formulae defined above, V is N, one of W, X and Y is $CR^4$ and the other two are CH. In another embodiment V is N, Y is CH, one of W and X is $CR^4$ and the other is CH.

In compounds of the invention $R^4$ is selected from halo, —$OR^6$, —$NR^6R^7$, —$COR^8$, —$C(O)OR^8$, —$CON(R^8)_2$ and —$R^6$, wherein each of $R^6$ and $R^7$ is independently H or a group selected from $C_1$-$C_6$ alkyl, $C_3$-$C_{10}$ cycloalkyl, $C_6$-$C_{10}$ aryl, 4- to 10-membered heterocyclyl and 4- to 10-membered heteroaryl, the group being unsubstituted or substituted, and wherein $R^8$ is H or $C_1$-$C_6$ alkyl, each $R^8$ being the same or different when two are present.

In one embodiment $R^4$ is halo, —$OR^6$, —$NR^6R^7$ or a group selected from $C_1$-$C_6$ alkyl, $C_3$-$C_{10}$ cycloalkyl, $C_6$-$C_{10}$ aryl, 4- to 10-membered heterocyclyl and 4- to 10-membered heteroaryl, the group being unsubstituted or substituted. When substituted, the group is typically substituted by a group Q as defined above. When $R^4$ is —$OR^6$ in which $R^6$ is substituted $C_1$-$C_6$ alkyl, the substituent may be $C_1$-$C_6$ alkoxy such that $R^6$ is $C_1$-$C_6$ alkoxyalkyl. When $R^4$ is —$OR^6$ in which $R^6$ is a $C_4$-$C_{10}$ heterocyclyl group, the heterocyclyl group may be, for instance, azetidinyl which is unsubstituted or substituted, for example substituted by $C_1$-$C_6$ alkyl such as methyl. When $R^4$ is —$OR^6$ in which $R^6$ is $C_1$-$C_6$ alkyl, one or more H atoms in the alkyl group may be replaced by D. For instance, $R^4$ may be a group —$OCD_3$.

Typically $R^4$ is halo (for instance Cl), —$OR^6$, —$NR^6R^7$, $C_1$-$C_6$ alkyl, $C_3$-$C_6$ cycloalkyl, phenyl, furanyl, thienyl, imidazolyl, pyridyl, pyrimidyl, azetidinyl, pyrrolindinyl, piperidinyl, piperazinyl or morpholinyl, each of which is unsubstituted or substituted by a group Q as defined above. When $R^4$ is substituted, a preferred substituent is halo or $C_1$-$C_6$ alkyl. For instance, when $R^4$ is substituted $C_1$-$C_6$ alkyl it may be a mono-, di- or trihalo-substituted $C_1$-$C_6$ alkyl group such as a difluoroalkyl or trifluoroalkyl group. When $R^4$ is substituted azetidinyl, pyrrolidinyl, piperidinyl, piperazinyl or morpholinyl, the substituent is typically $C_1$-$C_6$ alkyl. Another preferred substituent for piperidinyl, piperazinyl and morpholinyl is a bridgehead carbon atom linking two ring atoms.

Specific compounds of the invention include the following:

2-[4-(Methylamino)phenyl]-N-[(3S)-2-oxo-5-phenyl-1,3-dihydro-1,4-benzodiazepin-3-yl]pyrazolo[1,5-a]pyrimidine-3-carboxamide;

2-[4-(Methylamino)phenyl]-N-[(3S)-2-oxo-5-phenyl-1,3-dihydro-1,4-benzodiazepin-3-yl]pyrazolo[1,5-a]pyrimidine-3-carboxamide;

N-[(3S)-9-fluoro-2-oxo-5-phenyl-1,3-dihydro-1,4-benzodiazepin-3-yl]-2-(2-fluorophenyl)pyrazolo[1,5-a]pyrimidine-3-carboxamide;

N-[(3S)-2-oxo-5-phenyl-1,3-dihydro-1,4-benzodiazepin-3-yl]-2-phenylpyrazolo[1,5-a]pyrimidine-3-carboxamide;

N-[(3S)-2-Oxo-5-phenyl-1,3-dihydro-1,4-benzodiazepin-3-yl]-2-[4-(propan-2-ylamino)phenyl]pyrazolo[1,5-a]pyrimidine-3-carboxamide;

2-(1-Methyl-2,3-dihydroindol-6-yl)-N-[(3S)-2-oxo-5-phenyl-1,3-dihydro-1,4-benzodiazepin-3-yl]pyrazolo[1,5-a]pyrimidine-3-carboxamide;

2-(2-Fluoro-4-methoxyphenyl)-N-[(3S)-2-oxo-5-phenyl-1,3-dihydro-1,4-benzodiazepin-3-yl]pyrazolo[1,5-a]pyrimidine-3-carboxamide;

2-(2-Fluoro-4-propan-2-yloxyphenyl)-N-[(3S)-2-oxo-5-phenyl-1,3-dihydro-1,4-benzodiazepin-3-yl]pyrazolo[1,5-a]pyrimidine-3-carboxamide;

2-[2-Fluoro-4-(methylamino)phenyl]-N-[(3S)-2-oxo-5-phenyl-1,3-dihydro-1,4-benzodiazepin-3-yl]pyrazolo[1,5-a]pyrimidine-3-carboxamide;

N-[(3S)-9-Fluoro-2-oxo-5-phenyl-1,3-dihydro-1,4-benzodiazepin-3-yl]-2-phenylpyrazolo[1,5-a]pyrimidine-3-carboxamide;

6-Chloro-N-[(3S)-9-fluoro-2-oxo-5-phenyl-1,3-dihydro-1,4-benzodiazepin-3-yl]-2-methylimidazo[1,2-b]pyridazine-3-carboxamide;

6-Chloro-2-methyl-N-[(3S)-2-oxo-5-phenyl-1,3-dihydro-1,4-benzodiazepin-3-yl]imidazo[1,2-b]pyridazine-3-carboxamide;

N-[(3S)-9-Fluoro-2-oxo-5-phenyl-1,3-dihydro-1,4-benzodiazepin-3-yl]-6-(furan-3-yl)-2-methylpyrazolo[1,5-a]pyrimidine-3-carboxamide;

2-(2-Fluoro-5-methylphenyl)-N-[(3S)-2-oxo-5-phenyl-1,3-dihydro-1,4-benzodiazepin-3-yl]pyrazolo[1,5-a]pyrimidine-3-carboxamide;

2-(2-Fluoro-5-methylphenyl)-N-[(3S)-9-fluoro-2-oxo-5-phenyl-1,3-dihydro-1,4-benzodiazepin-3-yl]pyrazolo[1,5-a]pyrimidine-3-carboxamide;

2-(5-Chloropyridin-3-yl)-N-[(3S)-2-oxo-5-phenyl-1,3-dihydro-1,4-benzodiazepin-3-yl]pyrazolo[1,5-a]pyrimidine-3-carboxamide;

2-(5-Chloropyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide 2-(6-Cyclopropylpyridin-3-yl)-N-[(3S)-2-oxo-5-phenyl-1,3-dihydro-1,4-benzodiazepin-3-yl]pyrazolo[1,5-a]pyrimidine-3-carboxamide 2-(6-Cyclopropylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide 2-(5-Cyclopropylpyridin-3-yl)-N-[(3S)-2-oxo-5-phenyl-1,3-dihydro-1,4-benzodiazepin-3-yl]pyrazolo[1,5-a]pyrimidine-3-carboxamide 2-(2-Fluoro-5-methylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide 2-(2-Fluorophenyl)-6-methyl-N-[(3S)-2-oxo-5-phenyl-1,3-dihydro-1,4-benzodiazepin-3-yl]pyrazolo[1,5-a]pyrimidine-3-carboxamide N-[(3S)-9-Fluoro-2-oxo-5-phenyl-1,3-dihydro-1,4-benzodiazepin-3-yl]-2-(2-fluorophenyl)-6-methylpyrazolo[1,5-a]pyrimidine-3-carboxamide 2-(2,4-Difluorophenyl)-5-methyl-N-[(3S)-2-oxo-5-phenyl-1,3-dihydro-1,4-benzodiazepin-3-yl]pyrazolo[1,5-a]pyrimidine-3-carboxamide 2-(2,4-Difluorophenyl)-N-[(3S)-9-fluoro-2-oxo-5-phenyl-1,3-dihydro-1,4-benzodiazepin-3-yl]-5-methylpyrazolo[1,5-a]pyrimidine-3-carboxamide 2-(2-Fluorophenyl)-7-methyl-N-[(3S)-2-oxo-5-phenyl-1,3-dihydro-1,4-benzodiazepin-3-yl]pyrazolo[1,5-a]pyrimidine-3-carboxamide N-[(3S)-9-Fluoro-2-oxo-5-phenyl-1,3-dihydro-1,4-benzodiazepin-3-yl]-2-(2-fluorophenyl)-7-methylpyrazolo[1,5-a]pyrimidine-3-carboxamide 2-(2-Fluorophenyl)-5-(morpholin-4-yl)-N-[(3S)-2-oxo-5-phenyl-2,3-dihydro-1H-1,4-benzodiazepin-3-yl]pyrazolo[1,5-a]pyrimidine-3-carboxamide N-[(3S)-9-Fluoro-2-oxo-5-phenyl-1,3-dihydro-1,4-benzodiazepin-3-yl]-2-(2-fluorophenyl)-5-pyrrolidin-1-ylpyrazolo[1,5-a]pyrimidine-3-carboxamide 2-(2-Fluorophenyl)-N-[(3S)-2-oxo-5-phenyl-1,3-dihydro-1,4-benzodiazepin-3-yl]-5-pyrrolidin-1-ylpyrazolo[1,5-a]pyrimidine-3-carboxamide 2-(2,3-Difluorophenyl)-N-[(3S)-9-fluoro-2-oxo-5-phenyl-1,3-dihydro-1,4-benzodiazepin-3-yl]pyrazolo[1,5-a]pyrimidine-3-carboxamide 2-(2,3-Difluorophenyl)-N-[(3S)-2-oxo-5-phenyl-1,3-dihydro-1,4-benzodiazepin-3-yl]pyrazolo[1,5-a]pyrimidine-3-carboxamide 2-(2,6-Difluorophenyl)-N-[(3S)-9-fluoro-2-oxo-5-phenyl-1,3-dihydro-1,4-benzodiazepin-3-yl]pyrazolo[1,5-a]pyrimidine-3-carboxamide 2-(2-Fluoro-4-pyrrolidin-1-ylphenyl)-N-[(3S)-2-oxo-5-phenyl-1,3-dihydro-1,4-benzodiazepin-3-yl]pyrazolo[1,5-a]pyrimidine-3-carboxamide 6-Methyl-N-[(3S)-2-oxo-5-phenyl-1,3-dihydro-1,4-benzodiazepin-3-yl]-2-[5-(trifluoromethyl)pyridin-3-yl]imidazo[1,2-b]pyridazine-3-carboxamide N-[(3S)-9-fluoro-2-oxo-5-phenyl-1,3-dihydro-1,4-benzodiazepin-3-yl]-6-methyl-2-[5-(trifluoromethyl)pyridin-3-yl]imidazo[1,2-b]pyridazine-3-carboxamide 2-[6-(Cyclopropylamino)-2-fluoropyridin-3-yl]-N-[(3S)-2-oxo-5-phenyl-1,3-dihydro-1,4-benzodiazepin-3-yl]pyrazolo[1,5-a]pyrimidine-3-carboxamide 2-(6-Methylpyridin-3-yl)-N-[(3S)-2-oxo-5-phenyl-1,3-dihydro-1,4-benzodiazepin-3-yl]pyrazolo[1,5-a]pyrimidine-3-carboxamide N-[(3S)-9-fluoro-2-oxo-5-phenyl-1,3-dihydro-1,4-benzodiazepin-3-yl]-2-(6-methylpyridin-3-yl)pyrazolo[1,5-a]pyrimidine-3-carboxamide 2-[6-(2-methoxyethyl)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide N-[(3S)-9-fluoro-2-oxo-5-phenyl-1,3-dihydro-1,4-benzodiazepin-3-yl]-2-(2-methylpyridin-4-yl)pyrazolo[1,5-a]pyrimidine-3-carboxamide 2-(6-Ethoxypyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide 2-(6-Ethylpyridin-3-yl)-N-[(3S)-2-oxo-5-phenyl-1,3-dihydro-1,4-benzodiazepin-3-yl]pyrazolo[1,5-a]pyrimidine-3-carboxamide 2-(6-Ethylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide 2-(6-Ethyl-2-methylpyridin-3-yl)-N-[(3S)-2-oxo-5-phenyl-2,3-dihydro-1H-1,4-benzodiazepin-3-yl]pyrazolo[1,5-a]pyrimidine-3-carboxamide 2-(6-Ethyl-2-methylpyridin-3-yl)-N-[(3S)-9-fluoro-2-oxo-5-phenyl-2,3-dihydro-1H-1,4-benzodiazepin-3-yl]pyrazolo[1,5-a]pyrimidine-3-carboxamide 2-(6-Propan-2-ylpyridin-3-yl)-N-[(3S)-2-oxo-5-phenyl-1,3-dihydro-1,4-benzodiazepin-3-yl]pyrazolo[1,5-a]pyrimidine-3-carboxamide 2-(6-Propan-2-ylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide 2-[2-Methyl-6-(propan-2-ylamino)pyridin-3-yl]-N-[(3S)-2-oxo-5-phenyl-1,3-dihydro-1,4-benzodiazepin-3-yl]pyrazolo[1,5-a]pyrimidine-3-carboxamide 2-[2-Methyl-6-(propan-2-ylamino)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide 2-[4-Methyl-6-(propan-2-ylamino)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide N-[(3S)-9-fluoro-2-oxo-5-phenyl-1,3-dihydro-1,4-benzodiazepin-3-yl]-2-(1-methylindazol-5-yl)pyrazolo[1,5-a]pyrimidine-3-carboxamide N-[(3S)-9-fluoro-2-oxo-5-phenyl-1,3-dihydro-1,4-benzodiazepin-3-yl]-2-(5-methylpyridin-3-yl)pyrazolo[1,5-a]pyrimidine-3-carboxamide 2-[6-(Ethylamino)-2-fluoropyridin-3-yl]-N-[(3S)-2-oxo-5-phenyl-1,3-dihydro-1,4-benzodiazepin-3-yl]pyrazolo[1,5-a]pyrimidine-3-carboxamide 2-[6-(Ethylamino)-2-fluoropyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide 2-[6-(3-Methylmorpholin-4-yl)pyridin-3-yl]-N-[(3S)-2-oxo-5-phenyl-1,3-dihydro-1,4-benzodiazepin-3-yl]pyrazolo[1,5-a]pyrimidine-3-carboxamide 2-[6-(3-Methylmorpholin-4-yl)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide 2-[2-Fluoro-6-(propan-2-ylamino)pyridin-3-yl]-N-[(3S)-2-oxo-5-phenyl-1,3-dihydro-1,4-benzodiazepin-3-yl]pyrazolo[1,5-a]pyrimidine-3-carboxamide N-[(3S)-9-Fluoro-2-oxo-5-phenyl-1,3-dihydro-1,4-benzodiazepin-3-yl]-2-[2-fluoro-6-(propan-2-ylamino)pyridin-3-yl]pyrazolo[1,5-a]pyrimidine-3-carboxamide N-[(3S)-9-fluoro-2-oxo-5-phenyl-1,3-dihydro-1,4-benzodiazepin-3-yl]-2-(1-methylpyrrolo[2,3-b]pyridin-5-yl)pyrazolo[1,5-a]pyrimidine-3-carboxamide N-[(3S)-9-fluoro-2-oxo-5-phenyl-1,3-dihydro-1,4-benzodiazepin-3-yl]-2-(6-morpholin-4-ylpyridin-3-yl)pyrazolo[1,5-a]pyrimidine-3-carboxamide N-[(3S)-2-oxo-5-phenyl-1,3-dihydro-1,4-benzodiazepin-3-yl]-2-[6-(propan-2-ylamino)pyridin-3-yl]pyrazolo[1,5-a]pyrimidine-3-carboxamide N-[(3S)-9-Fluoro-2-oxo-5-phenyl-1,3-dihydro-1,4-benzodiazepin-3-yl]-2-[6-(propan-2-ylamino)pyridin-3-yl]pyrazolo[1,5-a]pyrimidine-3-carboxamide N-[(3S)-9-Fluoro-2-oxo-5-phenyl-1,3-dihydro-1,4-benzodiazepin-3-yl]-2-(1H-pyrrolo[2,3-b]pyridin-5-yl)pyrazolo[1,5-a]pyrimidine-3-carboxamide N-[(3S)-9-fluoro-2-oxo-5-phenyl-1,3-dihydro-1,4-benzodiazepin-3-yl]-2-(6-methoxypyridin-3-yl)pyrazolo[1,5-a]pyrimidine-3-carboxamide 2-[6-(2-Hydroxy-2-methylpropyl)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide N-[(3S)-9-fluoro-2-oxo-5-phenyl-1,3-dihydro-1,4-benzodiazepin-3-yl]-2-(5-fluoropyridin-2-yl)-6-methylimidazo[1,2-b]pyridazine-3-carboxamide N-[(3S)-9-Fluoro-2-oxo-5-phenyl-1,3-dihydro-1,4-benzodiazepin-3-yl]-2-(2-fluorophenyl)-6-morpholin-4-ylimidazo[1,2-b]pyridazine-3-carboxamide
N-[(3S)-9-fluoro-2-oxo-5-phenyl-1,3-dihydro-1,4-benzodiazepin-3-yl]-6-[(1S,4S)-5-methyl-2,5-diazabicyclo[2.2.1]heptan-2-yl]-2-phenylimidazo[1,2-b]pyridazine-3-carboxamide
N-[(3S)-9-fluoro-2-oxo-5-phenyl-1,3-dihydro-1,4-benzodiazepin-3-yl]-6-[(1R,4R)-5-methyl-2,5-diazabicyclo[2.2.1]heptan-2-yl]-2-phenylimidazo[1,2-b]pyridazine-3-carboxamide
N-[(3S)-9-fluoro-2-oxo-5-phenyl-1,3-dihydro-1,4-benzodiazepin-3-yl]-6-[(1R,4R)-2-oxa-5-azabicyclo[2.2.1]heptan-5-yl]-2-phenylimidazo[1,2-b]pyridazine-3-carboxamide
N-[(3S)-9-fluoro-2-oxo-5-phenyl-1,3-dihydro-1,4-benzodiazepin-3-yl]-6-morpholin-4-yl-2-phenylimidazo[1,2-b]pyridazine-3-carboxamide
N-[(3S)-9-fluoro-2-oxo-5-phenyl-1,3-dihydro-1,4-benzodiazepin-3-yl]-2-(2-fluorophenyl)-5-[(1R,4R)-5-methyl-2,5-diazabicyclo[2.2.1]heptan-2-yl]pyrazolo[1,5-a]pyrimidine-3-carboxamide
2-(2-Fluoro-6-methylpyridin-3-yl)-N-[(3S)-2-oxo-5-phenyl-1,3-dihydro-1,4-benzodiazepin-3-yl]pyrazolo[1,5-a]pyrimidine-3-carboxamide
2-(2-Methoxy-6-methylpyridin-3-yl)-N-[(3S)-2-oxo-5-phenyl-1,3-dihydro-1,4-benzodiazepin-3-yl]pyrazolo[1,5-a]pyrimidine-3-carboxamide
N-[(3S)-2-oxo-5-phenyl-1,3-dihydro-1,4-benzodiazepin-3-yl]-2-phenylimidazo[1,2-b]pyridazine-3-carboxamide
2-(2,4-Difluorophenyl)-N-[(3S)-2-oxo-5-phenyl-1,3-dihydro-1,4-benzodiazepin-3-yl]imidazo[1,2-b]pyridazine-3-carboxamide
2-(2,4-Difluorophenyl)-N-[(3S)-9-fluoro-2-oxo-5-phenyl-1,3-dihydro-1,4-benzodiazepin-3-yl]imidazo[1,2-b]pyridazine-3-carboxamide
2-(2,4-Difluorophenyl)-6-methyl-N-[(3S)-2-oxo-5-phenyl-1,3-dihydro-1,4-benzodiazepin-3-yl]imidazo[1,2-b]pyridazine-3-carboxamide
2-(2,4-Difluorophenyl)-N-[(3S)-9-fluoro-2-oxo-5-phenyl-1,3-dihydro-1,4-benzodiazepin-3-yl]-6-methylimidazo[1,2-b]pyridazine-3-carboxamide
6-Methyl-N-[(3S)-2-oxo-5-phenyl-1,3-dihydro-1,4-benzodiazepin-3-yl]-2-phenylimidazo[1,2-b]pyridazine-3-carboxamide
N-[(3S)-9-Fluoro-2-oxo-5-phenyl-1,3-dihydro-1,4-benzodiazepin-3-yl]-6-methyl-2-phenylimidazo[1,2-b]pyridazine-3-carboxamide
6-(Azetidin-1-yl)-N-[(3S)-9-fluoro-2-oxo-5-phenyl-1,3-dihydro-1,4-benzodiazepin-3-yl]-2-(2-fluorophenyl)imidazo[1,2-b]pyridazine-3-carboxamide
N-[(3S)-9-fluoro-2-oxo-5-phenyl-1,3-dihydro-1,4-benzodiazepin-3-yl]-2-(2-fluorophenyl)-6-(4-methylpiperazin-1-yl)imidazo[1,2-b]pyridazine-3-carboxamide
N-[(3S)-9-fluoro-2-oxo-5-phenyl-1,3-dihydro-1,4-benzodiazepin-3-yl]-6-methyl-2-pyridin-3-ylimidazo[1,2-b]pyridazine-3-carboxamide
6-Methyl-2-(2-methylpyridin-4-yl)-N-[(3S)-2-oxo-5-phenyl-1,3-dihydro-1,4-benzodiazepin-3-yl]imidazo[1,2-b]pyridazine-3-carboxamide
N-[(3S)-9-fluoro-2-oxo-5-phenyl-1,3-dihydro-1,4-benzodiazepin-3-yl]-6-methyl-2-(2-methylpyridin-4-yl)imidazo[1,2-b]pyridazine-3-carboxamide
2-(3-Fluoropyridin-4-yl)-6-methyl-N-[(3S)-2-oxo-5-phenyl-1,3-dihydro-1,4-benzodiazepin-3-yl]imidazo[1,2-b]pyridazine-3-carboxamide
N-[(3S)-9-fluoro-2-oxo-5-phenyl-1,3-dihydro-1,4-benzodiazepin-3-yl]-2-(3-fluoropyridin-4-yl)-6-methylimidazo[1,2-b]pyridazine-3-carboxamide
2-(5-Fluoropyridin-3-yl)-6-methyl-N-[(3S)-2-oxo-5-phenyl-1,3-dihydro-1,4-benzodiazepin-3-yl]imidazo[1,2-b]pyridazine-3-carboxamide
N-[(3S)-9-fluoro-2-oxo-5-phenyl-1,3-dihydro-1,4-benzodiazepin-3-yl]-2-(5-fluoropyridin-3-yl)-6-methylimidazo[1,2-b]pyridazine-3-carboxamide
N-[(3S)-9-fluoro-2-oxo-5-phenyl-1,3-dihydro-1,4-benzodiazepin-3-yl]-6-methyl-2-(5-methylpyridin-3-yl)imidazo[1,2-b]pyridazine-3-carboxamide
6-Methyl-2-(6-morpholin-4-ylpyridin-3-yl)-N-[(3S)-2-oxo-5-phenyl-1,3-dihydro-1,4-benzodiazepin-3-yl]imidazo[1,2-b]pyridazine-3-carboxamide
N-[(3S)-9-fluoro-2-oxo-5-phenyl-1,3-dihydro-1,4-benzodiazepin-3-yl]-6-methyl-2-(6-morpholin-4-ylpyridin-3-yl)imidazo[1,2-b]pyridazine-3-carboxamide
6-(Ethylamino)-N-[(3S)-9-fluoro-2-oxo-5-phenyl-1,3-dihydro-1,4-benzodiazepin-3-yl]-2-(2-fluorophenyl)imidazo[1,2-b]pyridazine-3-carboxamide
N-[(3S)-9-fluoro-2-oxo-5-phenyl-1,3-dihydro-1,4-benzodiazepin-3-yl]-2-phenylimidazo[1,2-b]pyridazine-3-carboxamide
N-[(3S)-9-Fluoro-2-oxo-5-phenyl-1,3-dihydro-1,4-benzodiazepin-3-yl]-2-(2-fluorophenyl)-6-(1-methylazetidin-3-yl)oxyimidazo[1,2-b]pyridazine-3-carboxamide
N-[(3S)-9-Fluoro-2-oxo-5-phenyl-1,3-dihydro-1,4-benzodiazepin-3-yl]-6-(1-methylazetidin-3-yl)oxy-2-phenylimidazo[1,2-b]pyridazine-3-carboxamide
N-[(3S)-9-Fluoro-2-oxo-5-phenyl-1,3-dihydro-1,4-benzodiazepin-3-yl]-2-(2-fluorophenyl)-6-(2-methoxyethoxy)imidazo[1,2-b]pyridazine-3-carboxamide
6-Methoxy-N-[(3S)-2-oxo-5-phenyl-1,3-dihydro-1,4-benzodiazepin-3-yl]-2-phenylimidazo[1,2-b]pyridazine-3-carboxamide
N-[(3S)-2-oxo-5-phenyl-1,3-dihydro-1,4-benzodiazepin-3-yl]-2-phenyl-6-(trideuteriomethoxy)imidazo[1,2-b]pyridazine-3-carboxamide
N-[(3S)-9-fluoro-2-oxo-5-phenyl-1,3-dihydro-1,4-benzodiazepin-3-yl]-6-methoxy-2-phenylimidazo[1,2-b]pyridazine-3-carboxamide
N-[(3S)-9-fluoro-2-oxo-5-phenyl-1,3-dihydro-1,4-benzodiazepin-3-yl]-2-phenyl-6-(trideuteriomethoxy)imidazo[1,2-b]pyridazine-3-carboxamide
N-[(3S)-9-fluoro-2-oxo-5-phenyl-1,3-dihydro-1,4-benzodiazepin-3-yl]-2-(2-fluorophenyl)-6-methoxyimidazo[1,2-b]pyridazine-3-carboxamide
6-Chloro-N-[(3S)-9-fluoro-2-oxo-5-phenyl-1,3-dihydro-1,4-benzodiazepin-3-yl]-2-(2-fluorophenyl)imidazo[1,2-b]pyridazine-3-carboxamide
6-Chloro-2-(6-ethylpyridin-3-yl)-N-[(3S)-9-fluoro-2-oxo-5-phenyl-1,3-dihydro-1,4-benzodiazepin-3-yl]imidazo[1,2-b]pyridazine-3-carboxamide
N-[(3S)-9-fluoro-2-oxo-5-phenyl-1,3-dihydro-1,4-benzodiazepin-3-yl]-6-methoxy-2-(5-methylpyridin-3-yl)imidazo[1,2-b]pyridazine-3-carboxamide
N-[(3S)-9-fluoro-2-oxo-5-phenyl-1,3-dihydro-1,4-benzodiazepin-3-yl]-2-(3-fluoropyridin-4-yl)-6-methoxyimidazo[1,2-b]pyridazine-3-carboxamide
N-[(3S)-9-fluoro-2-oxo-5-phenyl-1,3-dihydro-1,4-benzodiazepin-3-yl]-6-methoxy-2-(6-methylpyridin-3-yl)imidazo[1,2-b]pyridazine-3-carboxamide
2-(6-Ethylpyridin-3-yl)-6-methoxy-N-[(3S)-9-fluoro-2-oxo-5-phenyl-1,3-dihydro-1,4-benzodiazepin-3-yl]imidazo[1,2-b]pyridazine-3-carboxamide 6-Ethoxy-2-(6-ethylpyridin-3-yl)-N-[(3S)-9-fluoro-2-oxo-5-phenyl-1,3-dihydro-1,4-benzodiazepin-3-yl]imidazo[1,2-b]pyridazine-3-carboxamide 2-(6-Ethylpyridin-3-yl)-N-[(3S)-9-fluoro-2-oxo-5-phenyl-2,3-dihydro-1H-1,4-benzodiazepin-3-yl]-6-($^{2}$H$_3$)methoxyimidazo[1,2-b]pyridazine-3-carboxamide 2-(6-[(3S*)-3-methylmorpholin-4-yl]pyridin-3-yl)-N-[(3S)-2-oxo-5-phenyl-2,3-dihydro-1H-1,4-benzodiazepin-3-yl]pyrazolo[1,5-a]pyrimidine-3-carboxamide N-[(3S)-9-fluoro-2-oxo-5-phenyl-2,3-dihydro-1H-1,4-benzodiazepin-3-yl]-2-{6-[(3S*)-3-methylmorpholin-4-yl]pyridin-3-yl}pyrazolo[1,5-a]pyrimidine-3-carboxamide N-[(3S)-9-fluoro-2-oxo-5-phenyl-1,3-dihydro-1,4-benzodiazepin-3-yl]-2-(1H-indazol-5-yl)imidazo[1,2-b]pyridazine-3-carboxamide and the pharmaceutically acceptable salts thereof.

The compounds of the invention may contain asymmetric or chiral centres, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Compounds of Formula (I) containing one or more chiral centre may be used in enantiomerically or diastereoisomerically pure form, or in the form of a mixture of isomers.

The present invention embraces all geometric and positional isomers of compounds of the invention as defined above. For example, if a compound of the invention incorporates a double bond or a fused ring, the cis- and trans-forms, as well as mixtures thereof, are embraced within the scope of the invention. Both the single positional isomers and mixture of positional isomers are also within the scope of the present invention.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol tautomerizations. Valence tautomers include interconversions by reorganization of some of the bonding electrons.

Compounds of the invention can be prepared by the synthetic methods described in the Examples that follow, or by analogy with such methods using appropriate starting materials and methodologies familiar to the skilled chemist.

A benzodiazepine derivative of formula (I) can be converted into a pharmaceutically acceptable salt thereof, and a salt can be converted into the free compound, by conventional methods. For instance, a benzodiazepine derivative of formula (I) can be contacted with a pharmaceutically acceptable acid to form a pharmaceutically acceptable salt. A pharmaceutically acceptable salt is a salt with a pharmaceutically acceptable acid or base.

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the present invention have been found in biological tests to be inhibitors of respiratory syncytial virus (RSV). They possess a combination of potent anti-RSV activity with favourable bioavailability and physicochemical characteristics. This combination of properties makes the compounds therapeutically useful and superior as drug candidates to many compounds disclosed in the prior art references discussed earlier.

Accordingly, the present invention further provides a compound which is a benzodiazepine derivative of formula (I), as defined above, or a pharmaceutically acceptable salt thereof, for use in a method of treating the human or animal body by therapy.

The invention also provides a compound of the invention as defined above for use in a method treating or preventing an RSV infection. Still further, the present invention provides the use of a compound of the invention as defined above in the manufacture of a medicament for use in treating or preventing an RSV infection. A subject suffering from or susceptible to an RSV infection may thus be treated by a method comprising the administration thereto of a compound of the invention as defined above. The condition of the subject may thereby be improved or ameliorated.

The RSV infection is typically a respiratory tract infection. The RSV infection may be an infection in a child, for instance a child under ten years of age or an infant under two years of age. In one embodiment the invention provides a compound as defined above for use in treating or preventing an RSV infection in paediatric patients. Alternatively the infection may be an infection in a mature or elderly adult, for instance an adult over 60 years of age, an adult over 70 years of age, or an adult over 80 years of age. The invention further provides a compound for use in treating or preventing an RSV infection in geriatric patients.

The RSV infection may be an infection in an immunocompromised individual or an individual suffering from COPD or CHF. In another embodiment, the RSV infection is an infection in a non-compromised individual, for instance an individual who is otherwise healthy.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection, infusion, or by inhalation or nebulisation. The compound is preferably given by oral administration.

The dosage depends on a variety of factors including the age, weight and condition of the patient and the route of administration. Daily dosages can vary within wide limits and will be adjusted to the individual requirements in each particular. Typically, however, the dosage adopted for each route of administration when a compound is administered alone to adult humans is 0.0001 to 650 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A unit dose form such as a tablet or a capsule will usually contain 1-250 mg of active ingredient. For example, a compound of formula (I) could be administered to a human patient at a dose of between 100-250 mg either once a day, twice or three times a day. For example, a compound of formula (I) could be administered to a human patient at a dose of between 100-250 mg either once a day, twice or three times a day.

The compounds of formula (I) and pharmaceutically acceptable salts thereof may be used on their own. Alternatively, they may be administered in the form of a pharmaceutical composition. The present invention therefore also provides a pharmaceutical composition comprising a compound of formula (I) or a pharmaceutically acceptable salt thereof as hereinbefore defined, in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The compounds of the invention may be administered in a variety of dosage forms. Thus, they can be administered orally, for example as tablets, troches, lozenges, aqueous or oily suspensions, solutions, dispersible powders or granules. The compounds of the invention may also be administered parenterally, whether subcutaneously, intravenously, intramuscularly, intrasternally, transdermally, by infusion techniques or by inhalation or nebulisation. The compounds may also be administered as suppositories.

Solid oral forms of the pharmaceutical composition of the invention may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulfates; and, in general, non-toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. Further suitable carriers for suspensions include sterile water, hydroxypropylmethyl cellulose (HPMC), polysorbate 80, polyvinylpyrrolidone (PVP), aerosol AOT (i.e. sodium 1,2-bis(2-ethylhexoxycarbonyl)ethanesulphonate), pluronic F127 and/or captisol (i.e. sulfobutylether-beta-cyclodextrin).

The compounds of the invention may, for example, be formulated as aqueous suspensions in a carrier selected from:

(i) 0.5% w/v hydroxypropylmethyl cellulose (HPMC)/0.1% w/v polysorbate 80;

(ii) 0.67% w/v polyvinylpyrrolidone (PVP)/0.33% w/v aerosol AOT (sodium 1,2-bis(2-ethylhexoxycarbonyl)ethanesulphonate);

(iii) 1% w/v pluronic F 127; and (iv) 0.5% w/v polysorbate 80.

The carriers may be prepared by standard procedures known to those of skill in the art. For example, each of the carriers (i) to (iv) may be prepared by weighing the required amount of excipient into a suitable vessel, adding approximately 80% of the final volume of water and magnetically stirring until a solution is formed. The carrier is then made up to volume with water. The aqueous suspensions of compounds of formula I may be prepared by weighing the required amount of a compound of formula I into a suitable vessel, adding 100% of the required volume of carrier and magnetically stirring.

Solutions for injection or infusion may contain as carrier, for example, sterile water or preferably they may be in the form of sterile, aqueous, isotonic saline solutions.

The compounds of the invention may also be administered in conjunction with other compounds used for the treatment of viral infections. Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment or prevention of a viral infection, particularly infection by RSV.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Suitable therapeutic agents for use in the combination therapies include (i) RSV fusion inhibitors (ii) other RSV nucleocapsid (N)-protein inhibitors (iii) other RSV protein inhibitors, such as those that inhibit the phosphoprotein (P) protein and large (L) protein;

iv) nucleoside or polymerase inhibitors that inhibit the L Protein;

(v) anti-RSV monoclonal antibodies, such as the F-protein antibodies;

(vi) immunomodulating toll-like receptor compounds;

(vii) other respiratory virus anti-virals, such as anti-influenza and anti-rhinovirus compounds; and/or (viii) anti-inflammatory compounds.

The RSV nucleocapsid (N)-protein plays a pivotal role in viral transcription and replication, mediating the interaction between the genomic RNA and the virally encoded RNA-dependent RNA polymerase. The RSV P- and L-proteins are components of RSV's virally encoded RNA-dependent RNA polymerase.

According to a further aspect of the invention, there is provided a compound of the formula (I) or a pharmaceutically acceptable salt thereof as hereinbefore defined in combination with one or more of the therapeutic agents listed as (i) to (vi) above for use in the treatment of RSV.

The Examples that follow serve to illustrate the invention further. The Preparatory Examples relate to the preparation of starting materials and intermediates used to prepare the compounds of the Examples. Neither the Examples nor the Preparatory Examples limit the invention in any way.

EXAMPLES

Reagents were obtained from commercial sources and were used without further purification. Anhydrous solvents were purchased from commercial suppliers, used as supplied and stored under $N_2$. Reactions were performed with anhydrous solvents under an atmosphere of $N_2$ unless otherwise noted. All temperatures are in ° C. TLC was performed on aluminium backed silica gel plates with fluorescence indicator at 254 nM (median pore size 60 Å). Flash column chromatography was performed using a Biotage Isolera One system using KP-Sil or Ultra silica gel columns or an Isco CombiFlash Rf using FlashPure or RediSep Rf/RediSep Rf Gold silica gel columns. Reverse phase column chromatography was performed on an Isco CombiFlash Rf using Teledyne Isco RediSep Rf C18 reverse phase columns. Ion exchange chromatography was performed on Isolute SCX-2 silica-propylsulfonic acid solid phase extraction cartridges, washing with appropriate solvents selected from water, MeCN and MeOH. Elution of basic compounds was performed with $NH_3$ in MeOH (0.7 N or 7 N depending on substrate).

Preparative HPLC was performed at ambient column temperature by the following methods. HPLC Method 1: Gemini NX (30 mm×150 mm, 5 μm) column at 42 mL/min and UV detection at 210 nm. HPLC Method 2: Waters X-Select CSH C18 (30×100 mm, 5 μm) column at 50 mL/min and UV detection at 215 nm. HPLC Method 3: Waters X-select CDH C18 (19×50 mm, 5 μM) column at 42 mL/min and UV detection across all wavelengths with photodiode array. HPLC Method 4: Waters XSelect CSH C18, (30×100 mm, 5 μm) column at 42 mL and UV detection across all wavelengths with photodiode array. Preparative chiral HPLC was performed at ambient column temperature on a Gilson HPLC system (UV detection at 230 nm) with a ChiralPAK IC (20×250 mm; 5 μm) at 15 mL/min. Analytical chiral HPLC was performed at ambient column temperature on an Agilent 1100 HPLC (UV detection at 260 nM) with a ChiralPAK IC column (2.1×150 mm; particle size 3 μm) with a flow rate of 0.4 mL/min and a 10 min run time. Preparative Chiral SFC was performed using a Waters SFC prep 15 (UV detection by DAD at 210-400 nm; flow rate 15 mL/min; column temperature 40° C.; 120 bar back pressure) and a Phenomenex Lux® Cellulose-4 column (1×25 cm; 5 μm). Analytical Chiral SFC was performed using a Waters SFC ACQUITY $UPC^2$ (UV detection by DAD at 220-400 nm; flow rate 1.5 mL/min; column temperature 40° C.; 1750 psi back pressure) with 3 min run time on a Phenomenex Lux® Cellulose-4 (1×25 cm; 5 μm) columns.

NMR spectra were recorded on a 400 or 500 MHz spectrometer at ambient probe temperature (nominal 298 K). Chemical shifts (δ) are given in ppm and calibrated by using the residual peak of the solvent as the internal standard ($CDCl_3$, δ=7.26 ppm; DMSO-$d_6$, δ=2.50 ppm). Coupling constants are given in Hertz (Hz). LRMS were recorded using an Advion Plate Express expression[L] compact mass spectrometer equipped with an APCI ion source.

LCMS analysis was performed using a Waters Acquity UPLC with either a CSH C18 or BEH C18 column (2.1×30 mm) at 40° C. at 0.77 mL/min with a linear 5-95% acetonitrile gradient appropriate for the lipophilicity of the compound over 3 or 10 minutes. The aqueous portion of the mobile phase was 0.1% formic acid (CSH C18 column) or 10 mM ammonium bicarbonate (BEH C18 column). LC-UV chromatograms were recorded using a Waters Acquity photodiode array detector between 210 and 400 nm. Mass spectra were recorded using a Waters Acquity QDa detector with ESI switching between positive and negative ion mode.

Method A: 3 min Acidic
Method B: 3 min Basic
Method C: 10 min Acidic
Method D: 10 min Basic
Method E: 1 min Basic
Method F: 1 min Acidic Preparatory examples (3S)-3-amino-5-phenyl-1,3-dihydro-1,4-benzodiazepin-2-one and (3S)-3-amino-9-fluoro-5-phenyl-1,3-dihydro-1,4-benzodiazepin-2-one were prepared using methods described in WO/2004/026843, WO/2005/090319, and WO/2017/015449.

| | |
|---|---|
| APCI | Atmospheric pressure chemical ionization |
| DIPEA | N,N-Diisopropylethylamine |
| DMF | N,N-Dimethylformamide |
| DMSO | Dimethyl sulfoxide |
| dppf | (diphenylphosphino)ferrocene |
| ES | Electrospray ionisation |
| h | Hour(s) |
| LCMS | Liquid chromatography-mass spectrometry |
| LRMS | Low resolution mass spectrometry |
| MTBE | Methyl tert-butyl ether |
| MWI | Microwave irradiation |
| rt | room temperature |
| THF | Tetrahydrofuran |
| HATU | 1-[Bis(dimethylamino)methylene]-1H-1,2,3-triazolo[4,5-b]pyridinium 3-oxid hexafluorophosphate, N-[(dimethylamino)-1H-1,2,3-triazolo-[4,5-b]pyridin-1-ylmethylene]-N-methylmethanaminium hexafluorophosphate N-oxide |
| CDI | Carbonyldiimidazole |
| CV | Column volume |
| eq- | Equivalents |
| Pd-170 | XPhos Pd(crotyl)Cl |

PREPARATORY EXAMPLES

1A

Ethyl-5-amino-3-bromo-1H-pyrazole-4-carbaxylate

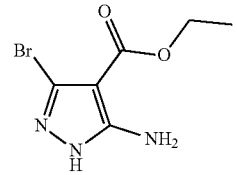

A solution of N-bromosuccinimide (13.77 g, 77.34 mmol) in MeCN (270 mL) was added dropwise over 25 min to a cooled (0° C.) solution of 5-amino-1H-pyrazole-4-carboxylic acid ethyl ester (10.00 g, 64.45 mmol) in THF (250 mL).

The reaction was allowed to attain rt and stirred overnight. The reaction mixture was adsorbed onto silica gel, the volatiles removed under reduced pressure and the residue purified by column chromatography [10-50% (EtOH: CH$_2$Cl$_2$:NH$_4$OH; 50:8:1) in CH$_2$Cl$_2$] to afford a beige solid, which was triturated with CH$_2$Cl$_2$ (~20 mL) to afford a white solid (5.93 g, 39%). LRMS (APCI+) m/z 234.1/236.1 [M+H]$^+$. $^1$H NMR (400 MHz, DMSO-d$_6$) δ 12.16 (s, 1H), 6.25 (s, 2H), 4.18 (q, J=7.1 Hz, 2H), 1.25 (t, J=7.1 Hz, 3H).

2A Ethyl 2-bromopyrazolo[1,5-a]pyrimidine-3-carbaxylate

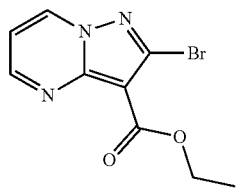

A solution of intermediate 1A (2.27 g, 9.70 mmol) and 1,1,3,3-tetramethoxypropane (1.93 mL, 11.64 mmol) in AcOH (33.9 mL) was heated at 70° C. for 68 h. After cooling to rt, the volatiles were removed under reduced pressure, the residue dissolved in EtOAc (50 mL), and neutralised with sat. aq. NaHCO$_3$ until pH≈7. The mixture was extracted with CH$_2$Cl$_2$ (3×50 mL), and the combined organics dried (Na$_2$SO$_4$) and concentrated in vacuo. The residue was purified by column chromatography (0 to 3% MeOH in CH$_2$Cl$_2$) to afford a beige solid (2.31 g, 88%). LCMS (method A): m/z 292.0 [M+Na]$^+$ at 0.93 min. $^1$H NMR (500 MHz, DMSO-d$_6$) δ 9.24 (dd, J=7.0, 1.8 Hz, 1H), 8.86 (dd, J=4.3, 1.8 Hz, 1H), 7.33 (dd, J=6.9, 4.2 Hz, 1H), 4.33 (q, J=7.1 Hz, 2H), 1.33 (t, J=7.1 Hz, 3H).

3A Ethyl 2-bromo-5-methylpyrazolo[1,5-a]pyrimidine-3-carbaxylate

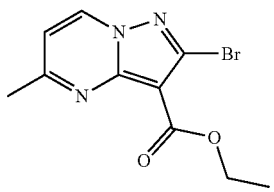 [SMILES: CCOC(=O)c1c(Br)nn2ccc(C)nc12]

A solution of intermediate 1A (877 mg, 3.750 mmol) and 4,4-dimethoxybutan-2-one (0.99 mL, 7.490 mmol) in toluene (6.3 mL) was heated at 100° C. for 19 h. The volatiles were removed under reduced pressure and the residue purified by column chromatography (30-57% EtOAc in heptane) to afford a white solid (539 mg, 51%). $^1$H NMR (400 MHz, DMSO-d$_6$) δ 9.07 (d, J=7.1 Hz, 1H), 7.21 (d, J=7.1 Hz, 1H), 4.30 (d, J=7.1 Hz, 2H), 2.62 (s, 3H), 1.32 (t, J=7.1 Hz, 3H). LRMS (APCI+) m/z 240.2 [M-OCH$_2$CH$_3$]$^+$ 4A Ethyl 6-bromo-2-methylpyrazolo[1,5-a]pyrimidine-3-carboxylate

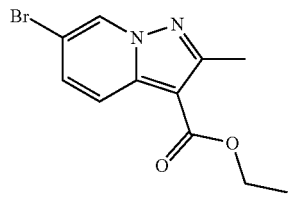 [SMILES: CCOC(=O)c1c(C)nn2cc(Br)ccc12]

5-Amino-3-methyl-1H-pyrazole-4-carboxylic acid ethyl ester (1.64 g, 9.69 mmol) and AcOH (8.32 mL, 145.41 mmol) were added to a solution of 2-bromomalonaldehyde (1.50 g, 9.94 mmol) in EtOH (19.4 mL) and heated at 75° C. overnight. The volatiles were removed under reduced pressure, CH$_2$Cl$_2$ (75 mL) and sat. aq. NaHCO$_3$ added (50 mL), and the aqueous layer extracted with CH$_2$Cl$_2$ (2×50 mL). The combined organic extracts were washed with sat. aq. NaHCO$_3$ and brine (25 mL each), dried (Na$_2$SO$_4$) and the solvent removed under reduced pressure. Purification by column chromatography (18-50% EtOAc in heptane) afforded a white solid (1.98 g, 72%). $^1$H NMR (400 MHz, DMSO-d$_6$) δ 9.65 (d, J=2.2 Hz, 1H), 8.85 (d, J=2.2 Hz, 1H), 4.30 (q, J=7.1 Hz, 2H), 2.60 (s, 3H), 1.31 (t, J=7.1 Hz, 3H). LRMS (APCI+) m/z 238.1 [M-OCH$_2$CH$_3$]$^+$ 5A 3-Fluoro-N-methyl-4-(4,4,5,5-tetramethyl-1,3,2-diaxaborolan-2-yl)aniline

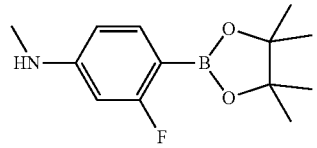

Sodium triacetoxyborohydride (268 mg, 1.27 mmol) was added to a solution of 3-fluoro-4-(4,4,5,5-tetramethyl-1,3,2-dioxaborolan-2-yl)aniline (300 mg, 1.27 mmol), formaldehyde (0.1 mL, 1.33 mmol) and AcOH (0.11 mL, 1.90 mmol) in CH$_2$Cl$_2$ (6 mL) and stirred at rt for 3 h. Further AcOH (0.11 mL, 1.90 mmol) and sodium triacetoxyborohydride (268 mg, 1.27 mmol) were added, and the reaction stirred at rt overnight. The reaction mixture was partitioned between CH$_2$Cl$_2$ (10 mL) and water (10 mL), separated and the organic layer passed through a hydrophobic frit and the solvent removed under reduced pressure. The residue was purified by column chromatography (0-100% (EtOAc in isohexanes) to afford a yellow solid (100 mg, 28%). LCMS (method A) m/z 252.2 [M+H]$^+$ (ES+) at 1.48 min.

6A Ethyl 2-phenylpyrazolo[1,5-a]pyrimidine-3-carboxylate

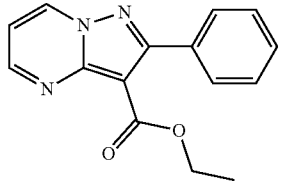 [SMILES: CCOC(=O)c1c(-c2ccccc2)nn2cccnc12]

A mixture of intermediate 2A (300 mg, 1.11 mmol), phenylboronic acid (167 mg, 1.37 mmol) and $K_2CO_3$ (464 mg, 3.36 mmol) in 1,4-dioxane:water (2:1, 3.0 mL) was degassed with $N_2$ for 5 min. $Pd(PPh_3)_4$ (192 mg, 0.170 mmol) was added, the reaction mixture further degassed with $N_2$ for 5 min, then heated to 100° C. overnight. The reaction was cooled to rt, diluted with $CH_2Cl_2$ (10 mL), and the organic layer washed with brine (3×10 mL), dried ($Na_2SO_4$) and concentrated in vacuo. The residue was purified by column chromatography (0-80% EtOAc in hexane) to afford a yellow solid (111 mg, 36%). LCMS (method A) m/z 222 [M+H]$^+$ (ES+) at 1.13 min. $^1$H NMR (500 MHz, CDCl$_3$) δ 8.79 (dd, J=4.2, 1.8 Hz, 1H), 8.75 (dd, J=6.9, 1.9 Hz, 1H), 7.79-7.75 (m, 2H), 7.49-7.45 (min, 3H), 7.03 (dd, J=6.9, 4.1 Hz, 1H), 4.38 (q, J=7.1 Hz, 2H), 1.29 (t, J=7.1 Hz, 3H).

The following intermediate compounds were prepared by an analogous procedure to that described for intermediate 6A. Preparatory examples 6M and 6N were prepared from the corresponding boronic acid pinacol ester. Preparatory example 6O was prepared with 2 eq. of (2,3-difluorophenyl) boronic acid.

TABLE 1

Examples prepared via Suzuki procedure

| Preparatory Example | Name | R | $^1$H NMR δ (500 MHz) | LCMS (ES+) m/z |
|---|---|---|---|---|
| 6B | Ethyl 2-(2-fluorophenyl)pyrazolo[1,5-a]pyrimidine-3-carboxylate | 2-fluorophenyl | (CDCl$_3$) 8.81 (dd, J = 4.2, 1.9 Hz, 1H), 8.77 (dd, J = 7.0, 1.8 Hz, 1H), 7.30-7.23 (m, 2H), 7.22-7.14 (m, 1H), 7.05 (dd, J = 6.9, 4.1 Hz, 1H), 4.32 (q, J = 7.1 Hz, 2H), 1.20 (t, J = 7.1 Hz, 3H) | (method A) 308.14 [M + Na]$^+$ at 1.13 min |
| 6C | Ethyl 2-[4-(methylamino)phenyl]pyrazolo[1,5-a]pyrimidine-3-carboxylate | 4-(methylamino)phenyl | (CDCl3) 8.81-8.70 (m, 2H), 7.77-7.71 (m, 2H), 6.99 (dd, J = 6.9, 4.2 Hz, 1H), 6.78-6.73 (m, 2H), 4.44 (q, J = 7.1 Hz, 2H), 1.37 (t, J = 7.1 Hz, 3H) | (method A) 297.17 [M + Na]$^+$ at 0.86 min |
| 6D | Ethyl 2-[4-(propan-2-ylamino)phenyl]pyrazolo[1,5-a]pyrimidine-3-carboxylate | 4-(isopropylamino)phenyl | — | (method A) 325.14 [M + H]$^+$ at 0.91 min |
| 6E | Ethyl 2-(1-methyl-2,3-dihydroindol-5-yl)pyrazolo[1,5-a]pyrimidine-3-carboxylate | 1-methyl-2,3-dihydroindol-5-yl | (CDCl$_3$) 8.73 (dd, J = 4.2, 1.8 Hz, 1H), 8.70 (dd, J = 6.9, 1.8 Hz, 1H), 7.62 (d, J = 8.2 Hz, 1H), 7.58 (s, 1H), 6.97 (dd, J = 6.9, 4.2 Hz, 1H), 6.63 (s, 1H), 4.41 (q, J = 7.1 Hz, 2H), 3.56-3.39 (m, 2H), 3.12-3.00 (m, 2H), 2.87 (s, 3H), 1.35 (t, J = 7.1 Hz, 3H) | (method A) 322.15 [M + H]$^+$ at 1.15 min |
| 6F | Ethyl 2-(2,4-difluorophenyl)pyrazolo[1,5-a]pyrimidine-3-carboxylate | 2,4-difluorophenyl | (CDCl$_3$) 8.82 (dd, J = 4.1, 1.8 Hz, 1H), 8.76 (dd, J = 7.0, 1.9 Hz, 1H), 7.06 (dd, J = 7.0, 4.1 Hz, 1H), 7.05-6.97 (m, 1H), 6.98-6.90 (m, 1H), 4.34 (q, J = 7.1 Hz, 2H), 1.24 (t, J = 7.1 Hz, 3H) | (method A) 326.11 [M + Na]$^+$ at 1.18 min |

TABLE 1-continued

Examples prepared via Suzuki procedure

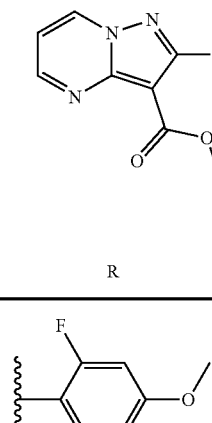

| Preparatory Example | Name | R | ¹H NMR δ (500 MHz) | LCMS (ES+) m/z |
|---|---|---|---|---|
| 6G | Ethyl 2-(2-fluoro-4-methoxyphenyl)pyrazolo[1,5-a]pyrimidine-3-carboxylate | 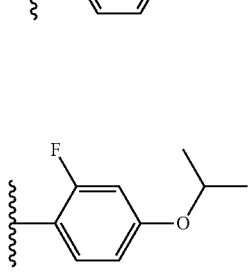 | (CDCl$_3$) 8.81 (dd, J = 4.2, 1.8 Hz, 1H), 8.77 (dd, J = 7.0, 1.8 Hz, 1H), 7.74-7.66 (m, 1H), 7.05 (dd, J = 6.9, 4.1 Hz, 1H), 6.84 (dd, J = 8.5, 2.5 Hz, 1H) 6.76 (dd, J = 11.8, 2.4 Hz, 1H), 4.37 (q, J = 7.1 Hz, 2H), 3.89 (s, 3H), 1.28 (td, J = 7.2, 2.0 Hz, 3H) | (method A) 338.46 [M + Na]$^+$ at 1.15 min |
| 6H | Ethyl 2-(2-fluoro-4-propan-2-yloxyphenyl)pyrazolo[1,5-a]pyrimidine-3-carboxylate | 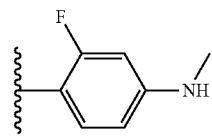 [SMILES: *c1ccc(NC)cc1F] | (DMSO-d$_6$) 9.28 (dd, J = 7.0, 1.7 Hz, 1H), 8.83 (dd, J = 4.2, 1.8 Hz, 1H), 7.48 (t, J = 8.5 Hz, 1H), 7.31 (dd, J = 7.0, 4.2 Hz, 1H), 6.93 (dd, J = 12.5, 2.4 Hz, 1H), 6.87 (dd, J = 8.5, 2.4 Hz, 1H), 4.73 (hept, J = 6.1 Hz, 1H), 4.03 (q, J = 7.1 Hz, 1H), 1.99 (s, 1H), 1.31 (d, J = 6.0 Hz, 6H), 1.16-1.12 (m, 3H) | (method A) 366.16 [M + Na]$^+$ at 1.37 min |
| 6I | Ethyl 2-[2-fluoro-4-(methylamino)phenyl]pyrazolo[1,5-a]pyrimidine-3-carboxylate | 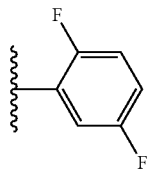 [SMILES: *c1cc(F)ccc1F] | — | (method A) 269.06 [M − OCH$_2$CH$_3$]$^+$ at 1.05 min |
| 6J | Ethyl 2-(2,5-difluorophenyl)pyrazolo[1,5-a]pyrimidine-3-carboxylate | 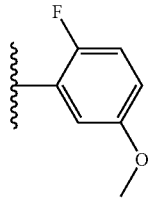 [SMILES: *c1cc(OC)ccc1F] | (CDCl$_3$) 8.83 (dd, J = 4.1, 1.8 Hz, 1H), 8.77 (dd, J = 7.0, 1.9 Hz, 1H), 7.33-7.28 (m, 1H), 7.19-7.11 (m, 2H), 7.08 (dd, J = 7.0, 4.1 Hz, 1H), 4.34 (q, J = 7.1 Hz, 2H), 1.23 (t, 7.1 Hz, 3H) | (method A) 326.09 [M + Na]$^+$ at 1.18 min |
| 6K | Ethyl-2-(2-fluoro-5-methoxyphenyl)pyrazolo[1,5-a]pyrimidine-3-carboxylate | 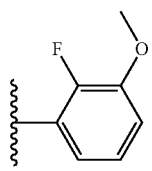 [SMILES: *c1cccc(OC)c1F] | (CDCl$_3$) 8.83 (dd, J = 4.2, 1.8 Hz, 1H), 8.79 (dd, J = 6.9, 1.8 Hz, 1H), 7.43-7.36 (m, 1H), 7.14-7.11 (m, 1H), 7.10-7.06 (m, 1H), 7.03-6.97 (m, 1H), 4.36 (q, J = 7.1 Hz, 2H), 3.86 (s, 3H), 1.25 (t, J = 7.1 Hz, 3H) | (method E) 338.09 [M + Na]$^+$ at 0.56 min |
| 6L | Ethyl 2-(2-fluoro-3-methoxyphenyl)pyrazolo[1,5-a]pyrimidine-3-carboxylate | | (CDCl$_3$) 8.81 (dd, J = 4.1, 1.8 Hz, 1H), 8.76 (dd, J = 7.0, 1.8 Hz, 1H), 7.22-7.02 (m, 4H), 4.32 (q, J = 7.1 Hz, 2H), 3.94 (s, 3H), 1.21 (t, J = 7.1 Hz, 3H) | (method A) 338.08 [M + Na]$^+$ at 1.11 min |

TABLE 1-continued

Examples prepared via Suzuki procedure

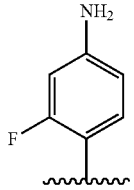

| Preparatory Example | Name | R | $^1$H NMR δ (500 MHz) | LCMS (ES+) m/z |
|---|---|---|---|---|
| 6M | Ethyl 2-(4-amino-2-fluorophenyl)pyrazolo [1,5-a]pyrimidine-3-carboxylate | 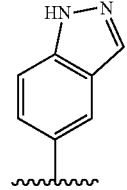 [SMILES: *c1ccc2[nH]ncc2c1] | 9.23 (dd, J = 7.0, 1.7 Hz, 1H), 8.77 (dd, J = 4.1, 1.8 Hz, 1H), 6.46 (dd, J = 8.3, 2.1 Hz, 1H), 6.39 (dd, J = 13.1, 2.1 Hz, 1H), 5.72 (s, 2H), 4.18 (q, J = 7.1 Hz, 2H), 1.17 (t, J = 7.1 Hz, 3H). | (method A) 255.2 [M − OCH$_2$CH$_3$]$^+$ at 0.86 min |
| 6N | Ethyl 2-(1H-indazol-5-yl)pyrazolo[1,5-a]pyrimidine-3-carboxylate | 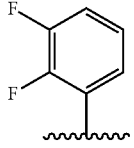 | 13.20 (s, 1H), 9.27 (dd, J = 6.9, 1.8 Hz, 1H), 8.81 (m, 1H), 8.18 (t, J = 1.2 Hz, 2H), 7.73 (dd, J = 8.7, 1.6 Hz, 1H), 7.61 (m, 1H), 7.29 (dd, J = 6.9, 4.2 Hz, 1H), 4.24 (q, J = 7.1 Hz, 2H), 1.20 (t, J = 7.1 Hz, 3H). | (method A) 308.3 [M + H]$^+$ at 0.89 min |
| 6O | Ethyl 2-(2,3-difluorophenyl)pyrazolo [1,5-a]pyrimidine-3-carboxylate | 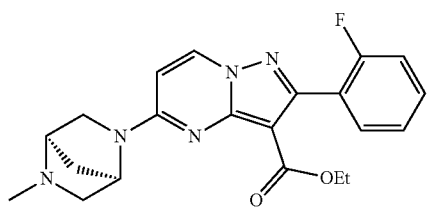 | 9.34 (dd, J = 7.0, 1.7 Hz, 1H), 8.89 (dd, J = 4.2, 1.8 Hz, 1H), 4.19 (q, J = 7.1 Hz, 2H), 1.13 (t, J = 7.1 Hz, 3H). | (method A) 258.5 [M − OCH$_2$CH$_3$]$^+$ at 1.20 min |

6P Ethyl 2-(2-fluorophenyl)-5-[(1R,4R)-5-methyl-2,5-diazabicyclo[2.2.1]heptan-2-yl]pyrazolo[1,5-a]pyrimidine-3-carboxylate

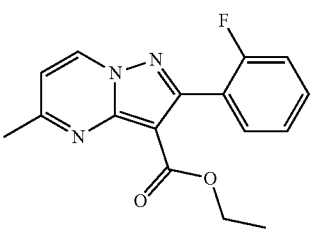 [SMILES: CCOC(=O)c1c(-c2ccccc2F)nn2ccc(C)nc12]

A solution of intermediate 24C (149 mg, 0.386 mmol), 2-fluorophenylboronic acid (141 mg, 1.00 mmol) and K$_2$CO$_3$ (161 mg, 1.162 mmol) in 1,4-dioxane/water (2:1, 1.9 mL) was sparged with N$_2$ for ~5 minutes. Pd(PPh$_3$)$_4$ (134 mg, 0.116 mmol) was added and the reaction heated at 100° C. overnight. The reaction mixture was diluted with CH$_2$Cl$_2$ (25 mL) and acidified (pH≈4) with AcOH. The mixture was purified by ion exchange chromatography (2 g SCX-2). The resulting solution was concentrated under reduced pressure to afford a brown solid (124 mg, 73%). LCMS (method A) m/z 396.4 [M+H]$^+$ (ES+) at 0.74 min. $^1$H NMR (500 MHz, CDCl$_3$) 8.33 (d, J=7.6 Hz, 1H), 7.58-7.50 (m, 1H), 7.46-7.38 (m, 1H), 7.24 (t, J=7.6 Hz, 1H), 7.15 (t, J=9.1 Hz, 1H), 6.29-6.18 (m, 1H), 4.28-4.18 (m, 2H), 4.04-3.92 (m, 1H), 3.86-3.73 (m, 1H), 3.62-3.50 (m, 1H), 3.21-3.03 (m, 1H), 2.61 (s, 3H), 2.55-2.46 (m, 1H), 2.26-2.12 (m, 1H), 2.05-1.93 (m, 1H), 1.40-1.31 (m, 1H), 1.19 (t, J=7.1 Hz, 3H).

7A Ethyl 2-(2-fluorophenyl)-5-methylpyrazolo[1,5-a]pyrimidine-3-carboxylate

Prepared by an analogous procedure to that described for intermediate 6A from intermediate 3A. $^1$H NMR (400 MHz, DMSO-d$_6$) δ 9.15 (d, J=7.1 Hz, 1H), 7.60-7.49 (m, 2H), 7.37-7.28 (m, 2H), 7.22 (d, J=7.1 Hz, 1H), 4.13 (q, J=7.1 Hz, 2H), 2.64 (s, 3H), 1.08 (t, J=7.1 Hz, 3H). LRMS (APCI+) m/z 254.3 [M-OCH$_2$CH$_3$]$^+$

8A Ethyl 6-(furan-3-yl)-2-methylpyrazolo[1,5-a]pyrimidine-3-carboxylate

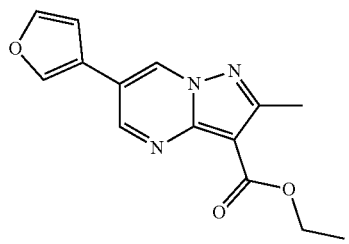 [SMILES: CCOC(=O)c1c(C)nn2cc(-c3ccoc3)cnc12]

A solution of intermediate 4A (200 mg, 0.70 mmol), furan-3-boronic acid (118 mg, 1.06 mmol), and $K_2CO_3$ (292 mg, 2.11 mmol) in 1,4-dioxane/water (3:1; 3.52 mL) in a microwave reactor vial was degassed with $N_2$ for ~10 min. Pd(dppf)Cl$_2$ (39 mg, 0.05 mmol) was added, and the sealed vial heated at 80° C. for 16 h. The reaction was cooled to rt, diluted with EtOAc and filtered through a pad of Celite® on glass microfiber filter paper, washing with EtOAc. The solvent was removed under reduced pressure, and the residue purified by column chromatography (18-70% EtOAc in heptane). The resultant solid triturated with cold (0° C.) Et$_2$O/heptane (1:1) followed by heptane (2×) and dried under reduced pressure to afford a pink solid (85 mg, 45%). $^1$H NMR (400 MHz, DMSO-d$_6$) δ 9.50 (d, J=2.2 Hz, 1H), 9.14 (d, J=2.2 Hz, 1H), 8.45-8.43 (m, 1H), 7.85 (t, J=1.7 Hz, 1H), 7.19 (dd, J=1.9, 0.9 Hz, 1H), 4.30 (q, J=7.1 Hz, 2H), 2.61 (s, 3H), 1.33 (t, J=7.1 Hz, 3H). LRMS (APCI+) m/z 226.2 [M-OCH$_2$CH$_3$]$^+$

9A 2-(2-Fluorophenyl)pyrazolo[1,5-a]pyrimidine-3-carboxylic acid

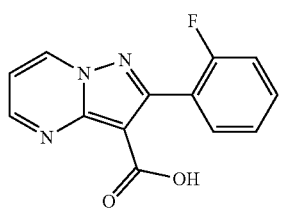 [SMILES: O=C(O)c1c(-c2ccccc2F)nn2cccnc12]

A solution of intermediate 6B (124 mg, 0.320 mmol) and LiOH (1.5 M aq; 0.9 mL, 1.350 mmol) in 1:1 THF/MeOH (4 mL) was stirred at rt overnight. The reaction mixture was diluted with water (20 mL) and washed with EtOAc (2×25 mL). The aqueous layer was acidified by dropwise addition of 1 M HCl (aq) until pH≈2, then extracted with CHCl$_3$/iPrOH (3:1; 3×25 mL). The combined organic extracts were dried (Na$_2$SO$_4$), and the solvent removed under reduced pressure to afford a yellow solid (48 mg, 56%). LCMS (method A) m/z 280.4 [M+Na]$^+$ at 0.82 min. $^1$H NMR (500 MHz, DMSO-d$_6$) 12.19 (br s, 1H), 9.29 (dd, J=6.9, 1.8 Hz, 1H), 8.84 (dd, J=4.2, 1.8 Hz, 1H), 7.63-7.49 (m, 2H), 7.36-7.26 (m, 2H).

The following intermediate compounds were prepared by an analogous procedure to that described for intermediate 9A.

TABLE 2

Preparatory Examples prepared via general ester hydrolysis procedure

| Preparatory Example | Name | R | $^1$H NMR δ (500 MHz) | LCMS (Method A) (ES+) m/z |
|---|---|---|---|---|
| 9B | 2-[4-(Methylamino)phenyl]pyrazolo[1,5-a]pyrimidine-3-carboxylic acid | 4-(methylamino)phenyl | (DMSO-d$_6$) δ 9.24 (dd, J = 6.9, 1.7 Hz, 1H), 8.76 (dd, J = 4.1, 1.8 Hz, 1H), 7.77 (d, J = 8.2 Hz, 2H), 7.25 (dd, J = 6.9, 4.2 Hz, 1H), 7.17 (br s, 1H), 2.82 (s, 3H). | 291.10 [M + Na]$^+$ at 0.59 min |
| 9C | 2-(2,4-Difluorophenyl)pyrazolo[1,5-a]pyrimidine-3-carboxylic acid | 2,4-difluorophenyl | (CDCl$_3$) 8.87 (dd, J = 7.0, 1.7 Hz, 1H), 8.80 (dd, J = 4.3, 1.7 Hz, 1H), 7.64-7.56 (m, 1H), 7.16 (dd, J = 7.0, 4.3 Hz, 1H), 7.05-6.93 (m, 2H) | 258.09 [M – OCH$_2$CH$_3$]$^+$ at 0.88 min |
| 9D | 2-(2,5-Difluorophenyl)pyrazolo[1,5-a]pyrimidine-3-carboxylic acid | 2,5-difluorophenyl | (DMSO-d$_6$) 12.39 (br s, 1H), 9.30 (dd, J = 7.0, 1.8 Hz, 1H), 8.85 (dd, J = 4.2, 1.8 Hz, 1H), 7.46-7.41 (m, 1H), 7.41-7.36 (m, 2H), 7.33 (dd, J = 7.0, 4.1 Hz, 1H) | 258.10 [M – OCH$_2$CH$_3$]$^+$ at 0.87 min |

TABLE 2-continued

Preparatory Examples prepared via general ester hydrolysis procedure

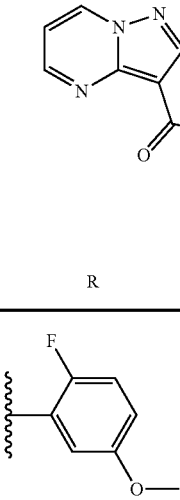

| Preparatory Example | Name | R | $^1$H NMR δ (500 MHz) | LCMS (Method A) (ES+) m/z |
|---|---|---|---|---|
| 9E | 2-(2-Fluoro-5-methoxyphenyl)pyrazolo[1,5-a]pyrimidine-3-carboxylic acid | 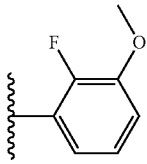 | (DMSO-$d_6$) 12.24 (br s, 1H), 9.33-9.26 (m, 1H), 8.85-8.81 (m, 1H), 7.33-7.29 (m, 1H), 7.26-7.21 (m, 1H), 7.11-7.04 (m, 2H), 3.79 (s, 3H) | 310.04 [M + Na]$^+$ at 0.85 min |
| 9F | 2-(2-Fluoro-3-methoxyphenyl)pyrazolo[1,5-a]pyrimidine-3-carboxylic acid | 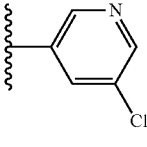 | (DMSO-$d_6$) 12.28 (br s, 1H), 9.28 (dd, J = 7.0, 1.8 Hz, 1H), 8.82 (dd, J = 4.2, 1.8 Hz, 1H), 7.30 (dd, J = 7.0, 4.1 Hz, 1H), 7.28 (dd, J = 8.1, 1.7 Hz, 1H), 7.25-7.20 (m, 1H), 7.11-7.07 (m, 1H), 3.89 (s, 3H) | 270.11 [M − OCH$_2$CH$_3$]$^+$ at 0.84 min |
| 9G | 2-Bromopyrazolo[1,5-a]pyrimidine-3-carboxylic acid | Br | (DMSO-$d_6$) 12.71 (br s, 1H), 9.22 (dd, J = 7.0, 1.7 Hz, 1H), 8.82 (dd, J = 4.2, 1.8 Hz, 1H), 7.30 (dd, J = 7.0, 4.2 Hz, 1H) | 263.9/265.9 [M + Na]$^+$ at 0.57 min |
| 9H | 2-(5-Chloropyridin-3-yl)pyrazolo[1,5-a]pyrimidine-3-carboxylic acid | 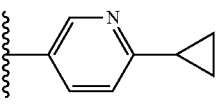 [SMILES: *c1ccc(C2CC2)nc1] | 12.59 (s, 1H), 9.33 (dd, J = 7.0, 1.8 Hz, 1H), 8.90-8.84 (m, 2H), 8.74 (d, J = 2.4 Hz, 1H), 8.31 (t, J = 2.1 Hz, 1H), 7.35 (dd, J = 7.0, 4.2 Hz, 1H) | (method A) 275.5 [M + H]+ at 0.80 min |
| 9I | 2-(6-Cyclopropylpyridin-3-yl)pyrazolo[1,5-a]pyrimidine-3-carboxylic acid | 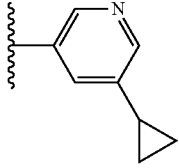 [SMILES: *c1cncc(C2CC2)c1] | 12.45 (s, 1H), 9.31-9.26 (m, 1H), 8.84-8.79 (m, 1H), 8.77-8.72 (m, 1H), 8.01 (dd, J = 8.1, 2.2 Hz, 1H), 7.41 (d, J = 8.1 Hz, 1H), 7.30 (dd, J = 7.0, 4.2 Hz, 1H), 2.22-2.13 (m, 1H), 1.06-0.95 (m, 4H). | (method A) 281.2 [M + H]+ at 0.57 min |
| 9J | 2-(5-Cyclopropylpyridin-3-yl)pyrazolo[1,5-a]pyrimidine-3-carboxylic acid | | Not available | (method A) 281.2 [M + H]+ at 0.57 min |

9K 6-Methyl-2-[5-(trifluoromethyl)pyridin-3-yl]imidazo[1,2-b]pyridazine-3-carboxylic acid

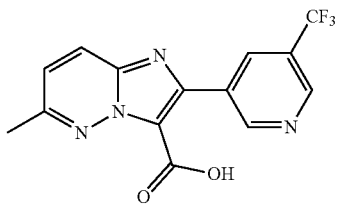

Prepared by an analogous procedure to that described for intermediate 9A with heating at 40° C. LCMS (method A) m/z 322.7 [M+H]$^+$ at 1.03 min. $^1$H NMR (500 MHz, DMSO-d$_6$) 13.48 (s, 1H), 9.30 (d, J=2.0 Hz, 1H), 9.03 (d, J=2.2 Hz, 1H), 8.62-8.58 (m, 1H), 8.24 (d, J=9.3 Hz, 1H), 7.44 (d, J=9.3 Hz, 1H), 2.62 (s, 3H).

10A 2-(2-Chlorophenyl)pyrazolo[1,5-a]pyrimidine-3-carboxylic acid

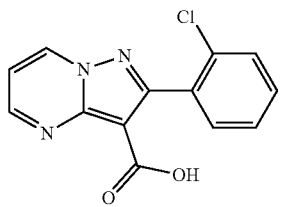 [SMILES: O=C(O)c1c(-c2ccccc2Cl)nn2cccnc12]

A mixture of intermediate 9G (250 mg, 1.03 mmol), 2-chlorobenzeneboronic acid (170 mg, 1.08 mmol) and K$_2$CO$_3$ (432 mg, 3.13 mmol) in 1,4-dioxane:water (2:1, 3.0 mL) was degassed with N$_2$ for 5 min. Pd(PPh$_3$)$_4$ (119 mg, 0.100 mmol) was added, the reaction mixture further degassed with N$_2$ for 5 min, then heated to 100° C. overnight. The reaction was cooled to rt and concentrated under reduced pressure. NaOH (2 M aq; 30 mL) was added and the solution washed with MTBE (3×50 mL). The aqueous solution was acidified with 1 M aq. HCl (pH≈2) and extracted with CHCl$_3$/iPrOH (3:1; 3×50 mL). The combined organic extracts were dried (MgSO$_4$) and concentrated in vacuo to afford a white solid (105 mg, 30%). LCMS (Method A) m/z 255.99 [M-OCH$_2$CH$_3$]$^+$ at 0.86 min.

11A 2-(2-Fluorophenyl)-5-methylpyrazolo[1,5-a]pyrimidine-3-carboxylic acid

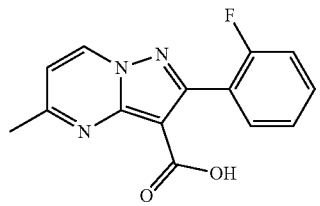 [SMILES: Cc1ccn2nc(-c3ccccc3F)c(C(=O)O)c2n1]

A solution of intermediate 7A (222 mg, 0.740 mmol) and LiOH (1 M aq, 2.23 mL, 2.230 mmol) in THF/MeOH (3:1; 3.7 mL) was heated at 50° C. for 16 h. The volatiles were removed under reduced pressure, and the residue was triturated with Et$_2$O, acidified with HCl (1 M; 2.2 mL) and sat. aq. NH$_4$Cl solution (5 mL) and extracted with MeOH/CH$_2$Cl$_2$ (1:4; 4×15 mL). The combined organic extracts were washed with brine (5 mL), dried (MgSO$_4$) and the solvent removed under reduced pressure to afford a pale yellow solid (151 mg, 75%). $^1$H NMR (400 MHz, DMSO-d$_6$) δ 12.16 (br s, 1H), 9.12 (d, J=7.1 Hz, 1H), 7.57-7.48 (m, 2H), 7.33-7.27 (m, 2H), 7.19 (d, J=7.1 Hz, 1H), 2.64 (s, 3H). LRMS (APCI+) m/z 272.2 [M+H]$^+$.

The following intermediate compounds were prepared an analogous procedure to that described for intermediate 11A.

| Preparatory Example | Name | Structure | $^1$H NMR δ (400 MHz, DMSO-d$_6$) | TLC R$_f$ |
|---|---|---|---|---|
| 11B | 2-(2-Fluorophenyl)-6-methylpyrazolo[1,5-a]pyrimidine-3-carboxylic acid | 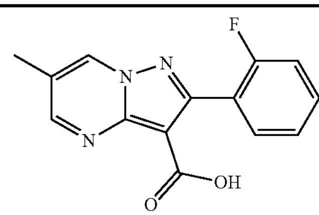 | 12.23 (s, 1H), 9.14 (dq, J = 2.2, 1.0 Hz, 1H), 8.74 (d, J = 2.1 Hz, 1H), 7.58-7.49 (m, 2H), 7.34-7.26 (m, 2H), 2.39 (d, J = 1.1 Hz, 3H). | 0.32 (EtOAc) |
| 11C | 2-(2,4-Difluorophenyl)-5-methylpyrazolo[1,5-a]pyrimidine-3-carboxylic acid | 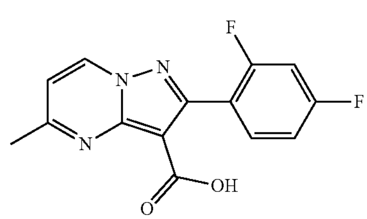 | 12.21 (s, 1H), 9.12 (d, J = 7.1 Hz, 1H), 7.65-7.56 (m, 1H), 7.37 (ddd, J = 10.4, 9.4, 2.5 Hz, 1H), 7.24-7.15 (m, 2H), 2.64 (s, 3H). | 0.46 (EtOAc) |

11D 2-(2-Fluorophenyl)-5-morpholin-4-ylpyrazolo[1,5-a]pyrimidine-3-carboxylic acid

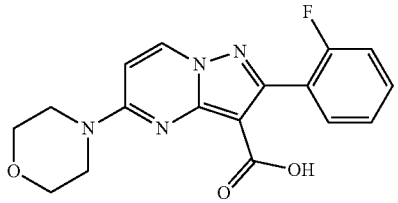 [SMILES: O=C(O)c1c(-c2ccccc2F)nn2ccc(N3CCOCC3)nc12]

A solution of intermediate 26D (192 mg, 0.518 mmol) and LiOH (1 M aq, 2.205 mL, 2.205 mmol) in THF/MeOH (3:1; 2.58 mL) was heated at 50° C. for 19 h. Further LiOH (1 M aq, 1.036 mL, 1.036 mmol) was added and the reaction heated for 23 h. Analogous workup to that described for intermediate 11A, followed by trituration with $Et_2O$, afforded an off-white solid (158 mg, 58%). $^1$H NMR (400 MHz, DMSO-$d_6$) δ 11.57 (s, 1H), 8.79 (d, J=7.9 Hz, 1H), 7.52-7.44 (m, 2H), 7.29-7.21 (m, 2H), 6.91 (d, J=7.9 Hz, 1H), 3.82-3.66 (m, 8H). LRMS (APCI+) m/z 343.1 [M+H]$^+$.

11E 2-(2-Fluorophenyl)-5-pyrrolidin-1-ylpyrazolo[1,5-a]pyrimidine-3-carboxylic acid

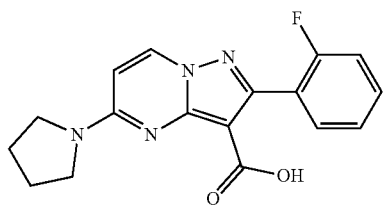 [SMILES: O=C(O)c1c(-c2ccccc2F)nn2ccc(N3CCCC3)nc12]

Prepared by an analogous procedure to that described for intermediate 11D. $^1$H NMR (400 MHz, DMSO-$d_6$) δ 11.42 (s, 1H), 8.75 (d, J=7.7 Hz, 1H), 7.54-7.44 (m, 2H), 7.32-7.22 (m, 2H), 6.59 (d, J=7.8 Hz, 1H), 3.68-3.49 (m, 4H), 2.08-1.89 (m, 4H). LRMS (APCI+) m/z 327.2 [M+H]$^+$.

12A 6-(Furan-3-yl)-2-methylpyrazolo[1,5-a]pyrimidine-3-carboxylic acid

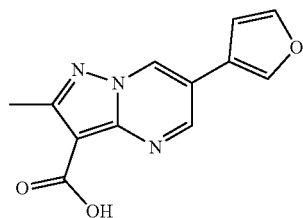 [SMILES: Cc1nn2cc(-c3ccoc3)cnc2c1C(=O)O]

A solution of ethyl 6-(furan-3-yl)-2-methylpyrazolo[1,5-a]pyrimidine-3-carboxylate intermediate 6A and LiOH (1 M aq; 0.94 mL, 0.94 mmol) in THF/MeOH (3:1, 4 mL) was heated at 50° C. for 2 h, then at 40° C. for 48 h. The volatiles were removed under reduced pressure and the crude triturated with $Et_2O$, then acidified with HCl (1 M aq, 0.8 mL), and sat. aq. NHaCl (5 mL) to pH≈2 and extracted with EtOAc/EtOH (~3:1; 3×25 mL). The combined organic extracts were washed with brine (5 mL), dried ($Na_2SO_4$) and the solvent removed under reduced pressure. The residue was suspended in water, filtered, washing with water and the obtained precipitate dried under reduced pressure to afford the crude product as a pale brown solid (56 mg, 74%). $^1$H NMR (400 MHz, DMSO-$d_6$) δ 12.30 (br s, 1H), 9.48 (d, J=2.3 Hz, 1H), 9.08 (d, J=2.3 Hz, 1H), 8.45 (s, 1H), 7.85 (s, 1H), 7.19 (s, 1H), 2.60 (s, 3H). LRMS (APCI+) m/z 244.2 [M+H]$^+$.

13A Ethyl 2-chloro-3-(2-fluorophenyl)-3-oxopropanoate

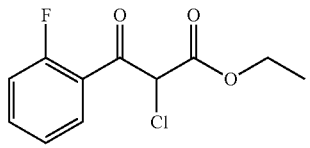 [SMILES: CCOC(=O)C(Cl)C(=O)c1ccccc1F]

A solution of ethyl (2-fluorobenzoyl)acetate (0.43 mL, 2.38 mmol) in MTBE (1 mL) was added dropwise to a stirred solution of sulfuryl dichloride (0.21 mL, 2.62 mmol) in MTBE (5 mL) at 0° C. and the reaction stirred at rt for 2 h. Further sulfuryl dichloride (0.08 mL, 0.95 mmol) was added, and the reaction stirred at rt overnight. The reaction was quenched with sat. aq. $NaHCO_3$ solution (60 mL) and EtOAc (60 mL) and stirred for 30 min. The organic layer was separated, washed with brine (30 mL), dried ($MgSO_4$) and concentrated under reduced pressure to afford a yellow oil (346 mg, 55%). $^1$H NMR (500 MHz, $CDCl_3$) δ 7.95 (td, J=7.6, 1.9 Hz, 1H), 7.65-7.57 (m, 1H), 7.33-7.26 (m, 1H), 7.24-7.14 (m, 1H), 5.63 (s, 1H), 4.30 (q, J=7.12H), 1.27 (t, J=7.1 Hz, 3H).

14A Ethyl-2-(2-fluorophenyl)imidazo[1,2-b]pyridazine-3-carboxylate

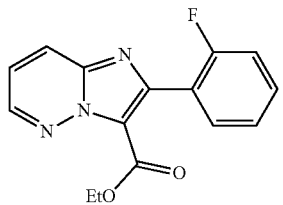 [SMILES: CCOC(=O)c1c(-c2ccccc2F)nc2cccnn12]

A solution of pyridazin-3-amine (201 mg, 2.110 mmol) and intermediate 13A (0.27 mL, 2.640 mmol) in EtOH (4 mL) was heated to 100° C. for 2 h by MWI. The reaction mixture was cooled to rt, evaporated in vacuo and the residue purified by column chromatography (0-100% EtOAc in isohexanes) to afford a yellow solid (70 mg, 9%). LCMS (Method A) m/z 286.01 [M+H]$^+$ at 1.13 min. $^1$H NMR (500 MHz, DMSO-$d_6$) δ 8.77 (dd, J=4.5, 1.7 Hz, 1H), 8.33 (dd, J=9.3, 1.7 Hz, 1H), 7.69 (td, J=7.5, 1.8 Hz, 1H), 7.58-7.48 (m, 2H), 7.38-7.29 (m, 2H), 4.23 (q, J=7.1 Hz, 2H), 1.11 (t, J=7.1 Hz, 3H).

15A Ethyl 2-(2-fluorophenyl)-6-methylimidazo[1,2-b]pyridazine-3-carboxylate

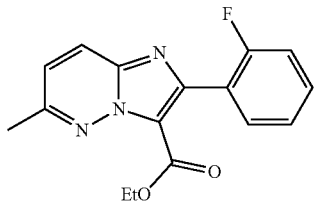 [SMILES: CCOC(=O)c1c(-c2ccccc2F)nc2ccc(C)nn12]

Prepared by an analogous procedure to that described for intermediate 14A. LCMS (Method A) m/z 300.14 [M+H]$^+$ at 1.21 min. $^1$H NMR (500 MHz, DMSO-d$_6$) δ 8.20 (d, J=9.3 Hz, 1H), 7.68 (td, J=7.5, 1.8 Hz, 1H), 7.56-7.48 (m, 1H), 7.42 (d, J=9.3 Hz, 1H), 7.37-7.27 (m, 2H), 4.21 (q, J=7.1 Hz, 2H), 2.60 (s, 3H), 1.10 (t, J=7.1 Hz, 3H).

16A 2-(2-Fluorophenyl)-6-methylimidazo[1,2-b]pyridazine-3-carboxylic acid

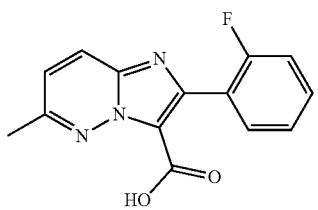

Prepared an analogous procedure to that described for intermediate 9A from intermediate 15A with heating at 40° C. for ~18 h. LCMS (method A) m/z 272.04 [M+H]$^+$ at 0.86 min. $^1$H NMR (500 MHz, DMSO-d$_6$) δ 13.01 (s, 1H), 8.18 (d, J=9.3 Hz, 1H), 7.65 (td, J=7.5, 1.8 Hz, 1H), 7.53-7.45 (m, 1H), 7.39 (d, J=9.3 Hz, 1H), 7.34-7.25 (m, 2H), 2.60 (s, 3H).

17A 3-Bromo-6-ethyl-2-methylpyridine

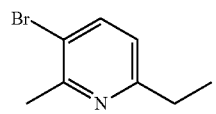

Pd(PPh$_3$)$_4$ (576 mg, 0.50 mmol) was added to a cooled (0° C.) solution of 3,6-dibromo-2-methylpyridine (2.5 g, 9.96 mmol) in THF (40 mL) under nitrogen, followed by dropwise addition of diethylzinc (1 M in hexane; 11.96 mL, 11.96 mmol). The reaction was stirred for 1 h at 0° C., then for 16 h at rt. The reaction was quenched with sat. aq. NH$_4$Cl (25 mL), diluted with EtOAc (10 mL) and the separated aqueous layer extracted with EtOAc (3×20 mL). The combined organic extracts were dried (Na$_2$SO$_4$) and the solvent removed under reduced pressure. Purification by column chromatography 0-10% EtOAc in isohexanes) afforded a colourless oil (1.3 g, 62%). LCMS (method B): m/z 200.1/202.1 [M+H]$^+$ at 1.35 min. $^1$H NMR (500 MHz, CDCl$_3$) 7.71 (d, J=8.1 Hz, 1H), 6.89 (d, J=8.1 Hz, 1H), 2.77 (q, J=7.6 Hz, 2H), 2.66 (s, 3H), 1.30 (t, J=7.6 Hz, 3H).

18A 5-Bromo-6-methyl-N-propan-2-ylpyridin-2-amine

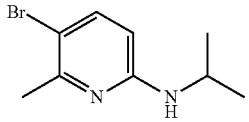

A solution of isopropylamine (5.09 mL, 59.2 mmol) and 3-bromo-6-fluoro-2-methylpyridine (2.5 g, 13.2 mmol) in DMSO (6 mL) was heated by MWI at 120° C. for 12 h. The reaction was diluted with water (100 mL), extracted with CH$_2$Cl$_2$ (3×15 mL), the combined organics dried (Na$_2$SO$_4$) and the solvent removed under reduced pressure. Purification by column chromatography (5-50% EtOAc in isohexanes) afforded a colourless oil (2.30 g, 76%). LCMS (method B): m/z 229.1/231.1 [M+H]$^+$ at 1.54 min. $^1$H NMR (500 MHz, CDCl$_3$) 7.48 (d, J=8.7 Hz, 1H), 6.11 (d, J=8.7 Hz, 1H), 4.38 (d, J=7.6 Hz, 1H), 3.80-3.74 (m, 1H), 2.47 (s, 3H), 1.23 (d, J=6.4 Hz, 6H).

18B 5-Bronro-4-methyl-N-propan-2-ylpyridin-2-amine

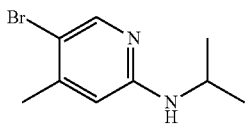

Prepared by an analogous procedure to that described for intermediate 18A from 5-bromo-2-fluoro-4-methylpyridine (2 g, 10.5 mmol) and isopropylamine (4.52 mL, 52.6 mmol). LCMS (method B): m/z 229.1/231.2 [M+H]$^+$ at 0.45 min. $^1$H NMR (500 MHz, CDCl$_3$) 8.09 (s, 1H), 6.27 (s, 1H), 4.40-4.22 (m, 1H), 3.84 (m, 1H), 2.30 (s, 3H), 1.23 (d, J=6.4 Hz, 6H).

19A 5-Bromo-2-(2-methoxyethyl)pyridine

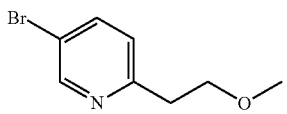

NaH (60% in mineral oil, 109 mg, 2.73 mmol) was added to a cooled (−78° C.) solution of 2-(5-bromopyridin-2-yl)ethanol (500 mg, 2.48 mmol) in THF (10 mL), stirred at -78° C. for 30 min, then MeI (0.17 mL, 2.73 mmol) added. The reaction mixture was allowed to attain rt and stirred overnight, then was quenched with sat. aq. NH$_4$Cl (5 mL). The separated aqueous layer was extracted with CH$_2$Cl$_2$ (3×10 mL), the combined organics dried (Na$_2$SO$_4$) and the solvent removed under reduced pressure. Purification by column chromatography (0-30% EtOAc in heptane) afforded a colourless oil (401 mg, 68%). LCMS (method B): m/z 216.5/218.5 [M+H]$^+$ at 1.00 min. $^1$H NMR (500 MHz, DMSO-d$_6$) 8.59 (dd, J=2.5, 0.7 Hz, 1H), 7.94 (dd, J=8.3, 2.5 Hz, 1H), 7.29 (dd, J=8.3, 0.7 Hz, 1H), 3.66 (t, J=6.6 Hz, 2H), 3.22 (s, 3H), 2.93 (t, J=6.5 Hz, 2H).

20A 1-(5-Bromopyridin-2-yl)-2-methylpropan-2-ol

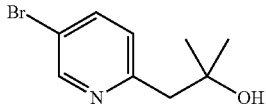

Lithium diisopropylamide (2 M in THF/heptane/ethylbenzene, 4.1 mL, 8.20 mmol) was added dropwise to a cooled (−78° C.) solution of 5-bromo-2-methylpyridine (1 g, 5.81 mmol) in THF (10 mL). The solution was stirred at −78° C. for 20 mins, then acetone (5.8 mL, 17.4 mmol) added dropwise. The reaction was allowed to attain room temperature and stirred for 3 h, then quenched with sat. aq. NH$_4$Cl (40 mL) and extracted with CH$_2$Cl$_2$ (2×50 mL). The combined organic extracts were dried (Na$_2$SO$_4$), concentrated under reduced pressure and purification by column chromatography (0-20% EtOAc in CH$_2$Cl$_2$) afforded a colourless oil (435 mg, 32%). LCMS (method B): m/z 214.1 [M-OH]$^+$ at 0.95 min. $^1$H NMR (500 MHz, CDCl$_3$) δ 8.59 (dd, J=2.5, 0.8 Hz, 1H), 7.78 (dd, J=8.3, 2.5 Hz, 1H), 7.07 (d, J=8.3 Hz, 1H), 2.90 (s, 2H), 1.24 (s, 6H).

21A Ethyl 2-bromo-6-methylpyrazolo[1,5-a]pyrimidine-3-carbaxylate

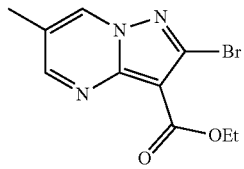 [SMILES: CCOC(=O)c1c(Br)nn2cc(C)cnc12]

A solution of intermediate 1A (963 mg, 4.11 mmol) and 3-ethoxymethacrolein (0.5 mL, 4.22 mmol) in AcOH (11.8 mL) was heated at 75° C. for 24 h. After cooling to rt, the volatiles were removed under reduced pressure. The residue was partitioned between EtOAc (50 mL) and sat. aq. NaHCO$_3$ (50 mL), and the separated aqueous phase extracted with EtOAc (3×50 mL). The combined organic layers were washed successively with sat. aq. NaHCO$_3$, water and brine (50 mL each), dried (Na$_2$SO$_4$) and the solvent removed under reduced pressure. Purification by column chromatography (30-79% EtOAc in heptane) afforded a white solid (936 mg, 80%). LRMS (APCI+) m/z 238.0, 240.0 [M-OCH$_2$CH$_3$]$^+$. $^1$H NMR (400 MHz, DMSO-d$_6$) δ 9.11 (d, J=1.1 Hz, 1H), 8.76 (d, J=2.2 Hz, 1H), 4.31 (d, J=7.1 Hz, 2H), 2.36 (d, J=1.1 Hz, 3H), 1.32 (t, J=7.1 Hz, 3H).

22A Ethyl 2-bromo-5-oxo-4H-pyrazolo[1,5-a]pyrimidine-3-carbaxylate

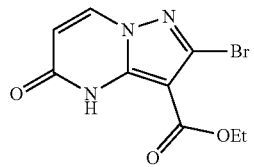 [SMILES: CCOC(=O)c1c(Br)nn2ccc(=O)[nH]c12]

Ethyl 5-amino-3-bromo-1H-pyrazole-4-carboxylate (7.88 g, 30.4 mmol) was added to a suspension of ethyl-3-ethoxyacrylate (6.58 mL, 45.6 mmol) and Cs$_2$CO$_3$ (15.1 g, 46.0 mmol) in DMF (120 mL) at rt, and the resulting mixture heated at 110° C. for 1.5 h. The reaction was cooled to rt, poured into ice-cold water (~500 mL) with acetic acid (3.48 mL, 60.8 mmol), with further rinsing of the reaction vessel with water (~100 mL). The resultant precipitate was collected by filtration, washing with water, and then dried under reduced pressure to afford an off-white solid (8.09 g, 87%). LCMS (method A): m/z 240.0/242.5 [M-OCH$_2$CH$_3$]$^+$ at 0.93 min. $^1$H NMR (500 MHz, DMSO-d$_6$) δ 11.77 (s, 1H), 8.49 (d, J=7.9 Hz, 1H), 6.16 (d, J=7.9 Hz, 1H), 4.30 (q, J=7.0 Hz, 2H), 1.28 (t, J=7.0 Hz, 3H).

23A Ethyl 2-bromo-5-chloropyrazolo[1,5-a]pyrimidine-3-carbaxylate

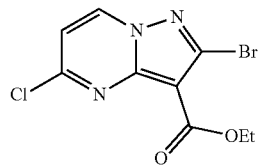 [SMILES: CCOC(=O)c1c(Br)nn2ccc(Cl)nc12]

A solution of intermediate 22A (8.09 g, 26.1 mmol) in POCl$_3$ (25 mL, 268 mmol) was refluxed for 3 h. The reaction was cooled to rt, and the volatiles removed under reduced pressure. The residue was diluted with CH$_2$Cl$_2$ (~200 mL) and poured slowly (caution: exotherm) into sat. aq. NaHCO$_3$ (300 mL). The resultant exotherm was controlled by addition of ice into the mixture. The phases were separated, and the aqueous layer was extracted with CH$_2$Cl$_2$ (2×200 mL). The combined organics were dried (Na$_2$SO$_4$) and the solvent removed under reduced pressure to afford a grey solid (7.94 g, 94%). LCMS (method A): m/z 326.6/328.5 [M+Na]$^+$ at 1.18 min. $^1$H NMR (500 MHz, DMSO-d$_6$) δ 9.27 (d, J=7.2 Hz, 1H), 7.44 (d, J=7.2 Hz, 1H), 4.33 (q, J=7.1 Hz, 2H), 1.32 (t, J=7.1 Hz, 3H).

24A Ethyl 2-bromo-5-morpholin-4-ylpyrazolo[1,5-a]pyrimidine-3-carbaxylate

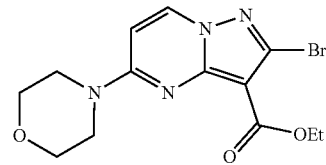 [SMILES: CCOC(=O)c1c(Br)nn2ccc(N3CCOCC3)nc12]

A solution of intermediate 23A (200 mg, 0.657 mmol), morpholine (75 μL, 0.857 mmol) and DIPEA (232 μL, 1.306 mmol) in DMF (3.28 mL) was heated in a sealed tube at 60° C. for 7 h. The reaction was cooled to rt, diluted with EtOAc (30 mL) and washed with sat. aq. NH$_4$Cl (3×10 mL). The aqueous washings were neutralised with sat. aq. NaHCO$_3$ (~20 mL) and extracted with EtOAc (3×25 mL). The combined organic layers were washed successively with water (3×30 mL) and brine (30 mL), dried (Na$_2$SO$_4$) and solvent removed under reduced pressure. Purification by column chromatography (35-100% EtOAc in heptane) afforded a white solid (194 mg, 83%). LRMS (APCI+) m/z 354.9/356.9 [M+H]+. 1H NMR (400 MHz, DMSO-d6) δ 8.70 (d, J=7.9 Hz, 1H), 6.88 (d, J=7.9 Hz, 1H), 4.19 (t, J=7.1 Hz, 2H), 3.80-3.67 (m, 8H), 1.29 (t, J=7.1 Hz, 3H).

24B Ethyl 2-bromo-5-pyrrolidin-1-ylpyrazolo[1,5-a]pyrimidine-3-carbaxylate

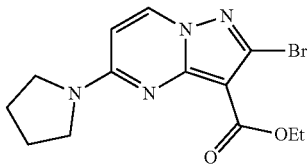 [SMILES: CCOC(=O)c1c(Br)nn2ccc(N3CCCC3)nc12]

A solution of intermediate 23A (300 mg, 0.985 mmol), pyrrolidine (107 μL, 1.286 mmol) and DIPEA (232 μL, 1.306 mmol) in DMF (4.23 mL) was heated in a sealed vial at 60° C. for 65 h. The reaction was cooled to rt and quenched with water. The resultant precipitate was collected by filtration, washing with water, then dissolved in EtOAc and washed with water (2×15 mL) and brine (15 mL), dried (Na2SO4) and the solvent removed under reduced pressure. Purification by column chromatography (33-70% EtOAc in heptane) afforded a white solid (280 mg, 84%). LRMS (APCI+) m/z 339.0/341.0 [M+H]+. 1H NMR (400 MHz, DMSO-d6) δ 8.62 (d, J=7.8 Hz, 1H), 6.52 (d, J=7.7 Hz, 1H), 4.19 (q, J=7.1 Hz, 2H), 3.59 (t, J=6.7 Hz, 2H), 3.49 (t, J=6.7 Hz, 2H), 2.07-1.87 (m, 4H), 1.30 (t, J=7.1 Hz, 3H).

24C Ethyl 2-bromo-5-[(1R,4R)-5-methyl-2,5-diazabicyclo[2.2.1]heptan-2-yl]pyrazolo[1,5-a]pyrimidine-3-carboxylate

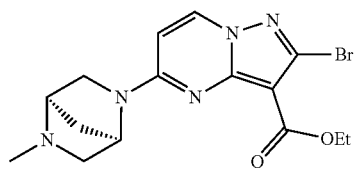 [SMILES: CCOC(=O)c1c(Br)nn2ccc(N3C[C@H]4C[C@@H]3CN4C)nc12]

A solution of intermediate 23A (519 mg, 1.551 mmol), (2R,5R)-1,2,5-trimethylpiperazine-1,4-diium dichloride (390 mg, 1.939 mmol) and DIPEA (1 mL, 5.741 mmol) in DMSO (6.5 mL) was heated at 70° C. for 66 h. The reaction mixture was cooled to rt, diluted with brine (25 mL), extracted with EtOAc (3×25 mL) and the solvent removed under reduced pressure. The residue was dissolved in MeOH (5 mL) and purified by ion exchange chromatography (2 g SCX-2). The aqueous fraction was also purified by ion exchange chromatography (2 g SCX-2). The combined solutions were concentrated under reduced pressure to afford a brown solid (444 mg, 59%). LCMS (method A) m/z 380.3/382.6 [M+Na]+ at 0.59 min. 1H NMR (500 MHz, CDCl3) δ 8.15 (d, J=7.7 Hz, 1H), 6.33-6.00 (m, 1H), 5.27-5.10 (m, 1H), 4.37 (q, J=7.1 Hz, 2H), 3.65 (s, 1H), 3.50-3.34 (m, 1H), 3.21-2.76 (m, 2H), 2.61 (s, 1H), 2.49 (s, 3H), 2.15-2.00 (m, 1H), 1.94-1.78 (m, 1H), 1.41 (t, J=7.1 Hz, 3H).

25A Ethyl 2-bromo-7-methylpyrazolo[1,5-a]pyrimidine-3-carbaxylate

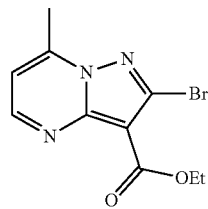 [SMILES: CCOC(=O)c1c(Br)nn2c(C)ccnc12]

A reaction vial was charged with ethyl 5-amino-3-bromo-1H-pyrazole-4-carboxylate (700 mg, 2.990 mmol), 4,4-dimethoxybutan-2-one (0.48 mL, 3.590 mmol), 70% ethanol (9.00 mL) and conc. HCl (0.25 mL, 2.99 mmol) and heated by MWI at 140° C. for 30 min. The reaction mixture was poured into sat. aq. NaHCO3 (100 mL), stirred for 15 min, and the precipitate collected by filtration, washing with water. The resulting solid was purified by column chromatography (0-20% CH2Cl2:EtOH:NH3 [50:8:1] in CH2Ch2), affording a white solid (568 mg, 669%). LRMS m/z [M+H]+. 1H NMR (400 MHz, DMSO-d6) δ 8.74 (d, J=4.4 Hz, 1H), 7.28 (dd, J=4.4, 1.0 Hz, 1H), 4.33 (q, J=7.1 Hz, 2H), 2.75 (d, J=0.8 Hz, 3H), 1.33 (t, J=7.1 Hz, 3H).

26A Ethyl 2-(2-fluorophenyl)-6-methylpyrazolo[1,5-a]pyrimidine-3-carboxylate

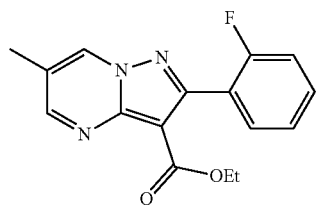 [SMILES: CCOC(=O)c1c(-c2ccccc2F)nn2cc(C)cnc12]

A solution of intermediate 21A (264 mg, 0.929 mmol), 2-fluorophenylboronic acid (195 mg, 1.394 mmol) and K2CO3 (389 mg, 2.813 mmol) in 1,4-dioxane/water (2:1, 2.79 mL) was sparged with N2 for ~10 minutes. Pd(PPh3)4 (149 mg, 0.139 mmol) was added and the reaction heated at 100° C. for 18 h. The reaction was cooled to rt, diluted with CH2Cl2 and filtered through a pad of Celite® on glass microfiber filter paper, washing with CH2Cl2. The solvent was removed under reduced pressure, and the residue purified by column chromatography (30-70% EtOAc in heptane) to afford a pale yellow solid (222 mg, 80%). LRMS (APCI+) m/z 254.1 [M-OCH2CH3]+. 1H NMR (400 MHz, DMSO-d6) δ 9.17 (dd, J=2.1, 1.1 Hz, 1H), 8.77 (d, J=2.2 Hz, 1H), 7.61-7.51 (m, 2H), 7.36-7.29 (m, 2H), 4.15 (q, J=7.1 Hz, 2H), 2.40 (d, J=1.1 Hz, 3H), 1.11 (t, J=7.1 Hz, 3H).

The following intermediates were prepared in an analogous manner to intermediate 26A.

| Preparatory Example | Name | Structure | ¹H NMR δ (400 MHz, DMSO-d₆) | LRMS (APCI⁺) m/z |
|---|---|---|---|---|
| 26B | Ethyl 2-(2-fluorophenyl)-7-methylpyrazolo[1,5-a]pyrimidine-3-carboxylate | 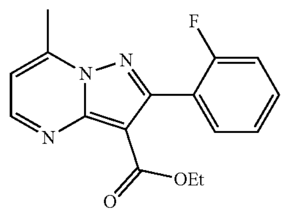 [SMILES: CCOC(=O)c1c(-c2ccccc2F)nn2c(C)ccnc12] | 8.76 (d, J = 4.4 Hz, 1H), 7.68-7.44 (m, 2H), 7.40-7.26 (m, 3H), 4.17 (q, J = 7.1 Hz, 2H), 2.81 (d, J = 0.9 Hz, 3H), 1.12 (t, J = 7.1 Hz, 3H). | 300.3 [M + H]⁺ |
| 26C | Ethyl 2-(2,4-difluorophenyl)-5-methylpyrazolo[1,5-a]pyrimidine-3-carboxylate | 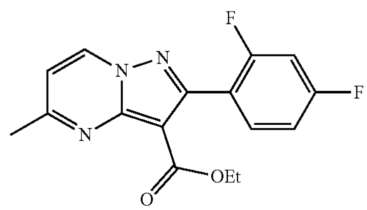 [SMILES: CCOC(=O)c1c(-c2ccc(F)cc2F)nn2ccc(C)nc12] | 9.15 (d, J = 7.1 Hz, 1H), 7.68-7.58 (m, 1H), 7.45-7.35 (m, 1H), 7.26-7.17 (m, 2H), 4.14 (q, J = 7.1 Hz, 2H), 2.64 (s, 3H), 1.11 (t, J = 7.1 Hz, 3H) | 272.1 [M − OEt]⁺ |
| 26D | Ethyl 2-(2-fluorophenyl)-5-morpholin-4-ylpyrazolo[1,5-a]pyrimidine-3-carboxylate | 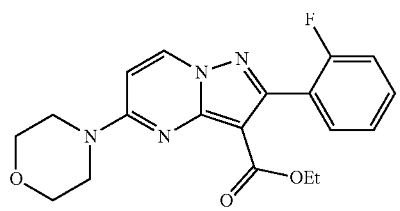 [SMILES: CCOC(=O)c1c(-c2ccccc2F)nn2ccc(N3CCOCC3)nc12] | 8.80 (d, J = 7.9 Hz, 1H), 7.66-7.44 (m, 2H), 7.31-7.21 (m, 2H), 6.91 (d, J = 7.9 Hz, 1H), 4.05 (q, J = 7.1 Hz, 2H), 3.81-3.67 (m, 8H), 1.09 (t, J = 7.1 Hz, 3H) | 325.0 [M − OEt]⁺ |
| 26E | Ethyl 2-(2-fluorophenyl)-5-pyrrolidin-1-ylpyrazolo[1,5-a]pyrimidine-3-carboxylate | 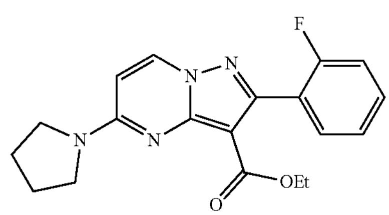 [SMILES: CCOC(=O)c1c(-c2ccccc2F)nn2ccc(N3CCCC3)nc12] | 8.71 (d, J = 7.7 Hz, 1H), 7.53-7.45 (m, 2H), 7.29-7.22 (m, 2H), 6.56 (d, J = 7.7 Hz, 1H), 4.04 (q, J = 7.1 Hz, 2H), 3.57 (d, J = 39.2 Hz, 4H), 2.05-1.91 (m, 4H), 1.10 (t, J = 7.1 Hz, 3H). | 355.4 [M + H]⁺ |

27A Ethyl 2-(5-chloropyridin-3-yl)pyrazolo[1,5-a]pyrimidine-3-carboxylate

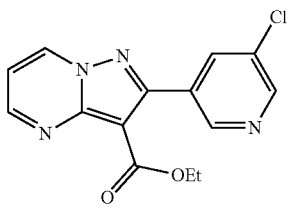 [SMILES: CCOC(=O)c1c(-c2cncc(Cl)c2)nn2cccnc12]

A reaction vessel was charged with intermediate 2A (502 mg, 1.86 mmol), (5-chloropyridin-3-yl)boronic acid (583 mg, 3.70 mmol), K₃PO₄ (621 mg, 2.92 mmol), XPhos (63 mg, 0.133 mmol) and XPhos Pd(crotyl)Cl (Pd-170; 122 mg, 0.180 mmol), then sparged with N₂ for 5 minutes. THF (9 mL) and water (3 mL) were added, the reaction mixture sparged with N₂ for 5 minutes, then heated at 65° C. for 3 h. The reaction was cooled to rt, diluted with CH₂Cl₂ (50 mL), and washed with brine (50 mL). The aqueous layer was extracted with CH₂Cl₂ (2×50 mL), and the combined organic layers dried (Na₂SO₄) and the solvent removed under reduced pressure. Purification by column chromatography (0-3.5% MeOH in CH₂Cl₂) afforded a yellow solid (409 mg, 70%). LCMS (method A) m/z 303.2 [M+H]⁺ (ES+) at 1.06 min. ¹H NMR (500 MHz, DMSO-d₆) 9.35 (dd, J=7.0, 1.8 Hz, 1H), 8.90 (dd, J=4.2, 1.8 Hz, 1H), 8.86 (d, J=1.8 Hz, 1H), 8.76 (d, J=2.4 Hz, 1H), 8.32 (t, J=2.1 Hz, 1H), 7.38 (dd, J=7.0, 4.2 Hz, 1H), 4.25 (q, J=7.1 Hz, 2H), 1.22 (t, J=7.1 Hz, 3H).

The following intermediates were prepared in an analogous manner to intermediate 27A. Preparatory example 27G was prepared from the corresponding boronic acid pinacol ester.

TABLE 1

Preparatory examples prepared by Suzuki-Miyaura coupling with Pd-170

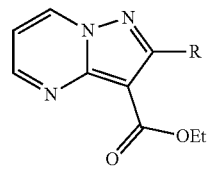

| Preparatory Example | Name | R | $^1$H NMR δ (500 MHz) | LCMS (ES+) m/z |
|---|---|---|---|---|
| 27B | Ethyl 2-(2-fluoro-6-methylpyridin-3-yl)pyrazolo[1,5-a]pyrimidine-3-carboxylate | 6-methyl-2-fluoropyridin-3-yl | (CDCl$_3$) 8.85 (dd, J = 4.2, 1.8 Hz, 1H), 8.78 (dd, J = 7.0, 1.8 Hz, 1H), 7.93 (dd, J = 9.3, 7.5 Hz, 1H), 7.22-7.17 (m, 1H), 7.09 (dd, J = 7.0, 4.2 Hz, 1H), 4.37 (q, J = 7.1 Hz, 2H), 2.62 (s, 3H), 1.26 (t, J = 7.1 Hz, 3H). | (method A) 301.3 [M + H]$^+$ at 0.98 min |
| 27C | Ethyl 2-(6-cyclopropylpyridin-3-yl)pyrazolo[1,5-a]pyrimidine-3-carboxylate | 6-cyclopropylpyridin-3-yl | (CDCl$_3$) 8.84-8.78 (m, 2H), 8.75 (dd, J = 6.9, 1.8 Hz, 1H), 7.97 (dd, J = 8.1, 2.2 Hz, 1H), 7.23 (d, J = 8.1 Hz, 1H), 7.05 (dd, J = 6.9, 4.1 Hz, 1H), 4.39 (q, J = 7.1 Hz, 2H), 2.15-2.07 (m, 1H), 1.31 (t, J = 7.1 Hz, 3H), 1.15-1.07 (m, 2H), 1.10-1.01 (m, 2H). | (method A) 309.3 [M + H]$^+$ at 0.78 min |
| 27D | Ethyl 2-(5-methylpyridin-3-yl)pyrazolo[1,5-a]pyrimidine-3-carboxylate | 5-methylpyridin-3-yl | (CDCl$_3$) 8.85-8.80 (m, 1H), 8.80-8.74 (m, 2H), 8.56-8.50 (m, 1H), 7.94-7.88 (m, 1H), 7.07 (dd, J = 6.9, 4.1 Hz, 1H), 4.38 (q, J = 7.1 Hz, 2H), 2.43 (s, 3H), 1.29 (t, J = 7.1 Hz, 3H) | (method A) 283.3 [M + H]$^+$ at 0.60 min |
| 27E | Ethyl 2-(2,6-difluoropyridin-3-yl)pyrazolo[1,5-a]pyrimidine-3-carboxylate | 2,6-difluoropyridin-3-yl | (DMSO-d$_6$) 9.35 (dd, J = 7.0, 1.7 Hz, 1H), 8.91 (dd, J = 4.2, 1.8 Hz, 1H), 8.42-8.34 (m, 1H), 7.42-7.34 (m, 2H), 4.20 (q, J = 7.1 Hz, 2H), 1.15 (t, J = 7.1 Hz, 3H). | (method A) 259.2 [M + H]$^+$ at 1.08 min |
| 27F | Ethyl 2-(2-fluoro-5-methylpyridin-3-yl)pyrazolo[1,5-a]pyrimidine-3-carboxylate | 2-fluoro-5-methylpyridin-3-yl | (CDCl$_3$) 8.86 (dd, J = 4.1, 1.8 Hz, 1H), 8.79 (dd, J = 7.0, 1.8 Hz, 1H), 8.18-8.13 (m, 1H), 7.88-7.82 (m, 1H), 7.14-7.08 (m, 1H), 4.36 (q, J = 7.1 Hz, 2H), 2.43 (s, 2H), 1.25 (t, J = 7.1 Hz, 2H) | (method A) 301.3 [M + H]$^+$ at 1.00 min |
| 27G | Ethyl 2-(6-methylpyridin-3-yl)pyrazolo[1,5-a]pyrimidine-3-carboxylate | 6-methylpyridin-3-yl | (DMSO-d$_6$) 9.32 (dd, J = 6.9, 1.7 Hz, 1H), 8.86 (dd, J = 4.2, 1.8 Hz, 1H), 8.80-8.75 (m, 1H), 8.03 (dd, J = 8.0, 2.3 Hz, 1H), 7.38 (d, J = 8.0 Hz, 1H), 7.33 (dd, J = 7.0, 4.2 Hz, 1H), 4.25 (q, J = 7.1 Hz, 2H), 2.55 (s, 3H), 1.22 (t, J = 7.1 Hz, 3H). | (method A) 283.3 [M + H]$^+$ at 0.56 min |

28A Ethyl 2-(6-methaxypyridin-3-yl)pyrazolo[1,5-a]pyrimidine-3-carboxylate

XPhos Pd G2 (59 mg, 0.076 mmol) was added to a suspension of intermediate 2A (170 mg, 0.504 mmol), (6-methoxypyridin-3-yl)boronic acid (154 mg, 1.008 mmol) and CsF (348 mg, 2.266 mmol) in 1,4-dioxane:water (4:1; 5 mL), the reaction mixture sparged with $N_2$, then heated at 100° C. overnight. The reaction was cooled to rt, diluted with water and EtOAc (10 mL each), and the separated aqueous layer extracted with EtOAc (3×10 mL). The combined organic layers were washed with brine (20 mL), dried ($Na_2SO_4$) and the solvent removed under reduced pressure. Purification by column chromatography (0-100% EtOAc in hexane) afforded a yellow solid (149 mg, 99%). LCMS (method A) m/z 299.3 [M+H]$^+$ (ES+) at 1.00 min. $^1$H NMR (500 MHz, DMSO-d$_6$) 9.30 (dd, J=6.9, 1.8 Hz, 1H), 8.85 (dd, J=4.2, 1.8 Hz, 1H), 8.54 (dd, J=2.4, 0.8 Hz, 1H), 8.07 (dd, J=8.6, 2.5 Hz, 1H), 7.32 (dd, J=6.9, 4.2 Hz, 1H), 6.94 (dd, J=8.6, 0.8 Hz, 1H), 4.26 (q, J=7.1 Hz, 2H), 3.93 (s, 3H), 1.24 (t, J=7.1 Hz, 3H).

The following intermediates were prepared in an analogous manner to intermediate 28A. Preparatory examples 29C and 29D were prepared from the corresponding boronic acid pinacol ester.

TABLE 2

Preparatory examples prepared by Suzuki-Miyaura coupling with XPhos Pd G2

| Preparatory Example | Name | R | $^1$H NMR δ (500 MHz, DMSO-d$_6$) | LCMS (ES+) m/z |
|---|---|---|---|---|
| 28B | Ethyl 2-(6-ethoxypyridin-3-yl)pyrazolo[1,5-a]pyrimidine-3-carboxylate | | 9.30 (dd, J = 6.9, 1.7 Hz, 1H), 8.84 (dd, J = 4.2, 1.7 Hz, 1H), 8.51 (d, J = 2.4 Hz, 1H), 8.06 (dd, J = 8.6, 2.4 Hz, 1H), 7.32 (dd, J = 6.9, 4.2 Hz, 1H), 6.91 (d, J = 8.6 Hz, 1H), 4.38 (q, J = 7.0 Hz, 2H), 4.26 (q, J = 7.1 Hz, 2H), 1.36 (t, J = 7.0 Hz, 3H), 1.23 (t, J = 7.1 Hz, 3H). | (method A) 313.3 [M + H]$^+$ at 1.14 min |
| 28C | Ethyl 2-(1H-pyrrolo[2,3-b]pyridin-5-yl)pyrazolo[1,5-a]pyrimidine-3-carboxylate | | 11.83 (s, 1H), 9.31 (dd, J = 6.9, 1.7 Hz, 1H), 8.85 (dd, J = 4.2, 1.8 Hz, 1H), 8.56 (d, J = 2.1 Hz, 1H), 8.34 (d, J = 2.1 Hz, 1H), 7.58-7.53 (m, 1H), 7.32 (dd, J = 6.9, 4.2 Hz, 1H), 6.56 (dd, J = 3.4, 1.7 Hz, 1H), 4.26 (q, J = 7.1 Hz, 2H), 1.21 (t, J = 7.1 Hz, 3H). | (method A) 308.3 [M + H]$^+$ at 0.98 min |
| 28D | Ethyl 2-(1-methylpyrrolo[2,3-b]pyridin-5-yl)pyrazolo[1,5-a]pyrimidine-3-carboxylate | | 9.32 (dd, J = 6.9, 1.8 Hz, 1H), 8.85 (dd, J = 4.2, 1.7 Hz, 1H), 8.61 (d, J = 2.0 Hz, 1H), 8.34 (d, J = 2.1 Hz, 1H), 7.61 (d, J = 3.5 Hz, 1H), 7.32 (dd, J = 6.9, 4.2 Hz, 1H), 6.58 (d, J = 3.4 Hz, 1H), 4.25 (q, J = 7.1 Hz, 2H), 3.89 (s, 3H), 1.21 (t, J = 7.1 Hz, 3H). | (method A) 322.3 [M + H]$^+$ at 0.98 min |

28E Ethyl 2-(2,6-difluorophenyl)pyrazolo[1,5-a]pyrimidine-3-carboxylate

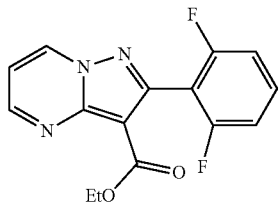 [SMILES: CCOC(=O)c1c(-c2c(F)cccc2F)nn2cccnc12]

Prepared by an analogous procedure to that described for intermediate 28A from intermediate 2A (76 mg, 0.276 mmol) and 2,6-difluorophenylboronic acid (440 mg, 2.786 mmol) using Xphos Pd G2 (57 mg, 0.072 mmol) and CsF (169 mg, 1.272 mmol) in 1,4-dioxane:water (3:1; 4 mL). White solid (74 mg, 0.244 mmol). LCMS (method A) m/z 283.0 [M+H]$^+$ (ES+) at 0.49 min. $^1$H NMR (500 MHz, DMSO-d$_6$) 9.35 (dd, J=7.0, 1.7 Hz, 1H), 8.91 (dd, J=4.2, 1.8 Hz, 1H), 7.68-7.58 (m, 1H), 7.38 (dd, J=7.0, 4.2 Hz, 1H), 7.30-7.22 (m, 2H), 4.15 (q, J=7.1 Hz, 2H), 1.09 (t, J=7.1 Hz, 3H).

29A Ethyl 2-(2-methylpyridin-4-yl)pyrazolo[1,5-a]pyrimidine-3-carboxylate

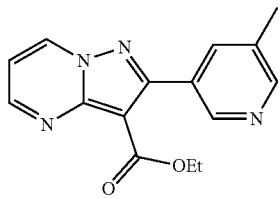 [SMILES: CCOC(=O)c1c(-c2cncc(C)c2)nn2cccnc12]

XPhos Pd G2 (59 mg, 0.076 mmol) was added to a suspension of intermediate 2A (170 mg, 0.504 mmol), 2-methyl-4-(4,4,5,5-tetramethyl-1,3,2-dioxaborolan-2-yl)pyridine (221 mg, 1.00 mmol) and CsF (347 mg, 2.266 mmol) in 1,4-dioxane:water (4:1; 5 mL), the reaction mixture sparged with N$_2$, and heated at 70° C. overnight. The reaction was cooled to rt, retreated with XPhos Pd G2 (59 mg, 0.076 mmol), 2-methyl-4-(4,4,5,5-tetramethyl-1,3,2-dioxaborolan-2-yl)pyridine (221 mg, 1.01 mmol) and CsF (347 mg, 2.266 mmol) and reaction was heated to 70° C. overnight. Analogous workup and purification to that described for intermediate 28A afforded a yellow solid. (75 mg, 53%). LCMS (method A) m/z 283.0 [M+H]$^+$ (ES+) at 0.49 min. $^1$H NMR (500 MHz, DMSO-d$_6$) 9.32 (dd, J=7.0, 1.7 Hz, 1H), 8.87 (dd, J=4.2, 1.7 Hz, 1H), 8.56 (d, J=5.1 Hz, 1H), 7.61-7.57 (m, 1H), 7.52 (dd, J=5.1, 1.7 Hz, 1H), 7.36 (dd, J=7.0, 4.2 Hz, 1H), 4.25 (q, J=7.1 Hz, 2H), 2.55 (s, 3H), 1.21 (t, J=7.1 Hz, 3H).

30A Ethyl 2-(6-fluoropyridin-3-yl)pyrazolo[1,5-a]pyrimidine-3-carboxylate

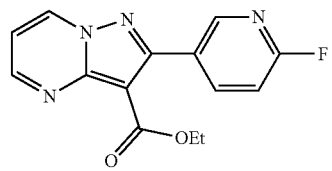 [SMILES: CCOC(=O)c1c(-c2ccc(F)nc2)nn2cccnc12]

XPhos Pd G2 (198 mg, 0.25 mmol) was added to a suspension of intermediate 2A (1 g, 3.59 mmol), 2-fluoropyridine-5-boronic acid (607 mg, 4.31 mmol) and K$_3$PO$_4$ (1.53 g, 7.21 mmol) in 1,4-dioxane:water (4:1; 10 mL), the reaction mixture sparged with N$_2$, and heated at 100° C. for 4 h. Analogous workup and purification to that described for intermediate 28A afforded a yellow solid (850 mg, 83%). LCMS (method A) m/z 287.4 [M+H]$^+$ (ES+) at 0.96 min. $^1$H NMR (500 MHz, DMSO-d$_6$) 9.36-9.31 (m, 1H), 8.89 (dd, J=4.2, 1.8 Hz, 1H), 8.58 (d, J=2.5 Hz, 1H), 8.35 (td, J=8.2, 2.5 Hz, 1H), 7.39-7.31 (m, 2H), 4.25 (q, J=7.1 Hz, 2H), 1.22 (t, J=7.1 Hz, 3H).

31A Ethyl 2-(6-ethylpyridin-3-yl)pyrazolo[1,5-a]pyrimidine-3-carboxylate

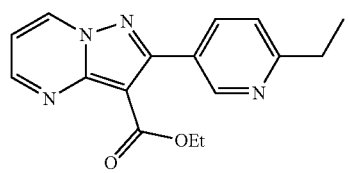 [SMILES: CCOC(=O)c1c(-c2ccc(CC)nc2)nn2cccnc12]

KOAc (633 mg, 6.45 mmol) was added to a suspension of bis(pinacolato)diboron (600 mg, 2.36 mmol) and 5-bromo-2-ethylpyridine (400 mg, 2.15 mmol) in dioxane (3.3 mL). The mixture was sparged with N$_2$, Pd(dppf)Cl$_2$ (118 mg, 0.161 mmol) added, and heated at 100° C. for 1 h. The reaction was cooled to rt, diluted with EtOAc (30 mL) and filtered through Celite, washing with EtOAc (40 mL). The filtrate was concentrated under reduced pressure to afford a red oil (501 mg) and the residue taken directly to the next reaction. A portion of the crude residue (251 mg, 1.08 mmol) was suspended in 1,4-dioxane:water (4:1; 5 mL), intermediate 2A (170 mg, 0.504 mmol) and CsF (347 mg, 2.266 mmol) added, followed by XPhos Pd G2 (59 mg, 0.076 mmol). The reaction was sparged with N$_2$ for 5 minutes then heated at 100° C. for 2 h. Analogous workup and purification to that described for intermediate 28A afforded an orange solid (112 mg, 73%). LCMS (method A) m/z 297.4 [M+H]+ (ES+) at 0.66 m. $^1$H NMR (500 MHz, DMSO-d$_6$) 9.32 (dd, J=6.9, 1.8 Hz, 1H), 8.86 (dd, J=4.2, 1.8 Hz, 1H), 8.79 (dd, J=2.3, 0.9 Hz, 1H), 8.05 (dd, J=8.0, 2.3 Hz, 1H), 7.39 (d, J=8.0 Hz, 1H), 7.33 (dd, J=6.9, 4.2 Hz, 1H), 4.25 (q, J=7.1 Hz, 2H), 2.83 (q, J=7.6 Hz, 2H), 1.28 (t, J=7.6 Hz, 3H), 1.22 (t, J=7.1 Hz, 3H).

The following intermediates were prepared in an analogous manner to intermediate 31A. Preparatory examples 31F and 31G were subject to additional purification by ion exchange chromatography (SCX-2). The reaction for 31G was heated at 70° C.

TABLE 3

*Preparatory examples prepared by Suzuki-Miyaura coupling*

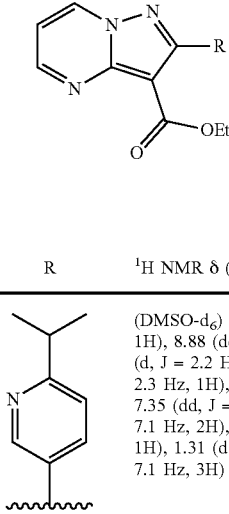

| Preparatory Example | Name | R | ¹H NMR δ (500 MHz) | LCMS (ES+) m/z |
|---|---|---|---|---|
| 31B | Ethyl 2-(6-propan-2-ylpyridin-3-yl)pyrazolo[1,5-a]pyrimidine-3-carboxylate | 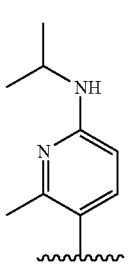 [SMILES: *c1ccc(NC(C)C)nc1C] | (DMSO-$d_6$) 9.33 (dd, J = 7.0, 1.7 Hz, 1H), 8.88 (dd, J = 4.2, 1.7 Hz, 1H), 8.82 (d, J = 2.2 Hz, 1H), 8.07 (dd, J = 8.0, 2.3 Hz, 1H), 7.42 (d, J = 8.1 Hz, 1H), 7.35 (dd, J = 6.9, 4.2 Hz, 1H), 4.26 (q, J = 7.1 Hz, 2H), 3.12 (hept, J = 7.3 Hz, 1H), 1.31 (d, J = 7.0 Hz, 6H), 1.23 (t, J = 7.1 Hz, 3H) | (method B) 311.3 [M + H]⁺ at 1.14 min |
| 31C | Ethyl 2-[2-methyl-6-(propan-2-ylamino)pyridin-3-yl]pyrazolo[1,5-a]pyrimidine-3-carboxylate | 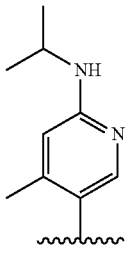 [SMILES: *c1cnc(NC(C)C)cc1C] | (DMSO-$d_6$) 9.24 (dd, J = 6.9, 1.8 Hz, 1H), 8.82 (dd, J = 4.2, 1.8 Hz, 1H), 7.35-7.18 (m, 2H), 6.43 (d, J = 7.8 Hz, 1H), 6.32 (d, J = 8.5 Hz, 1H), 4.17 (q, J = 7.1 Hz, 2H), 4.03 (dt, J = 13.3, 6.7 Hz, 1H), 2.17 (s, 3H), 1.21-1.13 (m, 9H). | (method B) 340.4 [M + H]⁺ at 1.11 min |
| 31D | Ethyl 2-[4-methyl-6-(propan-2-ylamino)pyridin-3-yl]pyrazolo[1,5-a]pyrimidine-3-carboxylate | 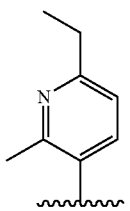 [SMILES: *c1ccc(CC)nc1C] | Not available | (method B) 340.4 [M + H]⁺ at 1.08 min |
| 31E | Ethyl 2-(6-ethyl-2-methylpyridin-3-yl)pyrazolo[1,5-a]pyrimidine-3-carboxylate | | (CDCl₃) 8.86 (dd, J = 4.2, 1.8 Hz, 1H), 8.78 (dd, J = 6.9, 1.8 Hz, 1H), 7.58 (d, J = 7.8 Hz, 1H), 7.16-7.07 (m, 2H), 4.27 (q, J = 7.1 Hz, 2H), 2.89 (q, J = 7.6 Hz, 2H), 2.45 (s, 3H), 1.36 (t, J = 7.6 Hz, 3H), 1.15 (t, J = 7.1 Hz, 3H). | (method B) 310.7 [M + H]⁺ at 1.01 min |
| 33F | Ethyl 2-[6-(2-methoxyethyl)pyridin-3-yl]pyrazolo[1,5-a]pyrimidine-3-carboxylate | 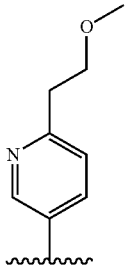 [SMILES: *c1ccc(CCOC)nc1] | (DMSO-$d_6$) 9.32 (dd, J = 6.9, 1.7 Hz, 1H), 8.86 (dd, J = 4.2, 1.8 Hz, 1H), 8.80 (dd, J = 2.3, 0.8 Hz, 1H), 8.05 (dd, J = 8.0, 2.3 Hz, 1H), 7.42 (dd, J = 8.1, 0.8 Hz, 1H), 7.34 (dd, J = 7.0, 4.2 Hz, 1H), 4.25 (q, J = 7.1 Hz, 2H), 3.74 (t, J = 6.6 Hz, 2H), 3.26 (s, 3H), 3.04 (t, J = 6.6 Hz, 2H), 1.22 (t, J = 7.1 Hz, 3H). | (method B) 327.3 [M + H]⁺ at 0.90 min |

TABLE 3-continued

Preparatory examples prepared by Suzuki-Miyaura coupling

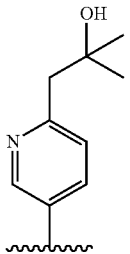 [SMILES: *c1ccc(CC(C)(C)O)nc1]

| Preparatory Example | Name | R | $^1$H NMR δ (500 MHz) | LCMS (ES+) m/z |
|---|---|---|---|---|
| 31G | Ethyl 2-[6-(2-hydroxy-2-methylpropyl)pyridin-3-yl]pyrazolo[1,5-a]pyrimidine-3-carboxylate | OH on pyridine-CH$_2$-C(CH$_3$)$_2$-OH | (DMSO-d$_6$) 9.32 (dd, J = 7.0, 1.7 Hz, 1H), 8.89-8.84 (m, 1H), 8.79 (d, J = 2.3 Hz, 1H), 8.08-8.00 (m, 1H), 7.43 (d, J = 8.1 Hz, 1H), 7.36-7.32 (m, 1H), 4.73 (s, 1H), 4.29-4.20 (m, 2H), 2.92 (s, 2H), 1.22-1.18 (m, 3H), 1.14 (s, 6H). | (method B) 340.7 [M + H]$^+$ at 0.86 min |

32A Ethyl 2-(5-cyclopropylpyridin-3-yl)pyrazolo[1,5-a]pyrimidine-3-carboxylate

33A Ethyl 2-[6-(propan-2-ylamino)pyridin-3-yl]pyrazolo[1,5-a]pyrimidine-3-carbaxylate

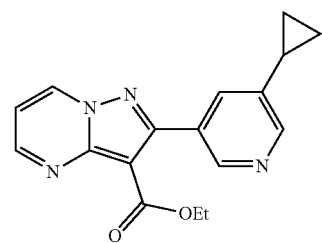 [SMILES: CCOC(=O)c1c(-c2cncc(C3CC3)c2)nn2cccnc12]

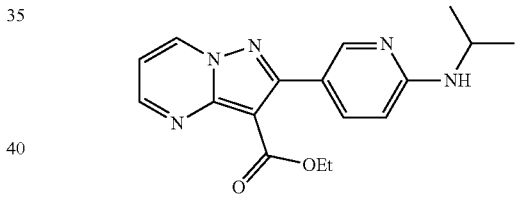

Potassium cyclopropyltrifluoroborate (143 mg, 0.964 mmol), K$_2$CO$_3$ (187 mg, 1.353 mmol), 2-dicyclohexylphosphino-2',6'-diisopropoxybiphenyl (RuPhos; 29 mg, 0.063 mmol), and Pd(OAc)$_2$ (7.1 mg, 0.031 mmol) were added to a solution of intermediate 27A (95 mg, 0.313 mmol) in toluene (1.7 mL) and water (0.2 mL) under N$_2$ and the reaction heated by MWI at 130° C. for 2 h. The reaction mixture was combined with a second batch performed with 49 mg of 27A (total input 144 mg, 0.476 mmol). The combined reaction mixtures were diluted with CH$_2$Cl$_2$ (25 ml) and washed with brine (25 mL). The aqueous layer was extracted with CH$_2$Cl$_2$ (2×25 mL), the combined organic extracts dried (Na$_2$SO$_4$), and the solvent removed under reduced pressure. Purification by column chromatography (0-3% MeOH in CH$_2$Cl$_2$) afforded an amber oil (104 mg, 71% combined yield). LCMS (method A) m/z 309.3 [M+H]$^+$ (ES+) at 0.80 min. $^1$H NMR (500 MHz, CDCl$_3$) 8.88-8.83 (m, 1H), 8.83-8.76 (m, 2H), 8.55-8.50 (m, 1H), 7.86-7.81 (m, 1H), 7.10 (dd, J=7.0, 4.1 Hz, 1H), 4.41 (q, J=7.1 Hz, 2H), 2.07-2.01 (m, 1H), 1.33 (t, J=7.1 Hz, 3H), 1.16-1.07 (m, 2H), 0.91-0.80 (m, 2H).

DIPEA (0.18 mL, 1.04 mmol) and isopropylamine (0.36 mL, 4.22 mmol) were added to a solution of intermediate 30A (240 mg, 0.84 mmol) in DMSO (2 mL) and heated at 100° C. overnight. The reaction mixture was partitioned between EtOAc (10 mL) and sat. aq. NH$_4$Cl (10 mL). The separated aqueous layer was extracted with EtOAc (3×10 mL), and the combined organic layers were washed with brine (20 mL), dried (Na$_2$SO$_4$) and concentrated under reduced pressure. Purification by column chromatography (0-100% EtOAc in hexane) afforded a yellow solid. (127 mg, 42%). LCMS (method B): m/z 326.4 [M+H]$^+$ at 1.06 min. $^1$H NMR (500 MHz, DMSO-d$_6$) 9.23 (dd, J=6.9, 1.8 Hz, 1H), 8.78 (dd, J=4.2, 1.8 Hz, 1H), 8.38 (d, J=2.5 Hz, 1H), 7.75 (dd, J=8.7, 2.4 Hz, 1H), 7.25 (dd, J=6.9, 4.2 Hz, 1H), 6.73 (d, J=7.6 Hz, 1H), 6.51 (dd, J=8.8, 0.8 Hz, 1H), 4.27 (q, J=7.1 Hz, 2H), 4.14-4.02 (m, 1H), 1.26 (t, J=7.1 Hz, 3H), 1.18 (d, J=6.4 Hz, 6H).

The following intermediates were prepared in an analogous manner to intermediate 33A. The reaction for intermediate 33C was heated at 50° C. for 3 h.

TABLE 4

Preparatory examples prepared by Suzuki-Miyaura coupling

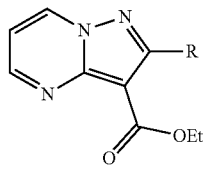

| Preparatory Example | Name | Structure | $^1$H NMR δ (500 MHz) | LCMS (ES+) m/z |
|---|---|---|---|---|
| 33B | Ethyl 2-(6-morpholin-4-ylpyridin-3-yl)pyrazolo[1,5-a]pyrimidine-3-carboxylate | 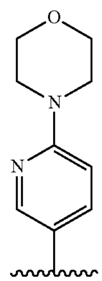 [SMILES: *c1ccc(N2CCOCC2)nc1] | (DMSO-$d_6$) 9.26 (dd, J = 6.9, 1.8 Hz, 1H), 8.81 (dd, J = 4.2, 1.8 Hz, 1H), 8.53 (dd, J = 2.4, 0.7 Hz, 1H), 7.96 (dd, J = 8.9, 2.4 Hz, 1H), 7.28 (dd, J = 6.9, 4.2 Hz, 1H), 6.93 (d, J = 8.9 Hz, 1H), 4.27 (q, J = 7.1 Hz, 2H), 3.75-3.70 (m, 4H), 3.55 (dd, J = 5.7, 4.1 Hz, 4H), 1.26 (t, J = 7.1 Hz, 3H) | (method A) 354.7 [M + H]$^+$ at 0.93 min |
| 33C | Ethyl 2-[6-(cyclopropylamino)-2-fluoropyridin-3-yl]pyrazolo[1,5-a]pyrimidine-3-carboxylate | 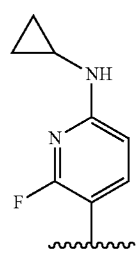 [SMILES: *c1ccc(NC2CC2)nc1F] | (DMSO-$d_6$) 9.26 (dd, J = 7.0, 1.7 Hz, 1H), 8.81 (dd, J = 4.2, 1.7 Hz, 1H), 7.78 (t, J = 9.0 Hz, 1H), 7.49 (d, J = 2.6 Hz, 1H), 7.29 (dd, J = 7.0, 4.2 Hz, 1H), 6.58 (d, J = 8.5 Hz, 1H), 4.21 (q, J = 7.1 Hz, 2H), 2.61-2.54 (m, 1H), 1.19 (t, J = 7.1 Hz, 3H), 0.79-0.70 (m, 2H), 0.51-0.45 (m, 2H). | (method A) 342.3 [M + H]$^+$ at 1.11 min |

34A Ethyl 2-[6-(ethylamino)-2-fluoropyridin-3-yl]pyrazolo[1,5-a]pyrimidine-3-carbaxylate 35A Ethyl 2-[2-fluoro-6-(propan-2-ylamino)pyridin-3-yl]pyrazolo[1,5-a]pyrimidine-3-carboxylate

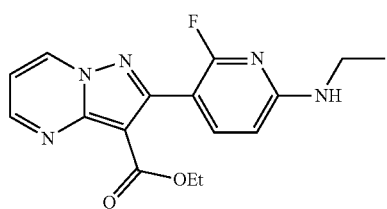 [SMILES: CCNc1ccc(-c2nn3cccnc3c2C(=O)OCC)c(F)n1]

DIPEA (99 µL, 0.57 mmol) and ethylamine (2 M in THF; 583 µL, 1.12 mmol) were added to a solution of intermediate 27E (144 mg, 0.47 mmol) in DMSO (2 mL) and heated by MWI at 100° C. for 30 min. Analogous workup to that described for intermediate 33A followed by purification by column chromatography (0-2% MeOH in CH$_2$Cl$_2$) afforded a yellow solid (84 mg, 52%). LCMS (method A): m/z 352.3 [M+Na]$^+$ at 1.09 min. $^1$H NMR (500 MHz, CDCl$_3$) 8.80 (dd, J=4.2, 1.8 Hz, 1H), 8.75 (dd, J=7.0, 1.8 Hz, 1H), 7.84-7.78 (m, 1H), 7.04 (dd, J=7.0, 4.2 Hz, 1H), 6.37-6.33 (m, 1H), 4.40 (q, J=7.1 Hz, 2H), 3.40 (q, J=7.2 Hz, 2H), 1.35-1.29 (m, 6H).

DIPEA (116 µL, 0.67 mmol) and isopropylamine (117 µL, 1.36 mmol) were added to a solution of intermediate 27E (168 mg, 0.55 mmol) in DMSO (2 mL) and stirred at rt for 4 h, then heated at 40° C. for 1 h. Analogous workup to that described for intermediate 33A followed by purification by column chromatography (0-3% MeOH in CH$_2$Cl$_2$) afforded a white solid (89 mg, 46%). LCMS (method A): m/z 344.2 [M+H]$^+$ at 1.19 min. $^1$H NMR (500 MHz, DMSO-$d_6$) 9.24 (dd, J=7.0, 1.7 Hz, 1H), 8.80 (dd, J=4.2, 1.8 Hz, 1H), 7.67 (dd, J=9.9, 8.3 Hz, 1H), 7.27 (dd, J=6.9, 4.2 Hz, 1H), 7.14 (d, J=7.6 Hz, 1H), 6.43 (dd, J=8.2, 1.8 Hz, 1H), 4.20 (q, J=7.1 Hz, 2H), 4.01-3.90 (m, 1H), 1.22-1.15 (m, 9H).

36A Ethyl 2-[6-(3-methylmorpholin-4-yl)pyridin-3-yl]pyrazolo[1,5-a]pyrimidine-3-carbaxylate

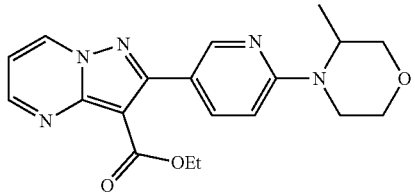 [SMILES: CCOC(=O)c1c(-c2ccc(N3CCOCC3C)nc2)nn2cccnc12]

A solution of intermediate 30A (150 mg, 0.49 mmol), 3-methylmorpholine (39 µL mL, 0.50 mmol) and DIPEA (107 µL, 0.62 mmol) in DMSO (2 mL) was heated at 100° C. overnight. Further 3-methylmorpholine (330 µL, 2.42 mmol) and DIPEA (600 µL, 3.45 mmol) were added and the mixture heated at 145° C. overnight. The reaction mixture was cooled to rt, diluted with EtOAc (25 mL) and washed with sat. aq. NaHCO$_3$ (3×25 mL). The organic layer was dried (Na$_2$SO$_4$), the solvent removed under reduced pressure, and the residue purified by column chromatography (0-4% MeOH in CH$_2$Cl$_2$) to afford a brown oil (140 mg, 65%). LCMS (method A): m/z 368.4 [M+H]$^+$ at 0.75 min. $^1$H NMR (500 MHz, CDCl$_3$) 8.81-8.77 (m, 1H), 8.77-8.74 (m, 1H), 8.70-8.66 (m, 1H), 8.04-8.00 (m, 1H), 7.07-7.01 (m, 1H), 6.71-6.67 (m, 1H), 4.49-4.41 (m, 3H), 4.10-4.04 (m, 1H), 4.00-3.96 (m, 1H), 3.88-3.79 (m, 2H), 3.72-3.63 (m, 1H), 3.34-3.30 (m, 1H), 1.39 (t, J=7.1 Hz, 3H), 1.34-1.30 (m, 3H).

37A Ethyl 2-(1-methylindazol-5-yl)pyrazolo[1,5-a]pyrimidine-3-carbaxylate

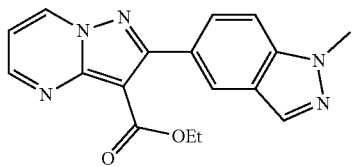 [SMILES: CCOC(=O)c1c(-c2ccc3c(cnn3C)c2)nn2cccnc12]

NaH (60% dispersion in mineral oil, 55 mg, 1.38 mmol) was added to a cooled (0° C.) solution of intermediate 6N (139 mg, 0.45 mmol) in DMF (2 mL) and the reaction stirred for 30 min at 0° C. Methyl iodide (34 µL, 0.54 mmol) was added and the reaction stirred at rt for 4 h. The reaction was quenched with water (5 mL), diluted with EtOAc (25 mL) and the organic layer washed with brine (3×25 mL), dried (Na$_2$SO$_4$) and the solvent removed under reduced pressure. Purification by column chromatography (0-2% MeOH in CH$_2$C2) afforded a white solid (47 mg, 32%). LCMS (method A): m/z 322.7 [M+H]$^+$ at 1.00 min. $^1$H NMR (500 MHz, CDCl$_3$) 8.81-8.73 (m, 2H), 8.20 (dd, J=1.6, 1.0 Hz, 1H), 8.07 (d, J=1.0 Hz, 1H), 7.83 (dd, J=8.7, 1.6 Hz, 1H), 7.48 (dt, J=8.8, 1.0 Hz, 1H), 7.03 (dd, J=6.9, 4.1 Hz, 1H), 4.39 (q, J=7.1 Hz, 2H), 4.13 (s, 3H), 1.29 (t, J=7.1 Hz, 3H).

38A Ethyl 2-(2-fluoro-4 pyrrolidin-1-ylphenyl)pyrazolo[1,5-a]pyrimidine-3-carbaxylate

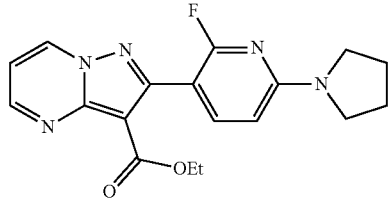 [SMILES: CCOC(=O)c1c(-c2ccc(N3CCCC3)nc2F)nn2cccnc12]

1,4-Dibromobutane (67 µL, 0.57 mmol) was added to a solution of intermediate 6M (170 mg, 0.57 mmol), K$_2$CO$_3$ (156 mg, 1.13 mmol) and KI (45 mg, 1.15 mmol) in MeCN (10 mL) and the reaction heated to 90° C. for ~3 days. The volatiles were removed under reduced pressure, and the residue partitioned between EtOAc (10 mL) and water (10 mL). The separated aqueous layer was extracted with EtOAc (3×10 mL), and the combined organic layers washed with brine (20 mL), dried (Na$_2$SO$_4$) and concentrated under reduced pressure. Purification by column chromatography (0-100% EtOAc in hexane) afforded an orange solid (120 mg, 49%). LCMS (method A): m/z 355.1 [M+H]$^+$ at 1.43 min. $^1$H NMR (500 MHz, DMSO-d$_6$) 9.24 (dd, J=6.9, 1.8 Hz, 1H), 8.78 (dd, J=4.1, 1.8 Hz, 1H), 7.25 (dd, J=6.9, 4.2 Hz, 1H), 6.45 (dd, J=8.6, 2.3 Hz, 1H), 6.39 (dd, J=13.8, 2.3 Hz, 1H), 4.19 (q, J=7.1 Hz, 2H), 3.31-3.25 (m, 4H), 2.02-1.94 (m, 4H), 1.18 (t, J=7.1 Hz, 3H).

39A Ethyl 6-ethylpyridine-3-carbaxylate

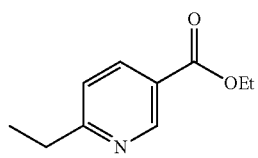

EtMgBr (3.0 M solution in Et$_2$O; 41 mL, 123 mmol) was added dropwise to a cooled (−75° C.) solution of ethyl 6-chloropyridine-3-carboxylate (15.11 g, 81.41 mmol), iron (III) acetylacetonate (2.99 g, 8.30 mmol) and 1-methylpyrrolidin-2-one (11 mL, 114.3 mmol) in THF (400 mL). The mixture was stirred at −75° C. for 1 h, then allowed to warm to 0° C. and quenched by dropwise addition of water (250 mL). The resulting mixture was extracted with EtOAc (3×250 mL), and the combined organic layers concentrated under reduced pressure. The residue was diluted with EtOAc (250 mL), washed with brine (3×250 mL), dried (Na$_2$SO$_4$), and the solvent removed under reduced pressure. Purification by column chromatography (0-15% EtOAc in iso-hexanes) afforded a yellow oil (13.45 g, 90%). LCMS (method A) m/z 180.3 [M+H]$^+$ (ES+) at 0.98 min. $^1$H NMR (500 MHz, DMSO-d$_6$) 8.99 (d, J=2.3 Hz, 1H), 8.19 (dd, J=8.1, 2.3 Hz, 1H), 7.43 (d, J=8.1 Hz, 1H), 4.33 (q, J=7.1 Hz, 2H), 2.83 (q, J=7.6 Hz, 2H), 1.32 (t, J=7.1 Hz, 3H), 1.24 (t, J=7.6 Hz, 3H).

40A 6-Ethylpyridine-3-carboxylic acid

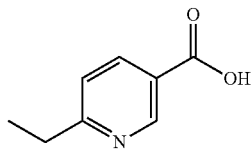

A solution of intermediate 39A (13.45 g, 73.30 mmol) and LiOH (9.22 g, 219.67 mmol) in MeOH:THF:water (1:1:1; 23 mL) was stirred at rt overnight. The reaction mixture was acidified (pH≈4-5) by dropwise addition of 1 M aq. HCl and extracted with CHCl$_3$/iPrOH (3:1; 3×250 mL). The combined organic layers were dried (Na$_2$SO$_4$), and the solvent was removed under reduced pressure. The aqueous phase was acidified (pH≈3-4) by dropwise addition of 1 M aq. HCl and extracted with CHCl$_3$/iPrOH (3:1; 3×250 mL). The combined organic layers were dried (Na$_2$SO$_4$), and the solvent was removed under reduced pressure, and combined with the residue from the previous organic extracts to afford an off-white solid (8.05 g, 71%). LCMS (method A) m/z 152.4 [M+H]$^+$ (ES+) at 0.26 min. $^1$H NMR (500 MHz, DMSO-d$_6$) 13.23 (s, 1H), 8.98 (d, J=2.2 Hz, 1H), 8.17 (dd, J=8.1, 2.2 Hz, 1H), 7.40 (d, J=8.1 Hz, 1H), 2.83 (q, J=7.6 Hz, 2H), 1.25 (t, J=7.6 Hz, 3H).

41A Ethyl 3-(5-fluoropyridin-2-yl)-3-oxopropanoate

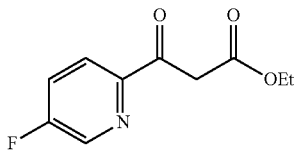 [SMILES: CCOC(=O)CC(=O)c1ccc(F)cn1]

CDI (1.21 g, 7.44 mmol) was added to a solution of 5-fluoropyridine-2-carboxylic acid (1 g, 7.09 mmol) in THF (10 mL) and refluxed for 1 h. The reaction was cooled to rt, potassium 3-ethoxy-3-oxopropanoic acid (1.33 g, 7.80 mmol) then MgCl$_2$ (0.81 g, 8.50 mmol) added, and heated to 60° C. overnight. The volatiles were removed under reduced pressure and the residue partitioned between sat. aq. NH$_4$Cl (50 mL) and EtOAc (50 mL). The separated aqueous was extracted with EtOAc (50 mL), and the combined organics dried (Na$_2$SO$_4$) and concentrated under reduced pressure. Purification by column chromatography (0-50% EtOAc in isohexanes) afforded a colourless oil (450 mg, 29%). LCMS (method A) m/z 166.3 [M-OCH$_2$CH$_3$]$^+$ (ES+) at 0.88 min. $^1$H NMR (500 MHz, DMSO-d$_6$) 8.73 (d, J=2.7 Hz, 1H), 8.11 (dd, J=8.7, 4.7 Hz, 1H), 7.99-7.91 (m, 1H), 4.16-4.00 (m, 4H), 1.14 (t, J=7.1 Hz, 3H).

42A Ethyl 3-(2-methylpyridin-4-yl)-3-oxopropanoate

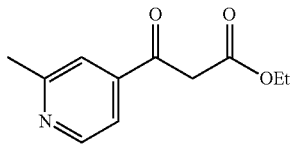

Potassium 3-ethoxy-3-oxopropanoic acid (2.05 g, 12.03 mmol) and NEt$_3$ (4.57 mL, 32.81 mmol) were added to a cooled (0° C.) suspension of MgCl$_2$ (1.25 g, 13.13 mmol) in MeCN (25 mL) and stirred at rt for 3 h (vial A). In a separate vial, CDI (1.86 g, 11.48 mmol) was added to a suspension of 2-methylpyridine-4-carboxylic acid (1.5 g, 10.94 mmol) in THF:MeCN (1:1; 20 mL) and stirred at 40° for 3 h (vial B). After this time, the contents of vial A were added via pipette to vial B, and the combined reaction stirred at rt for 18 h. The reaction mixture was poured into ice-water (~10 mL), acidified with conc. HCl to pH≈6, and extracted with EtOAc (2×15 mL). The organics were washed with brine (50 mL), dried (MgSO$_4$) and concentrated under reduced pressure to give a yellow oil (2.05 g, 90%), which was used without further purification. LCMS (method F) m/z 208.3 [M+H]$^+$ (ES+) at 0.88 min.

The following intermediates were prepared in an analogous manner to intermediate 42A.

TABLE 5

Preparatory Examples prepared by general ketoester procedure

| Preparatory Example | Name | R$^1$ | $^1$H NMR δ (500 MHz) | LCMS (ES+) m/z |
|---|---|---|---|---|
| 42B | Ethyl 3-(3-fluoropyridin-4-yl)-3-oxopropanoate | | Not available | (method A) 212.6 [M + H]$^+$ at 1.01 min. |

TABLE 5-continued

Preparatory Examples prepared by general ketoester procedure

| Preparatory Example | Name | R[1] | $^1$H NMR δ (500 MHz) | LCMS (ES+) m/z |
|---|---|---|---|---|
| 42C | Ethyl 3-(5-fluoropyridin-3-yl)-3-oxopropanoate | 5-fluoropyridin-3-yl | (CDCl$_3$) δ 12.56 (s, 1H), 8.98 (t, J = 1.6 Hz, 1H), 8.81 (t, J = 1.6 Hz, 1H), 8.70 (d, J = 2.8 Hz, 1H), 8.55 (d, J = 2.8 Hz, 1H), 7.99-7.93 (m, 1H), 7.82-7.76 (m, 1H), 5.73 (s, 1H), 4.30 (q, J = 7.1 Hz, 2H), 4.24 (q, J = 7.2 Hz, 2H), 4.02 (s, 2H), 1.36 (t, J = 7.1 Hz, 3H), 1.28 (t, J = 7.2 Hz, 3H). (~1:1 ratio of keto/enol tautomers). | (method F) 212.3 [M + H]$^+$ at 0.49 min. |
| 42D | Ethyl 3-(5-methylpyridin-3-yl)-3-oxopropanoate | 5-methylpyridin-3-yl | (DMSO-d$_6$) 8.93 (d, J = 2.1 Hz, 1H), 8.67 (d, J = 2.1 Hz, 1H), 8.12 (dt, J = 2.3, 1.4 Hz, 1H), 4.28-4.19 (m, 2H), 4.12 (q, J = 7.0 Hz, 2H), 2.37 (d, J = 14.2 Hz, 3H), 1.24-1.14 (m, 3H) | (method A) 208.3 [M + H]$^+$ at 0.81 min. |
| 42E | Ethyl 3-oxo-3-[5-(trifluoromethyl)pyridin-3-yl]propanoate | 5-(trifluoromethyl)pyridin-3-yl | Not available | (method A) 262.23 [M + H]$^+$ at 1.24 min |
| 42F | Ethyl 3-(6-chloropyridin-3-yl)-3-oxopropanoate | 6-chloropyridin-3-yl | Not available | (method F) 228.1 [M + H]$^+$ at 0.56 min. |
| 42G | Ethyl 3-(6-methylpyridin-3-yl)-3-oxopropanoate | 6-methylpyridin-3-yl | Not available | (method F) 208.3 [M + H]$^+$ at 0.41 min. |
| 42H | Ethyl 3-(6-ethylpyridin-3-yl)-3-oxopropanoate | 6-ethylpyridin-3-yl | (CDCl$_3$) 9.11-9.05 (m, 1H), 8.25-8.15 (m, 1H), 7.33 (d, J = 8.1 Hz, 1H), 4.25 (q, J = 7.1 Hz, 2H), 4.00 (s, 2H), 2.94 (q, J = 7.6 Hz, 2H), 1.42-1.33 (m, 3H), 1.29 (t, J = 7.1 Hz, 3H). | (method A) 222.5 [M + H]$^+$ at 0.93 min. |

43A Ethyl 2-chloro-3-oxo-3-phenylpropanoate

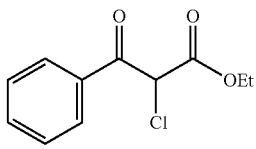 [SMILES: CCOC(=O)C(Cl)C(=O)c1ccccc1]

Sulfuryl dichloride (1.47 mL, 18.19 mmol) was added dropwise to a cooled (0° C.) solution of ethyl 3-oxo-3-phenylpropanoate (3 mL, 17.32 mmol) in CH$_2$Cl$_2$ (65 mL) and stirred at rt for 3 h. The reaction was partitioned between CH$_2$Cl$_2$ (30 mL) and sat. aq. NaHCO$_3$ (50 mL). The separated aqueous layer was extracted with CH$_2$Cl$_2$ (2×20 mL), and the combined organic layers were washed with brine (50 mL), passed through a phase separation cartridge, and concentrated under reduced pressure to afford a yellow oil (3.93 g, 80%). $^1$H NMR (500 MHz, CDCl$_3$) 8.04-8.00 (m, 2H), 7.68-7.63 (m, 1H), 7.55-7.51 (m, 2H), 5.63 (s, 1H), 4.34-4.29 (m, 2H), 1.27 (t, J=7.1 Hz, 3H).

43B Ethyl 2-chloro-3-(2,4-difluorophenyl)-3-oxopropanoate

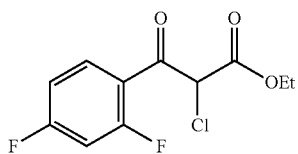

Prepared by an analogous procedure to that described for intermediate 43A. $^1$H NMR (500 MHz, CDCl$_3$) 8.07-8.00 (m, 1H), 7.08-7.03 (m, 1H), 6.96-6.91 (m, 1H), 5.60 (s, 1H), 4.32 (q, J=7.2, 0.7 Hz, 2H), 1.30 (t, J=7.1 Hz, 3H).

44A Ethyl 2-bromo-3-oxo-3-pyridin-3-ylpropanoate

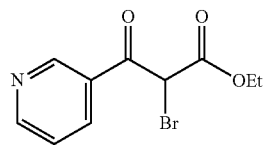 [SMILES: CCOC(=O)C(Br)C(=O)c1cccnc1]

Bromine (111 μL, 2.17 mmol) was added dropwise to a solution of ethyl 3-oxo-3-(3-pyridyl)propionate (400 mg, 2.07 mmol) in CHCl$_3$ (10 mL) and stirred at rt for 1 h. The reaction was diluted with CH$_2$Cl$_2$ (20 mL) washed with aq. Na$_2$S2O$_3$ (10% w/v; 50 mL), sat. aq NaHCO$_3$ (50 mL) and brine (50 mL), passed through a phase separation cartridge and concentrated under reduced pressure to afford an orange oil (501 mg, 62%) which was used without further purification. LCMS (method A) m/z 272.2/274.2 [M+H]$^+$ (ES+) at 1.02 min. $^1$H NMR (500 MHz, CDCl$_3$) 9.23-9.19 (m, 1H), 8.86-8.80 (m, 1H), 8.32-8.28 (m, 1H), 7.47 (ddt, J=7.3, 4.7, 1.6 Hz, 2H), 5.59 (s, 1H), 4.31 (q, J=7.2 Hz, 2H), 1.28 (t, J=7.2 Hz, 3H).

The following intermediates were prepared in an analogous manner to intermediate 44A.

TABLE 6

Preparatory Examples prepared by general bromination procedure

| Preparatory Example | Name | R$^1$ | $^1$H NMR δ (500 MHz) | LCMS (ES+) m/z |
|---|---|---|---|---|
| 44B | Ethyl 2-bromo-3-(5-fluoropyridin-2-yl)-3-oxopropanoate | 5-fluoropyridin-2-yl | (DMSO-d$_6$) 8.75 (d, J = 2.8 Hz, 1H), 8.19 (dd, J = 8.8, 4.6 Hz, 1H), 7.99 (td, J = 8.6, 2.8 Hz, 1H), 6.38 (s, 1H), 4.18-4.12 (m, 2H), 1.11 (t, J = 7.1 Hz, 3H). | (method A) 244.5/246.5 [M + H]$^+$ at 1.32 min |
| 44C | Ethyl 2-bromo-3-(3-fluoropyridin-4-yl)-3-oxopropanoate | 3-fluoropyridin-4-yl | (CDCl$_3$) 8.70 (d, J = 2.3 Hz, 1H), 8.65 (dd, J = 5.0, 1.3 Hz, 1H), 7.78 (dd, J = 6.0, 4.9 Hz, 1H), 5.64 (s, 1H), 4.33 (q, J = 7.2 Hz, 2H), 1.31 (t, J = 7.1 Hz, 3H). | (method F) 290.2/292.2 [M + H]$^+$ at 0.56 min |

TABLE 6-continued

Preparatory Examples prepared by general bromination procedure

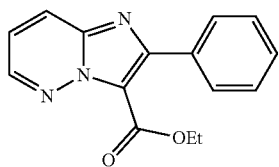 [SMILES: CCOC(=O)c1c(-c2ccccc2)nc2cccnn12]

| Preparatory Example | Name | R[1] | ¹H NMR δ (500 MHz) | LCMS (ES+) m/z |
|---|---|---|---|---|
| 44D | Ethyl 2-bromo-3-(2-methylpyridin-4-yl)-3-oxopropanoate | | (CDCl$_3$) 8.74 (dd, J = 5.2, 0.9 Hz, 1H), 7.65-7.62 (m, 1H), 7.61-7.54 (m, 1H), 5.58 (s, 1H), 4.36-4.27 (m, 2H), 2.68 (s, 3H), 1.31-1.26 (m, 3H | (method F) 286.2/288.2 [M + H]⁺ at 0.52 min |

45A Ethyl 2-phenylimidazo[1,2-b]pyridazine-3-carboxylate

A suspension of crude intermediate 43A (0.6 g, 1.85 mmol) and pyridazin-3-amine (0.18 g, 1.85 mmol) in EtOH (4 mL) was heated at 150° C. for 12 h by MWI. The reaction mixture was cooled to M1 evaporated under reduced pressure and the residue purified by column chromatography (0-100% EtOAc in isohexanes) to afford a brown solid (147 mg, 29%/). LCMS (method E) m/z 268.3 [M+H]+(ES+) at 0.55 min. ¹H NMR (500 MHz, CDCl$_3$) 8.60 (dd, J=4.5, 1.7 Hz, 1H), 8.07 (dd, J=9.1, 1.7 Hz, 1H), 7.86-7.79 (m, 2H), 7.52-7.42 (m, 3H), 7.26 (dd, J=9.1, 4.5 Hz, 1H), 4.42 (q, J=7.1 Hz, 2H), 1.29 (t, J=7.2 Hz, 3H).

The following intermediates were prepared in an analogous manner to intermediate 45A. Preparatory examples 45G to 45K were prepared from the corresponding crude 2-bromoketoester with 1.3 eq. of the corresponding pyridazin-3-amine.

| Preparatory Example | Name | Structure | ¹H NMR δ (500 MHz) | LCMS (ES+) m/z |
|---|---|---|---|---|
| 45B | Ethyl 6-methyl-2-phenylimidazo[1,2-b]pyridazine-3-carboxylate | 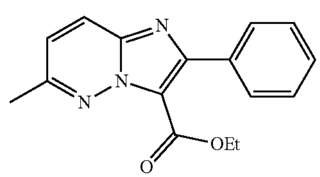 [SMILES: CCOC(=O)c1c(-c2ccccc2)nc2ccc(C)nn12] | Not available | (method E) 282.3 [M + H]⁺ at 0.58 min |
| 45C | Ethyl 6-chloro-2-phenylimidazo[1,2-b]pyridazine-3-carboxylate | 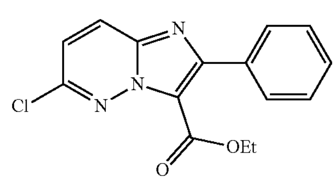 [SMILES: CCOC(=O)c1c(-c2ccccc2)nc2ccc(Cl)nn12] | Not available | (method F) 302.2 [M + H]⁺ at 0.65 min |
| 45D | Ethyl 6-chloro-2-(2-fluorophenyl)imidazo[1,2-b]pyridazine-3-carboxylate | 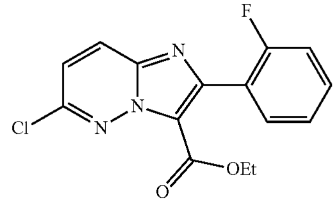 [SMILES: CCOC(=O)c1c(-c2ccccc2F)nc2ccc(Cl)nn12] | Not available | (method B) 319.7 [M + H]⁺ at 1.33 min |

-continued

| Preparatory Example | Name | Structure | ¹H NMR δ (500 MHz) | LCMS (ES+) m/z |
|---|---|---|---|---|
| 45E | Ethyl 2-(2,4-difluorophenyl)imidazo[1,2-b]pyridazine-3-carboxylate | 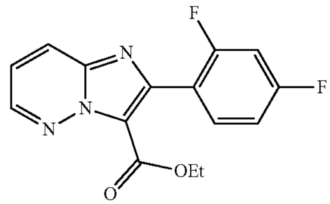 [SMILES: CCOC(=O)c1c(-c2ccc(F)cc2F)nc2cccnn12] | (CDCl₃) 8.64 (dd, J = 4.5, 1.7 Hz, 1H), 8.09 (dd, J = 9.2, 1.7 Hz, 1H), 7.70 (td, J = 8.4, 6.4 Hz, 1H), 7.33-7.27 (m, 1H), 7.08-7.00 (m, 1H), 6.97-6.90 (m, 1H), 4.37 (q, J = 7.1 Hz, 2H), 1.23 (t, J = 7.1 Hz, 3H). | (method B) 304.2 [M + H]⁺ at 1.19 min |
| 45F | Ethyl 2-(2,4-difluorophenyl)-6-methylimidazo[1,2-b]pyridazine-3-carboxylate | 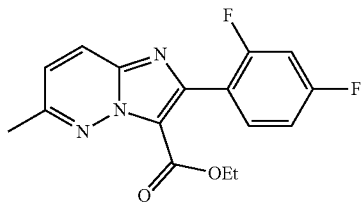 [SMILES: CCOC(=O)c1c(-c2ccc(F)cc2F)nc2ccc(C)nn12] | (CDCl₃) 7.95 (d, J = 9.3 Hz, 1H), 7.68 (td, J = 8.4, 6.4 Hz, 1H), 7.16 (d, J = 9.3 Hz, 1H), 7.07-6.99 (m, 1H), 6.93 (ddd, J = 10.0, 8.9, 2.5 Hz, 1H), 4.36 (q, J = 7.1 Hz, 2H), 2.73 (s, 3H), 1.23 (t, J = 7.1 Hz, 3H). | (method B) 318.3 [M + H]⁺ at 1.28 min |
| 45G | Ethyl 6-methyl-2-pyridin-3-ylimidazo[1,2-b]pyridazine-3-carboxylate | 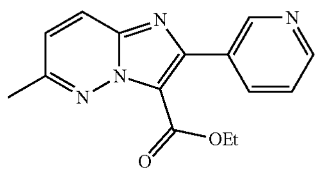 | (CDCl₃) 9.05-9.00 (d, 1H), 8.68 (dd, J = 4.9, 1.7 Hz, 1H), 8.15 (dt, J = 7.9, 2.0 Hz, 1H), 7.96 (d, J = 9.3 Hz, 1H), 7.42 (ddd, J = 7.9, 4.9, 0.9 Hz, 1H), 7.19-7.15 (m, 1H), 4.41 (q, J = 7.1 Hz, 2H), 2.78-2.70 (s, 3H), 1.35-1.26 (t, 7.1 Hz, 3H). | (method A) 283.3 [M + H]⁺ at 0.67 min |
| 45H | Ethyl 2-(5-fluoropyridin-2-yl)-6-methylimidazo[1,2-b]pyridazine-3-carboxylate | 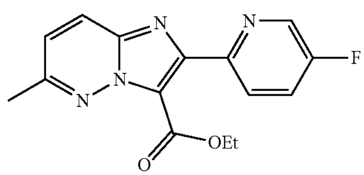 [SMILES: CCOC(=O)c1c(-c2ccc(F)cn2)nc2ccc(C)nn12] | (DMSO-d₆) 8.62 (d, J = 2.9 Hz, 1H), 8.17 (d, J = 9.4 Hz, 1H), 8.08 (dd, J = 8.7, 4.6 Hz, 1H), 7.87 (td, J = 8.8, 3.0 Hz, 1H), 7.35 (d, J = 9.4 Hz, 1H), 4.36 (q, J = 7.1 Hz, 2H), 2.57 (s, 3H), 1.25 (t, J = 7.1 Hz, 3H) | (method A) 301.3 [M + H]⁺ at 1.07 min |
| 45I | Ethyl 6-methyl-2-(2-methylpyridin-4-yl)imidazo[1,2-b]pyridazine-3-carboxylate | 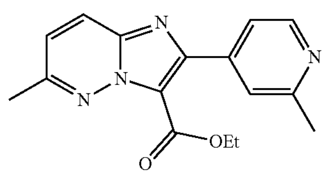 | Not available | (method F) 297.4 [M + H]⁺ at 0.37 min |
| 45J | Ethyl 2-(3-fluoropyridin-4-yl)-6-methylimidazo[1,2-b]pyridazine-3-carboxylate | 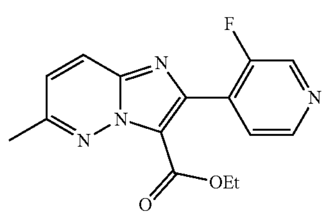 [SMILES: CCOC(=O)c1c(-c2ccncc2F)nc2ccc(C)nn12] | Not available | (method F) 301.3 [M + H]⁺ at 0.50 min |
| 45K | Ethyl 6-chloro-2-(3-fluoropyridin-4-yl)imidazo[1,2-b]pyridazine-3-carboxylate | 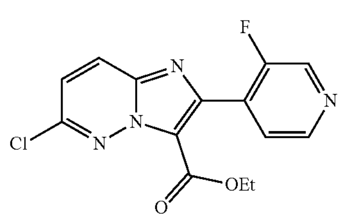 [SMILES: CCOC(=O)c1c(-c2ccncc2F)nc2ccc(Cl)nn12] | (CDCl₃) 8.64-8.58 (m, 2H), 8.06 (d, J = 9.5 Hz, 1H), 7.73 (t, J = 5.5 Hz, 1H), 7.35 (d, J = 9.5 Hz, 1H), 4.41 (q, J = 7.1 Hz, 2H), 1.27 (t, J = 7.1 Hz, 3H) | (method C) 321.2 [M + H]⁺ at 1.09 min |

46A Ethyl 6-methyl-2-[S-(trifluoromethyl)pyridin-3-yl]imidazo[1,2-b]pyridazine-3-carbaxylate

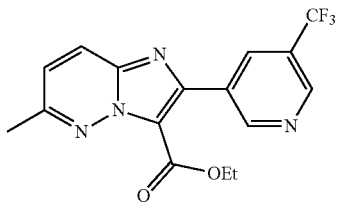 [SMILES: CCOC(=O)c1c(-c2cncc(C(F)(F)F)c2)nc2ccc(C)nn12]

A solution of bromine (186 µL, 3.63 mmol) in CH$_2$Cl$_2$ (5 mL) was added dropwise to a cooled (0° C.) solution of intermediate 42E (2.7 mL, 3.46 mmol) in CH$_2$Cl$_2$ (20 mL) and stirred at rt overnight. The reaction was diluted with CH$_2$Cl$_2$ (50 mL), washed with sat. aq NaHCO$_3$ (100 mL), dried (Na$_2$SO$_4$) and concentrated under reduced pressure to afford an orange oil (918 mg) which was used directly in the next reaction. The residue was dissolved in EtOH (3 mL), 6-methylpyridazin-3-amine (383 mg, 3.51 mmol) added, and the mixture heated at 150° C. for 3 h by MWI. The reaction mixture was cooled to rt, evaporated under reduced pressure and the residue purified by column chromatography (0-100% EtOAc in isohexanes) to afford an off-white solid (185 mg, 20%). LCMS (method A) m/z 351.3 [M+H]$^+$ (ES+) at 1.28 min. $^1$H NMR (500 MHz, DMSO-d$_6$) 9.25 (d, J=2.0 Hz, 1H), 9.08-9.03 (m, 1H), 8.60-8.55 (m, 1H), 8.25 (d, J=9.3 Hz, 1H), 7.47 (d, J=9.4 Hz, 1H), 4.30 (q, J=7.1 Hz, 2H), 2.62 (s, 3H), 1.19 (t, J=7.1 Hz, 3H).

The following intermediates were prepared by in an analogous manner to intermediate 46A with heating by MWI at 140° C.

| Preparatory Example | Name | Structure | $^1$H NMR δ (500 MHz, CDCl$_3$) | LCMS (ES+) m/z |
|---|---|---|---|---|
| 46B | Ethyl 6-methyl-2-(5-methylpyridin-3-yl)imidazo[1,2-b]pyridazine-3-carboxylate | 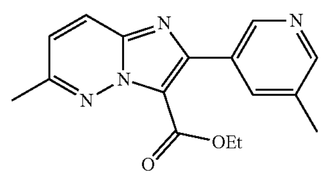 | Not available | (method F) 297.3 [M + H]$^+$ at 0.41 min |
| 46C | Ethyl 6-chloro-2-(5-methylpyridin-3-yl)imidazo[1,2-b]pyridazine-3-carboxylate | 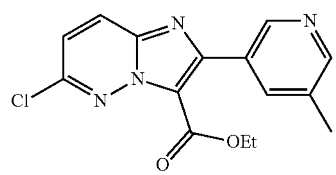 [SMILES: CCOC(=O)c1c(-c2cncc(C)c2)nc2ccc(Cl)nn12] | Not available | (method F) 317.2/319.2 [M + H]$^+$ at 0.45 min |
| 46D | Ethyl 2-(5-fluoropyridin-3-yl)-6-methylimidazo[1,2-b]pyridazine-3-carboxylate | 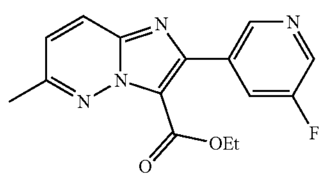 [SMILES: CCOC(=O)c1c(-c2cncc(F)c2)nc2ccc(C)nn12] | 8.97 (s, 1H) 8.57 (d, J = 2.7 Hz, 1H), 8.11 (d, J = 9.1 Hz, 1H), 7.98 (d, J = 9.3 Hz, 1H), 7.21 (d, J = 9.3 Hz, 1H), 4.46 (q, J = 7.1 Hz, 2H), 2.74 (s, 3H), 1.36 (t, J = 7.1 Hz, 3H). | (method F) 301.3 [M + H]$^+$ at 0.54 min |
| 46E | Ethyl 6-chloro-2-(6-methylpyridin-3-yl)imidazo[1,2-b]pyridazine-3-carboxylate | 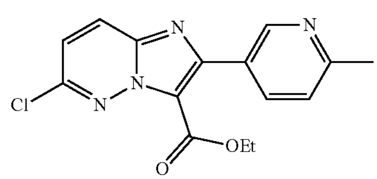 [SMILES: CCOC(=O)c1c(-c2ccc(C)nc2)nc2ccc(Cl)nn12] | 9.08 (s, 1H), 8.38 (d, J = 8.1 Hz, 1H), 8.03 (d, J = 9.4 Hz, 1H), 7.44 (d, J = 8.1 Hz, 1H), 7.33 (d, J = 9.4 Hz, 1H), 4.48 (q, J = 7.1 Hz, 2H), 2.81 (s, 3H), 1.39 (t, J = 7.1 Hz, 3H). | (method F) 317.2/319.2 [M + H]$^+$ at 0.41 min |
| 46F | Ethyl 6-chloro-2-(6-ethylpyridin-3-yl)imidazo[1,2-b]pyridazine-3-carboxylate | 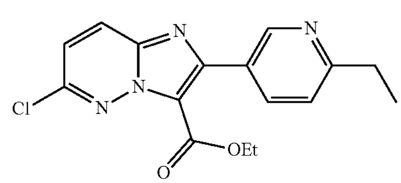 [SMILES: CCOC(=O)c1c(-c2ccc(CC)nc2)nc2ccc(Cl)nn12] | 9.03 (s, 1H), 8.24-8.20 (m, 1H), 8.02 (d, J = 9.4 Hz, 1H), 7.40-7.34 (m, 1H), 7.31 (d, J = 9.4 Hz, 1H), 4.46 (q, J = 7.1 Hz, 2H), 3.03-2.99 (m, 2H), 1.41 (t, J = 7.6 Hz, 3H), 1.37 (t, J = 7.1 Hz, 3H). | (method A) 331.3/333.3 [M + H]$^+$ at 0.87 min |

47A Ethyl 6-methyl-2-(6-morpholin-4 ylpyridin-3 yl)imidazo[1,2-b]pyridazine-3-carbaxylate

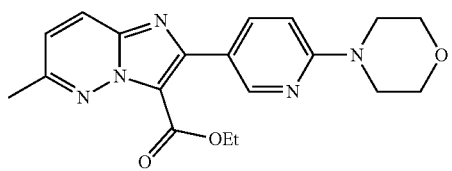 [SMILES: CCOC(=O)c1c(-c2ccc(N3CCOCC3)nc2)nc2ccc(C)nn12]

A solution of bromine (720 μL, 14.02 mmol) in CH$_2$Cl$_2$ (10 mL) was added dropwise to a cooled (0° C.) solution of intermediate 42F (3.04 g, 13.35 mmol) in CH$_2$Cl$_2$ (40 mL) and stirred at rt for 2 h. The reaction was diluted with CH$_2$Cl$_2$ (50 mL), washed with sat. aq. NaHCO$_3$ (100 mL) and brine (100 mL), passed through a phase separation cartridge, and concentrated under reduced pressure to afford a yellow oil (4.15 g) which was used directly in the next reaction. The crude residue was dissolved in EtOH (15 mL), 6-methylpyridazin-3-amine (1.11 g, 10.15 mmol) added and the mixture heated by MWI at 140° C. for 2.5 h. The reaction was cooled to rt, evaporated under reduced pressure and the residue purified by column chromatography (0-10% MeOH in CH$_2$Cl$_2$) to afford a yellow solid (2.24 g) which was used directly in the next reaction. The crude residue (200 mg) was dissolved in DMSO (6 mL) and treated with morpholine (0.07 mL, 0.85 mmol), followed by DIPEA (0.3 mL, 1.70 mmol) and stirred for 18 h at rt. Additional morpholine (0.07 mL, 0.85 mmol) and DIPEA (0.3 mL, 1.70 mmol) were added and the mixture was stirred at rt for a further 4 days. The reaction diluted with water (20 mL) and extracted with EtOAc (3×20 mL). The combined organic extracts were washed with brine (3×20 mL), dried (MgSO$_4$), and the solvent removed under reduced pressure to afford a light yellow solid (230 mg). LCMS (method F) m/z 368.3 [M+H]$^+$ (ES+) at 0.42 min. $^1$H NMR (500 MHz, CDCl$_3$) δ 8.69 (d, J=2.4 Hz, 1H), 8.02 (dd, J=8.8, 2.4 Hz, 1H), 7.91 (d, J=9.2 Hz, 1H), 7.12 (d, J=9.2 Hz, 1H), 6.72 (d, J=8.8 Hz, 1H), 4.44 (q, J=7.2 Hz, 2H), 3.87 (t, J=4.9 Hz, 4H), 3.65-3.60 (m, 4H), 2.70 (s, 3H), 1.37 (t, J=7.1 Hz, 3H).

48A Ethyl 6-(azetidin-1-yl)-2-(2-fluorophenyl)imidazo[1,2-b]pyridazine-3-carbaxylate

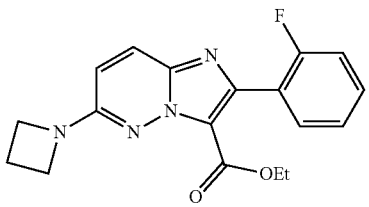 [SMILES: CCOC(=O)c1c(-c2ccccc2F)nc2ccc(N3CCC3)nn12]

A solution of intermediate 45D (72 mg, 0.230 mmol), azetidine (50 μL, 0.680 mmol), DIPEA (240 μL, 1.350 mmol) in DMSO (3 mL) was heated at 100° C. for 18 h. The reaction mixture was cooled to rt, diluted with water (20 mL), and extracted with EtOAc (3×20 mL). The combined organics were washed with brine (50 mL), passed through a phase separation cartridge and concentrated under reduced pressure to give an orange solid (68 mg, 85%) which was used without further purification. LCMS (method E) m/z 341.4 [M+H]$^+$ (ES+) at 0.62 min. $^1$H NMR (500 MHz, CDCl$_3$) 7.77 (d, J=9.6 Hz, 1H), 7.66 (td, J=7.4, 1.8 Hz, 1H), 7.44-7.36 (m, 1H), 7.25 (td, J=7.5, 1.2 Hz, 1H), 7.16-7.10 (m, 1H), 6.57 (d, J=9.6 Hz, 1H), 4.32 (q, J=7.2 Hz, 2H), 4.21 (t, J=7.5 Hz, 4H), 2.55-2.45 (m, 2H), 1.21 (t, J=7.1 Hz, 3H).

The following intermediates were prepared in an analogous manner to intermediate 48A.

| Preparatory Example | Name | Structure | $^1$H NMR δ (500 MHz, DMSO-d$^6$) | LCMS (ES+) m/z |
|---|---|---|---|---|
| 48B | Ethyl 2-(2-fluorophenyl)-6-morpholin-4-ylimidazo[1,2-b]pyridazine-3-carboxylate | 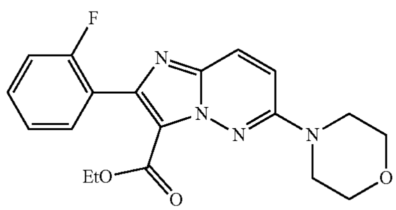 [SMILES: CCOC(=O)c1c(-c2ccccc2F)nc2ccc(N3CCOCC3)nn12] | Not available | (method C) 371.4 [M + H]$^+$ at 1.27 min. |
| 48C | Ethyl 6-morpholin-4-yl-2-phenylimidazo[1,2-b]pyridazine-3-carboxylate | 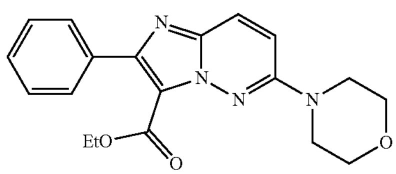 [SMILES: CCOC(=O)c1c(-c2ccccc2)nc2ccc(N3CCOCC3)nn12] | 8.02 (d, J = 9.9 Hz, 1H), 7.79-7.74 (m, 2H), 7.47-7.36 (m, 4H), 4.29 (q, J = 7.0 Hz, 2H), 3.78-3.72 (m, 4H), 3.56-3.50 (m, 4H), 1.23 (t, J = 7.1 Hz, 3H). | (method A) 353.4 [M + H]$^+$ at 1.28 min |
| 48D | Ethyl 6-[(1R,4R)-5-methyl-2,5-diazabicyclo[2.2.1]heptan-2-yl]-2-phenylimidazo[1,2-b]pyridazine-3-carboxylate | 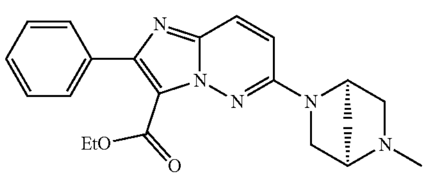 [SMILES: CCOC(=O)c1c(-c2ccccc2)nc2ccc(N3C[C@H]4C[C@@H]3CN4C)nn12] | 7.94 (d, J = 9.8 Hz, 1H), 7.79-7.73 (m, 2H), 7.46-7.40 (m, 2H), 7.40-7.35 (m, 1H), 7.10 (d, J = 9.8 Hz, 1H), 4.65 (s, 1H), 4.30 (q, J = 7.0 Hz, 2H), 3.59 (d, J = 10.0 Hz, 1H), 3.53 (s, 1H), 3.37 (d, J = 9.9 Hz, 1H), 3.17 (d, J = 5.2 Hz, 1H), 2.86 (d, J = 9.7 Hz, 1H), 2.32 (s, 2H), 1.96-1.91 (m, 1H), 1.81 (d, J = 9.6 Hz, 1H), 1.25 (t, J = 7.1 Hz, 3H). | (method A) 378.0 [M + H]$^+$ at 0.75 min |

48E Ethyl 2-(2 fluorophenyl)-6-(4-methylpiperazin-1 yl)imidazo[1,2-b]pyridazine-3-carbaxylate

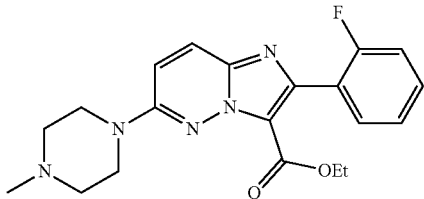 [SMILES: CCOC(=O)c1c(-c2ccccc2F)nc2ccc(N3CCN(C)CC3)nn12]

Prepared by an analogous procedure to that described for intermediate 48A with intermediate 45D (162 mg, 0.42 mmol), 1-methylpiperazine (240 μL, 2.15 mmol) and DIPEA (240 μL, 1.35 mmol) in DMSO (5 mL). LCMS (method B) m/z 384.4 [M+H]+(ES+) at 1.21 min. $^1$H NMR (500 MHz, CDCl$_3$) 7.81 (d, J=9.9 Hz, 1H), 7.65 (td, J=7.4, 1.8 Hz, 1H), 7.43-7.38 (m, 1H), 7.25 (td, J=7.5, 1.1 Hz, 1H), 7.13 (ddd, J=9.7, 8.3, 1.2 Hz, 1H), 7.01 (d, J=9.9 Hz, 1H), 4.31 (q, J=7.2 Hz, 2H), 3.67 (t, J=5.1 Hz, 4H), 2.61-2.55 (m, 4H), 2.39 (s, 3H), 1.20 (t, J=7.1 Hz, 3H).

49A Ethyl 6-(ethylamino)-2-(2-fluorophenyl)imidazo[1,2-b]pyridazine-3-carbaxylate

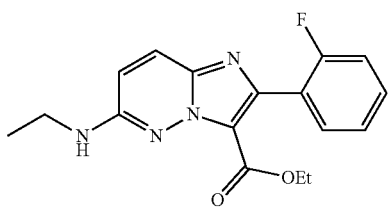 [SMILES: CCNc1ccc2nc(-c3ccccc3F)c(C(=O)OCC)n2n1]

A solution of intermediate 45D (80 mg, 0.21 mmol), ethylamine (70% w/w in water; 68 μL, 0.85 mmol), DIPEA (296 μL, 1.70 mmol) in DMSO (6 mL) was heated at 100° C. for 18 h. Additional ethylamine (70% w/w in water; 1 mL, 17.97 mmol) was added and the reaction mixture was heated at 100° C. for a further 2 h. The reaction mixture was cooled to rt, diluted with water (10 mL), and extracted with EtOAc (2×10 mL). The combined organics were washed with brine (20 mL), dried (MgSO$_4$), and the solvent removed under reduced pressure to afford an orange solid (74 mg, 85%) which was used without further purification. LCMS (method B) m/z 329.4 [M+H]$^+$ (ES+) at 1.30 min.

50A Ethyl 6-[(1R,4R)-2-oxa-5-azabicyclo[2.2.1]heptan-5-yl]-2-phenylimidazo[1,2-b]pyridazine-3-carbaxylate

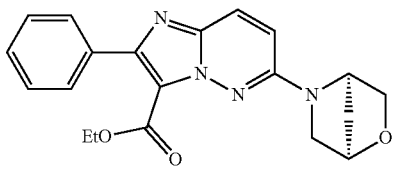 [SMILES: CCOC(=O)c1c(-c2ccccc2)nc2ccc(N3C[C@H]4C[C@@H]3CO4)nn12]

A solution of intermediate 45C (150 mg, 0.5 mmol), (1R,4R)-2-oxa-5-azoniabicyclo[2.2.1]heptane chloride (81 mg, 0.6 mmol), DIPEA (296 μL, 1.7 mmol) in DMSO (2 mL), was heated at 100° C. overnight. The reaction mixture was cooled to rt, treated with further (1R,4R)-2-oxa-5-azoniabicyclo[2.2.1]heptane chloride (40 mg, 0.3 mmol) and DIPEA (113 μL, 0.646 mmol) and heated to 100° C. overnight. The reaction mixture was cooled to rt, diluted with water (20 mL) and extracted with EtOAc (2×20 mL). The combined organic extracts were washed with brine (3×40 mL), passed through a phase separation cartridge, and concentrated under reduced pressure. Purification by column chromatography (0-100% EtOAc in isohexanes) afforded an off-white solid (86 mg, 46%). LCMS (method A) m/z 365.3 [M+H]$^+$ (ES+) at 1.22 min. $^1$H NMR (500 MHz, DMSO-d$_6$) δ 7.98 (d, J=9.8 Hz, 1H), 7.76 (d, J=7.3 Hz, 2H), 7.47-7.40 (m, 2H), 7.40-7.35 (m, 1H), 7.14 (d, J=9.8 Hz, 1H), 4.89 (s, 1H), 4.71 (s, 1H), 4.30 (q, J=7.1 Hz, 2H), 3.81 (d, J=7.5 Hz, 1H), 3.75 (d, J=7.5 Hz, 1H), 3.54 (d, J=10.2 Hz, 1H), 3.40 (d, J=10.2 Hz, 1H), 1.98 (d, J=9.9 Hz, 1H), 1.92 (d, J=9.9 Hz, 1H), 1.25 (t, J=7.1 Hz, 3H).

51A Ethyl 6-[(1S,4S)-5-methyl-2,S-diazabicyclo[2.2.1]heptan-2-yl]-2-phenylimidazo[1,2-b]pyridazine-3-carboxylate

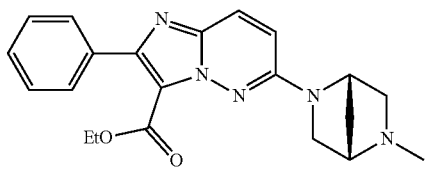 [SMILES: CCOC(=O)c1c(-c2ccccc2)nc2ccc(N3C[C@@H]4C[C@H]3CN4C)nn12]

A solution of intermediate 45C (175 mg, 0.58 mmol), (2S,5S)-1,2,5-trimethylpiperazine-1,4-diium dibromide (204 mg, 0.70 mmol), DIPEA (0.61 mL, 3.48 mmol) in DMSO (2 mL), was heated at 70° C. overnight. The reaction mixture was cooled to rt, treated with further (1R,4R)-2-oxa-5-azoniabicyclo[2.2.1]heptane chloride (200 mg, 0.690 mmol) and DIPEA (0.61 mL, 3.480 mmol) and heated to 70° C. over the weekend. The reaction mixture was cooled to rt, diluted with brine (10 mL) and extracted with EtOAc (4×10 mL). The combined organic extracts were washed with brine (10 mL), passed through a phase separation cartridge, and concentrated under reduced pressure to afford an off-white solid (143 mg, 65%). LCMS (method A) m/z 378.4 [M+H]$^+$ (ES+) at 0.74 min. $^1$H NMR (500 MHz, DMSO-d$_6$) 7.95 (d, J=9.8 Hz, 1H), 7.79-7.73 (m, 2H), 7.46-7.41 (m, 2H), 7.41-7.35 (m, 1H), 7.10 (d, J=9.8 Hz, 1H), 4.65 (s, 1H), 4.30 (q, J=7.1 Hz, 2H), 4.09 (q, J=5.2 Hz, 1H), 3.62-3.57 (m, 1H), 3.38 (d, J=10.1 Hz, 1H), 3.17 (d, J=5.2 Hz, 2H), 2.87 (d, J=9.6 Hz, 1H), 2.33 (s, 2H), 1.95-1.92 (m, 1H), 1.85-1.79 (m, 1H), 1.25 (t, J=7.1 Hz, 3H).

52A 2-(2-Fluorophenyl)-7-methylpyrazolo[1,5-a]pyrimidine-3-carboxylic acid

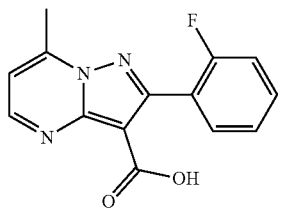 [SMILES: Cc1ccnc2c(C(=O)O)c(-c3ccccc3F)nn12]

A solution of intermediate 26B (190 mg, 0.635 mmol) and 5 M aq. NaOH (0.635 mL, 3.174 mmol) in EtOH/water (3:1, 4 mL) was heated at 75° C. for 1 h. The reaction was cooled to rt and the EtOH removed under reduced pressure. The residual aqueous solution was diluted with water (5 mL) and acidified (pH≈1) with 1 M HCl (aq). The resulting precipitate was collected by filtration and purified by column chromatography (0-10/6 EtOH in EtOAc) to give a pale yellow solid (128 mg, 74%). LRMS (APCI+) m/z 272.3 [M+H]$^+$

53A 2-(2,3-Difluorophenyl)pyrazolo[1,5-a]pyrimidine-3-carboxylic acid

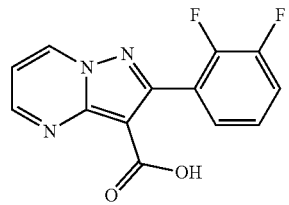 [SMILES: O=C(O)c1c(-c2cccc(F)c2F)nn2cccnc12]

A solution of intermediate 60 (129 mg, 0.425 mmol) and LiOH (1.5 M aq; 2.83 mL, 4.25 mmol) in THF/MeOH (1:1; 4 mL) was stirred at 40° C. overnight. The reaction was cooled to rt and washed with MTBE (3×10 mL). The aqueous layer was acidified (pH 1) with 1 M HCl (aq), then extracted with CHCl$_3$/iPrOH (3:1; 3×10 mL). The combined organic extracts were dried (Na$_2$SO$_4$) and concentrated under reduced pressure to afford an orange solid (135 mg, 97%) which was used without further purification. LCMS (Method A) m/z 258.7 [M-OCH$_2$CH$_3$]$^+$ at 0.89 min. $^1$H NMR (500 MHz, DMSO-d$_6$) 12.39 (s, 1H), 9.31 (dd, J=7.0, 1.8 Hz, 1H), 8.85 (dd, J=4.2, 1.8 Hz, 1H), 7.63-7.53 (m, 1H), 7.43-7.36 (m, 1H), 7.37-7.29 (m, 2H).

The following intermediate compounds were prepared by an analogous procedure to that described for 53A.

| Preparatory Example | Name | Structure | $^1$H NMR δ (500 MHz, DMSO-d$_6$) | LCMS (ES+) m/z |
|---|---|---|---|---|
| 53B | 2-(2,6-Difluorophenyl)pyrazolo[1,5-a]pyrimidine-3-carboxylic acid | 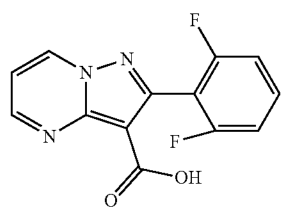 [SMILES: O=C(O)c1c(-c2c(F)cccc2F)nn2cccnc12] | 12.38 (s, 1H), 9.31 (dd, J = 6.9, 1.8 Hz, 1H), 8.87 (dd, J = 4.2, 1.8 Hz, 1H), 7.64-7.54 (m, 1H), 7.35 (dd, J = 7.0, 4.2 Hz, 1H), 7.29-7.19 (m, 2H). | (method A) 258.6 [M − OCH$_2$CH$_3$]$^+$ at 0.84 min |
| 53C | 2-(2-Fluoro-4-pyrrolidin-1-ylphenyl)pyrazolo[1,5-a]pyrimidine-3-carboxylic acid | 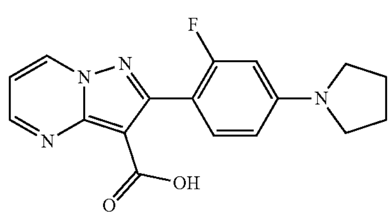 [SMILES: O=C(O)c1c(-c2ccc(N3CCCC3)cc2F)nn2cccnc12] | 12.14 (s, 1H), 9.22 (dd, J = 6.9, 1.8 Hz, 1H), 8.75 (dd, J = 4.2, 1.8 Hz, 1H), 7.40-7.33 (m, 1H), 7.23 (dd, J = 6.9, 4.1 Hz, 1H), 6.44 (dd, J = 8.6, 2.4 Hz, 1H), 6.38 (dd, J = 13.6, 2.3 Hz, 1H), 3.32-3.26 (m, 4H), 2.01-1.95 (m, 4H). | (method A) 327.5 [M + H]$^+$ at 1.15 min |

54A 2-(2-Fluoro-5-methylpyridin-3-yl)pyrazolo[1,5-a]pyrimidine-3-carboxylic acid

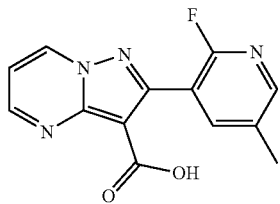

A solution of intermediate 27F (334 mg, 0.855 mmol) and LiOH (1.5 M aq; 2 mL, 3 mmol) in THF (9 mL) was heated at 40° C. overnight. Further LiOH (1.5 M aq; 2 mL, 3 mmol) and MeOH (2 mL) were added and the reaction heated at 60° C. for 2 h. The reaction mixture was cooled to rt, was diluted with water (20 mL) and washed with MTBE (2×25 mL). The aqueous layer was acidified (pH≈4) by dropwise addition of 1 M aq. HCl and extracted with CHCl$_3$/iPrOH (3:1; 3×25 mL). The combined organic extracts were dried (Na$_2$SO$_4$), and the solvent removed under reduced pressure to afford an orange solid (200 mg, 70%). LCMS (method A) m/z 273.6 [M+H]$^+$ at 0.74 min. $^1$H NMR (500 MHz, CDCl$_3$) 12.27 (s, 1H), 9.30 (dd, J=7.0, 1.7 Hz, 1H), 8.85 (dd, J=4.1, 1.8 Hz, 1H), 8.18-8.14 (m, 1H), 7.98-7.92 (m, 1H), 7.33 (dd, J=7.0, 4.2 Hz, 1H), 2.37 (s, 3H).

55A 2-(2-Fluoro-5-methylphenyl)pyrazolo[1,5-a]pyrimidine-3-carboxylic acid

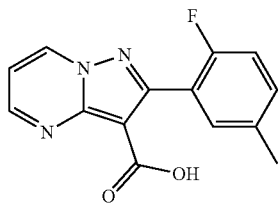 [SMILES: Cc1ccc(F)c(-c2nn3cccnc3c2C(=O)O)c1]

A mixture of intermediate 2A (250 mg, 0.907 mmol), (2-fluoro-5-methylphenyl)boronic acid (172 mg, 1.117 mmol) and K$_2$CO$_3$ (432 mg, 2.721 mmol) in 1,4-dioxane:water (2:1, 3.0 mL) was sparged with N$_2$ for 5 min. Pd(PPh$_3$)$_4$ (157 mg, 0.136 mmol) was added, the reaction degassed with N$_2$ for 5 min, then heated to 100° C. overnight. The reaction was cooled to rt, 2 M aq. NaOH (3.0 mL) added, then stirred at rt for 30 h. The mixture was concentrated under reduced pressure to remove 1,4-dioxane, then diluted with water (30 mL) and washed with MTBE (3×20 mL). The aqueous solution was acidified (pH≈2) with 1 M aq. HCl and extracted with CHCl$_3$/iPrOH (3:1; 3×50 mL). The combined organic extracts were dried (Na$_2$SO$_4$) and concentrated under reduced pressure to afford a brown solid (238 mg, 74%). LCMS (method A) m/z 294.0 [M+Na]$^+$ at 0.94 min. $^1$H NMR (500 MHz, DMSO-d$_6$) 12.26 (s, 1H), 9.28 (dd, J=7.0, 1.8 Hz, 1H), 8.83 (dd, J=4.2, 1.8 Hz, 1H), 7.35 (m, 1H), 7.31 (m, 2H), 7.19 (m, 1H), 2.36 (s, 3H).

56A 2-(2-Fluorophenyl)-6-(1-methylazeidin-3-yl)oxyimidazo[1,2-b]pyridazine-3-carboxylic acid

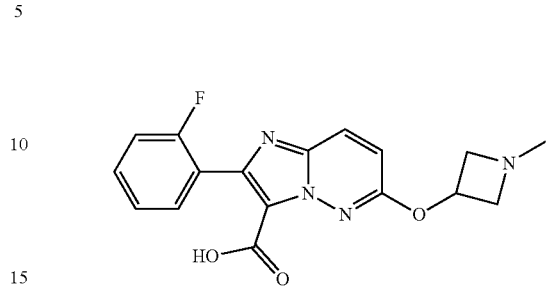

NaH (60% dispersion in mineral oil, 31 mg, 0.774 mmol) was added to a cooled (0° C.) solution of 1-methylazetidin-3-ol hydrochloride (47 mg, 0.378 mmol) in DMF (4 mL) and stirred for 15 min. A solution of intermediate 45D (55 mg, 0.172 mmol) in DMF (2 mL) was then added, and the reaction stirred at rt for 1 h. LiOH (103 mg, 4.301 mmol) was added and the solution stirred for a further 1 h. The reaction was acidified to pH~4 with 1 M aq. HCl, the volatiles removed under reduced pressure and the residue purified by reverse phase column chromatography (5-65% MeCN in 10 mM (NH$_4$)$_2$CO$_3$ aq. solution) to afford an off-white solid (55 mg, 93%). LCMS (method B) m/z 343.4 [M+H]$^+$ (ES+) at 0.47 min.

56B 2-(2-Fluorophenyl)-6-(2-methoxyethoxy)imidazo[1,2-b]pyridazine-3-carboxylic acid

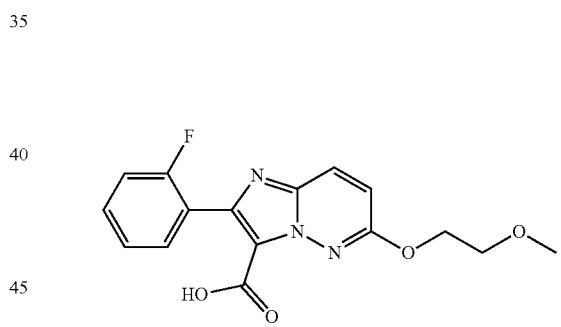

Prepared by an analogous procedure to that described for intermediate 56A. LCMS (method B) m/z 332.3 [M+H]$^+$ (ES+) at 0.49 min.

57A 6-(1-Methylazetidin-3-yl)oxy-2-phenylimidazo[1,2-b]pyridazine-3-carboxylic acid

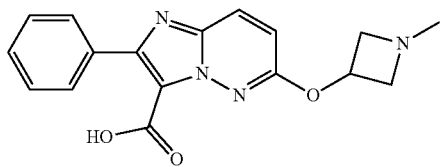 [SMILES: CN1CC(Oc2ccc3nc(-c4ccccc4)c(C(=O)O)n3n2)C1]

NaH (60% dispersion in mineral oil, 89 mg, 2.237 mmol) was added to a cooled (0° C.) solution of 1-methylazetidin-3-ol hydrochloride (135 mg, 1.094 mmol) in DMF (10 mL) and the mixture was stirred for 15 min. A solution of intermediate 45C (150 mg, 0.497 mmol) in DMF (2 mL) was added, the reaction mixture allowed to warm to rt and stirred for 2 h. A further suspension of NaH (89 mg, 2.237 mmol) and 1-methylazetidin-3-ol hydrochloride (135 mg, 1.094 mmol) in DMF (3 mL), which had been stirring in a separate flask at rt for 45 min, was added and the reaction stirred for a further 1 h. LiOH (298 mg, 12.43 mmol) was added and the solution stirred for 72 h at rt. The reaction was acidified to pH~4 with 1 M aq. HCl, the volatiles removed under reduced pressure and the residue purified by reverse phase column chromatography (5-65% MeCN in 10 mM $(NH_4)_2CO_3$ aq. solution) to afford a yellow solid (87 mg, 53%). LCMS (method B) m/z 324.6 $[M+H]^+$ (ES+) at 0.51 min.

58A 2-(6-Ethylpyridin-3-yl)-6-(trideuteriomethoxy) imidazo[1,2-b]pyridazine-3-carboxylic acid

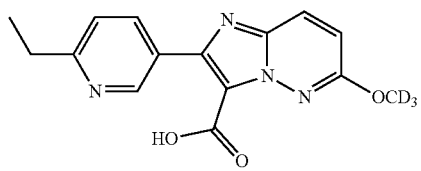

LiOH (1.5 M aq; 0.49 mL, 0.736 mmol) was added to a solution of intermediate 46F (52 mg, 0.147 mmol) in methanol-$d_4$ (1.2 mL, 29.5 mmol) and water (2 mL) and heated to 100° C. for 1 h by MWI. The reaction was cooled to rt, acidified with 1 M aq. HCl to pH~4, then concentrated under reduced pressure to afford a beige white solid (40 mg, 86%) which was used without further purification. LCMS (method A) m/z 301.7 $[M+H]^+$ (ES+) at 0.20 min.

EXAMPLES

1. 2-[4-(Methylamino)phenyl]-N-[(3S)-2-oxo-5-phenyl-1,3-dihydro-1,4-benzodiazepin-3-yl]pyrazolo[1,5-a]pyrimidine-3-carboxamide (Procedure A)

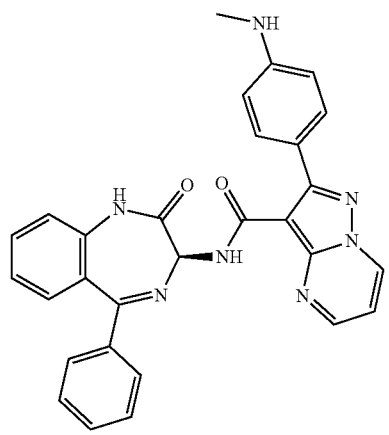 [SMILES: CNc1ccc(-c2nn3cccnc3c2C(=O)N[C@H]2N=C(c3ccccc3)c3ccccc3NC2=O)cc1]

Intermediate 9B (122 mg, 0.450 mmol) was added to a mixture of (3S)-3-amino-5-phenyl-1,3-dihydro-1,4-benzodiazepin-2-one (130 mg, 0.520 mmol), HATU (214 mg, 0.560 mmol) and $NEt_3$ (0.200 mL, 1.430 mmol) in DMF (3 mL) and the mixture was stirred at rt overnight. The reaction was quenched with water (15 mL) and the resultant precipitate filtered, washing with water (2×15 mL). The precipitate was dried under vacuum, dissolved with $CH_2Cl_2$, and purified by column chromatography (0-90% EtOAc in isohexanes) to afford a yellow solid (95 mg, 40%). LCMS (method D) 502.29 $[M+H]^+$ at 3.80 min. $^1$H NMR (500 MHz, DMSO-$d_6$) 10.98 (s, 1H), 9.91 (d, J=7.8 Hz, 1H), 9.31 (dd, J=6.9, 1.7 Hz, 1H), 8.87 (dd, J=4.3, 1.7 Hz, 1H), 7.81-7.74 (m, 2H), 7.68-7.42 (m, 6H), 7.37-7.32 (m, 2H), 7.31-7.24 (m, 2H), 6.58-6.51 (m, 2H), 5.98 (q, J=5.0 Hz, 1H), 5.52 (d, J=7.8 Hz, 1H), 2.71 (d, J=5.0 Hz, 3H).

The following compounds of the invention were prepared with (3S)-3-amino-5-phenyl-1,3-dihydro-1,4-benzodiazepin-2-one and (3S)-3-amino-9-fluoro-5-phenyl-1,3-dihydro-1,4-benzodiazepin-2-one by the amide coupling procedure A described for the compound of Example 1.

TABLE 3

Examples compounds prepared by amide coupling procedure A

| Example | Name | $R^1$ | $R^2$ | $^1$H NMR δ (500 MHz, DMSO-$d_6$) δ | LCMS (ES+) m./z |
|---|---|---|---|---|---|
| 2 | 2-(2-Fluorophenyl)-N-[(3S)-2-oxo-5-phenyl-1,3-dihydro-1,4-benzodiazepin-3-yl]pyrazolo[1,5-a]pyrimidine-3-carboxamide | H | (2-fluorophenyl) | 11.00 (s, 1H), 9.59 (d, J = 8.1 Hz, 1H), 9.43 (dd, J = 7.0, 1.7 Hz, 1H), 9.00 (dd, J = 4.3, 1.7 Hz, 1H), 7.65 (ddd, J = 8.5, 7.1, 1.6 Hz, 1H), 7.57-7.39 (m, 8H), 7.36-7.15 (m, 5H), 5.46 (d, J = 8.1 Hz, 1H) | (method C) m/z 491.24 $[M + H]^+$ at 4.05 min |

TABLE 3-continued

Examples compounds prepared by amide coupling procedure A

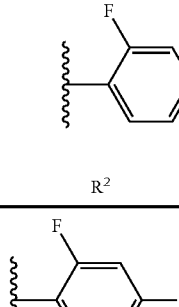

| Example | Name | R¹ | R² | ¹H NMR δ (500 MHz, DMSO-d$_6$) δ | LCMS (ES+) m./z |
|---|---|---|---|---|---|
| 3 | N-[(3S)-9-fluoro-2-oxo-5-phenyl-1,3-dihydro-1,4-benzodiazepin-3-yl]-2-(2-fluorophenyl)pyrazolo[1,5-a]pyrimidine-3-carboxamide | F | 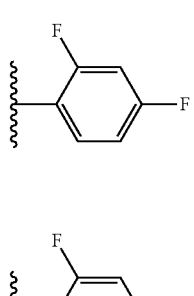 | 10.96 (s, 1H), 9.60 (d, J = 8.0 Hz, 1H), 9.42 (dt, J = 7.0, 1.4 Hz, 1H), 9.00 (dt, J = 4.3, 1.4 Hz, 1H), 7.66-7.39 (m, 9H), 7.35-7.20 (m, 3H), 7.15 (d, J = 7.9 Hz, 1H), 5.53 (d, J = 7.9 Hz, 1H) | (method C) 509.29 [M + H]⁺ at 4.14 min |
| 4 | 2-(2,4-difluorophenyl)-N-[(3S)-2-oxo-5-phenyl-1,3-dihydro-1,4-benzodiazepin-3-yl]pyrazolo[1,5-a]pyrimidine-3-carboxamide | H | 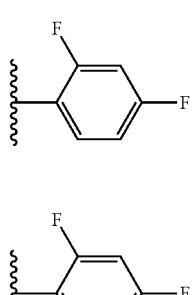 | 11.00 (s, 1H), 9.58 (d, J = 8.0 Hz, 1H), 9.42 (dd, J = 7.0, 1.7 Hz, 1H), 9.00 (dd, J = 4.3, 1.7 Hz, 1H), 7.67-7.62 (m, 1H), 7.61-7.56 (m, 1H), 7.53-7.49 (m, 1H), 7.49-7.40 (m, 5H), 7.34-7.29 (m, 3H), 7.29-7.23 (m, 1H), 7.19-7.13 (m, 1H), 5.45 (d, J = 8.0 Hz, 1H) | (method C) 509.19 [M + H]⁺ at 4.25 min |
| 5 | 2-(2,4-Difluorophenyl)-N-[(3S)-9-fluoro-2-oxo-5-phenyl-1,3-dihydro-1,4-benzodiazepin-3-yl]pyrazolo[1,5-a]pyrimidine-3-carboxamide | F | 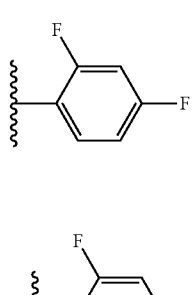 | 10.96 (s, 1H), 9.60 (d, J = 8.0 Hz, 1H), 9.42 (dd, J = 7.0, 1.7 Hz, 1H), 9.00 (dd, J = 4.3, 1.7 Hz, 1H), 7.63-7.56 (m, 2H), 7.54-7.49 (m, 3H), 7.47-7.40 (m, 3H), 7.33-7.27 (m, 2H), 7.20-7.12 (m, 2H), 5.53 (d, J = 7.9 Hz, 1H) | (method C) 527.20 [M + H]⁺ at 4.30 min |
| 6 | 2-(2,5-Difluorophenyl)-N-[(3S)-2-oxo-5-phenyl-1,3-dihydro-1,4-benzodiazepin-3-yl]pyrazolo[1,5-a]pyrimidine-3-carboxamide | H | 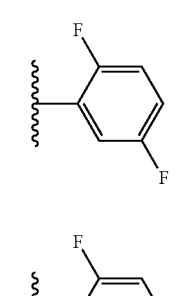 | 11.00 (s, 1H), 9.58 (d, J = 8.0 Hz, 1H), 9.44 (dd, J = 7.0, 1.7 Hz, 1H), 9.01 (dd, J = 4.3, 1.7 Hz, 1H), 7.66-7.62 (m, 1H), 7.54-7.49 (m, 1H), 7.48-7.42 (m, 5H), 7.41-7.34 (m, 2H), 7.34-7.28 (m, 3H), 7.28-7.23 (m, 1H), 5.46 (d, J = 8.0 Hz, 1H). | (method C) 509.24 [M + H]⁺ at 4.21 min |
| 7 | 2-(2,5-Difluorophenyl)-N-[(3S)-9-fluoro-2-oxo-5-phenyl-1,3-dihydro-1,4-benzodiazepin-3-yl]pyrazolo[1,5-a]pyrimidine-3-carboxamide | F | 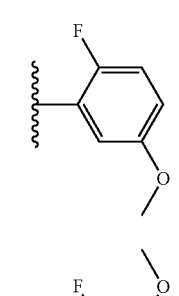 | 10.97 (s, 1H), 9.60 (d, J = 8.0 Hz, 1H), 9.44 (dd, J = 7.0, 1.7 Hz, 1H), 9.02 (dd, J = 4.3, 1.7 Hz, 1H), 7.63-7.56 (m, 1H), 7.55-7.48 (m, 3H), 7.48-7.42 (m, 3H), 7.41-7.34 (m, 2H), 7.34-7.28 (m, 2H), 7.15 (d, J = 7.9 Hz, 1H), 5.53 (d, J = 7.9 Hz, 1H). | (method C) 527.20 [M + H]⁺ at 4.26 min |
| 8 | 2-(2-Fluoro-5-methoxyphenyl)-N-[(3S)-9-fluoro-2-oxo-5-phenyl-1,3-dihydro-1,4-benzodiazepin-3-yl]pyrazolo[1,5-a]pyrimidine-3-carboxamide | F | 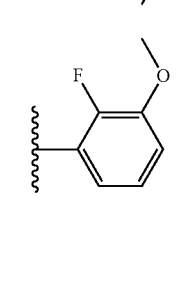 | 10.96 (s, 1H), 9.60 (d, J = 8.0 Hz, 1H), 9.43 (dd, J = 7.0, 1.7 Hz, 1H), 9.01 (dd, J = 4.3, 1.7 Hz, 1H), 7.63-7.57 (m, 1H), 7.55-7.49 (m, 3H), 7.48-7.40 (m, 3H), 7.34-7.29 (m, 1H), 7.19-7.13 (m, 2H), 7.06-7.02 (m, 2H), 5.54 (d, J = 7.8 Hz, 1H), 3.76 (s, 3H) | (method C) 539.20 [M + H]⁺ at 4.14 min |
| 9 | 2-(2-Fluoro-3-methoxyphenyl)-N-[(3S)-9-fluoro-2-oxo-5-phenyl-1,3-dihydro-1,4-benzodiazepin-3-yl]pyrazolo[1,5-a]pyrimidine-3-carboxamide | F |  | 10.95 (s, 1H), 9.59 (d, J = 8.0 Hz, 1H), 9.41 (dd, J = 7.0, 1.7 Hz, 1H), 8.99 (dd, J = 4.3, 1.7 Hz, 1H), 7.62-7.56 (m, 1H), 7.56-7.42 (m, 5H), 7.41 (dd, J = 7.0, 4.3 Hz, 1H), 7.34-7.28 (m, 1H), 7.27-7.21 (m, 1H), 7.21-7.13 (m, 2H), 7.06-7.00 (m, 1H), 5.53 (d, J = 7.9 Hz, 1H), 3.84 (s, 3H) | (method C) 539.15 [M + H]⁺ at 4.06 min |

TABLE 3-continued

Examples compounds prepared by amide coupling procedure A

| Example | Name | R¹ | R² | ¹H NMR δ (500 MHz, DMSO-d₆) δ | LCMS (ES+) m./z |
|---|---|---|---|---|---|
| 10 | 2-(2-Chlorophenyl)-N-[(3S)-9-fluoro-2-oxo-5-phenyl-1,3-dihydro-1,4-benzodiazepin-3-yl]pyrazolo[1,5-a]pyrimidine-3-carboxamide | F | 2-chlorophenyl | 10.95 (s, 1H), 9.55 (d, J = 8.0 Hz, 1H), 9.42 (dd, J = 7.0, 1.7 Hz, 1H), 9.01 (dd, J = 4.2, 1.7 Hz, 1H), 7.61-7.55 (m, 1H), 7.54-7.36 (m, 10H), 7.34-7.27 (m, 1H), 7.14 (d, J = 8.0 Hz, 1H), 5.50 (d, J = 8.0 Hz, 1H). | (method C) 525.10, 527.05 [M + H]⁺ at 4.26 min |
| 25 | 2-(2-Fluoro-5-methylphenyl)-N-[(3S)-2-oxo-5-phenyl-1,3-dihydro-1,4-benzodiazepin-3-yl]pyrazolo[1,5-a]pyrimidine-3-carboxamide | H | 2-fluoro-5-methylphenyl | 11.00 (s, 1H), 9.58 (d, J = 8.1 Hz, 1H), 9.41 (dd, J = 7.0, 1.7 Hz, 1H), 9.00 (dd, J = 4.3, 1.7 Hz, 1H), 7.65 (m, 1H), 7.55-7.37 (m, 6H), 7.37-7.20 (m, 5H), 7.11 (dd, J = 9.8, 8.4 Hz, 1H), 5.46 (d, J = 8.1 Hz, 1H), 2.32 (s, 3H). | (method C) 505.1 [M + H]+ at 4.39 min |
| 26 | 2-(2-Fluoro-5-methylphenyl)-N-[(3S)-9-fluoro-2-oxo-5-phenyl-1,3-dihydro-1,4-benzodiazepin-3-yl]pyrazolo[1,5-a]pyrimidine-3-carboxamide | F | 2-fluoro-5-methylphenyl | 10.96 (s, 1H), 9.60 (d, J = 8.0 Hz, 1H), 9.41 (dd, J = 7.0, 1.7 Hz, 1H), 9.00 (dd, J = 4.3, 1.7 Hz, 1H), 7.63-7.39 (m, 7H), 7.31 (m, 3H), 7.16 (d, J = 8.0 Hz, 1H), 7.11 (dd, J = 9.8, 8.0 Hz, 1H), 5.54 (d, J = 8.0 Hz, 1H), 2.33 (s, 3H) | (method C) 523.2 [M + H]+ at 4.45 min |
| 27 | 2-(5-Chloropyridin-3-yl)-N-[(3S)-2-oxo-5-phenyl-1,3-dihydro-1,4-benzodiazepin-3-yl]pyrazolo[1,5-a]pyrimidine-3-carboxamide | H | 5-chloropyridin-3-yl | 11.02 (s, 1H), 9.84 (d, J = 7.8 Hz, 1H), 9.46 (d, J = 7.1 Hz, 1H), 9.02 (d, J = 4.3 Hz, 1H), 8.96-8.92 (m, 1H), 8.70 (d, J = 2.4 Hz, 1H), 8.42-8.37 (m, 1H), 7.66 (t, J = 7.8 Hz, 1H), 7.55-7.48 (m, 2H), 7.47-7.41 (m, 3H), 7.37-7.31 (m, 2H), 7.31-7.24 (m, 1H), 5.52 (d, J = 7.8 Hz, 1H) | (method C) 508.3 [M + H]+ at 4.10 min |
| 28 | 2-(5-Chloropyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide | F | 5-chloropyridin-3-yl | 10.99 (s, 1H), 9.86 (d, J = 7.8 Hz, 1H), 9.50-9.44 (m, 1H), 9.05-9.00 (m, 1H), 8.96-8.93 (m, 1H), 8.73-8.69 (m, 1H), 8.42-8.38 (m, 1H), 7.61 (t, J = 9.2 Hz, 1H), 7.57-7.50 (m, 3H), 7.49-7.43 (m, 3H), 7.37-7.30 (m, 1H), 7.19 (d, J = 7.9 Hz, 1H), 5.61 (d, J = 7.7 Hz, 1H). | (method C) 526.3 [M + H]+ at 4.15 min |
| 29 | 2-(6-Cyclopropylpyridin-3-yl)-N-[(3S)-2-oxo-5-phenyl-1,3-dihydro-1,4-benzodiazepin-3-yl]pyrazolo[1,5-a]pyrimidine-3-carboxamide | H | 6-cyclopropylpyridin-3-yl | 11.00 (s, 1H), 9.82 (d, J = 7.8 Hz, 1H), 9.45-9.39 (m, 1H), 9.00-8.94 (m, 1H), 8.82-8.78 (m, 1H), 8.11-8.05 (m, 1H), 7.69-7.62 (m, 1H), 7.55-7.30 (m, 9H), 7.27 (t, J = 7.5 Hz, 1H), 5.50 (d, J = 7.8 Hz, 1H), 2.19-2.10 (m, 1H), 1.03-0.92 (m, 4H). | (method C) 514.4 [M + H]+ at 2.93 min |

TABLE 3-continued

Examples compounds prepared by amide coupling procedure A

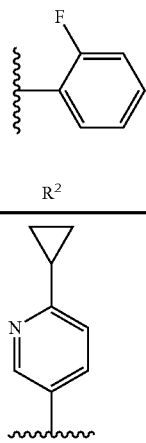

| Example | Name | R¹ | R² | ¹H NMR δ (500 MHz, DMSO-d₆) δ | LCMS (ES+) m./z |
|---|---|---|---|---|---|
| 30 | 2-(6-Cyclopropylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide | F | 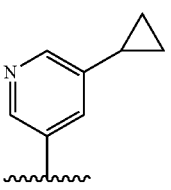 [SMILES: *c1cncc(C2CC2)c1] | 10.98 (s, 1H), 9.84 (d, J =7.7 Hz, 1H), 9.43 (d, J = 7.0 Hz, 1H), 9.01-8.95 (m, 1H), 8.83-8.78 (m, 1H), 8.08 (dd, J = 8.1, 2.2 Hz, 1H), 7.61 (t, J = 9.2 Hz, 1H), 7.57-7.50 (m, 3H), 7.50-7.43 (m, 2H), 7.43-7.38 (m, 1H), 7.38-7.29 (m, 2H), 7.18 (d, J = 7.9 Hz, 1H), 5.59 (d, J = 7.7 Hz, 1H), 2.20-2.11 (m, 1H), 1.03-0.93 (m, 4H). | (method C) 532.4 [M + H]+ at 2.96 min |
| 31 | 2-(5-Cyclopropylpyridin-3-yl)-N-[(3S)-2-oxo-5-phenyl-1,3-dihydro-1,4-benzodiazepin-3-yl]pyrazolo[1,5-a]pyrimidine-3-carboxamide | H | 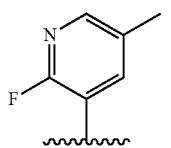 | 11.01 (s, 1H), 9.82 (d, J = 7.8 Hz, 1H), 9.46-9.41 (m, 1H), 9.01-8.96 (m, 1H), 8.75-8.71 (m, 1H), 8.46-8.41 (m, 1H), 7.86-7.81 (m, 1H), 7.66 (t, J = 7.8 Hz, 1H), 7.55-7.38 (m, 6H), 7.37-7.31 (m, 2H), 7.27 (t, J = 7.6 Hz, 1H), 5.50 (d, J = 7.8 Hz, 1H), 2.04-1.99 (m, 1H), 1.09-0.99 (m, 2H), 0.80-0.72 (m, 2H) | (method C) 514.4 [M + H]+ at 2.99 min |
| 32 | 2-(2-Fluoro-5-methylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide | F | 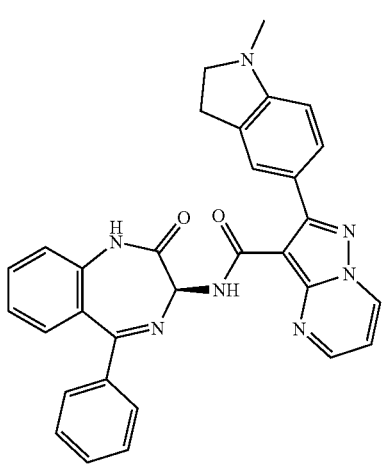 | 10.97 (s, 1H), 9.57 (d, J = 8.0 Hz, 1H), 9.46-9.40 (m, 1H), 9.06-8.98 (m, 1H), 8.16-8.09 (m, 1H), 7.93-7.88 (m, 1H), 7.63-7.56 (m, 1H), 7.55-7.48 (m, 3H), 7.48-7.41 (m, 3H), 7.35-7.28 (m, 1H), 7.15 (d, J = 8.0 Hz, 1H), 5.53 (d, J = 7.9 Hz, 1H), 2.33 (s, 3H). | (method C) 524.5 [M + H]+ at 3.85 min |

11. 2-(1-Methyl-2,3-dihydroindol-6-yl)-N-[(3S)-2-oxo-5-phenyl-1,3-dihydro-1,4-benzodiazepin-3-yl]pyrazolo[1,5-a]pyrimidine-3-carboxamide (Procedure B)

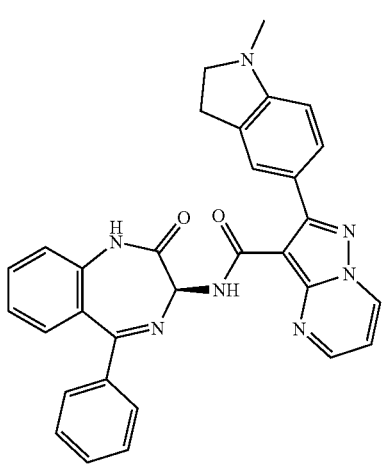 [SMILES: CN1CCc2cc(-c3nn4cccnc4c3C(=O)N[C@H]3N=C(c4ccccc4)c4ccccc4NC3=O)ccc21]

LiOH (1.5 M aq, 0.447 mL, 0.671 mmol) was added to a solution of intermediate 6E (12 mg, 0.038 mmol) in THF: MeOH (1:1, 4 mL) and the reaction mixture stirred at 40° C. overnight. The mixture was cooled to rt, neutralised with HCl (1 M aq, 0.671 mL, 0.671 mmol) and concentrated in vacuo. The crude product was dissolved in DMF (1.5 mL), NEt₃ (11 µL, 0.076 mmol), HATU (22 mg, 0.057 mmol) and (3S)-3-amino-5-phenyl-1,3-dihydro-1,4-benzodiazepin-2-one (13 mg, 0.052 mmol) added, and the reaction mixture was stirred at 40° C. for 2 h. The reaction was quenched with water (10 mL), and the resultant precipitate filtered, washing with water. The precipitate was purified by column chromatography (0 to 5% MeOH in CH₂Cl₂) to afford a yellow solid (6 mg, 29%). LCMS (Method C) 528.30 [M+H]⁺ at 4.13 min. ¹H NMR (500 MHz, DMSO-d₆) δ 10.99 (s, 1H), 9.91 (d, J=7.8 Hz, 1H), 9.33 (dd, J=6.9, 1.7 Hz, 1H), 8.89 (dd, J=4.3, 1.7 Hz, 1H), 7.72-7.63 (m, 3H), 7.56-7.42 (m, 5H), 7.38-7.23 (m, 4H), 6.52 (d, J=8.2 Hz, 1H), 5.53 (d, J=7.8 Hz, 1H), 3.36-3.26 (m, 2H), 2.92 (t, J=8.3 Hz, 2H), 2.76 (s, 3H).

The following compounds of the invention were prepared by the amide coupling procedure B described for the compound of Example 11.

TABLE 4

Compounds prepared by amide coupling procedure B

| Example | Name | R¹ | R² | ¹H NMR δ (500 MHz, DMSO-d$_6$) | LCMS (Method C) (ES+) m/z |
|---|---|---|---|---|---|
| 12 | N-[(3S)-2-oxo-5-phenyl-1,3-dihydro-1,4-benzodiazepin-3-yl]-2-phenylpyrazolo[1,5-a]pyrimidine-3-carboxamide | H | phenyl | 11.00 (s, 1H), 9.86 (d, J = 7.9 Hz, 1H), 9.41 (dd, J = 7.0, 1.7 Hz, 1H), 8.97 (dd, J = 4.3, 1.7 Hz, 1H), 7.90-7.83 (m, 2H), 7.69-7.62 (m, 1H), 7.56-7.42 (m, 8H), 7.39 (dd, J = 7.0, 4.2 Hz, 1H), 7.36-7.33 (m, 2H), 7.30-7.26 (m, 1H), 5.52 (d, J = 7.8 Hz, 1H). | 473.2 [M + H]⁺ at 4.15 min |
| 13 | N-[(3S)-2-Oxo-5-phenyl-1,3-dihydro-1,4-benzodiazepin-3-yl]-2-[4-(propan-2-ylamino)phenyl]pyrazolo[1,5-a]pyrimidine-3-carboxamide | H | 4-(propan-2-ylamino)phenyl | 10.98 (s, 1H), 9.91 (d, J = 7.8 Hz, 1H), 9.31 (dd, J = 6.9, 1.7 Hz, 1H), 8.86 (dd, J = 4.3, 1.7 Hz, 1H), 7.77-7.72 (m, 2H), 7.68-7.24 (m, 10H), 6.58-6.53 (m, 2H), 5.75 (d, J = 7.9 Hz, 1H), 5.52 (d, J = 7.8 Hz, 1H), 3.59 (dq, J = 13.2, 6.3 Hz, 1H), 1.14 (d, J = 6.3 Hz, 6H) | 530.3 [M + H]⁺ at 3.44 min |
| 14 | 2-(2-Fluoro-4-methoxyphenyl)-N-[(3S)-2-oxo-5-phenyl-1,3-dihydro-1,4-benzodiazepin-3-yl]pyrazolo[1,5-a]pyrimidine-3-carboxamide | H | 2-fluoro-4-methoxyphenyl | 10.99 (s, 1H), 9.58 (d, J = 8.0 Hz, 1H), 9.40 (dd, J = 7.0, 1.7 Hz, 1H), 8.97 (dd, J = 4.2, 1.7 Hz, 1H), 7.68-7.61 (m, 1H), 7.55-7.48 (m, 1H), 7.48-7.40 (m, 5H), 7.39 (dd, J = 7.0, 4.3 Hz, 1H), 7.35-7.28 (m, 2H), 7.28-7.23 (m, 1H), 6.89-6.81 (m, 2H), 5.45 (d, J = 8.0 Hz, 1H), 3.81 (s, 3H) | 521.25 [M + H]⁺ at 4.14 min |
| 15 | 2-(2-Fluoro-4-propan-2-yloxyphenyl)-N-[(3S)-2-oxo-5-phenyl-1,3-dihydro-1,4-benzodiazepin-3-yl]pyrazolo[1,5-a]pyrimidine-3-carboxamide | H | 2-fluoro-4-isopropoxyphenyl | 10.99 (s, 1H), 9.59 (d, J = 8.1 Hz, 1H), 9.39 (dd, J = 7.0, 1.7 Hz, 1H), 8.97 (dd, J = 4.3, 1.7 Hz, 1H), 7.64 (ddd, J = 8.5, 7.1, 1.7 Hz, 1H), 7.58-7.36 (m, 7H), 7.32 (ddd, J = 7.9, 4.0, 1.4 Hz, 2H), 7.29-7.23 (m, 1H), 6.86-6.77 (m, 2H), 5.46 (d, J = 8.0 Hz, 1H), 4.68 (hept, J = 6.1 Hz, 1H), 1.28 (d, J = 6.0 Hz, 6H) | 549.26 [M + H]⁺ at 4.84 min |
| 16 | 2-[2-Fluoro-4-(methylamino)phenyl]-N-[(3S)-2-oxo-5-phenyl-1,3-dihydro-1,4-benzodiazepin-3-yl]pyrazolo[1,5-a]pyrimidine-3-carboxamide | H | 2-fluoro-4-(methylamino)phenyl | 10.98 (s, 1H), 9.59 (d, J = 8.1 Hz, 1H), 9.35 (dd, J = 7.0, 1.7 Hz, 1H), 8.92 (dd, J = 4.3, 1.7 Hz, 1H), 7.68-7.61 (m, 1H), 7.54-7.40 (m, 5H), 7.37-7.30 (m, 2H), 7.31-7.20 (m, 3H), 6.39 (dd, J = 8.5, 2.2 Hz, 1H), 6.28 (dd, J = 13.1, 2.2 Hz, 1H), 6.24-6.18 (m, 1H), 5.46 (d, J = 8.1 Hz, 1H), 2.69 (d, J = 5.0 Hz, 3H) | 520.25 [M + H]⁺ at 3.83 min |

TABLE 4-continued

Compounds prepared by amide coupling procedure B

| Example | Name | R¹ | R² | ¹H NMR δ (500 MHz, DMSO-$d_6$) | LCMS (Method C) (ES+) m/z |
|---|---|---|---|---|---|
| 17 | N-[(3S)-9-Fluoro-2-oxo-5-phenyl-1,3-dihydro-1,4-benzodiazepin-3-yl]-2-phenylpyrazolo[1,5-a]pyrimidine-3-carboxamide | F | phenyl | 10.97 (s, 1H), 9.87 (d, J = 7.8 Hz, 1H), 9.41 (dd, J = 7.0, 1.7 Hz, 1H), 8.97 (dd, J = 4.2, 1.7 Hz, 1H), 7.99-7.82 (m, 2H), 7.70-7.59 (m, 1H), 7.57-7.51 (m, 3H), 7.50-7.42 (m, 5H), 7.40 (dd, J = 7.0, 4.3 Hz, 1H), 7.36-7.30 (m, 1H), 7.18 (d, J = 7.9 Hz, 1H), 5.59 (d, J = 7.8 Hz, 1H) | 492.2 [M + H]+ at 4.20 min |

18. N-[(3S)-9-fluoro-2-oxo-5-phenyl-1,3-dihydro-1,4-benzodiazepin-3-yl]-2-(2-fluorophenyl)imidazo[1,2-b]pyridazine-3-carboxamide 19. N-[(3S)-9-fluoro-2-oxo-5-phenyl-1,3-dihydro-1,4-benzodiazepin-3-yl]-2-(2-fluorophenyl)-6-methyl-imidazo[1,2-b]pyridazine-3-carboxamide

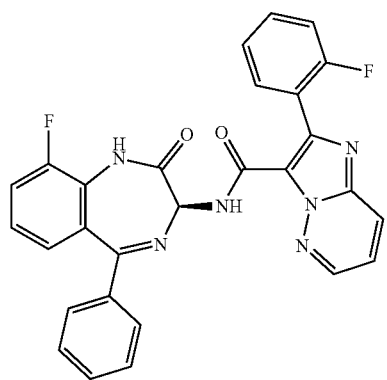 [SMILES: O=C(N[C@H]1N=C(c2ccccc2)c2cccc(F)c2NC1=O)c1c(-c2ccccc2F)nc2cccnn12]

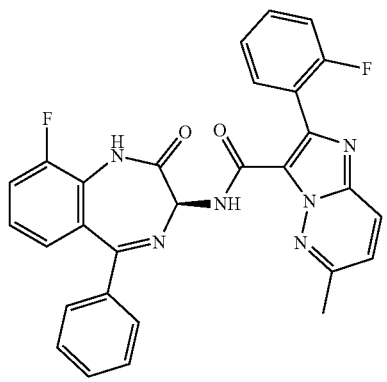 [SMILES: Cc1ccc2nc(-c3ccccc3F)c(C(=O)N[C@H]3N=C(c4ccccc4)c4cccc(F)c4NC3=O)n2n1]

Prepared by the amide coupling procedure B described for the compound of Example 11 from intermediate 14A. LCMS (Method C) m/z 509.1 [M+H]+ at 3.88 min. ¹H NMR (500 MHz, DMSO-$d_6$) δ 11.01 (s, 1H), 10.18 (d, J=7.6 Hz, 1H), 8.98 (dd, J=4.6, 1.6 Hz, 1H), 8.45 (dd, J=9.2, 1.6 Hz, 1H), 7.63-7.49 (m, 6H), 7.49-7.42 (m, 3H), 7.36-7.18 (m, 3H), 7.16 (d, J=7.9 Hz, 1H), 5.57 (d, J=7.5 Hz, 1H).

Prepared by the amide coupling procedure A described for the compound of Example 1 from intermediate 16A with heating at 40° C. overnight. LCMS (Method C) m/z 523.15 [M+H]+ at 4.12 min. ¹H NMR (500 MHz, DMSO-$d_6$) δ 11.01 (s, 1H), 10.59 (d, J=7.2 Hz, 1H), 8.33 (d, J=9.3 Hz, 1H), 7.63-7.41 (m, 9H), 7.36-7.28 (m, 1H), 7.28-7.20 (m, 2H), 7.20-7.14 (m, 1H), 5.53 (d, J=7.2 Hz, 1H), 2.75 (s, 3H).

20. 6-Chloro-N-[(3S)-9-fluoro-2-oxo-5-phenyl-1,3-dihydro-1,4-benzodiazepin-3-yl]-2-methylimidazo[1,2-b]pyridazine-3-carboxamide (Procedure C)

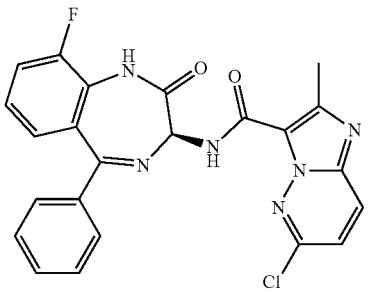 [SMILES: Cc1nc2ccc(Cl)nn2c1C(=O)N[C@H]1N=C(c2ccccc2)c2cccc(F)c2NC1=O]

HATU (205 mg, 0.540 mmol) was added to a solution of (3S)-3-amino-9-fluoro-5-phenyl-1,3-dihydro-1,4-benzodiazepin-2-one (121 mg, 0.45 mmol), 6-chloro-2-methylimidazo[1,2-b]pyridazine-3-carboxylic acid (99.8 mg, 0.47 mmol) and DIPEA (172 µL, 0.99 mmol) in anhydrous DMF (2.88 mL) under $N_2$ and the reaction stirred at rt for 24 h. The reaction was quenched with water, resulting in formation of an off-white precipitate, which was filtered and washed with water. The precipitate was dissolved in EtOAc, and the solvent removed under reduced pressure. Purification by column chromatography [10-37% (EtOH:$CH_2Cl_2$:$NH_4OH$; 50:8:1) in $CH_2Cl_2$] afforded a white solid (153 mg, 74%). $^1$H NMR (400 MHz, DMSO-$d_6$) δ 11.03 (s, 1H), 9.91 (d, J=7.1 Hz, 1H), 8.36 (d, J=9.5 Hz, 1H), 7.69-7.57 (m, 2H), 7.57-7.42 (m, 5H), 7.39-7.30 (m, 1H), 7.21 (d, J=7.9 Hz, 1H), 5.60 (d, J=7.2 Hz, 1H), 2.68 (s, 3H). LRMS (APCI+) m/z 463.3 [M+H]$^+$ The following compounds were prepared by the amide coupling procedure C described above for the compound of Example 20. Examples 40 and 41 were prepared with additional purification by HPLC method 1 (MeCN/water with 0.2% v/v formic acid; 25-100% for 18 min).

TABLE 5

Example compounds prepared by amide coupling procedure C

| Example | Name | R$^1$ | R$^2$ | $^1$H NMR δ (400 MHz, DMSO-$d_6$) | LRMS (APCI$^+$) |
|---|---|---|---|---|---|
| 21 | 6-Chloro-2-methyl-N-[(3S)-2-oxo-5-phenyl-1,3-dihydro-1,4-benzodiazepin-3-yl]imidazo[1,2-b]pyridazine-3-carboxamide | H | (imidazo[1,2-b]pyridazine with Cl and methyl) | 11.07 (s, 1H), 9.88 (d, J = 7.3 Hz, 1H), 8.35 (d, J = 9.5 Hz, 1H), 7.71-7.62 (m, 2H), 7.55-7.42 (m, 5H), 7.39-7.33 (m, 2H), 7.33-7.27 (m, 1H), 5.52 (d, J = 7.2 Hz, 1H), 2.67 (s, 3H) | 445.1 [M + H]$^+$ |
| 22 | 2-(2-Fluorophenyl)-5-methyl-N-[(3S)-2-oxo-5-phenyl-1,3-dihydro-1,4-benzodiazepin-3-yl]pyrazolo[1,5-a]pyrimidine-3-carboxamide | H | (pyrazolo[1,5-a]pyrimidine with 2-fluorophenyl and methyl) | 10.98 (s, 1H), 9.77 (d, J = 8.0 Hz, 1H), 9.26 (d, J = 7.1 Hz, 1H), 7.67-7.61 (m, 1H), 7.54-7.41 (m, 7H), 7.34-7.29 (m, 3H), 7.28-7.19 (m, 3H), 5.43 (d, J = 7.9 Hz, 1H), 2.74 (s, 3H) | 505.1 [M + H]$^+$ |
| 23 | N-[(3S)-9-Fluoro-2-oxo-5-phenyl-1,3-dihydro-1,4-benzodiazepin-3-yl]-2-(2-fluorophenyl)-5-methylpyrazolo[1,5-a]pyrimidine-3-carboxamide | F | (pyrazolo[1,5-a]pyrimidine with 2-fluorophenyl and methyl) | 10.94 (s, 1H), 9.81 (d, J = 7.8 Hz, 1H), 9.26 (d, J = 7.2 Hz, 1H), 7.63-7.56 (m, 1H), 7.55-7.42 (m, 7H), 7.34-7.19 (m, 4H), 7.15 (d, J = 7.9 Hz, 1H), 5.50 (d, J = 7.7 Hz, 1H), 2.75 (s, 3H) | 523.3 [M + H]$^+$ |

TABLE 5-continued

Example compounds prepared by amide coupling procedure C

| Example | Name | R¹ | R² | ¹H NMR δ (400 MHz, DMSO-d₆) | LRMS (APCI⁺) |
|---|---|---|---|---|---|
| 24 | N-[(3S)-9-Fluoro-2-oxo-5-phenyl-1,3-dihydro-1,4-benzodiazepin-3-yl]-6-(furan-3-yl)-2-methylpyrazolo[1,5-a]pyrimidine-3-carboxamide | F | (furan-3-yl / 2-methylpyrazolo[1,5-a]pyrimidine) | 11.00 (s, 1H), 9.61 (d, J = 2.1 Hz, 1H), 9.53 (d, J = 7.8 Hz, 1H), 9.29 (d, J = 2.1 Hz, 1H), 8.50 (dd, J = 1.5, 0.9 Hz, 1H), 7.87 (t, J = 1.7 Hz, 1H), 7.65-7.59 (m, 1H), 7.57-7.51 (m, 3H), 7.49-7.43 (m, 2H), 7.34 (s, 1H), 7.27-7.24 (m, 1H), 7.23-7.18 (m, 1H), 5.61 (d, J = 7.8 Hz, 1H), 2.64 (s, 3H) | 495.6 [M + H]⁺ |
| 33 | 2-(2-Fluorophenyl)-6-methyl-N-[(3S)-2-oxo-5-phenyl-1,3-dihydro-1,4-benzodiazepin-3-yl]pyrazolo[1,5-a]pyrimidine-3-carboxamide | H | (2-fluorophenyl / 6-methylpyrazolo[1,5-a]pyrimidine) | 11.00 (s, 1H), 9.55 (d, J = 8.1 Hz, 1H), 9.28 (dd, J = 2.1, 1.1 Hz, 1H), 8.91 (d, J = 2.0 Hz, 1H), 7.64 (ddd, J = 8.2, 7.0, 1.8 Hz, 1H), 7.54-7.41 (m, 7H), 7.33-7.19 (m, 5H), 5.44 (d, J = 8.1 Hz, 1H), 2.45 (d, J = 1.1 Hz, 3H). | 505.0 [M + H]⁺ |
| 34 | N-[(3S)-9-Fluoro-2-oxo-5-phenyl-1,3-dihydro-1,4-benzodiazepin-3-yl]-2-(2-fluorophenyl)-6-methylpyrazolo[1,5-a]pyrimidine-3-carboxamide | F | (2-fluorophenyl / 6-methylpyrazolo[1,5-a]pyrimidine) | 10.96 (s, 1H), 9.57 (d, J = 8.0 Hz, 1H), 9.28 (dd, J = 2.1, 1.2 Hz, 1H), 8.92 (d, J = 2.1 Hz, 1H), 7.62-7.42 (m, 8H), 7.34-7.19 (m, 3H), 7.15 (dd, J = 7.9, 1.3 Hz, 1H), 5.52 (d, J = 8.0 Hz, 1H), 2.45 (d, J = 1.1 Hz, 3H). | 523.1 [M + H]⁺ |
| 35 | 2-(2,4-Difluorophenyl)-5-methyl-N-[(3S)-2-oxo-5-phenyl-1,3-dihydro-1,4-benzodiazepin-3-yl]pyrazolo[1,5-a]pyrimidine-3-carboxamide | H | (2,4-difluorophenyl / 5-methylpyrazolo[1,5-a]pyrimidine) | 10.97 (s, 1H), 9.76 (d, J = 7.9 Hz, 1H), 9.26 (d, J = 7.1 Hz, 1H), 7.68-7.40 (m, 7H), 7.34-7.23 (m, 5H), 7.19-7.11 (m, 1H), 5.43 (d, J = 7.9 Hz, 1H), 2.74 (s, 3H). | 523.0 [M + H]⁺ |

TABLE 5-continued

Example compounds prepared by amide coupling procedure C

| Example | Name | R¹ | R² | ¹H NMR δ (400 MHz, DMSO-d₆) | LRMS (APCI⁺) |
|---|---|---|---|---|---|
| 36 | 2-(2,4-Difluorophenyl)-N-[(3S)-9-fluoro-2-oxo-5-phenyl-1,3-dihydro-1,4-benzodiazepin-3-yl]-5-methylpyrazolo[1,5-a]pyrimidine-3-carboxamide | F | 2,4-difluorophenyl-5-methylpyrazolo[1,5-a]pyrimidin-3-yl | 10.94 (s, 1H), 9.80 (d, J = 7.8 Hz, 1H), 9.26 (d, J = 7.1 Hz, 1H), 7.63-7.42 (m, 7H), 7.35-7.25 (m, 3H), 7.16 (d, J = 1.3 Hz, 2H), 5.50 (d, J = 7.7 Hz, 1H), 2.75 (s, 3H). | 541.4 [M + H]⁺ |
| 37 | 2-(2-Fluorophenyl)-7-methyl-N-[(3S)-2-oxo-5-phenyl-1,3-dihydro-1,4-benzodiazepin-3-yl]pyrazolo[1,5-a]pyrimidine-3-carboxamide | H | 2-fluorophenyl-7-methylpyrazolo[1,5-a]pyrimidin-3-yl | 11.00 (s, 1H), 9.69 (d, J = 8.1 Hz, 1H), 8.89 (d, J = 4.5 Hz, 1H), 7.65 (ddd, J = 8.2, 7.1, 1.7 Hz, 1H), 7.56-7.41 (m, 7H), 7.38 (dd, J = 4.5, 1.0 Hz, 1H), 7.36-7.16 (m, 5H), 5.46 (d, J = 8.1 Hz, 1H), 2.86 (d, J = 0.9 Hz, 3H). | 505.8 [M + H]⁺ |
| 38 | N-[(3S)-9-Fluoro-2-oxo-5-phenyl-1,3-dihydro-1,4-benzodiazepin-3-yl]-2-(2-fluorophenyl)-7-methylpyrazolo[1,5-a]pyrimidine-3-carboxamide | F | 2-fluorophenyl-7-methylpyrazolo[1,5-a]pyrimidin-3-yl | 10.97 (s, 1H), 9.71 (d, J = 8.0 Hz, 1H), 8.89 (d, J = 4.5 Hz, 1H), 7.60 (ddd, J = 10.3, 8.2, 1.3 Hz, 1H), 7.57-7.41 (m, 7H), 7.38 (dd, J = 4.6, 0.9 Hz, 1H), 7.35-7.20 (m, 3H), 7.15 (dt, J = 7.9, 1.0 Hz, 1H), 5.54 (d, J = 8.0 Hz, 1H), 2.86 (d, J = 0.8 Hz, 3H). | 524.0 [M + H]⁺ |

TABLE 5-continued

Example compounds prepared by amide coupling procedure C

| Example | Name | R¹ | R² | ¹H NMR δ (400 MHz, DMSO-d₆) | LRMS (APCI⁺) |
|---|---|---|---|---|---|
| 39 | 2-(2-Fluorophenyl)-5-(morpholin-4-yl)-N-[(3S)-2-oxo-5-phenyl-2,3-dihydro-1H-1,4-benzodiazepin-3-yl]pyrazolo[1,5-a]pyrimidine-3-carboxamide | H | (2-fluorophenyl-morpholinyl-pyrazolo[1,5-a]pyrimidine group) | 11.06 (s, 1H), 9.81 (d, J = 7.5 Hz, 1H), 8.88 (d, J = 7.9 Hz, 1H), 7.66-7.60 (m, 1H), 7.53-7.39 (m, 7H), 7.32-7.16 (m, 5H), 6.98 (d, J = 8.0 Hz, 1H), 5.33 (d, J = 7.5 Hz, 1H), 4.05-3.83 (m, 4H), 3.74 (t, J = 4.8 Hz, 4H). | 576.7 [M + H]+ |
| 40 | N-[(3S)-9-Fluoro-2-oxo-5-phenyl-1,3-dihydro-1,4-benzodiazepin-3-yl]-2-(2-fluorophenyl)-5-pyrrolidin-1-ylpyrazolo[1,5-a]pyrimidine-3-carboxamide | H | (2-fluorophenyl-pyrrolidinyl-pyrazolo[1,5-a]pyrimidine group) | 10.92 (s, 1H), 9.98 (d, J = 7.6 Hz, 1H), 8.80 (d, J = 7.8 Hz, 1H), 7.62-7.40 (m, 8H), 7.33-7.27 (m, 1H), 7.24-7.12 (m, 3H), 6.65 (d, J = 7.8 Hz, 1H), 5.44 (d, J = 7.6 Hz, 1H), 3.99-3.88 (m, 1H), 3.74-3.66 (m, 1H), 3.63-3.56 (m, 2H), 2.08-1.90 (m, 4H) | 578.6 [M + H]+ |
| 41 | 2-(2-Fluorophenyl)-N-[(3S)-2-oxo-5-phenyl-1,3-dihydro-1,4-benzodiazepin-3-yl]-5-pyrrolidin-1-ylpyrazolo[1,5-a]pyrimidine-3-carboxamide | F | (2-fluorophenyl-pyrrolidinyl-pyrazolo[1,5-a]pyrimidine group) | 10.95 (s, 1H), 9.95 (d, J = 7.7 Hz, 1H), 8.80 (d, J = 7.7 Hz, 1H), 7.66-7.60 (m, 1H), 7.53-7.40 (m, 7H), 7.33-7.15 (m, 5H), 6.64 (d, J = 7.7 Hz, 1H), 5.35 (d, J = 7.7 Hz, 1H), 3.97-3.87 (m, 1H), 3.74-3.66 (m, 1H), 3.60 (s, 2H), 2.07-1.91 (m, 4H) | 560.6 [M + H]+ |

42. 2-(2,3-Difluorophenyl)-N-[(3S)-9-fluoro-2-oxo-5-phenyl-1,3-dihydro-1,4-benzodiazepin-3-yl]pyrazolo[1,5-a]pyrimidine-3-carboxamide (Procedure D)

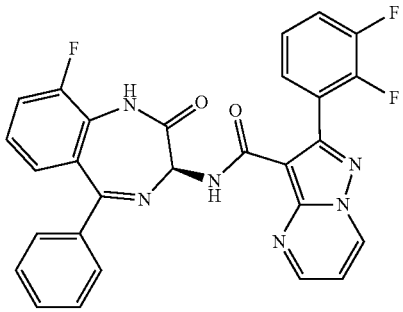 [SMILES: O=C(N[C@H]1N=C(c2ccccc2)c2cccc(F)c2NC1=O)c1c(-c2cccc(F)c2F)nn2cccnc12]

NEt$_3$ (59 μL, 0.423 mmol), HATU (79 mg, 0.206 mmol) and (3S)-3-amino-9-fluoro-5-phenyl-1,3-dihydro-1,4-benzodiazepin-2-one (56 mg, 0.206 mmol) were added to a solution of intermediate 53A (57 mg, 0.206 mmol) in DMF (2 mL), and the reaction mixture was stirred at 40° C. for 1 h. The reaction was quenched with water, and the resultant precipitate filtered, washing with water (100 mL). The precipitate was dissolved in CH$_2$Cl$_2$ (30 mL), concentrated under reduced pressure, and purified by column chromatography (0 to 5% MeOH in CH$_2$Cl$_2$) to afford an off-white solid (44 mg, 40%). LCMS (Method C) m/z 527.3 [M+H]$^+$ at 4.39 min. $^1$H NMR (500 MHz, DMSO-d$_6$) 10.97 (s, 1H), 9.61 (d, J=8.0 Hz, 1H), 9.44 (dd, J=7.0, 1.7 Hz, 1H), 9.02 (dd, J=4.3, 1.7 Hz, 1H), 7.61-7.57 (m, 1H), 7.57-7.48 (m, 4H), 7.47-7.42 (m, 3H), 7.39-7.33 (m, 1H), 7.33-7.26 (m, 2H), 7.16-7.13 (m, 1H), 5.54 (d, J=7.9 Hz, 1H).

The following compounds of the invention were prepared by the amide coupling procedure D described for the compound of Example 42.

TABLE 7

Example compounds prepared by amide coupling procedure D

| Example | Name | R$^1$ | R$^2$ | $^1$H NMR δ (500 MHz, DMSO-d$_6$) | LCMS (ES+) m/z |
|---|---|---|---|---|---|
| 43 | 2-(2,3-Difluorophenyl)-N-[(3S)-2-oxo-5-phenyl-1,3-dihydro-1,4-benzodiazepin-3-yl]pyrazolo[1,5-a]pyrimidine-3-carboxamide | H | 2,3-difluorophenyl-pyrazolo[1,5-a]pyrimidine | 11.01 (s, 1H), 9.59 (d, J = 8.0 Hz, 1H), 9.44 (dd, J = 7.0, 1.7 Hz, 1H), 9.02 (dd, J = 4.3, 1.7 Hz, 1H), 7.67-7.62 (m, 1H), 7.58-7.48 (m, 2H), 7.48-7.41 (m, 5H), 7.39-7.24 (m, 5H), 5.46 (d, J = 8.0 Hz, 1H) | (method C) 509.4 [M + H]$^+$ at 4.36 min |
| 44 | 2-(2,6-Difluorophenyl)-N-[(3S)-9-fluoro-2-oxo-5-phenyl-1,3-dihydro-1,4-benzodiazepin-3-yl]pyrazolo[1,5-a]pyrimidine-3-carboxamide | F | 2,6-difluorophenyl-pyrazolo[1,5-a]pyrimidine | 10.98 (s, 1H), 9.57 (d, J = 8.0 Hz, 1H), 9.46 (dd, J = 7.0, 1.7 Hz, 1H), 9.04 (dd, J = 4.3, 1.7 Hz, 1H), 7.63-7.50 (m, 5H), 7.49-7.44 (m, 3H), 7.35-7.28 (m, 1H), 7.22-7.13 (m, 3H), 5.54 (d, J = 8.0 Hz, 1H) | (method C) 527.3 [M + H]$^+$ at 4.24 min |

TABLE 7-continued

Example compounds prepared by amide coupling procedure D

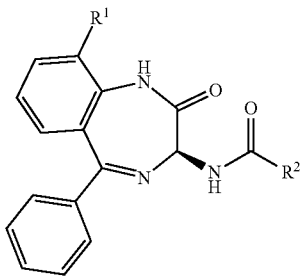

| Example | Name | R[1] | R[2] | $^1$H NMR δ (500 MHz, DMSO-d[6]) | LCMS (ES+) m/z |
|---|---|---|---|---|---|
| 45 | 2-(2-Fluoro-4-pyrrolidin-1-ylphenyl)-N-[(3S)-2-oxo-5-phenyl-1,3-dihydro-1,4-benzodiazepin-3-yl]pyrazolo[1,5-a]pyrimidine-3-carboxamide | H | (pyrrolidinyl-fluorophenyl-pyrazolo[1,5-a]pyrimidine group) | 10.98 (s, 1H), 9.58 (d, J = 8.0 Hz, 1H), 9.36 (dd, J = 7.0, 1.7 Hz, 1H), 8.93 (dd, J = 4.3, 1.7 Hz, 1H), 7.67-7.63 (m, 1H), 7.53-7.49 (m, 1H), 7.49-7.41 (m, 4H), 7.36-7.29 (m, 4H), 7.29-7.24 (m, 1H), 6.38 (dd, J = 8.6, 2.3 Hz, 1H), 6.30 (dd, J = 13.4, 2.3 Hz, 1H), 5.46 (d, J = 8.0 Hz, 1H), 3.28-3.22 (m, 4H), 1.99-1.92 (m, 4H). | (method C) 560.4 [M + H]+ at 4.95 min |
| 46 | 6-Methyl-N-[(3S)-2-oxo-5-phenyl-1,3-dihydro-1,4-benzodiazepin-3-yl]-2-[5-(trifluoromethyl)pyridin-3-yl]imidazo[1,2-b]pyridazine-3-carboxamide | H | (trifluoromethylpyridinyl-imidazo[1,2-b]pyridazine group) | 11.08 (s, 1H), 10.80 (d, J = 7.0 Hz, 1H), 9.37 (d, J = 2.0 Hz, 1H), 9.02-8.98 (m, 1H), 8.69-8.65 (m, 1H), 8.38 (d, J = 9.4 Hz, 1H), 7.70-7.63 (m, 1H), 7.55 (d, 1H), 7.52-7.40 (m, 5H), 7.36 (dd, J = 8.0, 1.4 Hz, 2H), 7.32-7.25 (m, 1H), 5.51 (d, J = 7.0 Hz, 1H), 2.75 (s, 3H). | (method C) 556.4 [M + H]+ at 4.52 min |
| 47 | N-[(3S)-9-fluoro-2-oxo-5-phenyl-1,3-dihydro-1,4-benzodiazepin-3-yl]-6-methyl-2-[5-(trifluoromethyl)pyridin-3-yl]imidazo[1,2-b]pyridazine-3-carboxamide | F | (trifluoromethylpyridinyl-imidazo[1,2-b]pyridazine group) | 11.05 (s, 1H), 10.84 (d, J = 6.9 Hz, 1H), 9.37 (d, J = 2.0 Hz, 1H), 9.02-8.98 (m, 1H), 8.69-8.64 (m, 1H), 8.38 (d, J = 9.4 Hz, 1H), 7.65-7.49 (m, 5H), 7.49-7.41 (m, 2H), 7.38-7.30 (m, 1H), 7.19 (d, J = 7.9 Hz, 1H), 5.60 (d, J = 6.9 Hz, 1H), 2.76 (s, 3H). | (method C) 574.3 [M + H]+ at 4.56 min |

48. 2-[6-(Cyclopropylamino)-2-fluoropyridin-3-yl]-N-[(3S)-2-oxo-5-phenyl-1,3-dihydro-1,4-benzodiazepin-3-yl]pyrazolo[1,5-a]pyrimidine-3-carboxamide (Procedure E)

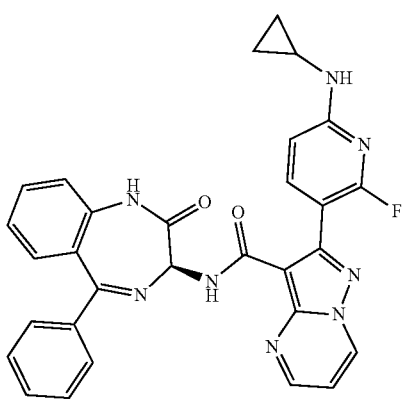 [SMILES: O=C(N[C@H]1N=C(c2ccccc2)c2ccccc2NC1=O)c1c(-c2ccc(NC3CC3)nc2F)nn2cccnc12]

A solution of intermediate 33C (70 mg, 0.205 mmol) and LiOH (1.5 M aq; 0.6 mL, 0.9 mmol) in THF/MeOH (1:1; 1 mL) was stirred at 40° C. overnight. The mixture was cooled to rt, neutralised with 1 M aq. HCl (0.92 mL, 0.920 mmol) and concentrated under reduced pressure. The crude residue was dissolved in DMF (1.26 mL), HATU (78 mg, 0.206 mmol), $NEt_3$ (57 μL, 0.41 mmol) and then (3S)-3-amino-5-phenyl-1,3-dihydro-1,4-benzodiazepin-2-one (41 mg, 0.205 mmol) added and the reaction stirred at 40° C. overnight. Analogous workup and purification to that described for Example 42 afforded a yellow solid (39 mg, 35%). LCMS (method C) m/z 547.3 [M+H]$^+$ at 4.13 min. $^1$H NMR (500 MHz, DMSO-d$_6$) 10.99 (s, 1H), 9.61 (d, J=8.0 Hz, 1H), 9.38 (dd, J=7.0, 1.7 Hz, 1H), 8.95 (dd, J=4.3, 1.7 Hz, 1H), 7.75-7.68 (m, 1H), 7.68-7.61 (m, 1H), 7.55-7.50 (m, 1H), 7.50-7.40 (m, 4H), 7.40-7.35 (m, 2H), 7.35-7.30 (m, 2H), 7.30-7.23 (m, 1H), 6.51 (d, J=8.1 Hz, 1H), 5.47 (d, J=8.0 Hz, 1H), 2.56-2.51 (m, 1H), 0.75-0.66 (m, 2H), 0.48-0.41 (m, 2H).

The following compounds of the invention were prepared by an analogous procedure to that described for the compound of Example 48 (amide coupling procedure E). The amide coupling procedure may be performed at rt or 40° C., and the stoichiometry of $NEt_3$ employed may be varied from 2 to 4 eq. For Examples 69-76 10 eq. of LiOH (1.5 M aq.) was used in the ester hydrolysis stage. Example 75 was subject to additional purification by reverse phase column chromatography (15-65% MeCN in water w/ 1% formic acid).

TABLE 8

Examples prepared by amide coupling procedure E

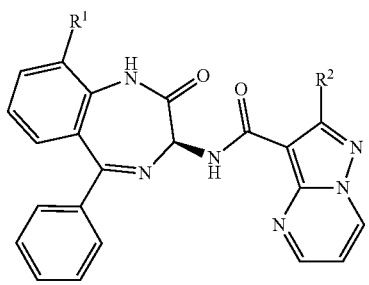

| Example | Name | R$^1$ | R$^2$ | $^1$H NMR δ (500 MHz, DMSO-d$_6$) | LCMS (ES+) m/z |
|---|---|---|---|---|---|
| 49 | 2-(6-Methylpyridin-3-yl)-N-[(3S)-2-oxo-5-phenyl-1,3-dihydro-1,4-benzodiazepin-3-yl]pyrazolo[1,5-a]pyrimidine-3-carboxamide | H | 6-methylpyridin-3-yl | 11.00 (s, 1H), 9.82 (d, J = 7.8 Hz, 1H), 9.43 (dd, J = 7.0, 1.7 Hz, 1H), 8.98 (dd, J = 4.3, 1.7 Hz, 1H), 8.85 (dd, J = 2.3, 0.9 Hz, 1H), 8.14 (dd, J = 8.0, 2.3 Hz, 1H), 7.66 (ddd, J = 8.4, 7.2, 1.6 Hz, 1H), 7.55-7.38 (m, 6H), 7.36-7.24 (m, 4H), 5.50 (d, J = 7.8 Hz, 1H), 2.52 (s, 3H). | (method C) 488.5 [M + H]$^+$ at 2.21 min |
| 50 | N-[(3S)-9-fluoro-2-oxo-5-phenyl-1,3-dihydro-1,4-benzodiazepin-3-yl]-2-(6-methylpyridin-3-yl)pyrazolo[1,5-a]pyrimidine-3-carboxamide | F | 6-methylpyridin-3-yl | 10.97 (s, 1H), 9.84 (d, J = 7.7 Hz, 1H), 9.43 (dd, J = 7.0, 1.7 Hz, 1H), 8.98 (dd, J = 4.3, 1.7 Hz, 1H), 8.85 (d, J = 2.3 Hz, 1H), 8.13 (dd, J = 8.1, 2.3 Hz, 1H), 7.64-7.57 (m, 1H), 7.56-7.49 (m, 3H), 7.49-7.43 (m, 2H), 7.41 (dd, J = 7.0, 4.3 Hz, 1H), 7.38-7.29 (m, 2H), 7.17 (d, J = 7.9 Hz, 1H), 5.58 (d, J = 7.7 Hz, 1H), 2.52 (s, 3H). | (method C) 506.3 [M + H]$^+$ at 2.19 min |

TABLE 8-continued

Examples prepared by amide coupling procedure E

| Example | Name | R¹ | R² | ¹H NMR δ (500 MHz, DMSO-d₆) | LCMS (ES+) m/z |
|---|---|---|---|---|---|
| 51 | 2-[6-(2-methoxy-ethyl)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide | F | 2-(2-methoxyethyl)pyridin-5-yl | 10.98 (s, 1H), 9.85 (d, J = 7.7 Hz, 1H), 9.44 (dd, J = 7.0, 1.7 Hz, 1H), 8.99 (dd, J = 4.3, 1.7 Hz, 1H), 8.89 (d, J = 2.2 Hz, 1H), 8.15 (dd, J = 8.0, 2.3 Hz, 1H), 7.61 (ddd, J = 9.8, 8.2, 1.3 Hz, 1H), 7.57-7.50 (m, 3H), 7.46 (dd, J = 8.2, 6.8 Hz, 2H), 7.42 (dd, J = 7.0, 4.3 Hz, 1H), 7.38-7.29 (m, 2H), 7.18 (d, J = 7.9 Hz, 1H), 5.59 (d, J = 7.7 Hz, 1H), 3.72 (t, J = 6.6 Hz, 2H), 3.25 (s, 3H), 3.01 (t, J = 6.6 Hz, 2H). | (method C) 550.4 [M + H]⁺ at 2.70 min |
| 52 | N-[(3S)-9-fluoro-2-oxo-5-phenyl-1,3-dihydro-1,4-benzodiazepin-3-yl]-2-(2-methylpyridin-4-yl)pyrazolo[1,5-a]pyrimidine-3-carboxamide | F | 2-methylpyridin-4-yl | 11.00 (s, 1H), 9.85 (d, J = 7.8 Hz, 1H), 9.43 (dd, J = 7.0, 1.7 Hz, 1H), 9.00 (dd, J = 4.2, 1.7 Hz, 1H), 8.53-8.48 (m, 1H), 7.71-7.68 (m, 1H), 7.66-7.57 (m, 2H), 7.57-7.40 (m, 6H), 7.37-7.29 (m, 1H), 7.18 (d, J = 7.9 Hz, 1H), 5.59 (d, J = 7.8 Hz, 1H), 2.52 (s, 3H) | (method C) 506.4 [M + H]⁺ at 2.04 min |
| 53 | 2-(6-Ethoxypyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide | F | 6-ethoxypyridin-3-yl | 10.99 (s, 1H), 9.86 (d, J = 7.7 Hz, 1H), 9.42 (dd, J = 7.0, 1.7 Hz, 1H), 8.97 (dd, J = 4.3, 1.7 Hz, 1H), 8.63-8.59 (m, 1H), 8.16 (dd, J = 8.6, 2.4 Hz, 1H), 7.65-7.57 (m, 1H), 7.52 (dt, J = 8.8, 2.1 Hz, 3H), 7.45 (dd, J = 8.3, 6.8 Hz, 2H), 7.44-7.37 (m, 1H), 7.37-7.29 (m, 1H), 7.18 (d, J = 8.2 Hz, 1H), 6.87-6.82 (m, 1H), 5.58 (d, J = 7.7 Hz, 1H), 4.35 (q, J = 7.1 Hz, 2H), 1.33 (t, J = 7.0 Hz, 3H). | (method C) 536.4 [M + H]⁺ at 4.34 min |
| 54 | 2-(6-Ethylpyridin-3-yl)-N-[(3S)-2-oxo-5-phenyl-1,3-dihydro-1,4-benzodiazepin-3-yl]pyrazolo[1,5-a]pyrimidine-3-carboxamide | H | 6-ethylpyridin-3-yl | 11.01 (s, 1H), 9.83 (d, J = 7.8 Hz, 1H), 9.44 (dd, J = 7.0, 1.7 Hz, 1H), 8.99 (dd, J = 4.3, 1.7 Hz, 1H), 8.88 (dd, J = 2.3, 0.8 Hz, 1H), 8.15 (dd, J = 8.1, 2.3 Hz, 1H), 7.68-7.64 (m, 1H), 7.55-7.43 (m, 5H), 7.41 (dd, J = 7.0, 4.3 Hz, 1H), 7.36-7.31 (m, 3H), 7.30-7.25 (m, 1H), 5.51 (d, J = 7.8 Hz, 1H), 2.80 (q, J = 7.6 Hz, 2H), 1.26 (t, J = 7.6 Hz, 3H). | (method C) 502.5 [M + H]⁺ at 2.56 min |
| 55 | 2-(6-Ethylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide | F | 6-ethylpyridin-3-yl | 10.98 (s, 1H), 9.84 (d, J = 7.7 Hz, 1H), 9.44 (dd, J = 7.0, 1.7 Hz, 1H), 8.99 (dd, J = 4.3, 1.6 Hz, 1H), 8.88 (dd, J = 2.3, 0.8 Hz, 1H), 8.15 (dd, J = 8.1, 2.3 Hz, 1H), 7.64-7.58 (m, 1H), 7.56-7.50 (m, 3H), 7.49-7.44 (m, 2H), 7.42 (dd, J = 7.0, 4.3 Hz, 1H), 7.36-7.30 (m, 2H), 7.18 (d, J = 7.9 Hz, 1H), 5.59 (d, J = 7.7 Hz, 1H), 2.80 (q, J = 7.6 Hz, 2H), 1.26 (t, J = 7.6 Hz, 3H) | (method C) 520.4 [M + H]⁺ at 2.53 min |

TABLE 8-continued

Examples prepared by amide coupling procedure E

| Example | Name | R¹ | R² | ¹H NMR δ (500 MHz, DMSO-d₆) | LCMS (ES+) m/z |
|---|---|---|---|---|---|
| 56 | 2-(6-Ethyl-2-methylpyridin-3-yl)-N-[(3S)-2-oxo-5-phenyl-2,3-dihydro-1H-1,4-benzodiazepin-3-yl]pyrazolo[1,5-a]pyrimidine-3-carboxamide | H | 6-ethyl-2-methylpyridin-3-yl | 10.99 (s, 1H), 9.63 (d, J = 7.9 Hz, 1H), 9.41 (dd, J = 7.0, 1.7 Hz, 1H), 9.00 (dd, J = 4.3, 1.7 Hz, 1H), 7.64 (m, 1H), 7.60 (d, J = 7.8 Hz, 1H), 7.55-7.48 (m, 1H), 7.50-7.42 (m, 4H), 7.45-7.38 (m, 2H), 7.31 (m, 2H), 7.26 (m, 1H), 7.13 (d, J = 7.8 Hz, 1H), 5.44 (d, J = 7.9 Hz, 1H), 2.75 (q, J = 7.6 Hz, 2H), 2.31 (s, 3H), 1.25 (t, J = 7.6 Hz, 3H). | (method C) 516.4 [M + H]⁺ at 2.16 min |
| 57 | 2-(6-Ethyl-2-methylpyridin-3-yl)-N-[(3S)-9-fluoro-2-oxo-5-phenyl-2,3-dihydro-1H-1,4-benzodiazepin-3-yl]pyrazolo[1,5-a]pyrimidine-3-carboxamide | F | 6-ethyl-2-methylpyridin-3-yl | 10.95 (s, 1H), 9.64 (d, J = 7.8 Hz, 1H), 9.41 (dd, J = 7.0, 1.7 Hz, 1H), 9.00 (dd, J = 4.3, 1.7 Hz, 1H), 7.62-7.56 (m, 2H), 7.56-7.49 (m, 3H), 7.48-7.43 (m, 2H), 7.41 (dd, J = 7.0, 4.3 Hz, 1H), 7.31 (td, J = 8.1, 4.9 Hz, 1H), 7.14 (t, J = 8.3 Hz, 2H), 5.52 (d, J = 7.9 Hz, 1H), 2.75 (q, J = 7.6 Hz, 2H), 2.31 (s, 3H), 1.25 (t, J = 7.6 Hz, 3H). | (method C) 534.3 [M + H]⁺ at 2.12 min |
| 58 | 2-(6-Propan-2-ylpyridin-3-yl)-N-[(3S)-2-oxo-5-phenyl-1,3-dihydro-1,4-benzodiazepin-3-yl]pyrazolo[1,5-a]pyrimidine-3-carboxamide | H | 6-isopropylpyridin-3-yl | 11.00 (s, 1H), 9.82 (d, J = 7.8 Hz, 1H), 9.43 (dd, J = 7.0, 1.7 Hz, 1H), 8.98 (dd, J = 4.3, 1.7 Hz, 1H), 8.88 (d, J = 2.3 Hz, 1H), 8.14 (dd, J = 8.1, 2.3 Hz, 1H), 7.68-7.63 (m, 1H), 7.54-7.39 (m, 6H), 7.36-7.31 (m, 3H), 7.29-7.25 (m, 1H), 5.50 (d, J = 7.8 Hz, 1H), 3.07 (hept, J = 7.1 Hz, 1H), 1.26 (d, J = 6.9 Hz, 6H). | 516.4 [M + H]⁺ at 2.92 min |
| 59 | 2-(6-Propan-2-ylpyridin-3-yl)-N-[(3S)-9-fluoro-2-oxo-5-phenyl-1,3-dihydro-1,4-benzodiazepin-3-yl]pyrazolo[1,5-a]pyrimidine-3-carboxamide | F | 6-isopropylpyridin-3-yl | 10.97 (s, 1H), 9.83 (d, J = 7.7 Hz, 1H), 9.43 (dd, J = 7.0, 1.7 Hz, 1H), 8.98 (dd, J = 4.3, 1.7 Hz, 1H), 8.88 (d, J = 2.2 Hz, 1H), 8.14 (dd, J = 8.1, 2.3 Hz, 1H), 7.63-7.58 (m, 1H), 7.55-7.49 (m, 3H), 7.48-7.43 (m, 2H), 7.41 (dd, J = 7.0, 4.3 Hz, 1H), 7.36-7.30 (m, 2H), 7.17 (d, J = 7.9 Hz, 1H), 5.58 (d, J = 7.7 Hz, 1H), 3.07 (hept, J = 6.9 Hz, 1H), 1.26 (d, J = 6.9 Hz, 6H). | 534.4 [M + H]⁺ at 2.91 min |
| 60 | 2-[2-Methyl-6-(propan-2-ylamino)pyridin-3-yl]-N-[(3S)-2-oxo-5-phenyl-1,3-dihydro-1,4-benzodiazepin-3-yl]pyrazolo[1,5-a]pyrimidine-3-carboxamide | H | 2-methyl-6-(isopropylamino)pyridin-3-yl | 10.99 (s, 1H), 9.67 (d, J = 7.9 Hz, 1H), 9.36 (dd, J = 7.0, 1.7 Hz, 1H), 8.94 (dd, J = 4.3, 1.7 Hz, 1H), 7.65 (ddd, J = 8.4, 7.2, 1.7 Hz, 1H), 7.55-7.41 (m, 5H), 7.39-7.19 (m, 5H), 6.39 (d, J = 7.8 Hz, 1H), 6.26 (d, J = 8.5 Hz, 1H), 5.46 (d, J = 7.9 Hz, 1H), 4.00 (h, J = 6.6 Hz, 1H), 2.18 (s, 3H), 1.15 (d, J = 6.6 Hz, 6H). | 516.4 [M + H]⁺ at 2.16 min |

TABLE 8-continued

Examples prepared by amide coupling procedure E

| Example | Name | R¹ | R² | ¹H NMR δ (500 MHz, DMSO-d₆) | LCMS (ES+) m/z |
|---|---|---|---|---|---|
| 61 | 2-[2-Methyl-6-(propan-2-ylamino)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide | F |  | 10.95 (s, 1H), 9.69 (d, J = 7.9 Hz, 1H), 9.36 (dd, J = 7.0, 1.7 Hz, 1H), 8.94 (dd, J = 4.3, 1.7 Hz, 1H), 7.65-7.56 (m, 1H), 7.57-7.42 (m, 5H), 7.36 (dd, J = 7.0, 4.3 Hz, 1H), 7.35-7.29 (m, 1H), 7.29 (d, J = 8.6 Hz, 1H), 7.16 (d, J = 7.9 Hz, 1H), 6.39 (d, J = 7.8 Hz, 1H), 6.27 (d, J = 8.5 Hz, 1H), 5.54 (d, J = 7.8 Hz, 1H), 4.00 (h, J = 6.4 Hz, 1H), 2.18 (s, 3H), 1.15 (d, J = 6.4 Hz, 6H). | (method C) 534.4 [M + H]⁺ at 3.75 min |
| 62 | 2-[4-Methyl-6-(propan-2-ylamino)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide | F |  | 10.95 (s, 1H), 9.67 (d, J = 7.9 Hz, 1H), 9.37 (dd, J = 7.0, 1.7 Hz, 1H), 8.95 (dd, J = 4.4, 1.7 Hz, 1H), 7.85 (s, 1H), 7.60 (t, J = 9.2 Hz, 1H), 7.57-7.42 (m, 5H), 7.41-7.27 (m, 2H), 7.15 (d, J = 7.9 Hz, 1H), 6.38 (d, J = 7.8 Hz, 1H), 6.29 (s, 1H), 5.53 (d, J = 7.7 Hz, 1H), 4.01 (m, 1H), 2.03 (s, 3H), 1.15 (s, 3H), 1.14 (s, 3H). | (method C) 534.4 [M + H]⁺ at 3.75 min |
| 63 | N-[(3S)-9-fluoro-2-oxo-5-phenyl-1,3-dihydro-1,4-benzodiazepin-3-yl]-2-(1-methylindazol-5-yl)pyrazolo[1,5-a]pyrimidine-3-carboxamide | F |  | 10.97 (s, 1H), 9.93 (d, J = 7.8 Hz, 1H), 9.41 (m, 1H), 8.96 (m, 1H), 8.43-8.35 (m, 1H), 8.12 (m, 1H), 7.92 (m, 1H), 7.66 (m, 1H), 7.61 (m, 1H), 7.56-7.50 (m, 3H), 7.49-7.43 (m, 2H), 7.39 (dd, J = 7.0, 4.3 Hz, 1H), 7.33 (td, J = 8.1, 5.0 Hz, 1H), 7.18 (d, J = 7.8 Hz, 1H), 5.62 (d, J = 7.8 Hz, 1H), 4.08 (s, 3H). | (method C) 545.4 [M + H]⁺ at 3.85 min |
| 64 | N-[(3S)-9-fluoro-2-oxo-5-phenyl-1,3-dihydro-1,4-benzodiazepin-3-yl]-2-(5-methylpyridin-3-yl)pyrazolo[1,5-a]pyrimidine-3-carboxamide | F |  | 10.97 (s, 1H), 9.88-9.79 (m, 1H), 9.47-9.38 (m, 1H), 9.05-8.94 (m, 1H), 8.80-8.72 (m, 1H), 8.49-8.42 (m, 1H), 8.08-7.99 (m, 1H), 7.64-7.57 (m, 1H), 7.56-7.49 (m, 3H), 7.49-7.38 (m, 3H), 7.36-7.28 (m, 1H), 7.20-7.14 (m, 1H), 5.62-5.57 (m, 1H), 2.39-2.27 (m, 3H). | (method C) 506.4 [M + H]⁺ at 2.46 min |
| 65 | 2-[6-(Ethylamino)-2-fluoropyridin-3-yl]-N-[(3S)-2-oxo-5-phenyl-1,3-dihydro-1,4-benzodiazepin-3-yl]pyrazolo[1,5-a]pyrimidine-3-carboxamide | H |  | 11.00 (s, 1H), 9.61 (d, J = 8.0 Hz, 1H), 9.37 (dd, J = 7.0, 1.7 Hz, 1H), 8.95 (dd, J = 4.3, 1.7 Hz, 1H), 7.69-7.58 (m, 2H), 7.56-7.48 (m, 1H), 7.51-7.45 (m, 2H), 7.48-7.41 (m, 2H), 7.40-7.34 (m, 1H), 7.36-7.30 (m, 2H), 7.30-7.24 (m, 1H), 7.19-7.13 (m, 1H), 6.40-6.34 (m, 1H), 5.48 (d, J = 8.0 Hz, 1H), 3.29-3.19 (m, 2H), 1.14 (t, J = 7.2 Hz, 3H). | (method C) 535.4 [M + H]⁺ at 3.97 min |

TABLE 8-continued

Examples prepared by amide coupling procedure E

| Example | Name | R¹ | R² | ¹H NMR δ (500 MHz, DMSO-d₆) | LCMS (ES+) m/z |
|---|---|---|---|---|---|
| 66 | 2-[6-(Ethylamino)-2-fluoropyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide | F | | 10.96 (s, 1H), 9.63 (d, J = 7.9 Hz, 1H), 9.37 (dd, J = 7.0, 1.7 Hz, 1H), 8.95 (dd, J = 4.3, 1.7 Hz, 1H), 7.66-7.57 (m, 2H), 7.57-7.48 (m, 3H), 7.51-7.42 (m, 2H), 7.40-7.28 (m, 2H), 7.19-7.14 (m, 2H), 6.40-6.34 (m, 1H), 5.55 (d, J = 7.9 Hz, 1H), 3.32-3.19 (m, 2H), 1.14 (t, J = 7.2 Hz, 3H). | (method C) 553.3 [M + H]⁺ at 4.03 min |
| 67 | 2-[6-(3-Methylmorpholin-4-yl)pyridin-3-yl]-N-[(3S)-2-oxo-5-phenyl-1,3-dihydro-1,4-benzodiazepin-3-yl]pyrazolo[1,5-a]pyrimidine-3-carboxamide | H | | 11.00 (s, 1H), 9.90-9.84 (m, 1H), 9.42-9.35 (m, 1H), 8.96-8.91 (m, 1H), 8.66 (d, J = 2.4 Hz, 1H), 8.09 (dd, J = 9.0, 2.4 Hz, 1H), 7.70-7.62 (m, 1H), 7.55-7.42 (m, 5H), 7.38-7.33 (m, 3H), 7.31-7.26 (m, 1H), 6.80 (d, J = 9.0 Hz, 1H), 5.52 (d, J = 7.8 Hz, 1H), 4.42-4.36 (m, 1H), 3.99-3.91 (m, 2H), 3.75-3.71 (m, 1H), 3.66-3.60 (m, 1H), 3.51-3.44 (m, 1H), 3.13-3.06 (m, 1H), 1.15 (d, J = 6.7 Hz, 3H). | (method D) 573.4 [M + H]⁺ at 3.86 min. |
| 68 | 2-[6-(3-Methylmorpholin-4-yl)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide | F | | 10.96 (s, 1H), 9.92-9.83 (m, 1H), 9.41-9.32 (m, 1H), 8.97-8.87 (m, 1H), 8.69-8.60 (m, 1H), 8.08 (dd, J = 8.9, 2.4 Hz, 1H), 7.66-7.58 (m, 1H), 7.57-7.49 (m, 3H), 7.50-7.42 (m, 2H), 7.39-7.28 (m, 2H), 7.18 (d, J = 7.9 Hz, 1H), 6.80 (d, J = 8.9 Hz, 1H), 5.59 (d, J = 7.7 Hz, 1H), 4.42-4.34 (m, 1H), 3.98-3.90 (m, 2H), 3.75-3.69 (m, 1H), 3.65-3.59 (m, 1H), 3.47 (td, J = 11.8, 3.2 Hz, 1H), 3.09 (td, J = 12.8, 3.8 Hz, 1H), 1.14 (d, J = 6.7 Hz, 3H). | (method D) 591.4 [M + H]⁺ at 3.87 min. |
| 69 | 2-[2-Fluoro-6-(propan-2-ylamino)pyridin-3-yl]-N-[(3S)-2-oxo-5-phenyl-1,3-dihydro-1,4-benzodiazepin-3-yl]pyrazolo[1,5-a]pyrimidine-3-carboxamide | H | | 11.00 (s, 1H), 9.62 (d, J = 8.0 Hz, 1H), 9.37 (dd, J = 7.0, 1.7 Hz, 1H), 8.94 (dd, J = 4.3, 1.7 Hz, 1H), 7.68-7.63 (m, 1H), 7.61 (dd, J = 9.9, 8.3 Hz, 1H), 7.54-7.50 (m, 1H), 7.49-7.42 (m, 4H), 7.37 (dd, J = 7.0, 4.3 Hz, 1H), 7.35-7.31 (m, 2H), 7.29-7.25 (m, 1H), 7.06 (d, J = 7.6 Hz, 1H), 6.36 (dd, J = 8.3, 1.8 Hz, 1H), 5.48 (d, J = 8.0 Hz, 1H), 3.93 (h, J = 6.7 Hz, 1H), 1.15 (d, J = 6.5 Hz, 6H). | (method C) 549.3 [M + H]⁺ at 4.33 min |

TABLE 8-continued

Examples prepared by amide coupling procedure E

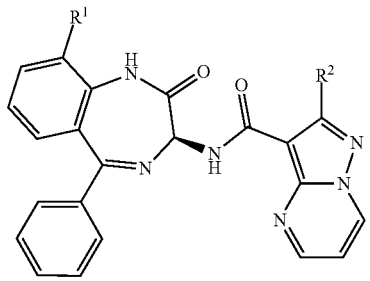

| Example | Name | R¹ | R² | ¹H NMR δ (500 MHz, DMSO-d₆) | LCMS (ES+) m/z |
|---|---|---|---|---|---|
| 70 | N-[(3S)-9-Fluoro-2-oxo-5-phenyl-1,3-dihydro-1,4-benzodiazepin-3-yl]-2-[2-fluoro-6-(propan-2-ylamino)pyridin-3-yl]pyrazolo[1,5-a]pyrimidine-3-carboxamide | F | (isopropylamino-fluoropyridinyl) | 10.96 (s, 1H), 9.63 (d, J = 8.0 Hz, 1H), 9.37 (dd, J = 7.0, 1.7 Hz, 1H), 8.95 (dd, J = 4.3, 1.7 Hz, 1H), 7.60 (ddd, J = 10.3, 8.3, 1.8 Hz, 2H), 7.56-7.49 (m, 3H), 7.48-7.43 (m, 2H), 7.37 (dd, J = 7.0, 4.3 Hz, 1H), 7.35-7.29 (m, 1H), 7.17 (d, J = 7.9 Hz, 1H), 7.06 (d, J = 7.6 Hz, 1H), 6.36 (dd, J = 8.3, 1.8 Hz, 1H), 5.55 (d, J = 7.9 Hz, 1H), 3.93 (h, J = 6.6 Hz, 1H), 1.15 (d, J = 6.5 Hz, 6H). | (method C) 567.4 [M + H]⁺ at 4.38 min |
| 71 | N-[(3S)-9-fluoro-2-oxo-5-phenyl-1,3-dihydro-1,4-benzodiazepin-3-yl]-2-(1-methylpyrrolo[2,3-b]pyridin-5-yl)pyrazolo[1,5-a]pyrimidine-3-carboxamide | F | (1-methylpyrrolopyridinyl) | 10.96 (s, 1H), 9.89 (d, J = 7.8 Hz, 1H), 9.43 (dd, J = 7.0, 1.6 Hz, 1H), 8.97 (dd, J = 4.3, 1.7 Hz, 1H), 8.70 (d, J = 2.0 Hz, 1H), 8.48 (d, J = 2.0 Hz, 1H), 7.63-7.56 (m, 1H), 7.57-7.49 (m, 4H), 7.48-7.42 (m, 2H), 7.39 (dd, J = 7.0, 4.3 Hz, 1H), 7.35-7.27 (m, 1H), 7.16 (d, J = 7.9 Hz, 1H), 6.53 (d, J = 3.5 Hz, 1H), 5.59 (d, J = 7.7 Hz, 1H), 3.85 (s, 3H) | (method C) 545.3 [M + H]⁺ at 3.84 min |
| 72 | N-[(3S)-9-fluoro-2-oxo-5-phenyl-1,3-dihydro-1,4-benzodiazepin-3-yl]-2-(6-morpholin-4-ylpyridin-3-yl)pyrazolo[1,5-a]pyrimidine-3-carboxamide | F | (morpholinophenyl) | 10.96 (s, 1H), 9.87 (d, J = 7.7 Hz, 1H), 9.38 (dd, J = 7.0, 1.7 Hz, 1H), 8.93 (dd, J = 4.3, 1.7 Hz, 1H), 8.65 (d, J = 2.4 Hz, 1H), 8.08 (dd, J = 8.9, 2.4 Hz, 1H), 7.64-7.57 (m, 1H), 7.57-7.49 (m, 3H), 7.49-7.42 (m, 2H), 7.39-7.29 (m, 2H), 7.18 (d, J = 7.9 Hz, 1H), 6.87 (d, J = 9.0 Hz, 1H), 5.58 (dd, J = 7.8, 1.5 Hz, 1H), 3.75-3.67 (m, 4H), 3.52 (t, J = 4.9 Hz, 4H). | (method C) 577.3 [M + H]⁺ at 2.77 min |
| 73 | N-[(3S)-2-oxo-5-phenyl-1,3-dihydro-1,4-benzodiazepin-3-yl]-2-[6-(propan-2-ylamino)pyridin-3-yl]pyrazolo[1,5-a]pyrimidine-3-carboxamide | H | (isopropylaminopyridinyl) | 11.00 (s, 1H), 9.88 (d, J = 7.8 Hz, 1H), 9.36 (dd, J = 6.9, 1.7 Hz, 1H), 8.91 (dd, J = 4.3, 1.7 Hz, 1H), 8.53 (d, J = 2.4 Hz, 1H), 7.90 (dd, J = 8.8, 2.4 Hz, 1H), 7.68-7.64 (m, 1H), 7.55-7.43 (m, 5H), 7.37-7.32 (m, 3H), 7.31-7.25 (m, 1H), 6.68 (d, J = 7.7 Hz, 1H), 6.45 (d, J = 8.8 Hz, 1H), 5.52 (d, J = 7.8 Hz, 1H), 4.05 (dq, J = 13.3, 6.7 Hz, 1H), 1.16 (d, J = 6.5 Hz, 6H). | (method C) 531.4 [M + H]⁺ at 2.43 min |

TABLE 8-continued

Examples prepared by amide coupling procedure E

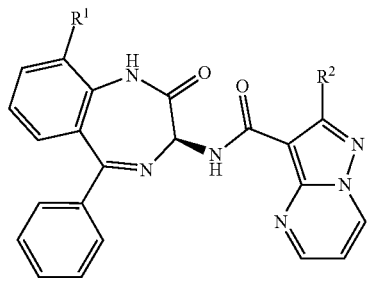

| Example | Name | R[1] | R[2] | $^1$H NMR δ (500 MHz, DMSO-d$_6$) | LCMS (ES+) m/z |
|---|---|---|---|---|---|
| 74 | N-[(3S)-9-Fluoro-2-oxo-5-phenyl-1,3-dihydro-1,4-benzodiazepin-3-yl]-2-[6-(propan-2-ylamino)pyridin-3-yl]pyrazolo[1,5-a]pyrimidine-3-carboxamide | F | | 10.95 (s, 1H), 9.89 (d, J = 7.8 Hz, 1H), 9.35 (dd, J = 6.9, 1.7 Hz, 1H), 8.90 (dd, J = 4.3, 1.7 Hz, 1H), 8.52 (d, J = 2.3 Hz, 1H), 7.89 (dd, J = 8.8, 2.4 Hz, 1H), 7.64-7.58 (m, 1H), 7.56-7.49 (m, 3H), 7.48-7.43 (m, 2H), 7.36-7.30 (m, 2H), 7.18 (d, J = 7.9 Hz, 1H), 6.67 (d, J = 7.7 Hz, 1H), 6.45 (d, J = 9.1 Hz, 1H), 5.59 (d, J = 7.7 Hz, 1H), 4.05 (dq, J = 6.7 Hz, 1H), 1.15 (d, J = 6.5 Hz, 6H). | (method C) 549.4 [M + H]+ at 2.41 min |
| 75 | N-[(3S)-9-Fluoro-2-oxo-5-phenyl-1,3-dihydro-1,4-benzodiazepin-3-yl]-2-(1H-pyrrolo[2,3-b]pyridin-5-yl)pyrazolo[1,5-a]pyrimidine-3-carboxamide | F | | 11.76 (s, 1H), 10.96 (s, 1H), 9.90 (d, J = 7.8 Hz, 1H), 9.42 (dd, J = 7.0, 1.7 Hz, 1H), 8.97 (dd, J = 4.3, 1.7 Hz, 1H), 8.65 (d, J = 2.1 Hz, 1H), 8.47-8.46 (m, 1H), 7.64-7.56 (m, 1H), 7.55-7.49 (m, 4H), 7.48-7.43 (m, 2H), 7.39 (dd, J = 7.0, 4.3 Hz, 1H), 7.31 (ddd, J = 8.0, 5.0 Hz, 1H), 7.16 (d, J = 7.9 Hz, 1H), 6.51 (dd, J = 3.5, 1.8 Hz, 1H), 5.60 (d, J = 7.8 Hz, 1H). | (method C) 531.4 [M + H]+ at 3.38 min |
| 76 | N-[(3S)-9-fluoro-2-oxo-5-phenyl-1,3-dihydro-1,4-benzodiazepin-3-yl]-2-(6-methoxypyridin-3-yl)pyrazolo[1,5-a]pyrimidine-3-carboxamide | F | | 10.96 (s, 1H), 9.85 (d, J = 7.7 Hz, 1H), 9.41 (dd, J = 7.0, 1.7 Hz, 1H), 8.97 (dd, J = 4.3, 1.7 Hz, 1H), 8.64 (d, J = 2.4 Hz, 1H), 8.17 (dd, J = 8.6, 2.4 Hz, 1H), 7.63-7.58 (m, 1H), 7.55-7.49 (m, 3H), 7.49-7.43 (m, 2H), 7.39 (dd, J = 7.0, 4.3 Hz, 1H), 7.35-7.29 (m, 1H), 7.18 (d, J = 7.9 Hz, 1H), 6.88 (d, J = 8.6 Hz, 1H), 5.58 (d, J = 7.7 Hz, 1H), 3.90 (s, 3H). | (method C) 522.3 [M + H]+ at 3.94 min |
| 126 | N-[(3S)-9-fluoro-2-oxo-5-phenyl-1,3-dihydro-1,4-benzodiazepin-3-yl]-2-(1H-indazol-5-yl)imidazo[1,2-b]pyridazine-3-carboxamide | F | | 13.15 (s, 1H), 10.96 (s, 1H), 9.93 (d, J = 7.8 Hz, 1H), 9.40 (dd, J = 6.9, 1.7 Hz, 1H), 8.96 (dd, J = 4.3, 1.7 Hz, 1H), 8.39 (t, J = 1.0 Hz, 1H), 8.14 (t, J = 1.3 Hz, 1H), 7.88 (dd, J = 8.7, 1.6 Hz, 1H), 7.65-7.50 (m, 5H), 7.49-7.43 (m, 2H), 7.39 (dd, J = 6.9, 4.3 Hz, 1H), 7.33 (td, J = 8.1, 5.0 Hz, 1H), 7.18 (d, J = 7.8 Hz, 1H), 5.61 (d, J = 7.8 Hz, 1H). | (method C) 531.4 [M + H]+ at 3.43 min |

77. 2-[6-(2-Hydroxy-2-methylpropyl)pyridin-3-yl]-N-[(3S)-9-fluoro-2-oxo-5-phenyl-1,3-dihydro-1,4-benzodiazepin-3-yl]pyrazolo[1,5-a]pyrimidine-3-carboxamide

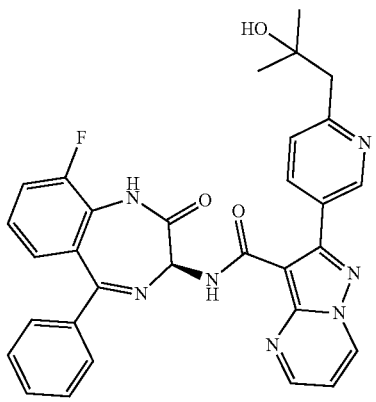 [SMILES: CC(C)(O)Cc1ccc(-c2nn3cccnc3c2C(=O)N[C@H]2N=C(c3ccccc3)c3cccc(F)c3NC2=O)cn1]

Prepared by the amide coupling procedure E described for the compound of Example 48, with additional purification by reverse phase column chromatography [5-40% MeCN (0.1% formic acid) in water (0.1% formic acid)], then preparative HPLC [method 3: 15-100% MeCN in water (0.1% formic acid)] to afford a white solid (9 mg, 5%). LCMS (method C) m/z 564.4 [M+H]$^+$ at 2.40 min. $^1$H NMR (500 MHz, DMSO-d$_6$) δ 10.97 (s, 1H), 9.86 (d, J=7.8 Hz, 1H), 9.43 (dd, J=7.0, 1.7 Hz, 1H), 8.98 (dd, J=4.3, 1.7 Hz, 1H), 8.89 (d, J=2.3 Hz, 1H), 8.16 (dd, J=8.1, 2.3 Hz, 1H), 7.64-7.56 (m, 1H), 7.56-7.49 (m, 3H), 7.49-7.28 (m, 5H), 7.18 (d, J=7.9 Hz, 1H), 5.59 (d, J=7.8 Hz, 1H), 4.72 (s, 1H), 2.88 (s, 2H), 1.12 (s, 6H).

The following compounds of the invention were prepared by an analogous procedure to that described for the compound of Example 48 (amide coupling procedure E). For Example 79, 10 eq. of LiOH (1.5 M aq.) was employed in the ester hydrolysis stage. Example 81 was subject to additional purification by reverse phase column chromatography [15-70% McCN in water w/0.1% (NH$_4$)$_2$CO$_3$].

TABLE 9

Imidazopyridazines prepared by amide coupling procedure E

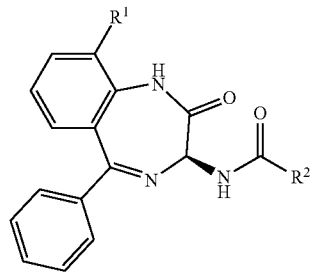

| Example | Name | R$^1$ | R$^2$ | $^1$H NMR δ (500 MHz, DMSO-d$_6$) | LCMS (ES+) m/z |
|---|---|---|---|---|---|
| 78 | N-[(3S)-9-fluoro-2-oxo-5-phenyl-1,3-dihydro-1,4-benzodiazepin-3-yl]-2-(5-fluoropyridin-2-yl)-6-methylimidazo[1,2-b]pyridazine-3-carboxamide | F | 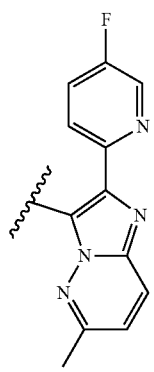 [SMILES: *c1c(-c2ccc(F)cn2)nc2ccc(C)nn12] | 10.98 (s, 1H), 10.93 (d, J = 7.3 Hz, 1H), 8.63 (d, J = 2.9 Hz, 1H), 8.25 (d, J = 9.3 Hz, 1H), 8.05 (dd, J = 8.8, 4.6 Hz, 1H), 7.86 (td, J = 8.8, 3.0 Hz, 1H), 7.65-7.58 (m, 1H), 7.57-7.50 (m, 3H), 7.50-7.42 (m, 3H), 7.34 (td, J = 8.1, 5.0 Hz, 1H), 7.20 (d, J = 7.9 Hz, 1H), 5.56 (d, J = 7.2 Hz, 1H), 2.67 (s, 3H). | (method C) 524.4 [M + H]$^+$ at 3.55 min |

TABLE 9-continued

Imidazopyridazines prepared by amide coupling procedure E

| Example | Name | R¹ | R² | ¹H NMR δ (500 MHz, DMSO-d₆) | LCMS (ES+) m/z |
|---|---|---|---|---|---|
| 79 | N-[(3S)-9-Fluoro-2-oxo-5-phenyl-1,3-dihydro-1,4-benzodiazepin-3-yl]-2-(2-fluorophenyl)-6-morpholin-4-ylimidazo[1,2-b]pyridazine-3-carboxamide | F | | 11.05 (s, 1H), 10.36 (d, J = 7.4 Hz, 1H), 8.15 (d, J = 10.0 Hz, 1H), 7.62-7.55 (m, 1H), 7.55-7.38 (m, 8H), 7.35-7.27 (m, 1H), 7.26-7.20 (m, 1H), 7.20-7.12 (m, 2H), 5.51 (d, J = 7.3 Hz, 1H), 3.80-3.65 (m, 8H). | (method C) 593.6 [M + H]⁺ at 4.40 min |
| 80 | N-[(3S)-9-fluoro-2-oxo-5-phenyl-1,3-dihydro-1,4-benzodiazepin-3-yl]-6-[(1S,4S)-5-methyl-2,5-diazabicyclo[2.2.1]heptan-2-yl]-2-phenylimidazo[1,2-b]pyridazine-3-carboxamide | F | | 11.01 (s, 1H), 10.77 (d, J = 7.2 Hz, 1H), 8.06 (d, J = 9.9 Hz, 1H), 7.87-7.82 (m, 2H), 7.64-7.42 (m, 6H), 7.39-7.28 (m, 5H), 7.18 (d, J = 8.0 Hz, 1H), 5.56 (d, J = 7.1 Hz, 1H), 4.90 (s, 1H), 3.68 (s, 1H), 3.54 (d, J = 10.4 Hz, 1H), 3.50 (s, 1H), 2.86 (d, J = 9.8 Hz, 1H), 2.69-2.57 (m, 1H), 2.31 (s, 3H), 1.92 (d, J = 9.6 Hz, 1H), 1.85 (d, J = 9.6 Hz, 1H). | (method C) 601.4 [M + H]⁺ at 2.60 min |
| 81 | N-[(3S)-9-fluoro-2-oxo-5-phenyl-1,3-dihydro-1,4-benzodiazepin-3-yl]-6-[(1R,4R)-5-methyl-2,5-diazabicyclo[2.2.1]heptan-2-yl]-2-phenylimidazo[1,2-b]pyridazine-3-carboxamide | F | | 11.04 (s, 1H), 10.77 (d, J = 7.4 Hz, 1H), 8.05 (d, J = 9.8 Hz, 1H), 7.86-7.81 (m, 2H), 7.59 (t, J = 9.2 Hz, 1H), 7.56-7.48 (m, 3H), 7.48-7.42 (m, 2H), 7.39-7.29 (m, 4H), 7.24-7.15 (m, 2H), 5.57 (d, J = 7.3 Hz, 1H), 5.07-4.84 (m, 1H), 3.91-3.69 (m, 1H), 3.52-3.46 (m, 2H), 2.87-2.81 (m, 1H), 2.67-2.59 (m, 1H), 2.30 (s, 3H), 1.94-1.88 (m, 1H), 1.85 (d, J = 9.4 Hz, 1H). | (method C) 601.4 [M + H]⁺ at 2.61 min |

TABLE 9-continued

Imidazopyridazines prepared by amide coupling procedure E

| Example | Name | R¹ | R² | ¹H NMR δ (500 MHz, DMSO-d$_6$) | LCMS (ES+) m/z |
|---|---|---|---|---|---|
| 82 | N-[(3S)-9-fluoro-2-oxo-5-phenyl-1,3-dihydro-1,4-benzodiazepin-3-yl]-6-[(1R,4R)-2-oxa-5-azabicyclo[2.2.1]heptan-5-yl]-2-phenylimidazo[1,2-b]pyridazine-3-carboxamide | F |  | 11.08 (s, 1H), 10.73 (d, J = 7.3 Hz, 1H), 8.10 (d, J = 9.8 Hz, 1H), 7.87-7.81 (m, 2H), 7.61 (t, J = 9.2 Hz, 1H), 7.56-7.40 (m, 5H), 7.40-7.29 (m, 4H), 7.23 (s, 1H), 7.20-7.15 (m, 1H), 5.58 (d, J = 7.2 Hz, 1H), 5.25 (s, 1H), 4.72 (s, 1H), 3.88-3.84 (m, 1H), 3.79 (d, J = 7.5 Hz, 1H), 3.69-3.64 (m, 2H), 2.04 (d, J = 9.8 Hz, 1H), 1.92 (d, J = 9.8 Hz, 1H). | (method C) 588.4 [M + H]⁺ at 4.14 min |
| 83 | N-[(3S)-9-fluoro-2-oxo-5-phenyl-1,3-dihydro-1,4-benzodiazepin-3-yl]-6-morpholin-4-yl-2-phenylimidazo[1,2-b]pyridazine-3-carboxamide | F |  | 11.07 (s, 1H), 10.50 (d, J = 7.2 Hz, 1H), 8.14 (d, J = 10.0 Hz, 1H), 7.87-7.82 (m, 2H), 7.61 (t, J = 9.2 Hz, 1H), 7.57-7.40 (m, 6H), 7.40-7.29 (m, 4H), 7.18 (d, J = 7.9 Hz, 1H), 5.57 (d, J = 7.2 Hz, 1H), 3.79-3.75 (m, 4H), 3.75-3.63 (m, 4H). | (method C) 576.4 [M + H]⁺ at 4.32 min |

84. N-[(3S)-9-fluoro-2-oxo-5-phenyl-1,3-dihydro-1,4-benzodiazepin-3-yl]-2-(2-fluorophenyl)[(1R,4R)-5-methyl-2,5-diazabicyclo[2.2.1]heptan-2-yl]pyrazolo[1,5-a]pyrimidine-3-carboxamide

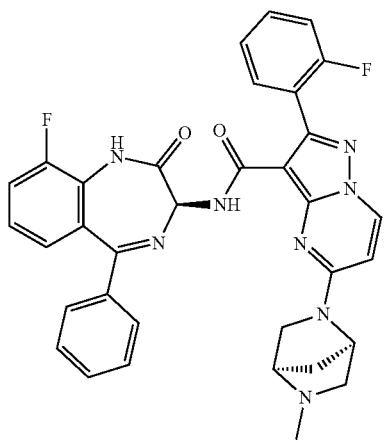 [SMILES: CN1C[C@H]2C[C@@H]1CN2c1ccn2nc(-c3ccccc3F)c(C(=O)N[C@H]3N=C(c4ccccc4)c4cccc(F)c4NC3=O)c2n1]

A solution of intermediate 6P (124 mg, 0.282 mmol) and LiOH (1.5 M aq; 0.55 mL, 0.825 mmol) in THF/MeOH (1:1; 2.18 mL) was stirred at rt overnight, then at 40° C. for 86 h. The mixture was cooled to rt, acidified (pH≈1) with 1 M aq. HCl (0.92 mL, 0.920 mmol) and concentrated under reduced pressure. A portion of the crude acid (52 mg, 0.135 mmol) was taken directly to the next reaction and dissolved in DME (1.5 mL). HATU (51 mg, 0. 135 mmol), NEt$_3$ (75 µL, 0.541 mmol) and then (3S)-3-amino-9-fluoro-5-phenyl-1,3-dihydro-1,4-benzodiazepin-2-one (36 mg, 0.135 mmol) were added and the reaction stirred at rt for 1 h. The reaction was quenched with water (5 mL), acidified (pH≈2) with AcOH, and purified by ion exchange chromatography (2 g SCX-2). The resulting residue was further purified by column chromatography [0-7% (0.7 N NH$_3$ in MeOH) in CH$_2$Cl$_2$] to afford a cream solid (13 mg, 15%) as a mixture of rotamers. 0.5H corresponds to 1H of a rotameric peak in the $^1$H NMR assignment. LCMS (method C) m/z 619.4 [M+H]$^+$ at 2.42 min. $^1$H NMR (500 MHz, DMSO-d$_6$) δ 11.08-10.89 (m, 1H), 10.02-9.92 (m, 1H), 8.85-8.75 (m, 1H), 7.61-7.54 (m, 1H), 7.54-7.39 (m, 6H), 7.34-7.25 (m, 1H), 7.24-7.10 (m, 3H), 6.85 (d, J=7.8 Hz, 0.5H), 6.54 (d, J=7.8 Hz, 0.5H), 5.49-5.43 (m, 1H), 5.40 (d, J=7.3 Hz, 0.5H), 4.82 (s, 0.5H), 4.16-4.09 (m, 0.5H), 3.68-3.60 (m, 0.5H), 3.58 (s, 0.5H), 3.52-3.43 (m, 1.5H), 2.95-2.87 (m, 0.5H), 2.84-2.77 (m, 0.5H), 2.70-2.63 (m, 0.5H), 2.37-2.27 (m, 3H), 2.01-1.94 (m, 0.5H), 1.93-1.79 (m, 2H), 1.75 (s, 1H).

85. 2-(2-Fluoro-6-methylpyridin-3-yl)-N-[(3S)-2-oxo-5-phenyl-1,3-dihydro-1,4-benzodiazepin-3-yl]pyrazolo[1,5-a]pyrimidine-3-carboxamide

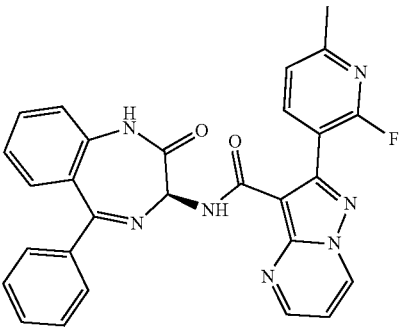 [SMILES: Cc1ccc(-c2nn3cccnc3c2C(=O)N[C@H]2N=C(c3ccccc3)c3ccccc3NC2=O)c(F)n1]

86. 2-(2-Methoxy-6-methylpyridin-3-yl)-N-[(3S)-2-oxo-5-phenyl-1,3-dihydro-1,4-benzodiazepin-3-yl]pyrazolo[1,5-a]pyrimidine-3-carboxamide

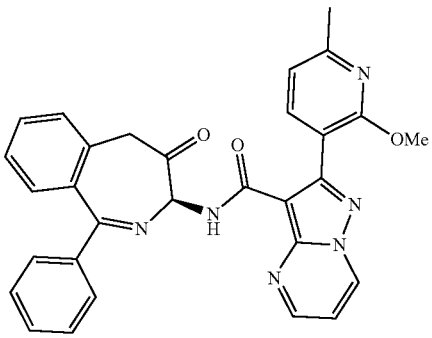 [SMILES: COc1nc(C)ccc1-c1nn2cccnc2c1C(=O)N[C@H]1N=C(c2ccccc2)c2ccccc2CC1=O]

A solution of intermediate 27B (227 mg, 0.717 mmol) and LiOH (1.5 M aq; 4.78 mL, 7.17 mmol) in THF/MeOH (1:1; 6 mL) was heated at 40° C. for 48 h. The reaction mixture was cooled to rt, was diluted with water (20 mL) and washed with MTBE (3×10 mL). The aqueous layer was acidified (pH≈1) with 1 M aq. HCl and extracted with CHCl$_3$/iPrOH (3:1; 3×10 mL). The combined organic extracts were dried (Na$_2$SO$_4$), and the solvent removed under reduced pressure to afford a white solid (151 mg) which was used without further purification. The residue was dissolved in DMF (1.5 mL), HATU (208 mg, 0.547 mmol), NEt$_3$ (123 µL, 0.882 mmol) and then (3S)-3-amino-5-phenyl-1,3-dihydro-1,4-benzodiazepin-2-one (137 mg, 0.546 mmol) were added, and the reaction stirred at 40° C. for 1 h. Analogous workup and purification to that described for Example 42 was followed by additional purification by preparative HPLC [method 2: 20-100% MeCN in water (0.1% formic acid)].

Example 85: White solid (28 mg, 8%). LCMS (method C) 506.4 [M+H]+ at 3.73 min. $^1$H NMR (500 MHz, DMSO-d$_6$) δ 11.01 (s, 1H), 9.56 (d, J=8.0 Hz, 1H), 9.43 (dd, J=7.0, 1.7 Hz, 1H), 9.01 (dd, J=4.3, 1.7 Hz, 1H), 7.96 (dd, J=9.6, 7.5 Hz, 1H), 7.68-7.61 (m, 1H), 7.54-7.48 (m, 1H), 7.48-7.40 (m, 5H), 7.34-7.23 (m, 4H), 5.45 (d, J=8.0 Hz, 1H), 2.47 (s, 3H).

Example 86: White solid (14 mg, 3%). LCMS (method C) m/z 518.5 [M+H]$^+$ at 3.96 min. $^1$H NMR (500 MHz, DMSO-d$_6$) δ 10.99 (s, 1H), 9.50 (d, J=8.0 Hz, 1H), 9.37 (dd, J=7.0, 1.7 Hz, 1H), 8.95 (dd, J=4.3, 1.7 Hz, 1H), 7.67-7.61 (m, 1H), 7.59 (d, J=7.4 Hz, 1H), 7.53-7.48 (m, 1H), 7.48-7.41 (m, 4H), 7.37 (dd, J=7.0, 4.3 Hz, 1H), 7.34-7.28 (m, 2H), 7.28-7.22 (m, 1H), 6.89 (d, J=7.4 Hz, 1H), 5.41 (d, J=7.9 Hz, 1H), 3.74 (s, 3H), 2.43 (s, 3H).

87. N-[(3S)-2-oxo-5-phenyl-1,3-dihydro-1,4-benzodiazepin-3-yl]-2-phenylimidazo[1,2-b]pyridazine-3-carboxamide (Procedure F)

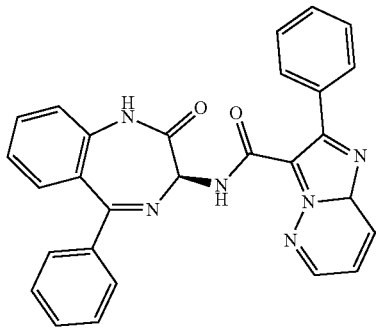

A solution of intermediate 45A (58 mg, 0.217 mmol) and LiOH.H$_2$O (91 mg, 2.174 mmol) in MeOH:THF:water (2:2:1; 5 mL) was heated to 50° C. for 2 h. The reaction mixture was cooled to rt, neutralised with 1 M aq. HCl to pH≈7, then concentrated under reduced pressure. The crude product was dissolved in DMF (1.5 mL), (3S)-3-amino-5-phenyl-1,3-dihydro-1,4-benzodiazepin-2-one (55 mg, 0.217 mmol) and NEt$_3$ (91 μL, 0.651 mmol) added, followed by HATU (83 mg, 0.217 mmol). The reaction was stirred at rt for 18 h, quenched with water (10 mL), and the resultant precipitate filtered, washing with water. The precipitate was dissolved in 10% MeOH/CH$_2$Cl$_2$, passed through a phase separation cartridge, concentrated under reduced pressure, and purified by column chromatography (0-10% MeOH in CH$_2$Cl$_2$) to afford an off-white solid (30 mg, 29%). LCMS (method D) m/z 473.4 [M+H]$^+$ at 3.89 min. $^1$H NMR (500 MHz, DMSO-d$_6$) δ 11.05 (s, 1H), 10.34 (d, J=7.4 Hz, 1H), 8.86 (dd, J=4.5, 1.6 Hz, 1H), 8.38 (dd, J=9.2, 1.6 Hz, 1H), 8.01-7.95 (m, 2H), 7.68 (ddd, J=8.6, 7.2, 1.6 Hz, 1H), 7.57-7.39 (m, 9H), 7.36 (dd, J=8.1, 1.4 Hz, 2H), 7.29 (ddd, J=8.3, 7.3, 1.2 Hz, 1H), 5.54 (d, J=7.4 Hz, 1H).

The following compounds of the invention were prepared by the amide coupling procedure F described for the compound of Example 87. The procedure was performed with 5 eq. of NEt$_3$ for Examples 95-105, and with 10 eq. of NEt$_3$ for Example 106. Example 107 was subject to additional purification by reverse phase column chromatography (5-60% MeCN in 10 mM (NH$_4$)$_2$CO$_3$ aq. solution).

TABLE 10

Example compounds prepared by amide coupling procedure F

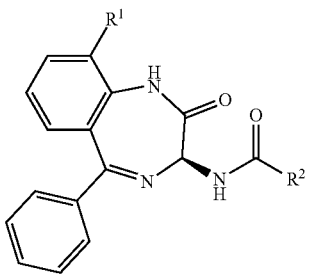

| Example | Name | R$^1$ | R$^2$ | $^1$H NMR δ (500 MHz, DMSO-d$_6$) | LCMS (ES+) m/z |
|---|---|---|---|---|---|
| 88 | 2-(2,4-Difluorophenyl)-N-[(3S)-2-oxo-5-phenyl-1,3-dihydro-1,4-benzodiazepin-3-yl]imidazo[1,2-b]pyridazine-3-carboxamide | H | 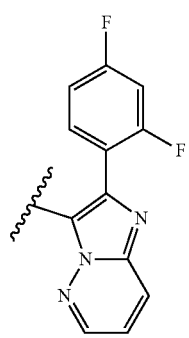 [SMILES: *c1c(-c2ccc(F)cc2F)nc2cccnn12] | 11.05 (s, 1H), 10.17 (d, J = 7.7 Hz, 1H), 8.99 (dd, J = 4.6, 1.6 Hz, 1H), 8.46 (dd, J = 9.3, 1.6 Hz, 1H), 7.69-7.63 (m, 1H), 7.66-7.58 (m, 2H), 7.56-7.49 (m, 1H), 7.51-7.42 (m, 4H), 7.37-7.31 (m, 2H), 7.31-7.24 (m, 2H), 7.17 (td, J = 8.4, 2.6 Hz, 1H), 5.48 (d, J = 7.6 Hz, 1H). | (method D) 509.4 [M + H]$^+$ at 4.02 min |

TABLE 10-continued

Example compounds prepared by amide coupling procedure F

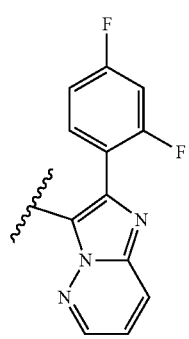 [SMILES: *c1c(-c2ccc(F)cc2F)nc2cccnn12]

| Example | Name | R$^1$ | R$^2$ | $^1$H NMR δ (500 MHz, DMSO-d$_6$) | LCMS (ES+) m/z |
|---|---|---|---|---|---|
| 89 | 2-(2,4-Difluorophenyl)-N-[(3S)-9-fluoro-2-oxo-5-phenyl-1,3-dihydro-1,4-benzodiazepin-3-yl]imidazo[1,2-b]pyridazine-3-carboxamide | F | 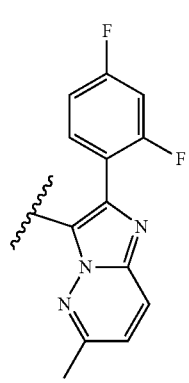 [SMILES: *c1c(-c2ccc(F)cc2F)nc2ccc(C)nn12] | 11.02 (s, 1H), 10.19 (d, J = 7.5 Hz, 1H), 8.99 (dd, J = 4.6, 1.6 Hz, 1H), 8.46 (dd, J = 9.3, 1.6 Hz, 1H), 7.66-7.57 (m, 3H), 7.56-7.44 (m, 5H), 7.36-7.24 (m, 2H), 7.20-7.13 (m, 2H), 5.57 (d, J = 7.5 Hz, 1H) | (method D) 527.3 [M + H]$^+$ at 3.96 min |
| 90 | 2-(2,4-Difluorophenyl)-6-methyl-N-[(3S)-2-oxo-5-phenyl-1,3-dihydro-1,4-benzodiazepin-3-yl]imidazo[1,2-b]pyridazine-3-carboxamide | H | 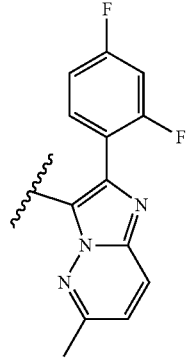 [SMILES: *c1c(-c2ccc(F)cc2F)nc2ccc(C)nn12] | 11.04 (s, 1H), 10.55 (d, J = 7.3 Hz, 1H), 8.34 (d, J = 9.4 Hz, 1H), 7.69-7.56 (m, 2H), 7.56-7.49 (m, 2H), 7.49-7.41 (m, 4H), 7.36-7.32 (m 2H), 7.31-7.23 (m, 2H), 7.16 (td, J = 8.6, 2.6 Hz, 1H), 5.45 (d, J = 7.3 Hz, 1H), 2.75 (s, 3H) | (method D) 523.4 [M + H]$^+$ at 4.20 min |
| 91 | 2-(2,4-Difluorophenyl)-N-[(3S)-9-fluoro-2-oxo-5-phenyl-1,3-dihydro-1,4-benzodiazepin-3-yl]-6-methylimidazo[1,2-b]pyridazine-3-carboxamide | F | | 11.02 (s, 1H), 10.59 (d, J = 7.2 Hz, 1H), 8.33 (d, J = 9.4 Hz, 1H), 7.65-7.57 (m, 2H), 7.57-7.42 (m, 6H), 7.33 (td, J = 8.0, 4.9 Hz, 1H), 7.27 (td, J = 9.8, 2.6 Hz, 1H), 7.20-7.12 (m, 2H), 5.53 (d, J = 7.1 Hz, 1H), 2.75 (s, 3H) | (method D) 541.4 [M + H]$^+$ at 4.22 min |

TABLE 10-continued

Example compounds prepared by amide coupling procedure F

| Example | Name | R¹ | R² | ¹H NMR δ (500 MHz, DMSO-d₆) | LCMS (ES+) m/z |
|---------|------|----|----|------------------------------|----------------|
| 92 | 6-Methyl-N-[(3S)-2-oxo-5-phenyl-1,3-dihydro-1,4-benzodiazepin-3-yl]-2-phenylimidazo[1,2-b]pyridazine-3-carboxamide | H | (structure) | 11.04 (s, 1H), 10.71 (d, J = 7.1 Hz, 1H), 8.28 (d, J = 9.3 Hz, 1H), 7.99-7.93 (m, 2H), 7.67 (ddd, J = 8.5, 7.2, 1.6 Hz, 1H), 7.56-7.33 (m, 11H), 7.33-7.26 (m, 1H), 5.50 (d, J = 7.1 Hz, 1H), 2.72 (s, 3H). | (method D) 487.5 [M + H]⁺ at 4.11 min |
| 93 | N-[(3S)-9-Fluoro-2-oxo-5-phenyl-1,3-dihydro-1,4-benzodiazepin-3-yl]-6-methyl-2-phenylimidazo[1,2-b]pyridazine-3-carboxamide | F | (structure) | 11.02 (s, 1H), 10.76 (d, J = 7.0 Hz, 1H), 8.29 (d, J = 9.3 Hz, 1H), 7.96 (d, 2H), 7.66-7.58 (m, 1H), 7.58-7.51 (m, 3H), 7.50-7.44 (m, 3H), 7.44-7.37 (m, 3H), 7.34 (td, J = 8.1, 4.9 Hz, 1H), 7.20 (d, J = 7.9 Hz, 1H), 5.59 (d, J = 7.0 Hz, 1H), 2.73 (s, 3H). | (method D) 505.4 [M + H]⁺ at 4.19 min |
| 94 | 6-(Azetidin-1-yl)-N-[(3S)-9-fluoro-2-oxo-5-phenyl-1,3-dihydro-1,4-benzodiazepin-3-yl]-2-(2-fluorophenyl)imidazo[1,2-b]pyridazine-3-carboxamide | F | (structure) | 10.96 (s, 1H), 10.65 (d, J = 7.3 Hz, 1H), 8.08 (d, J = 9.7 Hz, 1H), 7.59 (t, J = 9.2 Hz, 1H), 7.55-7.38 (m, 7H), 7.35-7.29 (m, 1H), 7.26-7.19 (m, 1H), 7.21-7.13 (m, 2H), 6.95 (d, J = 9.7 Hz, 1H), 5.50 (d, J = 7.3 Hz, 1H), 4.33-4.18 (m, 4H), 2.48-2.39 (m, 2H). | (method D) 564.4 [M + H]⁺ at 4.31 min |

TABLE 10-continued

Example compounds prepared by amide coupling procedure F

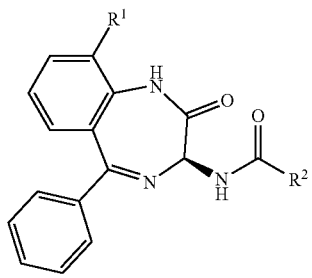

| Example | Name | R[1] | R[2] | $^1$H NMR δ (500 MHz, DMSO-$d_6$) | LCMS (ES+) m/z |
|---|---|---|---|---|---|
| 95 | N-[(3S)-9-fluoro-2-oxo-5-phenyl-1,3-dihydro-1,4-benzodiazepin-3-yl]-2-(2-fluorophenyl)-6-(4-methylpiperazin-1-yl)imidazo[1,2-b]pyridazine-3-carboxamide | F | *structure* | 11.02 (s, 1H), 10.37 (d, J = 7.4 Hz, 1H), 8.12 (d, J = 10.0 Hz, 1H), 7.63-7.27 (m, 10H), 7.27-7.11 (m, 3H), 5.51 (d, J = 7.3 Hz, 1H), 3.86-3.64 (m, 4H), 2.51-2.46 (m, 4H), 2.23 (s, 3H). | (method D) 607.3 [M + H]+ at 4.09 min |
| 96 | N-[(3S)-9-fluoro-2-oxo-5-phenyl-1,3-dihydro-1,4-benzodiazepin-3-yl]-6-methyl-2-pyridin-3-ylimidazo[1,2-b]pyridazine-3-carboxamide | F | *structure* | 11.03 (s, 1H), 10.80 (d, J = 7.0 Hz, 1H), 9.06 (dd, J = 2.3, 0.9 Hz, 1H), 8.58 (dd, J = 4.8, 1.7 Hz, 1H), 8.35 (d, J = 9.3 Hz, 1H), 8.30 (dt, J = 7.9, 2.0 Hz, 1H), 7.66-7.58 (m, 1H), 7.57-7.50 (m, 4H), 7.50-7.43 (m, 3H), 7.34 (td, J = 8.0, 4.9 Hz, 1H), 7.20 (d, J = 7.8 Hz, 1H), 5.59 (d, J = 6.9 Hz, 1H), 2.75 (s, 3H). | (method C) 506.5 [M + H]+ at 2.51 min |
| 97 | 6-Methyl-2-(2-methylpyridin-4-yl)-N-[(3S)-2-oxo-5-phenyl-1,3-dihydro-1,4-benzodiazepin-3-yl]imidazo[1,2-b]pyridazine-3-carboxamide | H | *structure* | 11.07 (s, 1H), 10.70 (d, J = 7.0 Hz, 1H), 8.49 (d, J = 5.2 Hz, 1H), 8.30 (d, J = 9.3 Hz, 1H), 7.83 (d, J = 1.6 Hz, 1H), 7.76 (dd, J = 5.2, 1.7 Hz, 1H), 7.68 (ddd, J = 8.5, 7.2, 1.6 Hz, 1H), 7.56-7.42 (m, 6H), 7.37 (dt, J = 8.1, 1.6 Hz, 2H), 7.30 (td, J = 7.5, 1.2 Hz, 1H), 5.51 (d, J = 7.0 Hz, 1H), 2.71 (s, 3H), 2.53 (s, 3H). | (method C) 502.5 [M + H]+ at 2.16 min |

TABLE 10-continued

Example compounds prepared by amide coupling procedure F

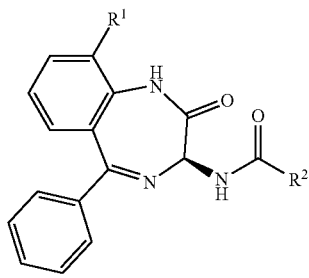

| Example | Name | R[1] | R[2] | $^1$H NMR δ (500 MHz, DMSO-d$_6$) | LCMS (ES+) m/z |
|---|---|---|---|---|---|
| 98 | N-[(3S)-9-fluoro-2-oxo-5-phenyl-1,3-dihydro-1,4-benzodiazepin-3-yl]-6-methyl-2-(2-methylpyridin-4-yl)imidazo[1,2-b]pyridazine-3-carboxamide | F | 2-methylpyridin-4-yl-imidazo[1,2-b]pyridazine | 11.04 (s, 1H), 10.74 (d, J = 6.9 Hz, 1H), 8.49 (d, J = 5.2 Hz, 1H), 8.31 (d, J = 9.4 Hz, 1H), 7.82 (d, J = 1.6 Hz, 1H), 7.76 (dd, J = 5.1, 1.7 Hz, 1H), 7.65-7.60 (m, 1H), 7.58-7.44 (m, 6H), 7.38-7.32 (m, 1H), 7.21 (d, J = 8.0 Hz, 1H), 5.60 (d, J = 6.9 Hz, 1H), 2.72 (s, 3H), 2.53 (s, 3H). | (method C) 520.5 [M + H]$^+$ at 2.21 min |
| 99 | 2-(3-Fluoropyridin-4-yl)-6-methyl-N-[(3S)-2-oxo-5-phenyl-1,3-dihydro-1,4-benzodiazepin-3-yl]imidazo[1,2-b]pyridazine-3-carboxamide | H | 3-fluoropyridin-4-yl-imidazo[1,2-b]pyridazine | 11.06 (s, 1H), 10.53 (d, J = 7.3 Hz, 1H), 8.62 (d, J = 1.6 Hz, 1H), 8.51 (dd, J = 4.8, 1.1 Hz, 1H), 8.38 (d, J = 9.4 Hz, 1H), 7.70-7.60 (m, 2H), 7.57 (d, J = 9.4 Hz, 1H), 7.55-7.49 (m, 1H), 7.49-7.41 (m, 4H), 7.34 (dt, J = 7.9, 1.6 Hz, 2H), 7.31-7.24 (m, 1H), 5.45 (d, J = 7.2 Hz, 1H), 2.76 (s, 3H). | (method C) 506.4 [M + H]$^+$ at 3.43 min |
| 100 | N-[(3S)-9-fluoro-2-oxo-5-phenyl-1,3-dihydro-1,4-benzodiazepin-3-yl]-2-(3-fluoropyridin-4-yl)-6-methylimidazo[1,2-b]pyridazine-3-carboxamide | F | 3-fluoropyridin-4-yl-imidazo[1,2-b]pyridazine | 11.03 (s, 1H), 10.58 (d, J = 7.2 Hz, 1H), 8.62 (d, J = 1.6 Hz, 1H), 8.51 (dd, J = 4.9, 1.1 Hz, 1H), 8.38 (d, J = 9.4 Hz, 1H), 7.65-7.56 (m, 3H), 7.55-7.43 (m, 5H), 7.33 (td, J = 8.1, 5.0 Hz, 1H), 7.18 (d, J = 8.0 Hz, 1H), 5.54 (d, J = 7.1 Hz, 1H), 2.76 (s, 3H). | (method C) 524.4 [M + H]$^+$ at 3.48 min |

TABLE 10-continued

Example compounds prepared by amide coupling procedure F

| Example | Name | R¹ | R² | ¹H NMR δ (500 MHz, DMSO-d₆) | LCMS (ES+) m/z |
|---|---|---|---|---|---|
| 101 | 2-(5-Fluoropyridin-3-yl)-6-methyl-N-[(3S)-2-oxo-5-phenyl-1,3-dihydro-1,4-benzodiazepin-3-yl]imidazo[1,2-b]pyridazine-3-carboxamide | H | | 11.08 (s, 1H), 10.78 (d, J = 7.0 Hz, 1H), 8.98 (t, J = 1.7 Hz, 1H), 8.61 (d, J = 2.8 Hz, 1H), 8.36 (d, J = 9.3 Hz, 1H), 8.26 (ddd, J = 10.3, 2.8, 1.6 Hz, 1H), 7.68 (ddd, J = 8.5, 7.2, 1.6 Hz, 1H), 7.57-7.48 (m, 4H), 7.48-7.42 (m, 2H), 7.37 (ddd, J = 8.1, 2.6, 1.3 Hz, 2H), 7.30 (td, J = 7.6, 1.2 Hz, 1H), 5.51 (d, J = 7.0 Hz, 1H), 2.75 (s, 3H). | (method C) 506.4 [M + H]⁺ at 3.77 min |
| 102 | N-[(3S)-9-fluoro-2-oxo-5-phenyl-1,3-dihydro-1,4-benzodiazepin-3-yl]-2-(5-fluoropyridin-3-yl)-6-methylimidazo[1,2-b]pyridazine-3-carboxamide | F | | 11.05 (s, 1H), 10.82 (d, J = 6.9 Hz, 1H), 8.98 (t, J = 1.7 Hz, 1H), 8.62 (d, J = 2.8 Hz, 1H), 8.36 (d, J = 9.3 Hz, 1H), 8.25 (ddd, J = 10.3, 2.8, 1.7 Hz, 1H), 7.62 (ddd, J = 10.1, 8.3, 1.4 Hz, 1H), 7.57-7.51 (m, 4H), 7.50-7.42 (m, 2H), 7.35 (td, J = 8.1, 5.0 Hz, 1H), 7.21 (d, J = 8.2 Hz, 1H), 5.60 (d, J = 6.9 Hz, 1H), 2.75 (s, 3H). | (method C) 524.4 [M + H]⁺ at 3.80 min |
| 103 | N-[(3S)-9-fluoro-2-oxo-5-phenyl-1,3-dihydro-1,4-benzodiazepin-3-yl]-6-methyl-2-(5-methylpyridin-3-yl)imidazo[1,2-b]pyridazine-3-carboxamide | F | | 11.03 (s, 1H), 10.79 (d, J = 7.0 Hz, 1H), 8.87 (d, J = 2.0 Hz, 1H), 8.42 (d, J = 2.1 Hz, 1H), 8.33 (d, J = 9.3 Hz, 1H), 8.13-8.09 (m, 1H), 7.62 (dd, J = 10.3, 8.1 Hz, 1H), 7.52 (dd, J = 8.5, 4.8 Hz, 4H), 7.49-7.43 (m, 2H), 7.34 (td, J = 8.1, 4.9 Hz, 1H), 7.20 (d, J = 7.9 Hz, 1H), 5.59 (d, J = 6.9 Hz, 1H), 2.74 (s, 3H), 2.36 (s, 3H). | (method C) 520.4 [M + H]⁺ at 2.51 min |

TABLE 10-continued

Example compounds prepared by amide coupling procedure F

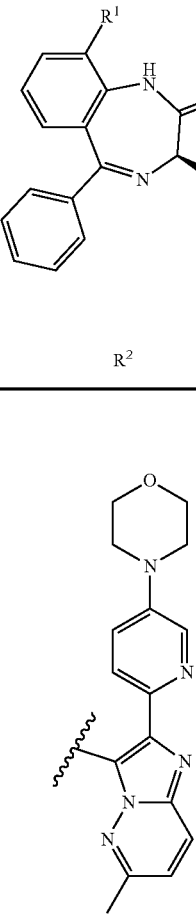

| Example | Name | R¹ | R² | ¹H NMR δ (500 MHz, DMSO-d$_6$) | LCMS (ES+) m/z |
|---|---|---|---|---|---|
| 104 | 6-Methyl-2-(6-morpholin-4-ylpyridin-3-yl)-N-[(3S)-2-oxo-5-phenyl-1,3-dihydro-1,4-benzodiazepin-3-yl]imidazo[1,2-b]pyridazine-3-carboxamide | H | 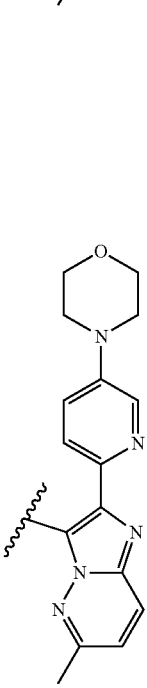 | 11.05 (s, 1H), 10.78 (d, J = 7.0 Hz, 1H), 8.74 (d, J = 2.3 Hz, 1H), 8.27 (d, J = 9.3 Hz, 1H), 8.16 (dd, J = 8.9, 2.4 Hz, 1H), 7.67 (t, J = 7.8 Hz, 1H), 7.56-7.42 (m, 6H), 7.39-7.33 (m, 2H), 7.30 (t, J = 7.5 Hz, 1H), 6.86 (d, J = 9.0 Hz, 1H), 5.50 (d, J = 6.9 Hz, 1H), 3.71 (t, J = 4.9 Hz, 4H), 3.52 (t, J = 4.8 Hz, 4H), 2.73 (s, 3H). | (method C) 573.4 [M + H]⁺ at 2.79 min |
| 105 | N-[(3S)-9-fluoro-2-oxo-5-phenyl-1,3-dihydro-1,4-benzodiazepin-3-yl]-6-methyl-2-(6-morpholin-4-ylpyridin-3-yl)imidazo[1,2-b]pyridazine-3-carboxamide | F | | 11.02 (s, 1H), 10.82 (d, J = 6.9 Hz, 1H), 8.74 (d, J = 2.4 Hz, 1H), 8.27 (d, J = 9.3 Hz, 1H), 8.16 (dd, J = 8.9, 2.4 Hz, 1H), 7.62 (t, J = 9.2 Hz, 1H), 7.53 (d, J = 7.5 Hz, 3H), 7.50-7.43 (m, 3H), 7.35 (td, J = 8.1, 4.9 Hz, 1H), 7.20 (d, J = 7.9 Hz, 1H), 6.86 (d, J = 9.0 Hz, 1H), 5.58 (d, J = 6.8 Hz, 1H), 3.71 (t, J = 4.8 Hz, 4H), 3.52 (t, J = 4.9 Hz, 4H), 2.73 (s, 3H). | (method C) 591.3 [M + H]⁺ at 2.80 min |

TABLE 10-continued

Example compounds prepared by amide coupling procedure F

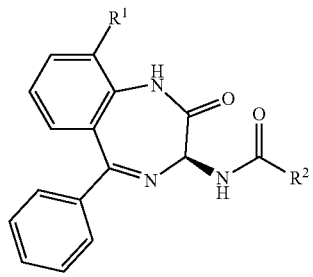

| Example | Name | R¹ | R² | ¹H NMR δ (500 MHz, DMSO-$d_6$) | LCMS (ES+) m/z |
|---|---|---|---|---|---|
| 106 | 6-(Ethylamino)-N-[(3S)-9-fluoro-2-oxo-5-phenyl-1,3-dihydro-1,4-benzodiazepin-3-yl]-2-(2-fluoro-phenyl)imidazo[1,2-b]pyridazine-3-carboxamide | F | 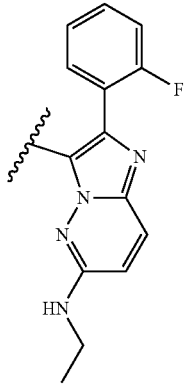 [SMILES: *c1c(-c2ccccc2F)nc2ccc(NCC)nn12] | 10.98 (s, 1H), 10.64 (d, J = 7.4 Hz, 1H), 7.93 (d, J = 9.8 Hz, 1H), 7.65-7.26 (m, 10H), 7.25-7.11 (m, 3H), 6.94 (d, J = 9.8 Hz, 1H), 5.51 (d, J = 7.3 Hz, 1H), 3.60-3.48 (m, 2H), 1.25 (t, J = 7.2 Hz, 3H). | (method D) 552.4 [M + H]⁺ at 4.27 min. |
| 107 | N-[(3S)-9-fluoro-2-oxo-5-phenyl-1,3-dihydro-1,4-benzodiazepin-3-yl]-2-phenylimidazo[1,2-b]pyridazine-3-carboxamide | F | 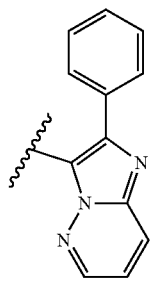 [SMILES: *c1c(-c2ccccc2)nc2cccnn12] | 11.01 (s, 1H), 10.36 (d, J = 7.3 Hz, 1H), 8.86 (d, J = 4.4 Hz, 1H), 8.38 (d, J = 9.2 Hz, 1H), 7.98 (d, J = 7.0 Hz, 2H), 7.62 (t, J = 9.2 Hz, 1H), 7.58-7.51 (m, 4H), 7.51-7.45 (m, 2H), 7.45-7.38 (m, 3H), 7.35-7.32 (m, 1H), 7.20 (d, J = 7.9 Hz, 1H), 5.62 (d, J = 7.0 Hz, 1H). | (method D) 491.4 [M + H]⁺ at 3.83 min |

108. N-[(3S)-9-Fluoro-2-oxo-5-phenyl-1,3-dihydro-1,4-benzodiazepin-3-yl]-2-(2-fluorophenyl)-6-(1-methylazetidin-3-yl)oxyimidazo[1,2-b]pyridazine-3-carboxamide

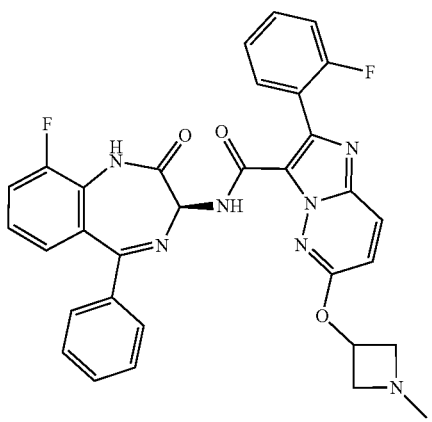 [SMILES: CN1CC(Oc2ccc3nc(-c4ccccc4F)c(C(=O)N[C@H]4N=C(c5ccccc5)c5cccc(F)c5NC4=O)n3n2)C1]

HATU (61 mg, 0.161 mmol) was added to a solution of crude intermediate 56A (55 mg, 0.161 mmol), (3S)-3-amino-9-fluoro-5-phenyl-1,3-dihydro-1,4-benzodiazepin-2-one (43 mg, 0.161 mmol) and NEt$_3$ (112 µL, 0.803 mmol) in DMF (3 mL) and the reaction stirred at rt overnight. Analogous workup and purification to that described for the compound of Example 87 afforded an off-white solid (30 mg, 31%). LCMS (method D) m/z 594.4 [M+H]$^+$ at 3.85 min. $^1$H NMR (500 MHz, DMSO-d$_6$) δ 11.08 (s, 1H), 9.89 (d, J=7.5 Hz, 1H), 8.33 (d, J=9.7 Hz, 1H), 7.65-7.41 (m, 8H), 7.37-7.16 (m, 5H), 5.55 (d, J=7.5 Hz, 1H), 5.51 (p, J=5.4 Hz, 1H), 3.92 (t, J=7.1 Hz, 1H), 3.85 (t, J=7.2 Hz, 1H), 3.27-3.19 (m, 2H), 2.22 (s, 3H).

109. N-[(3S)-9-Fluoro-2-oxo-5-phenyl-1,3-dihydro-1,4-benzodiazepin-3-yl]-6-(1-methylazetidin-3-yl)oxy-2-phenylimidazo[1,2-b]pyridazine-3-carboxamide

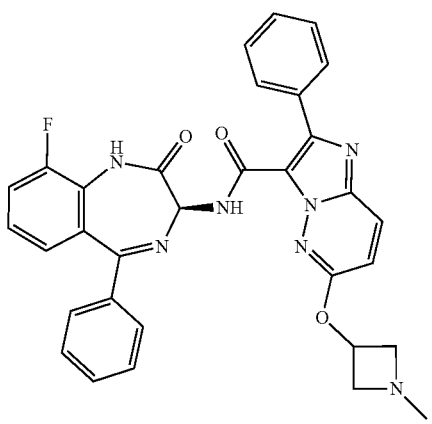 [SMILES: CN1CC(Oc2ccc3nc(-c4ccccc4)c(C(=O)N[C@H]4N=C(c5ccccc5)c5cccc(F)c5NC4=O)n3n2)C1]

Prepared by an analogous procedure to that described for the compound of Example 108. LCMS (method D) m/z 576.4 [M+H]$^+$ at 4.05 min. $^1$H NMR (500 MHz, DMSO-d$_6$) δ 11.07 (s, 1H), 10.01 (d, J=7.3 Hz, 1H), 8.29 (d, J=9.7 Hz, 1H), 7.93-7.84 (m, 2H), 7.63 (ddd, J=9.9, 8.2, 1.4 Hz, 1H), 7.60-7.52 (m, 3H), 7.51-7.44 (m, 2H), 7.43-7.31 (m, 4H), 7.22 (dd, J=9.4, 7.8 Hz, 2H), 5.62 (d, J=7.3 Hz, 1H), 5.45 (p, J=5.4 Hz, 1H), 3.91 (t, J=7.1 Hz, 1H), 3.85 (t, J=7.4 Hz, 1H), 3.22 (d, J=15.4 Hz, 2H), 2.23 (s, 3H).

110. N-[(3S)-9-Fluoro-2-oxo-5-phenyl-1,3-dihydro-1,4-benzodiazepin-3-yl]-2-(2-fluorophenyl)-6-(2-methoxyethoxy)imidazo[1,2-b]pyridazine-3-carboxamide

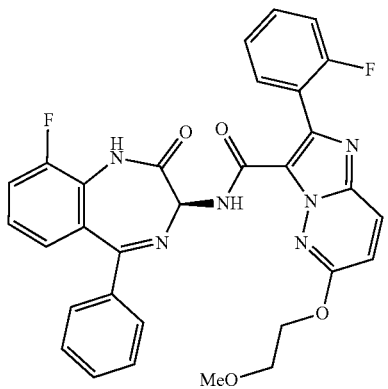 [SMILES: COCCOc1ccc2nc(-c3ccccc3F)c(C(=O)N[C@H]3N=C(c4ccccc4)c4cccc(F)c4NC3=O)n2n1]

Prepared by an analogous procedure to that described for the compound of Example 108 with 10 eq. NEt$_3$ in the amide coupling stage and additional purification by reverse phase column chromatography [10-60% MeCN in 10 mM (NH$_4$)$_2$CO$_3$ aq. solution]. LCMS (method D) m/z 582.6 [M+H]$^+$ at 4.20 min. $^1$H NMR (500 MHz, DMSO-d$_6$) δ 11.09 (s, 1H), 10.23 (d, J=7.2 Hz, 1H), 8.31 (d, J=9.7 Hz, 1H), 7.59 (t, J=9.2 Hz, 1H), 7.56-7.41 (m, 7H), 7.33 (t, J=7.0 Hz, 1H), 7.29 (d, J=9.8 Hz, 1H), 7.25 (td, J=7.5, 1.1 Hz, 1H), 7.23-7.18 (m, 1H), 7.17 (d, J=7.9 Hz, 1H), 5.52 (d, J=7.1 Hz, 1H), 4.84 (ddd, J=12.0, 5.8, 3.1 Hz, 1H), 4.71 (ddd, J=12.0, 5.4, 3.0 Hz, 1H), 3.78 (ddd, J=7.1, 4.5, 3.1 Hz, 2H), 3.33 (s, 3H).

111. 6-Methoxy-N-[(3S)-2-oxo-5-phenyl-1,3-dihydro-1,4-benzodiazepin-3-yl]-2-phenylimidazo[1,2-b]pyridazine-3-carboxamide

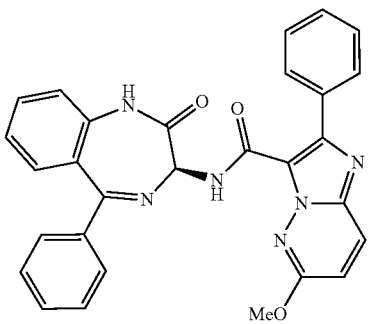 [SMILES: COc1ccc2nc(-c3ccccc3)c(C(=O)N[C@H]3N=C(c4ccccc4)c4ccccc4NC3=O)n2n1]

LiOH (1.5 M aq; 1.75 mL, 2.625 mmol) was added to a solution of intermediate 45C (180 mg, 0.597 mmol) in MeOH:water (1:1; 4 mL) and heated to 100° C. for 1 h by MWI. The reaction was cooled to rt, acidified with 1 M aq. HCl (3 mL) then concentrated under reduced pressure to afford an off-white solid (161 mg) which was taken directly to the next reaction. A portion of the crude residue (80 mg, 0.297 mmol) was dissolved in DMF (1.8 mL), HATU (113 mg, 0.298 mmol), NEt₃ (124 μL, 0.891 mmol), and (3S)-3-amino-5-phenyl-1,3-dihydro-1,4-benzodiazepin-2-one (75 mg, 0.297 mmol) added, and the reaction mixture was stirred at 40° C. overnight. Analogous workup and purification to that described for Example 42 afforded a white solid (32 mg, 22%). LCMS (method C) m/z 503.4 [M+H]⁺ at 4.32 min. ¹H NMR (500 MHz, DMSO-d₆) δ 11.06 (s, 1H), 10.36 (d, J=7.2 Hz, 1H), 8.26 (d, J=9.7 Hz, 1H), 7.92-7.86 (m, 2H), 7.70-7.63 (m, 1H), 7.55-7.32 (m, 10H), 7.32-7.25 (m, 1H), 7.22 (d, J=9.7 Hz, 1H), 5.51 (d, J=7.1 Hz, 1H), 4.21 (s, 3H).

The following compounds of the invention were prepared by an analogous procedure to that described for the compound of Example 111, with additional purification for Examples 113 and 114 by reverse phase column chromatography (10-65% MeCN in water w/0.1% formic acid).

| Example | Name | Structure | ¹H NMR δ (500 MHz, DMSO-d₆) | LCMS (ES+) m/z |
|---|---|---|---|---|
| 112 | N-[(3S)-2-oxo-5-phenyl-1,3-dihydro-1,4-benzodiazepin-3-yl]-2-phenyl-6-(trideuteriomethoxy)imidazo[1,2-b]pyridazine-3-carboxamide | 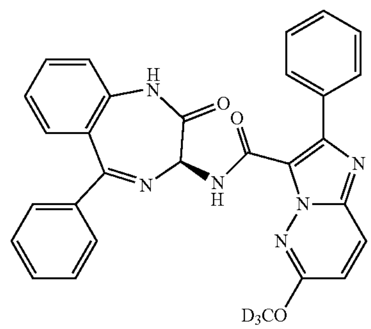 | 11.06 (s, 1H), 10.37 (d, J = 7.2 Hz, 1H), 8.26 (d, J = 9.7 Hz, 1H), 7.92-7.86 (m, 2H), 7.70-7.63 (m, 1H), 7.55-7.49 (m, 1H), 7.49-7.42 (m, 4H), 7.42-7.32 (m, 5H), 7.32-7.25 (m, 1H), 7.21 (d, J = 9.7 Hz, 1H), 5.51 (d, J = 7.2 Hz, 1H). | (method C) 506.4 [M + H]⁺ at 4.41 min |
| 113 | N-[(3S)-9-fluoro-2-oxo-5-phenyl-1,3-dihydro-1,4-benzodiazepin-3-yl]-6-methoxy-2-phenylimidazo[1,2-b]pyridazine-3-carboxamide | 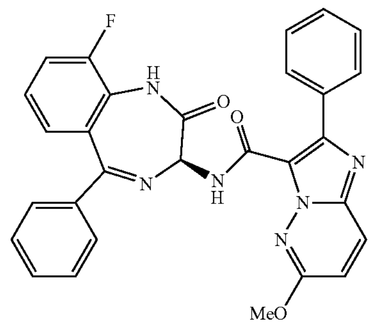 | 11.04 (s, 1H), 10.38 (d, J = 7.1 Hz, 1H), 8.27 (d, J = 9.7 Hz, 1H), 7.91-7.85 (m, 2H), 7.65-7.58 (m, 1H), 7.57-7.49 (m, 3H), 7.49-7.30 (m, 6H), 7.22 (d, J = 9.7 Hz, 1H), 7.19 (d, J = 7.9 Hz, 1H), 5.60 (d, J = 7.1 Hz, 1H), 4.21 (s, 3H). | (method C) 521.4 [M + H]⁺ at 4.51 min |
| 114 | N-[(3S)-9-fluoro-2-oxo-5-phenyl-1,3-dihydro-1,4-benzodiazepin-3-yl]-2-phenyl-6-(trideuteriomethoxy)imidazo[1,2-b]pyridazine-3-carboxamide | 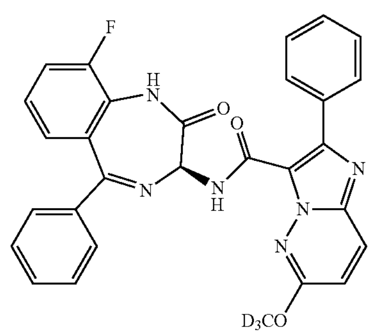 | 11.04 (s, 1H), 10.39 (d, J = 7.1 Hz, 1H), 8.27 (d, J = 9.7 Hz, 1H), 7.91-7.85 (m, 2H), 7.61 (ddd, J = 10.0, 8.1, 1.4 Hz, 1H), 7.56-7.49 (m, 3H), 7.48-7.43 (m, 2H), 7.42-7.36 (m, 3H), 7.36-7.30 (m, 1H), 7.22 (d, J = 9.7 Hz, 1H), 7.19 (d, J = 8.0 Hz, 1H), 5.60 (d, J = 7.1 Hz, 1H). | (method C) 524.4 [M + H]+ at 4.52 min. |

115. N-[(3S)-9-fluoro-2-oxo-5-phenyl-1,3-dihydro-1,4-benzodiazepin-3-yl]-2-(2-fluorophenyl)-6-methoxyimidazo[1,2-b]pyridazine-3-carboxamide

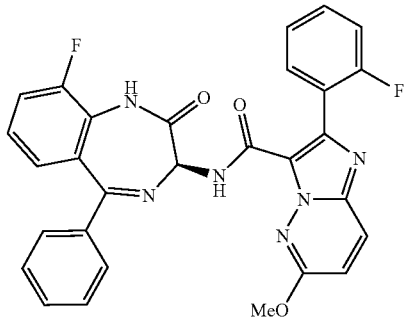 [SMILES: COc1ccc2nc(-c3ccccc3F)c(C(=O)N[C@H]3N=C(c4ccccc4)c4cccc(F)c4NC3=O)n2n1]

A solution of intermediate 45D (45 mg, 0.141 mmol) and LiOH—H$_2$O (59 mg, 1.41 mmol) in MeOH:THF:water (2:2:1; 5 mL) was heated at 50° C. for 18 h. The reaction was cooled to rt, acidified with 1 M aq. HCl to pH≈4 and the solvent removed under reduced pressure. The crude residue was dissolved in DME (1.5 mL), (3S)-3-amino-9-fluoro-5-phenyl-1,3-dihydro-1,4-benzodiazepin-2-one (40 mg, 0.141 mmol) and NEt$_3$ (39 µL, 0.281 mmol) added, followed by HATU (54 mg, 0.141 mmol). The reaction was stirred at rt for 3 h. Analogous workup and purification to that described for Example 42, followed by additional purification by reverse phase column chromatography [5-75% MeCN in 10 mM (NH$_4$)$_2$CO$_3$ aq. solution], afforded an off-white solid (18 mg, 23%). LCMS (Method C) m/z 539.4 [M+H]$^+$ at 4.13 min. $^1$H NMR (500 MHz, DMSO-d$_6$) δ 11.04 (s, 1H), 10.30 (d, J=7.2 Hz, 1H), 8.31 (d, J=9.7 Hz, 1H), 7.60 (t, 1H), 7.55-7.42 (m, 7H), 7.32 (td, J=8.0, 4.9 Hz, 1H), 7.29-7.15 (m, 4H), 5.54 (d, J=7.2 Hz, 1H), 4.24 (s, 3H).

116. 6-Chloro-N-[(3S)-9-fluoro-2-oxo-5-phenyl-1,3-dihydro-1,4-benzodiazepin-3-yl]-2-(2-fluorophenyl)imidazo[1,2-b]pyridazine-3-carboxamide

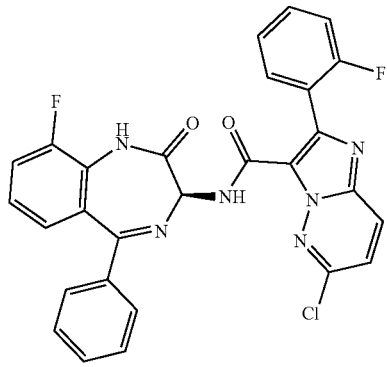 [SMILES: O=C(N[C@H]1N=C(c2ccccc2)c2cccc(F)c2NC1=O)c1c(-c2ccccc2F)nc2ccc(Cl)nn12]

A solution of intermediate 45D (45 mg, 0.141 mmol) and LiOH.H$_2$O (59 mg, 1.41 mmol) in THF:water (2:1; 3 mL) was heated to 50° C. for 3 h. The reaction mixture was cooled to rt, neutralised with 1 M aq. HCl to pH≈7, then concentrated under reduced pressure. The crude residue was dissolved in DMF (3 mL), (3S)-3-amino-9-fluoro-5-phenyl-1,3-dihydro-1,4-benzodiazepin-2-one (38 mg, 0.141 mmol) and NEt$_3$ (20 µL, 0.141 mmol) added, then HATU (54 mg, 0.141 mmol), and the reaction stirred at rt for 18 h. Analogous workup and purification to that described for Example 42, followed by purification by reverse phase column chromatography (15-75% McCN in 10 mM (NH$_4$)$_2$CO$_3$ aq. solution] afforded an off-white solid (13 mg, 17%). LCMS (method D) m/z 543.4 [M+H]$^+$ at 4.18 min. $^1$H NMR (500 MHz, DMSO-d$_6$) δ 11.01 (s, 1H), 9.92 (d, J=7.4 Hz, 1H), 8.50 (d, J=9.5 Hz, 1H), 7.73 (d, J=9.5 Hz, 1H), 7.65-7.58 (m, 2H), 7.58-7.44 (m, 6H), 7.37-7.22 (m, 3H), 7.18 (d, J=7.7 Hz, 1H), 5.54 (d, J=7.3 Hz, 1H).

117. 6-Chloro-2-(6-ethylpyridin-3-yl)-N-[(3S)-9-fluoro-2-oxo-5-phenyl-1,3-dihydro-1,4-benzodiazepin-3-yl]imidazo[1,2-b]pyridazine-3-carboxamide

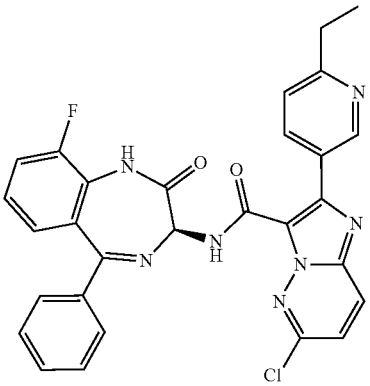 [SMILES: CCc1ccc(-c2nc3ccc(Cl)nn3c2C(=O)N[C@H]2N=C(c3ccccc3)c3cccc(F)c3NC2=O)cn1]

A solution of intermediate 46F (63 mg, 0.179 mmol) and 1.5 M aq. LiOH (0.359 mL, 0.538 mmol) in THF (3 mL) was stirred at rt overnight. The reaction mixture was acidified 1 M aq. HCl to pH≈4 and then concentrated under reduced pressure. The crude residue was dissolved in DMF (1.8 mL), (3S)-3-amino-9-fluoro-5-phenyl-1,3-dihydro-1,4-benzodiazepin-2-one (48 mg, 0.179 mmol) and NEt$_3$ (75 µL, 0.538 mmol) added, then HATU (68 mg, 0.179 mmol), and the reaction stirred at rt for 30 min. Analogous workup and purification to that described for Example 42 afforded a beige solid (50 mg, 48%). LCMS (method C) m/z 554.4 [M+H]$^+$ at 2.77 min. $^1$H NMR (500 MHz, DMSO-d$_6$) δ 11.04-11.00 (m, 1H), 10.18 (d, J=7.2 Hz, 1H), 9.05-9.00 (m, 1H), 8.46 (d, J=9.5 Hz, 1H), 8.26 (dd, J=8.1, 2.3 Hz, 1H), 7.67 (d, J=9.5 Hz, 1H), 7.66-7.60 (m, 1H), 7.59-7.53 (m, 3H), 7.48 (t, J=7.4 Hz, 2H), 7.39-7.31 (m, 2H), 7.21 (d, J=7.9 Hz, 1H), 5.61 (d, J=7.2 Hz, 1H), 2.82 (q, J=7.6 Hz, 2H), 1.28 (t, J=7.6 Hz, 3H).

118. N-[(3S)-9-fluoro-2-oxo-5-phenyl-1,3-dihydro-1,4-benzodiazepin-3-yl]-6-methoxy-2-(5-methylpyridin-3-yl)imidazo[1,2-b]pyridazine-3-carboxamide

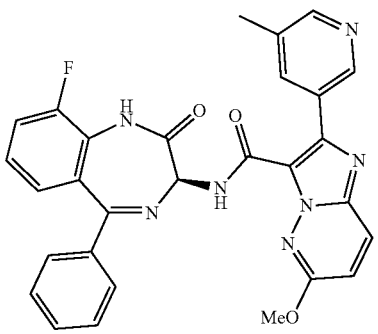 [SMILES: COc1ccc2nc(-c3cncc(C)c3)c(C(=O)N[C@H]3N=C(c4ccccc4)c4cccc(F)c4NC3=O)n2n1]

A solution of intermediate 46C (130 mg, 0.308 mmol) and LiOH (74 mg, 3.083 mmol) in MeOH:THF:water (4:3:3; 10 mL) was heated at 50° C. for 1 h. The reaction was cooled to rt, acidified with 1 M aq. HCl to pH≈4 and the solvent removed under reduced pressure. The crude residue was dissolved in DMF (6 mL), (3S)-3-amino-9-fluoro-5-phenyl-1,3-dihydro-1,4-benzodiazepin-2-one (83 mg, 0.308 mmol) and NEt$_3$ (214 µL, 1.539 mmol) added, then HATU (117 mg, 0.308 mmol), and the reaction was stirred at rt for 1 h. Analogous workup and purification to that described for Example 87 afforded a yellow solid (40 mg, 24%). LCMS (method C) m/z 536.4 [M+H]$^+$ at 2.63 min. $^1$H NMR (500 MHz, DMSO-d$_6$) δ 11.06 (s, 1H), 10.42 (d, J=7.1 Hz, 1H), 8.81 (d, J=2.0 Hz, 1H), 8.41 (s, 1H), 8.30 (d, J=9.7 Hz, 1H), 8.05 (s, 1H), 7.61 (t, J=9.3 Hz, 1H), 7.54-7.49 (m, 3H), 7.45 (t, J=7.5 Hz, 2H), 7.33 (d, J=5.9 Hz, 1H), 7.26 (d, J=9.7 Hz, 1H), 7.19 (d, J=8.0 Hz, 1H), 5.60 (d, J=6.9 Hz, 1H), 4.23 (s, 3H), 2.35 (s, 3H).

The following compounds of the invention were prepared by an analogous procedure to that described for the compound of Example 118.

| Example | Name | Structure | $^1$H NMR δ (500 MHz, DMSO-d$_6$) | LCMS (ES+) m/z |
|---|---|---|---|---|
| 119 | N-[(3S)-9-fluoro-2-oxo-5-phenyl-1,3-dihydro-1,4-benzodiazepin-3-yl]-2-(3-fluoropyridin-4-yl)-6-methoxy-imidazo[1,2-b]pyridazine-3-carboxamide | 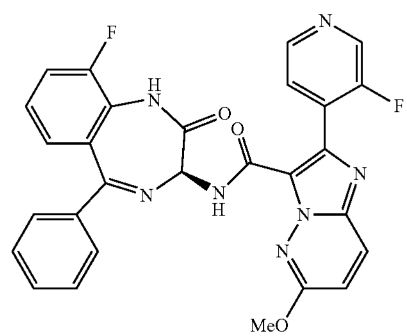 | 11.07 (s, 1H), 10.30 (d, J = 7.1 Hz, 1H), 8.61 (s, 1H), 8.50 (d, J = 4.9 Hz, 1H), 8.34 (d, J = 9.7 Hz, 1H), 7.64-7.56 (m, 2H), 7.56-7.51 (m, 1H), 7.51-7.46 (m, 2H), 7.49-7.42 (m, 2H), 7.36-7.28 (m, 2H), 7.17 (d, J = 7.9 Hz, 1H), 5.54 (d, J = 7.1 Hz, 1H), 4.25 (s, 3H). | (method C) 540.3 [M + H]$^+$ at 3.65 min |
| 120 | N-[(3S)-9-fluoro-2-oxo-5-phenyl-1,3-dihydro-1,4-benzodiazepin-3-yl]-6-methoxy-2-(6-methyipyridin-3-yl)imidazo[1,2-b]pyridazine-3-carboxamide | 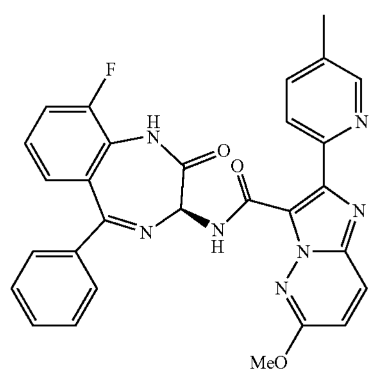 | 11.06 (s, 1H), 10.41 (d, J = 7.1 Hz, 1H), 8.88 (d, J = 2.3 Hz, 1H), 8.31 (d, J = 9.7 Hz, 1H), 8.13 (dd, J = 8.1, 2.3 Hz, 1H), 7.62 (t, J = 9.2 Hz, 1H), 7.57-7.48 (m, 3H), 7.46 (dd, J = 8.1, 6.8 Hz, 2H), 7.38-7.23 (m, 3H), 7.19 (d, J = 8.0 Hz, 1H), 5.60 (d, J = 7.0 Hz, 1H), 4.24 (s, 3H), 3.32 (s, 3H) | (method C) 536.4 [M + H]$^+$ at 2.44 min |

121. 2-(6-Ethylpyridin-3-yl)-6-methoxy-N-[(3S)-9-fluoro-2-oxo-5-phenyl-1,3-dihydro-1,4-benzodiazepin-3-yl]imidazo[1,2-b]pyridazine-3-carboxamide

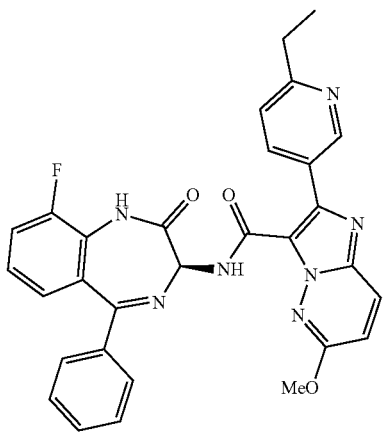 [SMILES: CCc1ccc(-c2nc3ccc(OC)nn3c2C(=O)N[C@H]2N=C(c3ccccc3)c3cccc(F)c3NC2=O)cn1]

LiOH (1.5 M aq; 0.643 mL, 0.965 mmol) was added to a solution of intermediate 46F (68 mg, 0.193 mmol) in THF:MeOH (1:1; 4 mL) and stirred at rt for 4 days. The reaction was acidified with 1 M aq. HCl then to pH≈4 and concentrated under reduced pressure to afford an off-white solid (123 mg) which was taken directly to the next reaction. A portion of the crude residue (58 mg, 0.193 mmol) was dissolved in DMF (1.5 mL), NEt$_3$ (81 µL, 0.579 mmol), and (3S)-3-amino-5-phenyl-1,3-dihydro-1,4-benzodiazepin-2-one (53 mg, 0.196 mmol) added, then HATU (74 mg, 0.195 mmol), and the reaction mixture was stirred at rt for 1 h. The reaction was quenched with water (15 mL), and the resultant precipitate filtered, washing with water (2×15 mL). The precipitate was dissolved in CH$_2$Cl$_2$, concentrated under reduced pressure, and purified by column chromatography (0 to 5% MeOH in CH$_2$Cl$_2$). Further purification by preparative HPLC Method 4 [20-100% MeCN in water (0.1% formic acid)] afforded a white solid (9.7 mg, 9%). LCMS (method C) m/z 550.1 [M+H]$^+$ at 1.02 min. $^1$H NMR (500 MHz, DMSO-d$_6$) δ 11.05 (s, 1H), 10.42 (d, J=7.0 Hz, 1H), 8.93-8.88 (m, 1H), 8.31 (d, J=9.7 Hz, 1H), 8.14 (dd, J=8.1, 2.3 Hz, 1H), 7.66-7.58 (m, 1H), 7.56-7.49 (m, 3H), 7.48-7.43 (m, 2H), 7.37-7.32 (m, 1H), 7.30 (d, J=8.1 Hz, 1H), 7.26 (d, J=9.7 Hz, 1H), 7.22-7.17 (m, 1H), 5.60 (d, J=7.1 Hz, 1H), 4.24 (s, 3H), 2.79 (q, J=7.6 Hz, 2H), 1.26 (t, J=7.6 Hz, 3H). 122. 6-Ethoxy-2-(6-ethylpyridin-3-yl)-N-[(3S)-9-fluoro-2-oxo-5-phenyl-1,3-dihydro-1,4-benzodiazepin-3-yl]imidazo[1,2-b]pyridazine-3-carboxamide

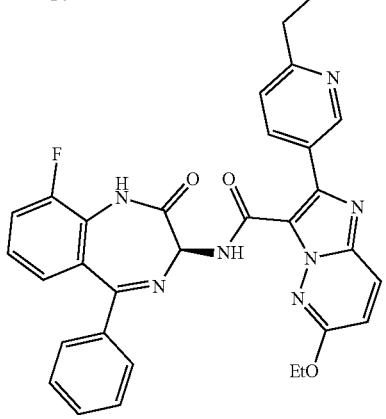

A solution of intermediate 46F (60 mg, 0.172 mmol) and 1.5 M aq. LiOH (0.572 mL, 0.858 mmol) in EtOH:THF (1:1; 4 mL) was heated at 50° C. for 1 h. The reaction was cooled to rt, acidified with 1 M aq. HCl to pH≈4 and the solvent removed under reduced pressure. The crude residue was dissolved in DMF (1.5 mL), (3S)-3-amino-9-fluoro-5-phenyl-1,3-dihydro-1,4-benzodiazepin-2-one (46 mg, 0.172 mmol) and NEt$_3$ (72 µL, 0.515 mmol) added, then HATU (68 mg, 0.178 mmol), and the reaction stirred at rt for 1.5 h. The reaction was diluted with EtOAc (50 mL), washed with brine (3×50 mL), dried (Na$_2$SO$_4$) and the solvent removed under reduced pressure. The residue was purified by column chromatography (0-3% MeOH in CH$_2$Cl$_2$), and reverse phase column chromatography [35-65% MeCN (0.1 formic acid) in water (0.1% formic acid)]. The obtained material was dissolved in CHCl$_3$/iPrOH (3:1; 25 mL), washed with sat. aq. NaHCO$_3$ (2×20 mL) and dried (Na$_2$SO$_4$) to afford a white solid (17 mg, 18%). LCMS (method C) m/z 540.3 [M+H]$^+$ at 3.63 min. $^1$H NMR (500 MHz, DMSO-d$_6$) δ 11.07 (s, 1H), 10.30 (d, J=7.2 Hz, 1H), 8.63-8.59 (m, 1H), 8.53-8.48 (m, 1H), 8.34 (d, J=9.8 Hz, 1H), 7.64-7.57 (m, 2H), 7.57-7.50 (m, 1H), 7.52-7.42 (m, 4H), 7.37-7.28 (m, 2H), 7.17 (d, J=7.9 Hz, 1H), 5.54 (d, J=7.1 Hz, 1H), 4.25 (s, 3H).

123. 2-(6-Ethylpyridin-3-yl)-N-[(3S)-9-fluoro-2-oxo-5-phenyl-2,3-dihydro-1H-1,4-benzodiazepin-3-yl]-6-($^2$H$_3$)methoxyimidazo[1,2-b]pyridazine-3-carboxamide

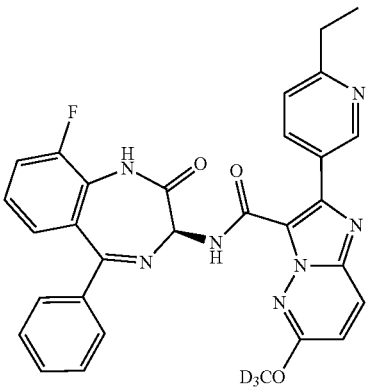

Prepared by the amide coupling procedure A described for the compound of Example 1. LCMS (method C) m/z 553.4 [M+H]$^+$ at 2.72 min. $^1$H NMR (500 MHz, DMSO-d$_6$) δ 11.05 (s, 1H), 10.41 (d, J=7.1 Hz, 1H), 8.92-8.87 (m, 1H), 8.30 (d, J=9.7 Hz, 1H), 8.14 (dd, J=8.1, 2.3 Hz, 1H), 7.65-7.57 (m, 1H), 7.55-7.48 (m, 3H), 7.47-7.42 (m, 2H), 7.36-7.31 (m, 1H), 7.30 (d, J=8.1 Hz, 1H), 7.25 (d, J=9.7 Hz, 1H), 7.19 (d, J=7.9 Hz, 1H), 5.59 (d, J=7.1 Hz, 1H), 2.78 (q, J=7.6 Hz, 2H), 1.25 (t, J=7.6 Hz, 3H).

124. 2-(6-[(3S*)-3-methylmorpholin-4-yl]pyridin-3-yl)-N-[(3S)-2-oxo-5-phenyl-2,3-dihydro-1H-1,4-benzodiazepin-3-yl]pyrazolo[1,5-a]pyrimidine-3-carboxamide

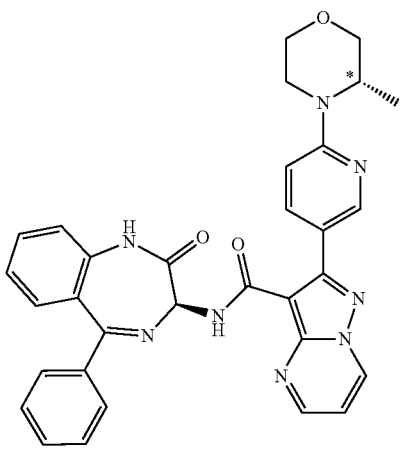 [SMILES: C[C@H]1COCCN1c1ccc(-c2nn3cccnc3c2C(=O)N[C@H]2N=C(c3ccccc3)c3ccccc3NC2=O)cn1]

Example 67 (40 mg) was purified by preparative chiral HPLC [70% MeCN in water (0.1% ammonia)] to afford the title compound as a single diastereomer of unknown absolute configuration, with the arbitrarily defined stereocenter marked by an asterisk. Second eluting enantiomer. Yellow solid (12 mg, 30%). Analytical chiral HPLC: 8.99 min. LCMS (method D) 573.4 [M+H]+ at 3.95 min. $^1$H NMR (500 MHz, DMSO-$d_6$) δ 11.00 (s, 1H), 9.87 (d, J=7.8 Hz, 1H), 9.38 (dd, J=7.0, 1.7 Hz, 1H), 8.93 (dd, J=4.3, 1.7 Hz, 1H), 8.66 (d, J=2.3 Hz, 1H), 8.09 (dd, J=8.9, 2.4 Hz, 1H), 7.70-7.63 (m, 1H), 7.56-7.41 (m, 5H), 7.39-7.32 (m, 3H), 7.32-7.25 (m, 1H), 6.80 (d, J=9.0 Hz, 1H), 5.52 (d, J=7.8 Hz, 1H), 4.42-4.36 (m, 1H), 3.98-3.91 (m, 2H), 3.73 (d, J=11.3 Hz, 1H), 3.63 (dd, J=11.3, 3.1 Hz, 1H), 3.48 (td, J=11.3, 3.1 Hz, 1H), 3.15-3.05 (m, 1H), 1.15 (d, J=6.7 Hz, 3H).

125. N-[(3S)-9-fluoro-2-oxo-5-phenyl-2,3-dihydro-1H-1,4-benzodiazepin-3-yl]-2-{6-[(3S*)-3-methyl-morpholin-4-yl]pyridin-3-yl}pyrazolo[1,5-a]pyrimidine-3-carboxamide

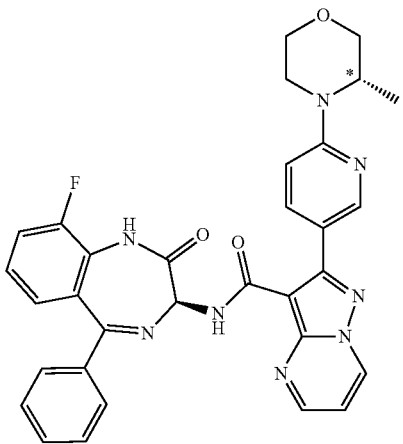 [SMILES: C[C@H]1COCCN1c1ccc(-c2nn3cccnc3c2C(=O)N[C@H]2N=C(c3ccccc3)c3cccc(F)c3NC2=O)cn1]

Example 68 (40 mg) was purified by preparative chiral SFC [50% MeOH:MeCN (1:1) w/0.1% ammonia] to afford the title compound as a single diastereomer of unknown absolute configuration, with the arbitrarily defined stereocenter marked by an asterisk. Second eluting enantiomer. Yellow solid (3.8 mg, 9%). Analytical SFC: 7.86 min. LCMS (method D) m/z 591.5 [M+H]+ at 3.94 min. $^1$H NMR (500 MHz, DMSO-$d_6$) δ 9.88 (d, J=7.8 Hz, 1H), 9.38 (dd, J=7.0, 1.7 Hz, 1H), 8.93 (dd, J=4.3, 1.7 Hz, 1H), 8.66 (d, J=2.3 Hz, 1H), 8.09 (dd, J=8.9, 2.3 Hz, 1H), 7.65-7.58 (m, 1H), 7.57-7.50 (m, 3H), 7.50-7.41 (m, 2H), 7.39-7.30 (m, 2H), 7.19 (d, J=7.9 Hz, 1H), 6.80 (d, J=8.9 Hz, 1H), 5.60 (d, J=7.7 Hz, 1H), 4.42-4.36 (m, 1H), 3.98-3.92 (m, 2H), 3.76-3.70 (m, 1H), 3.67-3.60 (m, 1H), 3.52-3.43 (m, 1H), 3.15-3.05 (m, 1H), 1.15 (d, J=6.7 Hz, 3H).

Example 127: Efficacy In Vitro

Compounds were subjected to RSV plaque reduction assays according to the following protocol. Plaque $EC_{50}$ and cell toxicity $CC_{50}$ values are a mean of at least two experiments and figures are rounded to whole units.

Plaque Reduction Assay.

Hep-G2 cells (ECACC, 85011430) were passaged in flasks and seeded in 24-well plates in DMEM containing antibiotics and supplemented with 10% FBS. During inoculation and subsequent incubation, cells were cultured in DMEM containing 2% FBS. 100 plaque forming unit/well of RSV (RSV A2 ECACC, 0709161v) was mixed with eight serial dilutions of compound. Subsequently, 100 μL of the virus/compound mixtures was added to confluent Hep-G2 cell monolayers. The cells and virus/compound mixtures were incubated at 37° C. in a humidified 5% $CO_2$ incubator for 2 h prior to removal of the inoculum and addition of 1 mL of overlay (DMEM containing 2% FBS and 0.8% CMC) containing compound dilutions. The cells and were incubated at 37° C. in a humidified 5% $CO_2$ incubator for 2 days.

Cells were washed with PBS before adding 75/25% v4v EtOH/MeOH, for 3 min. Fixative was removed and plates were washed with PBS. A pre-titrated amount of the primary antibody was added in 200 μL PBS/2% milk powder, and plates incubated for 90 min at 37° C. The plates were washed 3 times with PBS/0.05% Tween20 before addition of rabbit anti-goat horse radish peroxidase in 200 μL PBS/2% milk powder, and incubated for 1 h at 37° C. Following three wash steps with PBS/0.05% Tween20, 200 μL ready-to-use TrueBlue was added and plates were incubated at rt for 10-15 min before washing with water. After removal of water, plates were air-dried in the dark.

Plates were scanned and analysed using the Immunospot S6 Macro analyser, which is equipped with BioSpot analysis software for counting immunostained plaques (virospots). Plaque counts were used to calculate % c infection relative to the mean of the plaque count in the virus control wells for RSV. The $EC_{50}$ value was calculated as 50% reduction in signal, respectively, by interpolation of inhibition curves fitted with a 4-parameter nonlinear regression with a variable slope in Dotmatics. Plaque $EC_{50}$ and cell toxicity $CC_{50}$ values are a mean of at least two experiments and figures are rounded to whole units.

| Example | RSV A2 Plaque $EC_{50}$ (nM) | Cell Cytotoxicity $CC_{50}$ (nM) |
|---|---|---|
| 1 | 35 | >25,000 |
| 2 | 39 | >25,000 |

| Example | RSV A2 Plaque EC$_{50}$ (nM) | Cell Cytotoxicity CC$_{50}$ (nM) |
| --- | --- | --- |
| 3 | 90 | >25,000 |
| 4 | 62 | >25,000 |
| 5 | 39 | >25,000 |
| 6 | 94 | >25,000 |
| 7 | 107 | >25,000 |
| 8 | 54 | >25,000 |
| 9 | 73 | >25,000 |
| 10 | 77 | 21,081 |
| 11 | 89 | >25,000 |
| 12 | 153 | >25,000 |
| 13 | 94 | >25,000 |
| 14 | 41 | >25,000 |
| 15 | 91 | >25,000 |
| 16 | 18 | >25,000 |
| 17 | 90 | >25,000 |
| 18 | 28 | >25,000 |
| 19 | 31 | >25,000 |
| 20 | 114 | >25,000 |
| 21 | 147 | >25,000 |
| 22 | 33 | >25,000 |
| 23 | 21 | >25,000 |
| 24 | 104 | >25,000 |
| 25 | 116 | 15,397 |
| 26 | 53 | 8,766 |
| 27 | 61 | >25,000 |
| 28 | 41 | >25,000 |
| 28•HCl | 66 | >25,000 |
| 29 | 72 | >25,000 |
| 30 | 62 | >25,000 |
| 31 | 96 | >25,000 |
| 32 | 86 | >25,000 |
| 33 | 29 | >25,000 |
| 34 | 23 | >25,000 |
| 35 | 29 | >25,000 |
| 36 | 27 | >25,000 |
| 37 | 39 | >25,000 |
| 38 | 27 | >25,000 |
| 39 | 62 | >25,000 |
| 40 | 51 | >25,000 |
| 41 | 80 | >25,000 |
| 42 | 41 | >13,992 |
| 43 | 60 | >25,000 |
| 44 | 87 | >25,000 |
| 45 | 103 | >25,000 |
| 46 | 94 | >25,000 |
| 47 | 101 | >25,000 |
| 48 | 13 | >25,000 |
| 49 | 100 | >25,000 |
| 50 | 99 | >25,000 |
| 51 | 92 | >25,000 |
| 52 | 103 | >25,000 |
| 53 | 98 | >25,000 |
| 54 | 151 | >25,000 |
| 55 | 45 | >25,000 |
| 55•HCl | 91 | >25,000 |
| 56 | 63 | >25,000 |
| 57 | 56 | >25,000 |
| 58 | 69 | >25,000 |
| 59 | 60 | >25,000 |
| 60 | 41 | >25,000 |
| 61 | 25 | >25,000 |
| 62 | 74 | >25,000 |
| 63 | 66 | >25,000 |
| 64 | 100 | >18760 |
| 65 | 18 | >25,000 |
| 66 | 13 | >25,000 |
| 67 | 141 | >25,000 |
| 68 | 115 | >25,000 |
| 69 | 19 | >25,000 |
| 70 | 23 | >25,000 |
| 71 | 101 | >25,000 |
| 72 | 118 | >25,000 |
| 73 | 45 | >25,000 |
| 74 | 28 | >25,000 |
| 75 | 44 | >25,000 |
| 76 | 93 | >25,000 |
| 77 | 104 | >25,000 |
| 78 | 81 | >25,000 |
| 79 | 26 | >25,000 |
| 80 | 51 | 13,770 |
| 81 | 114 | 8,150 |
| 82 | 81 | >25,000 |
| 83 | 118 | >25,000 |
| 84 | 95 | 16,324 |
| 85 | 57 | >25,000 |
| 86 | 119 | >25,000 |
| 87 | 53 | >25,000 |
| 88 | 20 | >25,000 |
| 89 | 19 | >25,000 |
| 90 | 8 | >25,000 |
| 91 | 17 | >25,000 |
| 92 | 48 | >25,000 |
| 93 | 33 | >25,000 |
| 94 | 50 | >25,000 |
| 95 | 93 | >21,140 |
| 96 | 91 | >25,000 |
| 97 | 49 | >25,000 |
| 98 | 48 | >25,000 |
| 99 | 51 | >25,000 |
| 100 | 47 | >25,000 |
| 101 | 81 | >25,000 |
| 102 | 105 | >19,182 |
| 103 | 82 | >25,000 |
| 104 | 29 | >25,000 |
| 105 | 38 | >25,000 |
| 106 | 66 | >25,000 |
| 107 | 37 | >25,000 |
| 108 | 84 | 21,938 |
| 109 | 96 | >16,765 |
| 110 | 73 | >25,000 |
| 111 | 48 | >25,000 |
| 112 | 50 | >25,000 |
| 113 | 41 | >25,000 |
| 114 | 39 | >25,000 |
| 115 | 34 | >25,000 |
| 116 | 33 | >25,000 |
| 117 | 27 | >25,000 |
| 118 | 59 | >25,000 |
| 118•HCl | 49 | >25,000 |
| 119 | 28 | >25,000 |
| 120 | 101 | >25,000 |
| 121 | 42 | >25,000 |
| 122 | 100 | >25,000 |
| 123 | 45 | >25,000 |
| 124 | 83 | >25,000 |
| 125 | 87 | >25,000 |
| 126 | 56 | >25,000 |

Example 128: Thermodynamic Solubility

Test compound (2.5 mg of solid; n=1) was weighed in an amber glass vial and buffer (0.5 mL) was added (typically phosphate buffered saline pH 7.4). The solution was agitated at ambient temperature overnight using a vial roller system. The solution was then filtered (0.45 μm pore size; without pre-saturation). Duplicate aliquots (50 μL) are sampled from the filtrate and diluted with one volume of Milli-Q water and methanol (1:1 v/v) before analysis by HPLC-UV. A standard was prepared in DMSO at 10 mg/mL (n=1) which was then diluted 10-fold in Milli-Q water and methanol (1:1 v/v) to give a 1 mg/mL solution. The concentration of test compound in the filtrate was quantified relative to the concentration standard. Analysis was performed using a gradient HPLC-MS system.

| Example | Thermodynamic Solubility (μM) |
|---|---|
| 20 | 3.84 |
| 21 | 4.64 |

Example 129: In Vitro Pharmacokinetics

Compounds were subjected to the following assays to investigate liver microsomal stability and hepatocyte stability.

Microsomal Incubation: Experimental Procedure

Pooled liver microsomes were purchased from a reputable commercial supplier and stored at −80° C. prior to use. Microsomes (final protein concentration 0.5 mg/mL), 0.1 M phosphate buffer pH 7.4 and test compound (final substrate concentration 1 μM; final DMSO concentration 0.25%) were pre-incubated at 37° C. prior to the addition of NADPH (final concentration 1 mM) to initiate the reaction. The final incubation volume was 50 μL. A control incubation was included for each compound tested where 0.1 M phosphate buffer pH 7.4 was added instead of NADPH (minus NADPH). Two control compounds were included with each species. All incubations were performed singularly for each test compound. Each compound was incubated for 0, 5, 15, 30 and 45 min. The control (minus NADPH) was incubated for 45 min only. The reactions were stopped by transferring incubate into acetonitrile at the appropriate time points, in a 1:3 ratio. The termination plates are centrifuged at 3,000 rpm for 20 min at 4° C. to precipitate the protein. Following protein precipitation, the sample supernatants were combined in cassettes of up to 4 compounds, internal standard added, and samples analysed by LC-MS/MS. From a plot of ln peak area ratio (compound peak area/internal standard peak area) against time, the gradient of the line was determined. Subsequently, half-life ($t_{1/2}$) and intrinsic clearance ($CL_{int}$) were calculated. Compounds with low clearance (>80% remaining at 45 min) under the assay conditions are denoted as $t_{1/2}$>140 min.

| Example | Liver Microsomal Stability $t_{1/2}$ (min); rat/dog/human |
|---|---|
| 1 | 40.7/75.2/73.0 |
| 2 | >140/443/185 |
| 3 | >140/>140/330 |
| 4 | >140/236/>140 |
| 5 | >140/356/>140 |
| 7 | 125/150/644 |
| 10 | 110/380/>140 |
| 12 | >140/232/264 |
| 14 | 163/79.9/>140 |
| 16 | 39.1/39.4/89.8 |
| 18 | 50.3/414/741 |
| 19 | 28.6/>140/>140 |
| 20 | 101/>140/>140 |
| 21 | 62.2/177/129 |
| 23 | 33.3/902/399 |
| 24 | 25.6/119/>140 |
| 27 | 525/59.8/122 |
| 28 | 2680/257/852 |
| 29 | 909/73.9/313 |
| 30 | 266/293/181 |
| 32 | 77.1/227/335 |
| 34 | 65.0/86.4/>140 |
| 36 | 33.4/222/>140 |
| 37 | 50.5/117/>140 |
| 38 | 119/165/>140 |
| 39 | 32.3/15.3/79.8 |
| 42 | 170/730/>140 |

| Example | Liver Microsomal Stability $t_{1/2}$ (min); rat/dog/human |
|---|---|
| 43 | 2490/58.2/201 |
| 44 | 231/748/544 |
| 48 | 217/22.2/888 |
| 50 | 233/796/802 |
| 54 | 77/79/175 |
| 55 | 60.4/112/176 |
| 57 | 42.9/82.6/101 |
| 59 | 60.3/90.6/137 |
| 61 | 64.2/23.5/132 |
| 62 | 71.2/49.7/>140 |
| 63 | 227/152/113 |
| 64 | 102/215/1450 |
| 69 | 146/26.8/193 |
| 70 | 99.1/31.5/207 |
| 72 | 158/51.4/180 |
| 74 | 70.4/43.5/264 |
| 75 | 50.0/86.9/678 |
| 78 | 55.4/250/230 |
| 80 | 114/179/144 |
| 81 | 89.6/113/29.3 |
| 85 | 198/105/>140 |
| 87 | 86.0/67.5/4130 |
| 88 | 202/76.4/>140 |
| 89 | 186/1080/737 |
| 91 | 36.6/268/101 |
| 93 | 41.1/1420/2090 |
| 95 | 35.7/66.8/56.9 |
| 96 | 28.1/227/2570 |
| 100 | 27.4/82.2/908 |
| 106 | 87.4/288/47.5 |
| 107 | 87.4/187/298 |
| 108 | 68.6/173/77.9 |
| 109 | 68.9/260/77.9 |
| 113 | 87.4/241/518 |
| 114 | 122/330/246 |
| 115 | 145/467/150 |
| 116 | 57.4/>140/>140 |
| 118 | 48.5/143/119 |
| 119 | 51.8/444/161 |
| 126 | 413/33.8/312 |

Hepatocyte Incubation: Experimental Procedure

Cryopreserved pooled hepatocytes were purchased from a reputable commercial supplier and stored in liquid nitrogen prior to use. Williams E media supplemented with 2 mM L-glutamine and 25 mM HEPES and test compound (final substrate concentration 3 μM; final DMSO concentration 0.25%) are pre-incubated at 37° C. prior to the addition of a suspension of cryopreserved hepatocytes (final cell density $0.5 \times 10^6$ viable cells/mL in Williams E media supplemented with 2 mM L-glutamine and 25 mM HEPES) to initiate the reaction. The final incubation volume is 500 μL. Two control compounds were included with each species, alongside appropriate vehicle control. The reactions are stopped by transferring 50 μL of incubate to 100 μL acetonitrile containing internal standard at the appropriate time points. Samples were removed at 6 time points (0, 5, 15, 30, 45 and 60 min) over the course of a 60 min experiment. The termination plates are centrifuged at 2500 rpm at 4° C. for 30 min to precipitate the protein. Following protein precipitation, the sample supernatants were combined in cassettes of up to 4 compounds and analysed using generic LC-MS/MS conditions. From a plot of ln peak area ratio (compound peak area/internal standard peak area) against time, the gradient of the line is determined. Subsequently, half-life ($t_{1/2}$) and intrinsic clearance ($CL_{int}$) were calculated. Compounds with low clearance (>80% remaining at 60 min) under the assay conditions are denoted as $t_{1/2}$>186 min.

| Example | Liver Hepatocyte Stability $t_{1/2}$ (min); rat/dog/human |
|---|---|
| 2 | 237/67.1/8680 |
| 3 | 81.7/>186/257 |
| 18 | 66.4/127/694 |
| 19 | 95.8/>186/121 |
| 20 | 175/132/131 |
| 21 | 89.8/153/151 |
| 23 | 70.9/214/519 |
| 28 | >186/240/194 |
| 50 | 5800/>186/>186 |
| 55 | 85.9/146/>186 |
| 57 | 47.1/2600/>186 |
| 93 | 71.5/445/294 |
| 119 | 118/295/>186 |

Example 130: In Vivo Pharmacokinetics

The pharmacokinetics of compounds were studied in vivo in rats at doses of 1 mg/kg (IV) and 10 mg/kg (PO).
Rat Pharmacokinetics
Methods Male rats [Sprague Dawley (SD)] surgically prepared with a jugular vein cannula were treated with experimental compounds via intravenous administration (IV; n=3; 1 mg/kg) or oral administration (PO; n=3; 10 mg/kg). Compounds were formulated as a solution in 40:60 dimethylacetamide:saline (IV administration) and a solution of 10% DMSO, 20% cremaphor in water (70%) (PO administration). Animals were observed for any overt clinical signs or symptoms. Serial blood samples were collected via the cannula at 0.02, 0.08, 0.25, 0.5, 1, 2, 4, 6, 8 and 24 h post IV dosing of compound, and at 0.08, 0.25, 0.5, 1, 2, 4, 6, 8 and 24 h post oral dosing of compound, and plasma was prepared by centrifugation and stored immediately at −80° C. Samples were subsequently thawed, prepared for analysis by protein precipitation with acetonitrile, and analysed by tandem LCMS using electrospray ionisation using a matrix-matched calibration curve. PK parameters were calculated from the resulting data.

| Example | 2 | 28 | 50 | 55 | 57 |
|---|---|---|---|---|---|
| PO $AUC_{last}$ (hr*ng/mL) | 34228 | 11076 | 20044 | 14675 | 3663 |
| Cl (mL/min/kg) | 5.0 | 7.8 | 13.0 | 14.3 | 19.2 |
| $V_d$ (L/kg) | 1.3 | 1.8 | 0.94 | 1.2 | 0.6 |
| $C_{max}$ (ng/mL) | 2413 | 785 | 2038 | 1425 | 912 |
| C 8 h (ng/mL) | 2290 | 629 | 1003 | 753 | 142 |
| IV $t_{1/2}$ (h) | 3.1 | 3.1 | 1.2 | 2 | 1.4 |
| PO $t_{1/2}$ (h) | NR | 5.4 | 2.4 | 2.5 | 2.6 |
| F (%) | 103 | 54 | 152 | 113 | 48 |

Dog Pharmacokinetics

The pharmacokinetics of compounds were studied in vivo in dogs at doses of 0.5 mg/kg (IV) and 4 mg/kg (PO).
Methods Male Beagle dogs were treated with experimental compounds via intravenous administration (n=2; 0.5 mg/kg) or oral administration (n=2; 3 or 4 mg/kg). Compounds were formulated as a solution in 20% dimethylacetamide/80% (2-hydroxypropyl)-β-cyclodextrin (20% w/v) (IV administration) or a solution in 10% dimethylacetamide/90% (2-hydroxypropyl)-β-cyclodextrin (20% w/v) (PO administration). Animals were observed for any overt clinical signs or symptoms. Serial blood samples were collected from the jugular vein at 0.03, 0.08, 0.25, 0.5, 1, 2, 4, 6, 8 and 24 h post IV dosing of compound, and at 0.08, 0.25, 0.5, 1, 2, 4, 6, 8 and 24 h post oral dosing of compound, and plasma was prepared by centrifugation and stored immediately at −80° C. Samples were subsequently thawed, prepared for analysis by protein precipitation with acetonitrile, and analysed by tandem LCMS using electrospray ionisation using a matrix-matched calibration curve. PK parameters were calculated from the resulting data.

| Example | 2 | 20 | 50 | 55 |
|---|---|---|---|---|
| PO $AUC_{last}$ (hr*ng/mL) | 22322 | 43678 | 13334 | 20890 |
| Cl (mL/min/kg) | 1.3 | 1.6 | 1.7 | 1.5 |
| $V_d$ (L/kg) | 0.92 | 1.2 | 1.3 | 0.47 |
| $C_{max}$ (ng/mL) | 1920 | 3849 | 1201 | 3206 |
| C 8 h (ng/mL) | 968 | 1581 | 549 | 720 |
| IV $t_{1/2}$ (h) | 9.8 | 10.3 | 12.2 | 5.4 |
| PO $t_{1/2}$ (h) | 11.1 | 19.2 | 16.1 | 6.1 |
| F (%) | 55 | 118 | 65 | 65 |

Example 131: Aqueous Formulation

The compound of Example 1 is formulated as a solution in 30% w/v captisol (i.e. sulfobutylether-beta-cyclodextrin) at pH4 according to the following procedure. A carrier of 30% w/v captisol (i.e. sulfobutylether-beta-cyclodextrin) is prepared by weighing the required amount of captisol into a suitable vessel, adding approximately 80% of the final volume of water and magnetically stirring until a solution is formed. The carrier is then made up to volume with water.

An aqueous solution of a compound of Example 1 is prepared by weighing 175 mg of the compound into a suitable vessel and adding approximately 80% of the required volume of the carrier. Using an aqueous solution of hydrochloric acid, the pH is adjusted to pH2 and the resulting mixture is magnetically stirred until a solution is formed. The formulation is then made up to volume with carrier and the pH is adjusted to pH4 using an aqueous solution of sodium hydroxide.

Example 132: Tablet Composition

Tablets, each weighing 0.15 g and containing 25 mg of a compound of the invention are manufactured as follows:
Composition for 10.000 tablets
Compound of the invention (250 g)
Lactose (800 g)
Corn starch (415 g)
Talc powder (30 g)
Magnesium stearate (5 g)

The compound of the invention, lactose and half of the corn starch are mixed. The mixture is then forced through a sieve 0.5 mm mesh size. Corn starch (10 g) is suspended in warm water (90 mL). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 133: Injectable Formulation

| Compound of the invention | 200 mg |
|---|---|
| Hydrochloric Acid Solution 0.1M or | 4.0 to 7.0 |

| | |
|---|---|
| Sodium Hydroxide Solution 0.1M q.s. to pH | |
| Sterile water q.s. to | 10 mL |

The compound of the invention is dissolved in most of the water (35° C.-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 134: Intramuscular Injection

| | |
|---|---|
| Compound of the invention | 200 mg |
| Benzyl Alcohol | 0.10 g |
| Glycofurol 75 | 1.45 g |
| Water for injection q.s to | 3.00 mL |

The compound of the invention is dissolved in the glycofurol. The benzyl alcohol is then added and dissolved, and water added to 3 mL. The mixture is then filtered through a sterile micropore filter and sealed in sterile 3 mL glass vials (type 1).

Example 135: Syrup Formulation

| | |
|---|---|
| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbital solution and finally the flavour. The volume is made up with purified water and mixed well.

We claim:

1. 2-(2-Fluorophenyl)-N-[(3S)-2-oxo-5-phenyl-1,3-dihydro-1,4-benzodiazepin-3-yl]pyrazolo[1,5-a]pyrimidine-3-carboxamide or a pharmaceutically acceptable salt thereof.

2. A pharmaceutical composition which comprises: (a) 2-(2-Fluorophenyl)-N-[(3S)-2-oxo-5-phenyl-1,3-dihydro-1,4-benzodiazepin-3-yl]pyrazolo[1,5-a]pyrimidine-3-carboxamide or a pharmaceutically acceptable salt thereof; and (b) a pharmaceutically acceptable carrier or diluent.

* * * * *

UNITED STATES PATENT AND TRADEMARK OFFICE
CERTIFICATE OF CORRECTION

PATENT NO. : 11,634,425 B2
APPLICATION NO. : 17/845187
DATED : April 25, 2023
INVENTOR(S) : George Stuart Cockerill et al.

It is certified that error appears in the above-identified patent and that said Letters Patent is hereby corrected as shown below:

In the Specification

Column 24, Line 10, "(min, 3H)," should be --(m, 3H)--.

Column 24, Line 17, "60" should be --6O--.

Column 27, Line 39, "S-diazabicyclo" should be --5-diazabicyclo--.

Column 30, Line 30, "(in. 2H)" should be --(m, 2H)--.

Column 33, Line 1, "S-trifluoromethyl" should be --5-trifluoromethyl--.

Column 38, Line 26, "5-Bronro" should be --5-Bromo--.

Column 39, Line 27, "carbaxylate" should be --carboxylate--.

Column 39, Line 56, "carbaxylate" should be --carboxylate--.

Column 40, Line 17, "carbaxylate" should be --carboxylate--.

Column 40, Line 44, "carbaxylate" should be --carboxylate--.

Column 42, Line 2, "carbaxylate" should be --carboxylate--.

Column 42, Line 29, "Ch2" should be --$Cl_2$--.

Column 47, Line 1, "methaxypyridin" should be --methoxypyridin--.

Column 50, Line 57, "0.66 m." should be --0.66 min.--.

Signed and Sealed this
Sixth Day of June, 2023

*Katherine Kelly Vidal*

Katherine Kelly Vidal
*Director of the United States Patent and Trademark Office*

CERTIFICATE OF CORRECTION (continued)
U.S. Pat. No. 11,634,425 B2

Column 53, Line 26, "S-cyclopropylpyridin" should be --5-cyclopropylpyridin--.

Column 54, Line 27, "carbaxylate" should be --carboxylate--.

Column 55, Line 38, "carbaxylate" should be --carboxylate--.

Column 57, Line 2, "carbaxylate" should be --carboxylate--.

Column 57, Line 37, "carbaxylate" should be --carboxylate--.

Column 57, Line 62, "C2" should be --$Cl_2$--.

Column 58, Line 2, "carbaxylate" should be --carboxylate--.

Column 58, Line 35, "carbaxylate" should be --carboxylate--.

Column 60, Line 41, "90°/)" should be --90%)--.

Column 64, Line 25, "$Na_2S20_3$" should be --$Na_2S_2O_3$--.

Column 66, Line 21, "M1" should be --rt--.

Column 69, Line 1, "S-trifluoromethyl" should be --5-trifluoromethyl--.

Column 69, Line 2, "carbaxylate" should be --carboxylate--.

Column 71, Line 2, "carbaxylate" should be --carboxylate--.

Column 72, Line 8, "carbaxylate" should be --carboxylate--.

Column 73, Line 2, "carbaxylate" should be --carboxylate--.

Column 73, Line 28, "carbaxylate" should be --carboxylate--.

Column 73, Line 56, "carbaxylate" should be --carboxylate--.

Column 76, Line 18, "60" should be --6O--.

Column 78, Line 1, "methylazeidin" should be --methylazetidin--.

Column 123, Line 42, "DME" should be --DMF--.

Column 145, Line 27, "DME" should be --DMF--.

Column 147, Example 120/Name, "methyipyridin" should be --methylpyridin--.

Column 152, Line 38, "v4v" should be --v/v--.

Column 155, Line 41, insert --Results--.

Column 158, Line 46, "10.000" should be --10,000--.